United States Patent
Richelson et al.

(10) Patent No.: US 9,944,618 B2
(45) Date of Patent: Apr. 17, 2018

(54) INHIBITING NEUROTRANSMITTER REUPTAKE

(71) Applicants: Mayo Foundation for Medical Education and Research, Rochester, MN (US); Virginia Tech Intellectual Properties, Inc., Blacksburg, VA (US)

(72) Inventors: Elliott Richelson, Ponte Vedra Beach, FL (US); Abdul H. Fauq, Jacksonville, FL (US); Paul Carlier, Blacksburg, VA (US); Christopher J. Monceaux, Christiansburg, VA (US)

(73) Assignees: Mayo Foundation for Medical Education and Research, Rochester, MN (US); Virginia Tech Intellectual Properties, Inc., Blacksburg, VA (US)

( * ) Notice: Subject to any disclaimer, the term of this patent is extended or adjusted under 35 U.S.C. 154(b) by 0 days.

(21) Appl. No.: 14/776,397

(22) PCT Filed: Mar. 10, 2014

(86) PCT No.: PCT/US2014/022684
§ 371 (c)(1),
(2) Date: Sep. 14, 2015

(87) PCT Pub. No.: WO2014/159251
PCT Pub. Date: Oct. 2, 2014

(65) Prior Publication Data
US 2016/0024044 A1    Jan. 28, 2016

Related U.S. Application Data

(60) Provisional application No. 61/783,122, filed on Mar. 14, 2013.

(51) Int. Cl.
| | | |
|---|---|---|
| C07D 333/28 | (2006.01) | |
| C07C 259/06 | (2006.01) | |
| C07C 211/30 | (2006.01) | |
| A61K 31/138 | (2006.01) | |
| C07C 215/28 | (2006.01) | |
| C07C 215/68 | (2006.01) | |
| C07C 217/48 | (2006.01) | |
| C07C 217/62 | (2006.01) | |
| C07C 217/64 | (2006.01) | |
| C07C 233/43 | (2006.01) | |
| C07C 235/06 | (2006.01) | |
| C07C 235/08 | (2006.01) | |
| C07D 317/58 | (2006.01) | |
| C07D 319/18 | (2006.01) | |
| C07D 333/20 | (2006.01) | |
| C07D 261/08 | (2006.01) | |
| C07D 265/06 | (2006.01) | |

(Continued)

(52) U.S. Cl.
CPC .......... *C07D 333/28* (2013.01); *A61K 31/138* (2013.01); *C07C 211/30* (2013.01); *C07C 215/28* (2013.01); *C07C 215/30* (2013.01); *C07C 215/68* (2013.01); *C07C 217/48* (2013.01); *C07C 217/62* (2013.01); *C07C 217/64* (2013.01); *C07C 233/43* (2013.01); *C07C 235/06* (2013.01); *C07C 235/08* (2013.01); *C07C 235/14* (2013.01); *C07C 259/06* (2013.01); *C07C 323/32* (2013.01); *C07D 205/04* (2013.01); *C07D 207/12* (2013.01); *C07D 213/30* (2013.01); *C07D 213/38* (2013.01); *C07D 213/61* (2013.01); *C07D 213/64* (2013.01); *C07D 213/65* (2013.01); *C07D 215/06* (2013.01); *C07D 261/08* (2013.01); *C07D 265/06* (2013.01); *C07D 267/10* (2013.01); *C07D 271/06* (2013.01); *C07D 295/135* (2013.01); *C07D 295/185* (2013.01); *C07D 295/192* (2013.01); *C07D 317/58* (2013.01); *C07D 319/18* (2013.01); *C07D 333/20* (2013.01); *C07C 2101/02* (2013.01); *C07C 2101/04* (2013.01)

(58) Field of Classification Search
None
See application file for complete search history.

(56) References Cited

U.S. PATENT DOCUMENTS

| 6,069,177 A | 5/2000 | Carlier et al. |
|---|---|---|
| 6,184,222 B1 | 2/2001 | Heiligenstein |

(Continued)

FOREIGN PATENT DOCUMENTS

| WO | WO 2002/040006 | 5/2002 |
|---|---|---|
| WO | WO 2003/007929 | 1/2003 |

(Continued)

OTHER PUBLICATIONS

Parenty et al. Org. Let. 2002, 4(10), 1663-1666.*
https://en.wikipedia.org/wiki/Eschweiler%E2%80%93Clarke_reaction (Sep. 27, 2016).*
Beer et al., "DOV 216,303, a "triple" reuptake inhibitor: safety, tolerability, and pharmacokinetic profile," *J. Clin. Pharmacol.*, 2004, 44(12):1360-1367.
Berge et al., "Pharmaceutical Salts", *J. Pharm. Sci.*, 1977, 66: 1-19.
Bolden-Watson and Richelson, "Blockade by newly-developed antidepressants of biogenic amine uptake into rat brain synaptosomes," *Life Sci.*, 1993, 52:1023-1029.

(Continued)

*Primary Examiner* — Clinton Brooks
(74) *Attorney, Agent, or Firm* — Fish & Richardson P.C.

(57) ABSTRACT

This document relates to compounds as well as methods and materials involved in modulating neurotransmitter reuptake. For example, compounds, methods for synthesizing compounds, and methods for inhibiting neurotransmitter reuptake are provided. Specifically gamma-amino alcohol derivatives that inhibit the reuptake of neurotransmitters such as dopamine, serotonin, epinephrine or norepinephrine are provided as therapeutic agents for the treatment of depression or anxiety in a mammalian subject.

10 Claims, No Drawings

(51) Int. Cl.
    C07D 267/10      (2006.01)
    C07D 207/12      (2006.01)
    C07D 271/06      (2006.01)
    C07D 295/135     (2006.01)
    C07D 295/185     (2006.01)
    C07D 213/30      (2006.01)
    C07D 213/61      (2006.01)
    C07D 213/64      (2006.01)
    C07D 213/65      (2006.01)
    C07C 215/30      (2006.01)
    C07C 235/14      (2006.01)
    C07C 323/32      (2006.01)
    C07D 205/04      (2006.01)
    C07D 213/38      (2006.01)
    C07D 215/06      (2006.01)
    C07D 295/192     (2006.01)

(56) References Cited

U.S. PATENT DOCUMENTS

| | | | |
|---|---|---|---|
| 6,700,018 B2 * | 3/2004 | Richelson | A61K 31/137 564/355 |
| 6,914,080 B2 * | 7/2005 | Richelson | A61K 31/137 514/653 |
| 7,214,826 B2 | 5/2007 | Richelson et al. | |
| 8,440,724 B2 * | 5/2013 | Richelson | A61K 31/137 514/649 |
| 8,507,500 B2 | 8/2013 | Richelson et al. | |
| 2006/0069177 A1 | 3/2006 | Sachdev et al. | |
| 2007/0197662 A1 | 8/2007 | Richelson et al. | |
| 2008/0200556 A1 | 8/2008 | Richelson et al. | |
| 2008/0275272 A1 | 11/2008 | Richelson et al. | |
| 2010/0168246 A1 | 7/2010 | Richelson et al. | |
| 2012/0220665 A1 | 8/2012 | Richelson et al. | |

FOREIGN PATENT DOCUMENTS

| | | |
|---|---|---|
| WO | WO 2005/120200 | 12/2005 |
| WO | WO 2008/020056 | 8/2008 |
| WO | WO 2009/089479 | 7/2009 |
| WO | WO 2011/056773 | 5/2011 |
| WO | WO 2011/056788 | 5/2011 |
| WO | WO 2011/075470 | 6/2011 |

OTHER PUBLICATIONS

Carlier et al., "Gamma-Amino Alcohol Wide-Spectrum Reuptake Inhibitor Antidepressant Drug Candidates and Neurochemical Probes," *Proceedings of the Symposium on the Frontiers of Chemistry The Second Conference for Worldwide Chinese Young Chemists (CWCYC-2)*, Dec. 20-23, 1997, Hong Kong, pp. 127-128.

Carlier et al., "HMPA Promotes Retro-Aldol Reaction, Resulting in Syn-Selective Addition of Lithiated 1-Naphthylacetonitrile to Aromatic Aldehdes," *Org. Lett.*, 2000, 2(16):2443-2445.

Carlier et al., "Lead Optimization in the Development of SNDRI Antidepressant Drug Candidates and Species-Selective Dopamine Transporter Ligands," *Fifth Chemistry Postgraduate Research Symposium in Hong Kong*, Hong Kong, Apr. 25, 1998, Abstract O-55.

Carlier et al., "Synthesis of a Potent Wide-Spectrum Serotonin-, Norepinephrine-, Dopamine-Reuptake Inhibitor (SNDRI) and a Species-Selective Dopamine-Reuptake Inhibitor Based on the Gamma-Amino Alcohol Functional Group," *Bioorg. Med. Chem. Lett.*, 1998, 8:487-492.

Carlier et al., "Anti-Selective Aldol Reaction of Benzylic Nitriles and Synthesis of γ-Amino Alcohols," *J. Org. Chem.*, 1995, 60:7511-7517.

Carlier et al., "Synthesis of a potent wide-spectrum serotonin-, norepinephrine-, dopamine-reuptake inhibitor (SNDRI) and a species-specific dopamine-reuptake inhibitor based on the gamma-amino alcohol functional group," *Abstracts of Papers of the American Chemical Society 215th ACS National Meeting*, Mar. 29-Apr. 2, 1998, Abstract No. 154.

Carlier et al., "Synthetic Optimization and Structural Limitations of the Nitrile Aldol Reaction," *J. Org. Chem*... vol. 62, No. 18 (1997) 6316-6321.

Chen and Skolnick, "Triple uptake inhibitors: therapeutic potential in depression and beyond," *Exp. Opin. Investig. Drugs*, 2007, 16(9):1365-1377.

Cheng and Prusoff, "Relationship between the inhibition constant (K1) and the concentration of inhibitor which causes 50 percent inhibition (I50) of an enzymatic reaction," *Biochem Pharmacol.*, 22(23):3099-3108, Dec. 1, 1973.

Cryan et al., "Assessing antidepressant activity in rodents: recent developments and future needs," *Trends Pharmacol. Sci.*, 2002, 23(5):238-245.

Detke et al., "Active behaviors in the rat forced swimming test differentially produced by serotonergic and noradrenergic antidepressants," *Psychopharmacology*, 1995, 121:66-72.

Eisensamer et al., "Antidepressants are functional antagonists at the serotonin type 3 (5-HT3) receptor," *Mol. Psychiatry*, 2003, 8(12):994-1007.

GenBank® Accession No. NM_000238, "*Homo sapiens* potassium voltage-gated channel, subfamily H (eag-related), member 2 (KCNH2), transcript variant 1, mRNA," Feb. 14, 2012, 5 pages.

GenBank® Accession Nos. U04270, "Human putative potassium channel subunit (h-erg) mRNA, complete cds," Feb. 28, 1995, 3 pages.

Hanna et al., "Synthesis of Some Tropane Derivatives of Anticipated Activity on the Reuptake of Norepinephrine and/or Serotonins," *Biorganic & Medicinal Chemistry*, vol. 15:7765-7772 (2007).

King, ed., "Bioisosteres, conformational restriction and pro-drugs-case history: an example of a conformational restriction approach," *Medical Chemistry: Principles and Practice*, 1994, Chapter 14, pp. 206-209.

Liang and Richelson, "Triple Reuptake Inhibitors: Next-Generation Antidepressants," *Primary Psychiatry*, 2008, 15(4):50-56.

Liang et al., "Antidepressant-Like Pharmacological Profile of a Novel Triple Reuptake Inhibitor, (1S,2S)-3-(Methylamino)-2-(naphthalen-2-yl)-1-phenylpropan-1-ol (PRC200-SS)," *J. Pharmacol. Exp. Ther.*, 2008, 327(2):573-583.

Lo et al., "Anti-Selective Aldol of Benzylic Nitriles and Synthesis of γ-Hydroxyamine Antidepressant Analogs," *Second Symposium on Chemistry Postgraduate Research in Hong Kong*, Hong Kong, Mar. 11, 1995, Abstract OP-5.

Lowry et al., "Protein Measurement with the Folin Phenol Reagent," *J. Biol. Chem.*, 1951, 193:265-275.

May, "A Half Century in Medicinal Chemistry with Major Emphasis on Pain-Relieving Drugs and Their Antagonists," Med. Chem., 1992, 35(20), 3587-3594.

Munson and Rodbard, "LIGAND: A Versatile Computerized Approach for Characterization of Ligand-Binding Systems," *Analyt. Biochem.*, 1980, 107:220-239.

Pacholczyk et al., "Expression cloning of a cocaine-and antidepressant-sensitive human noradrenaline transporter," *Nature*, 1991, 350:350-354.

Pfenning and Richelson, "Methods for Studying Receptors with Cultured Cells of Nervous Tissue Origin," *Methods in Neurotransmitter Receptor Analysis*, 1990, Raven Press, New York, pp. 147-175.

Popik et al., "Pharmacological Profile of the "Triple" Monoamine Neurotransmitter Uptake Inhibitor, DOV 102,677," *Cell. Mol. Neurobiol.*, 2006, 26:857-873.

Porsolt et al., "Depression: a new animal model sensitive to antidepressant treatments," *Nature*, 1977, 266:730-732.

Pristupa et al., "Pharmacological Heterogeneity of the Cloned and Native Human Dopamine Transporter: Disassociation of [$3^H$]WIN 35,428 and [$3^H$]GBR 12,935 Binding," *Mol. Pharmacol.*, 1994, 45:125-135.

(56) References Cited

OTHER PUBLICATIONS

Ramamoorthy et al., "Antidepressant- and cocaine-sensitive human serotonin transporter: Molecular cloning, expression, and chromosomal localization," *Proc. Natl. Acad. Sci. USA*, 1993, 90:2542-2546.
Richelson and Pfenning, "Blockade by antidepressants and related compounds of biogenic amine uptake into rat brain synaptosomes: Most antidepressants selectively block norepinephrine uptake," *Eur. J. Pharmacol.*, 1984, 104:277-286.
Richelson et al., "A novel series of triple re-uptake inhibitor potential antidepressants," *IXth World Conference on Clinical Pharmacology and Therapeutics*, Quebec City, Canada, Jul. 30, 2008, Abstract 386.
Richelson, "Triple reuptake inhibitors as a new generation of antidepressant drugs," *J. Affect Disord.*, 2008, 107(Suppl 1):S36. (International Society for Affective Disorders, Cape Town, SA, Mar. 16, 2008).
Shaw et al., "Antidepressant-like effects of novel triple reuptake inhibitors, PRC025 and PRC050," *Eur. J. Pharmacol.*, 2007, 555:30-36.
Shaw et al., "Antidepressant-like effects of novel triple reuptake inhibitors, PRC025 and PRC050," *Program No. 447.8. 2005 Abstract Viewer/Itinerary Planner*, Washington, DC: Society for Neuroscience, 2005.
Shaw et al., "Antidepressant-like effects of PRC200, a novel norepinephrine, serotonin, and dopamine reuptake inhibitor," *Biol. Psychiatry*, 2006, 59(8):61S-62S, Abstract 196.
Shaw et al., "Reuptake inhibitors: What to expect from 'mega-antidepressants'," *Current Psychiatry*, 2007, 6(3):31-42.
Skolnick et al., "Antidepressant-like actions of DOV 21,947: a "triple" reuptake inhibitor," *Eur. J. Pharmacol.*, 2003, 461:99-104.
Skolnick et al., "Preclinical and Clinical Pharmacology of DOV 216,303, a "Triple" Reuptake Inhibitor," *CNS Drug Reviews*, 2006, 12(2):123-134.
Steru et al., "The tail suspension test: a new method for screening antidepressants in mice," *Psychopharmacology*, 1985, 85(3):367-370.
Tatsumi et al., "Pharmacological profile of antidepressants and related compounds at human monoamine transporters," *Eur. J. Pharmacol.*, 1997, 340:249-258.
International Search Report re PCT/US2002/022069, dated Dec. 9, 2002, 1 pages.
International Preliminary Examination Report re PCT/US2002/022069, completed Nov. 13, 2003, 3 pages.
Supplemental European Search Report in European Application No. 02761085.6, dated Mar. 14, 2007, 3 pages.
International Search Report and Written Opinion in International Application No. PCT/US2005/019866, dated May 24, 2007, 4 pages.
International Preliminary Report on Patentability in International Application No. PCT/US2005/019866, dated Jun. 19, 2007, 4 pages.
Supplemental European Search Report in European Application No. 05756359.5, dated Jan. 22, 2008, 3 pages.
International Search Report and Written Opinion in International Application No. PCT/US2009/030642, dated Aug. 28, 2009, 9 pages.
International Preliminary Report on Patentability in International Application No. PCT/US2009/030642, dated Jul. 13, 2010, 7 pages.
International Search Report and Written Opinion in International Application No. PCT/US2010/055065, dated Jul. 26, 2011, 12 pages.
International Search Report and Written Opinion in International Application No. PCT/US2010/055109, dated Jul. 26, 2011, 12 pages.
International Preliminary Report on Patentability in International Application No. PCT/US2010/055065, dated May 8, 2012, 9 pages.
International Preliminary Report on Patentability in International Application No. PCT/US2010/055109, dated May 8, 2012, 9 pages.
International Search Report and Written Opinion for PCT/US2014/022684, dated Sep. 18, 2014, 15 pages.
International Preliminary Report on Patentability for PCT/US2014/022684, dated Sep. 15, 2015, 9 pages.

* cited by examiner

INHIBITING NEUROTRANSMITTER REUPTAKE

CROSS-REFERENCE TO RELATED APPLICATIONS

This application is a National Stage application under 35 U.S.C. § 371 of International Application No. PCT/US2014/022684, having an International Filing Date of Mar. 10, 2014, which claims the benefit of U.S. Provisional Application Ser. No. 61/783,122, filed Mar. 14, 2013. The disclosure of the prior applications are considered part of (and are incorporated by reference in) the disclosure of this application.

BACKGROUND

1. Technical Field

This document relates to compounds as well as methods and materials involved in modulating neurotransmitter reuptake.

2. Background Information

Neuronal signals are transmitted from cell to cell at specialized sites of contact known as synapses. The usual mechanism of transmission is indirect. The cells are electrically isolated from one another, the pre-synaptic cell being separated from the postsynaptic cell by a narrow synaptic cleft. A change of electrical potential in the pre-synaptic cell triggers it to release signaling molecules known as neurotransmitters. The neurotransmitters rapidly diffuse across the synaptic cleft and provoke an electrical change in the postsynaptic cell by binding to neurotransmitter receptor-gated ion channels. After release, the excess neurotransmitters are rapidly removed, either by specific enzymes in the synaptic cleft or by reuptake into the pre-synaptic cell or surrounding glial cells. Reuptake is mediated by a variety of neurotransmitter transporters. Rapid removal ensures both spatial and temporal precision of signaling at a synapse. For example, rapid reuptake can prevent excess neurotransmitters from influencing neighboring cells and can clear the synaptic cleft before the next pulse of neurotransmitter release so that the timing of repeated, rapid signaling events is accurately communicated to the postsynaptic cell.

An imbalance of neurotransmitters in the brain can occur when not enough neurotransmitter is made and released from pre-synaptic cells or the reuptake of neurotransmitters by pre-synaptic cells is too rapid. If neurotransmitters such as serotonin, norepinephrine, or dopamine are not made and released in effective amounts or are cleared from the synaptic cleft too quickly, then cell-to-cell communication can be affected. Clinical manifestations of such imbalances include depression and anxiety disorders. Serotonin-, norepinephrine-, dopamine-reuptake inhibitors (SNDRIs) represent a class of potent, wide-spectrum antidepressant medications that inhibit the reuptake of these neurotransmitters back into pre-synaptic cells. Inhibiting neurotransmitter reuptake can increase the amount of neurotransmitter present in the synapse, thus helping to normalize the transmission of neuronal signals and alleviate the symptoms of depression and anxiety disorders.

SUMMARY

This document relates to compounds as well as methods and materials involved in modulating neurotransmitter reuptake. For example, this document provides compounds (e.g., amine compounds), methods for synthesizing compounds (e.g., amine compounds), and methods for inhibiting neurotransmitter reuptake. The compounds provided herein can be used as potent, wide-spectrum antidepressant medications for inhibiting neurotransmitter reuptake and treating anxiety or depressive disorders. In some cases, a compound provided herein can be used to treat pain. In addition, the methods provided herein for synthesizing compounds allow for synthesis in a reliable and efficient manner. In some cases, a compound provided herein can be used as a specific inhibitor to inhibit reuptake of one of serotonin, norepinephrine, or dopamine with little or no inhibitory activity for reuptake of the other two. For example, a compound provided herein can be used to inhibit dopamine reuptake with little or no ability to inhibit reuptake of serotonin and norepinephrine. In some cases, a compound provided herein can inhibit the reuptake of one or more of serotonin, norepinephrine, and dopamine with a Ki value of less than 50 nM when assessed in vitro while having an $IC_{50}$ value for a human cytochrome P450 2D6 (CYP2D6) polypeptide and/or a human ether-à-go-go-related gene (ERG) polypeptide that is greater than 1 µM.

In general, one aspect of this document features a composition comprising a compound selected from the group consisting of (a) Compound ID Nos. 1-110 and 112-172 and (b) enantiomers of any one of Compound ID Nos. 1-110 and 112-172, or a salt thereof.

In another aspect, this document features a method for inhibiting neurotransmitter reuptake in a mammal. The method comprises, or consists essentially of, administering a composition comprising a compound selected from the group consisting of (a) Compound ID Nos. 1-110 and 112-172 and (b) enantiomers of any one of Compound ID Nos. 1-110 and 112-172, or a salt thereof. The neurotransmitter reuptake can be norepinephrine or epinephrine reuptake. The neurotransmitter reuptake can be dopamine reuptake. The neurotransmitter reuptake can be serotonin reuptake. The mammal can be a human.

In another aspect, this document features a method for treating pain, depression, or anxiety, wherein the method comprises administering, to a mammal, a composition comprising a compound selected from the group consisting of (a) Compound ID Nos. 1-110 and 112-172 and (b) enantiomers of any one of Compound ID Nos. 1-110 and 112-172, or a salt thereof.

In another aspect, this document features a compound of formula I:

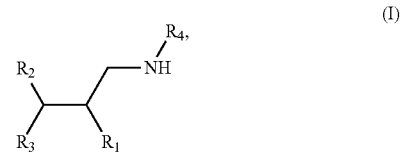

wherein $R_1$ is selected from naphthalen-2-yl and phenyl substituted at the 3 or 4 position or 3- and 4-positions with a substituent selected from halogen and lower alkyl;

$R_2$ is selected from phenyl and a 5- or 6-membered aromatic heterocycle each of which is optionally substituted with substituents selected from halo, methylsulfanyl, methanesulfonyl, hydroxyl, methyl, ethyl, alkoxy, dimethylamino, and 1,1,1-trifluoromethanesulfonamide;

optionally, two adjacent alkoxy groups are connected to form a 5- or 6-membered ring;

$R_3$ is hydrogen, hydroxyl, lower alkoxy, or halo; and $R_4$ is hydrogen or lower alkyl. In some cases, $R_2$ can be substituted with one or two substituents. In some cases, compound can have the formula Ia or Ib:

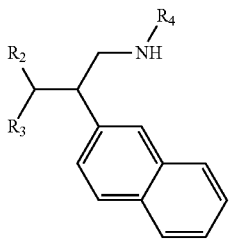

(Ia)

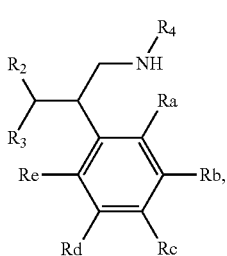

(Ib)

wherein $R_a$, $R_b$, $R_c$, $R_d$, and $R_e$ are selected from hydrogen, lower alkyl, and halo. In some cases, at least two of $R_a$, $R_b$, $R_c$, $R_d$, and $R_e$ can be hydrogen. The remaining $R_a$, $R_b$, $R_c$, $R_d$, and $R_e$ can be independently selected from ethyl, chloro, and bromo. $R_a$, $R_d$, and $R_e$ can be hydrogen; and $R_b$ and $R_c$ can be independently selected from ethyl, chloro, and bromo.

In another aspect, this document features a compound of formula II:

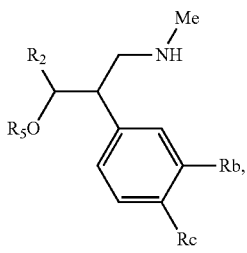

(II)

wherein $R_2$ is selected from phenyl and a 5- or 6-membered aromatic heterocycle each of which is optionally substituted with substituents selected from halo, methylsulfanyl, methanesulfonyl, ethyl, alkoxy, dimethylamino, and 1,1,1-trifluoromethanesulfonamide;

$R_5$ is hydrogen or lower alkyl; and $R_b$ and $R_c$ are independently hydrogen, halo, or lower alkyl. Each of $R_b$ and $R_c$ can be a unit other than hydrogen. The compound can have formula IIa:

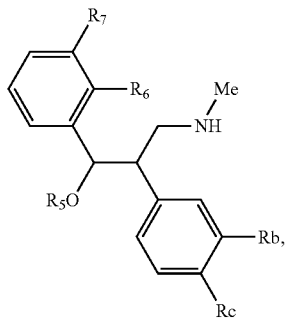

(IIa)

wherein $R_6$ and $R_7$ are independently selected from hydrogen, lower alkyl, halo, hydroxyl, lower alkoxy, methylsulfanyl, methanesulfonyl, dimethylamino, and 1,1,1-trifluoromethanesulfonamide. $R_6$ can be selected from hydrogen, lower alkyl, halo, hydroxyl, lower alkoxy, methylsulfanyl, and methsulfonyl; and $R_7$ can be selected from hydrogen, lower alkyl, halo, dimethylamino, methylsulfanyl, and 1,1,1-trifluoromethanesulfonamide.

In another aspect, this document features a compound selected from compounds described in Table 1, or a salt thereof.

In another aspect, this document features a pharmaceutical composition comprising a compound or a pharmaceutically-acceptable salt thereof as set forth in any of the above six paragraphs and a pharmaceutically-acceptable excipient or carrier.

In another aspect, this document features a pharmaceutical composition comprising a compound or a pharmaceutically-acceptable salt thereof as set forth in any of the above seven paragraphs and a pharmaceutically-acceptable excipient or carrier.

In another aspect, this document features the use of a compound as set forth in any of the above eight paragraphs in the manufacture of a medicament for the treatment of depression, anxiety, post-traumatic stress, social phobia, obsessive compulsive disorder, impulsivity, attention deficit disorder, attention deficit hyperactivity disorder, schizophrenia, movement disorders, restless leg syndrome, sleep disorder, narcolepsy, obesity, sexual dysfunction, or substance abuse. The depression can be severe refractory depression. The movement disorder can be Parkinson's disease.

In another aspect, this document features a method of treating depression, anxiety, post-traumatic stress, social phobia, obsessive compulsive disorder, impulsivity, attention deficit disorder, attention deficit hyperactivity disorder, schizophrenia, movements disorders, restless leg syndrome, sleep disorder, narcolepsy, obesity, sexual dysfunction, or substance abuse in a subject in need thereof, comprising administering to the subject a therapeutically effective amount of a compound as set forth in any of the above nine paragraphs. The depression can be severe refractory depression. The movement disorder can be Parkinson's disease.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

DETAILED DESCRIPTION

This document relates to compounds as well as methods and materials involved in modulating neurotransmitter reuptake. For example, this document provides compounds (e.g., amine compounds), methods for synthesizing compounds, and methods for inhibiting neurotransmitter reuptake. Examples of compounds provided herein include, without limitation, those set forth in Table 1 or any pharmaceutically acceptable salt thereof.

Other features and advantages of the invention will be apparent from the following detailed description and drawings, and from the claims.

TABLE 1

Compound Structures.

| Compound ID No. | Compound Reference No. | Structure | pKa (Base 1) | pKa (Base 2) | M.W. |
|---|---|---|---|---|---|
| 1 | 13341668 | 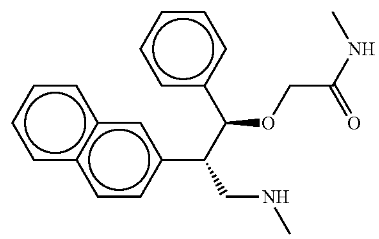 | 9.6 | | 362 |
| 2 | 13337869 | 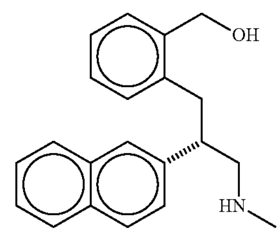 | 10 | | 305 |
| 3 | 13322896 | 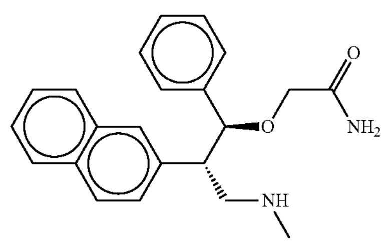 | 9.6 | | 348 |
| 4 | 13224752 | 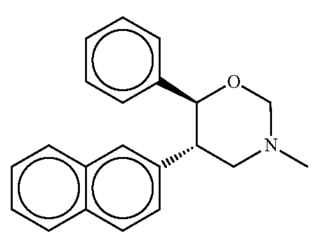 | 6.6 | | 303 |
| 5 | 13261591 | 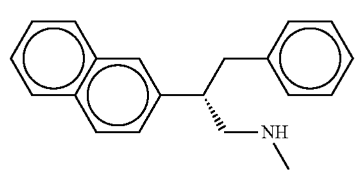 | 10.1 | | 275 |
| 6 | 13342106 | 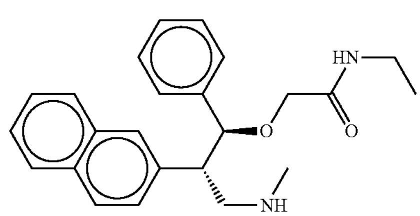 | 9.6 | | 377 |

TABLE 1-continued
Compound Structures.
| Compound ID No. | Compound Reference No. | Structure | pKa (Base 1) | pKa (Base 2) | M.W. |
|---|---|---|---|---|---|
| 7 | 13366080 | 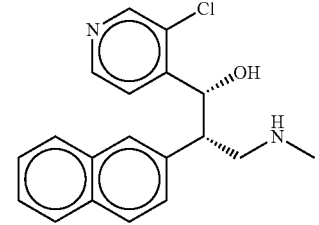 | 9.5 | 3 | 327 |
| 8 | 13371132 | 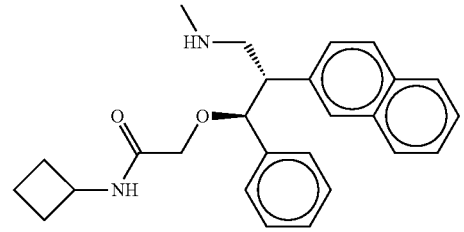 | 9.6 | | 403 |
| 9 | 13228373 | 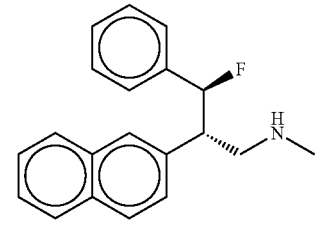 | 9.4 | | 293 |
| 10 | 13245751 | 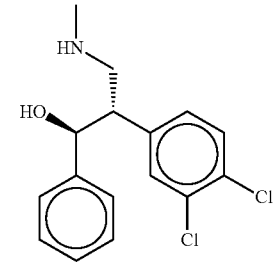 | 9.4 | | 310 |
| 11 | 13224757 | 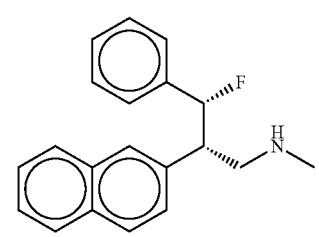 | 9.4 | | 293 |
| 12 | 13305851 | 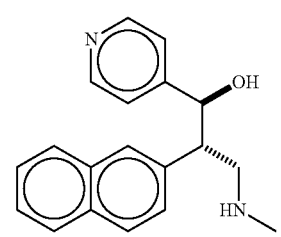 | 9.6 | 5.4 | 292 |

TABLE 1-continued

Compound Structures.

| Compound ID No. | Compound Reference No. | Structure | pKa (Base 1) | pKa (Base 2) | M.W. |
|---|---|---|---|---|---|
| 13 | 13349532 | 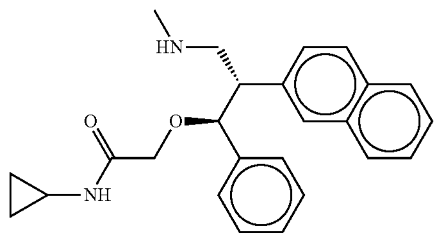 | | 9.6 | 389 |
| 14 | 13366816 | 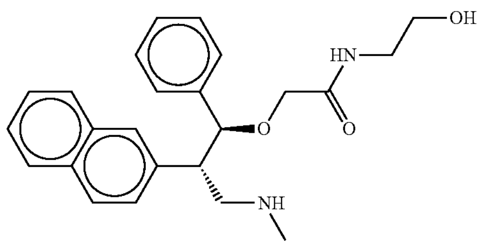 | | 9.6 | 393 |
| 15 | 13331487 | 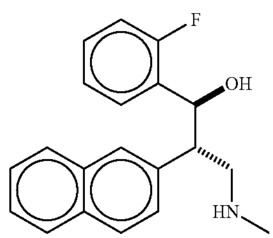 | | 9.7 | 309 |
| 16 | 13311940 | 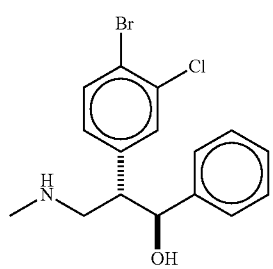 | | 9.4 | 355 |
| 17 | 13320979 | 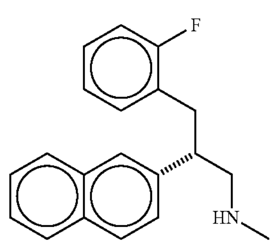 | | 10 | 293 |
| 18 | 13342139 | 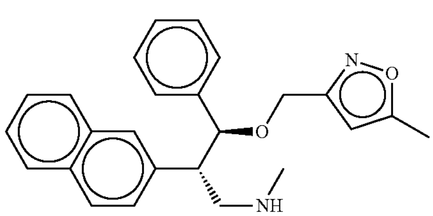 | | 9.6 | 386 |

TABLE 1-continued

Compound Structures.

| Compound ID No. | Compound Reference No. | Structure | pKa (Base 1) | pKa (Base 2) | M.W. |
|---|---|---|---|---|---|
| 19 | 13366419 | 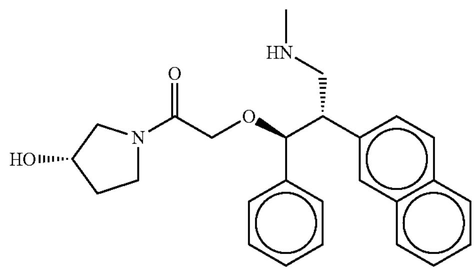 | | 9.6 | 419 |
| 20 | 13368447 | 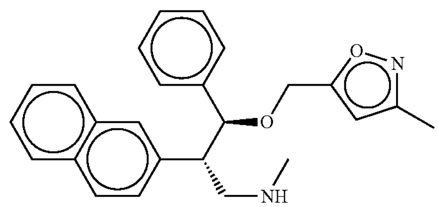 | | 9.6 | 386 |
| 21 | 13309710 | 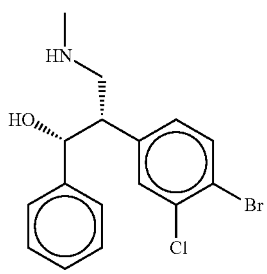 | | 9.4 | 355 |
| 22 | 13344312 | 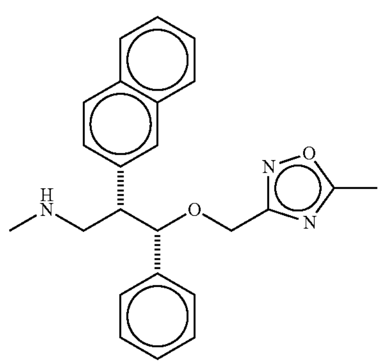 | | 9.6 | 387 |
| 23 | 13366125 | 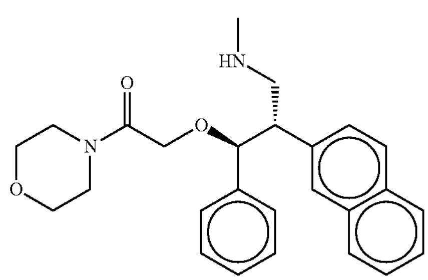 | | 9.6 | 419 |

TABLE 1-continued

Compound Structures.

| Compound ID No. | Compound Reference No. | Structure | pKa (Base 1) | pKa (Base 2) | M.W. |
|---|---|---|---|---|---|
| 24 | 13326653 | 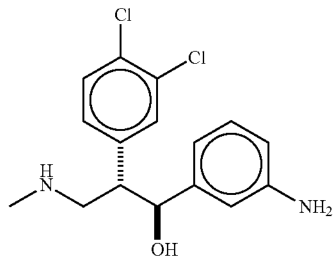 | 9.4 | 4.3 | 325 |
| 25 | 13341411 | 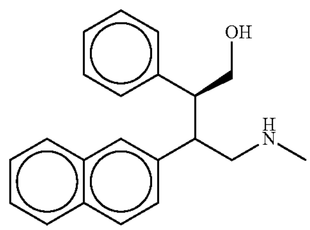 | 9.9 | | 305 |
| 26 | 13366118 | 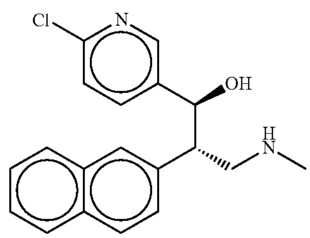 | 9.6 | | 327 |
| 27 | 13267551 | 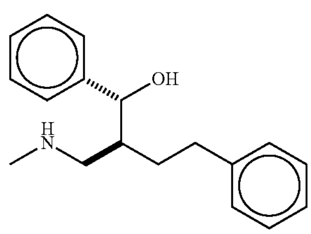 | 10.1 | | 269 |
| 28 | 13283201 | 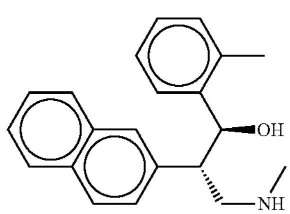 | 9.7 | | 305 |
| 29 | 13342110 | 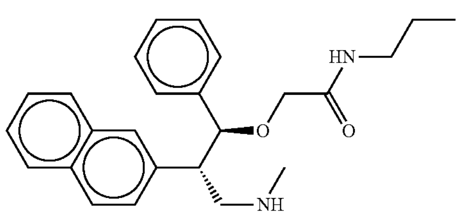 | 9.6 | | 391 |

TABLE 1-continued

Compound Structures.

| Compound ID No. | Compound Reference No. | Structure | pKa (Base 1) | pKa (Base 2) | M.W. |
|---|---|---|---|---|---|
| 30 | 13368783 | 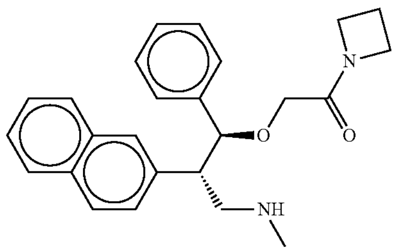 | | 9.6 | 389 |
| 31 | 13370608 | 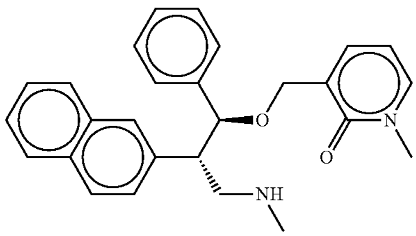 | | 9.6 | 413 |
| 32 | 13322893 | 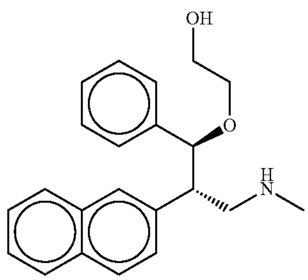 | | 9.6 | 335 |
| 33 | 13342019 | 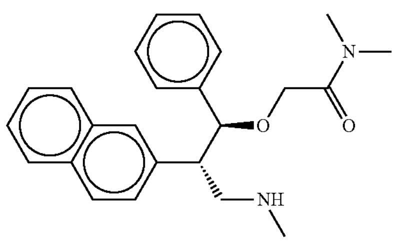 | | 9.6 | 377 |
| 34 | 13366421 | 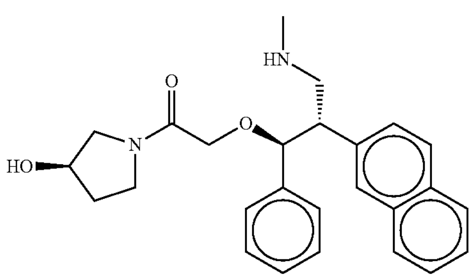 | | 9.6 | 419 |
| 35 | 13342107 | 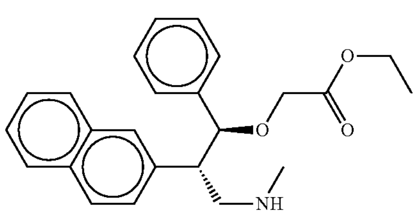 | | 9.6 | 377 |

TABLE 1-continued
Compound Structures.
| Compound ID No. | Compound Reference No. | Structure | pKa (Base 1) | pKa (Base 2) | M.W. |
|---|---|---|---|---|---|
| 36 | 13273128 | 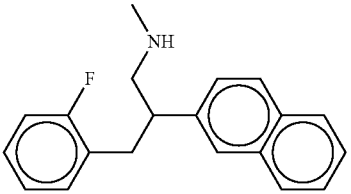<br>racemic | 10 | | 293 |
| 37 | 13283197 | 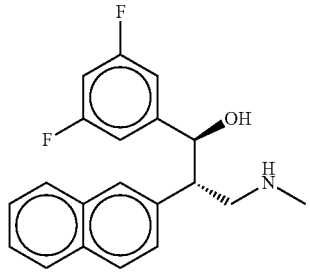 | 9.6 | | 327 |
| 38 | 13203584 | 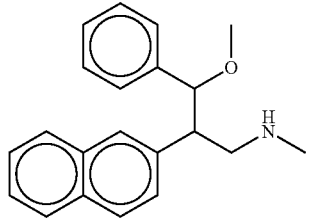 | 9.7 | | 305 |
| 39 | 13281862 | 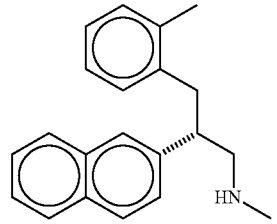 | 10.1 | | 289 |
| 40 | 13225597 | 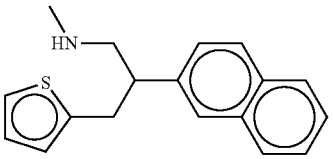<br>racemic | 10 | | 281 |
| 41 | 13225601 | 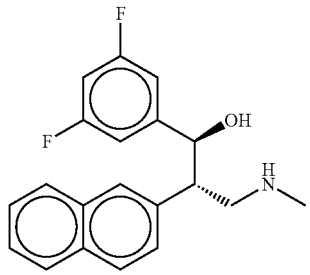<br>racemic | 9.6 | | 327 |

TABLE 1-continued

Compound Structures.

| Compound ID No. | Compound Reference No. | Structure | pKa (Base 1) | pKa (Base 2) | M.W. |
|---|---|---|---|---|---|
| 42 | 13320726 | 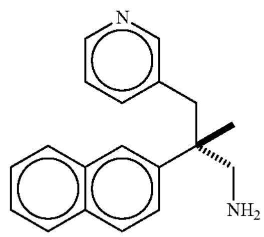 | 9.2 | 5.2 | 276 |
| 43 | 13267866 | racemic | 9.4 | | 355 |
| 44 | 13299100 | 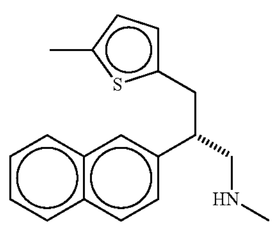 | 10 | | 295 |
| 45 | 13368878 | 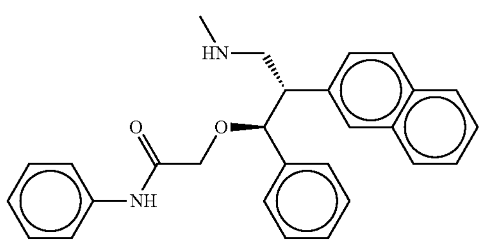 | 9.7 | | 425 |
| 46 | 13228482 | 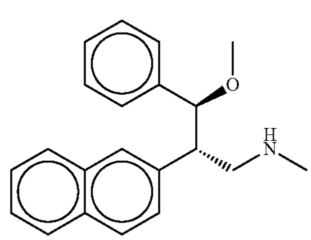 | 9.7 | | 305 |
| 47 | 13270298 | 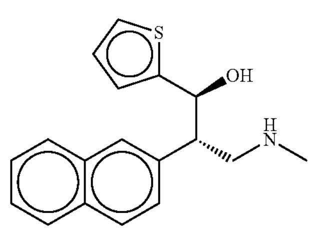 | 9.7 | | 297 |

TABLE 1-continued

Compound Structures.

| Compound ID No. | Compound Reference No. | Structure | pKa (Base 1) | pKa (Base 2) | M.W. |
|---|---|---|---|---|---|
| 48 | 13289328 | 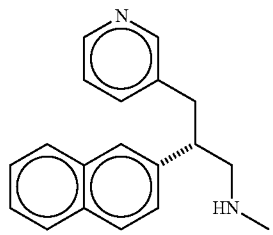 | 9.9 | | 276 |
| 49 | 13309941 | 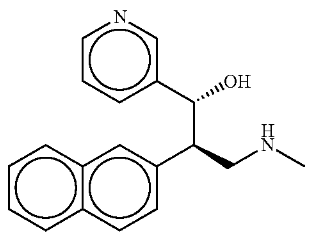 | 9.6 | 5.1 | 292 |
| 50 | 13341669 | 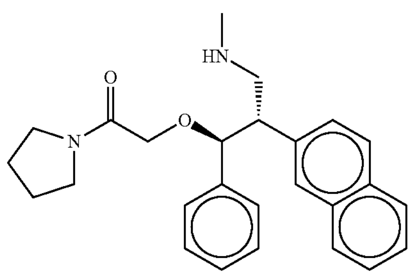 | 9.6 | | 403 |
| 51 | 13376700 | 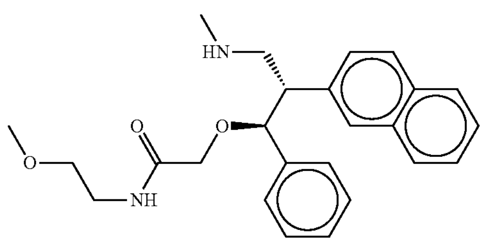 | 9.6 | | 407 |
| 52 | 13298151 | 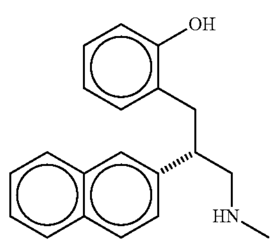 | 10 | | 291 |
| 53 | 13232819 | racemic | 9.4 | | 310 |

TABLE 1-continued
Compound Structures.
| Compound ID No. | Compound Reference No. | Structure | pKa (Base 1) | pKa (Base 2) | M.W. |
|---|---|---|---|---|---|
| 54 | 13243687 | 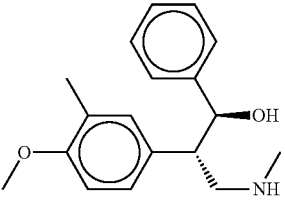 racemic | 10 | | 285 |
| 55 | 13283198 | 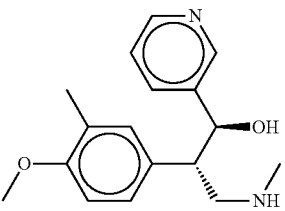 | 10 | | 285 |
| 56 | 13270295 | 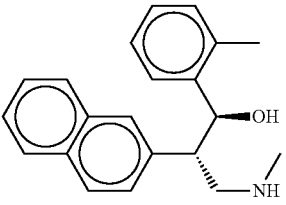 racemic | 9.7 | | 305 |
| 57 | 13299102 | 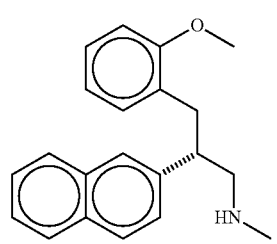 | 10.1 | | 305 |
| 58 | 13270525 | 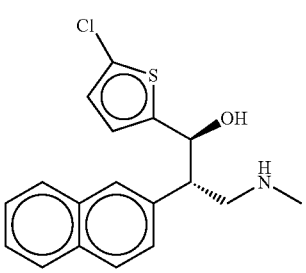 | 9.7 | | 332 |
| 59 | 13328855 | 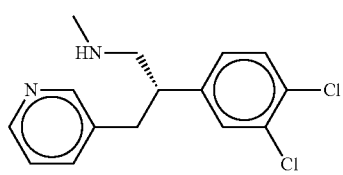 | 9.6 | 5.2 | 295 |

TABLE 1-continued

Compound Structures.

| Compound ID No. | Compound Reference No. | Structure | pKa (Base 1) | pKa (Base 2) | M.W. |
|---|---|---|---|---|---|
| 60 | 13328420 | 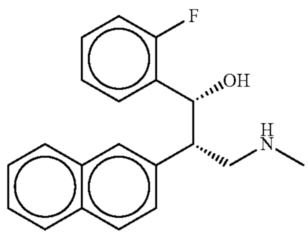 | 9.7 | | 309 |
| 61 | 13242271 | 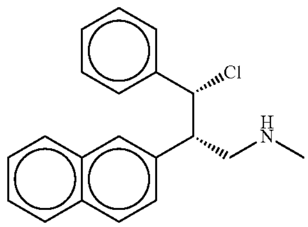 | 9.5 | | 310 |
| 62 | 13270294 | (racemic) | 9.6 | 5.1 | 292 |
| 63 | 13320582 | 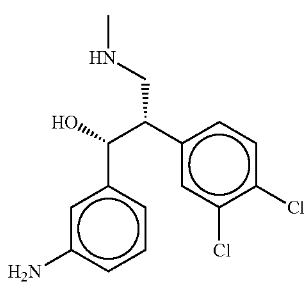 | 9.4 | 4.3 | 325 |
| 64 | 13342119 | 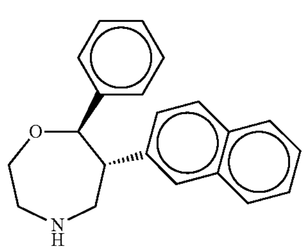 | 9.3 | | 303 |

TABLE 1-continued

Compound Structures.

| Compound ID No. | Compound Reference No. | Structure | pKa (Base 1) | pKa (Base 2) | M.W. |
|---|---|---|---|---|---|
| 65 | 13324681 | 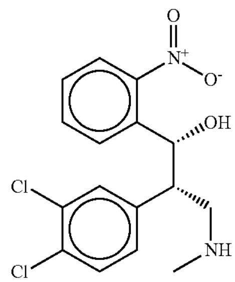 | 9.3 | | 355 |
| 66 | 13267288 | 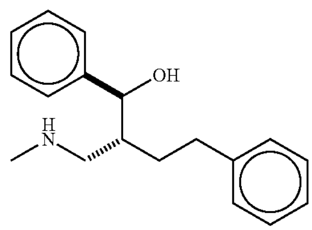 | 10.1 | | 269 |
| 67 | 13361259 | 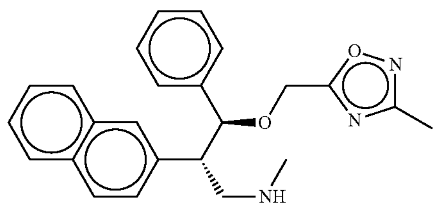 | 9.6 | | 387 |
| 68 | 13369076 | 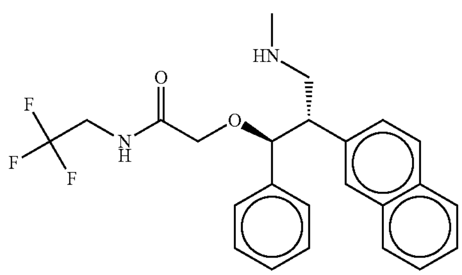 | 9.6 | | 430 |
| 69 | 13287084 | 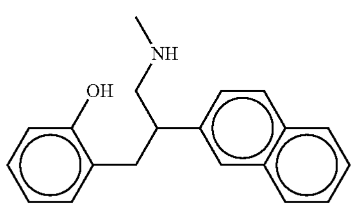 | 10 | | 291 |
| 70 | 13270228 | 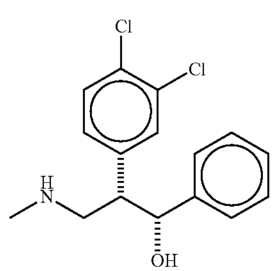 | 9.4 | | 310 |

TABLE 1-continued

Compound Structures.

| Compound ID No. | Compound Reference No. | Structure | pKa (Base 1) | pKa (Base 2) | M.W. |
|---|---|---|---|---|---|
| 71 | 13372931 | 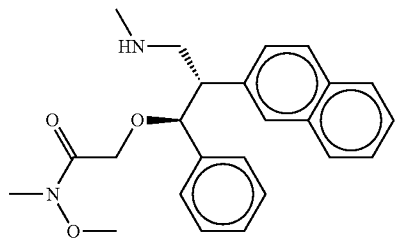 | 9.6 | | 393 |
| 72 | 13270293 | racemic | 9.6 | 4.1 | 292 |
| 73 | 13247827 | racemic | 9.3 | | 294 |
| 74 | 13287085 | 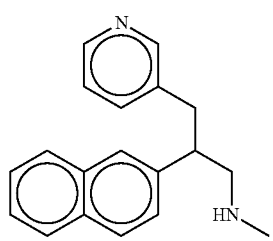 | 9.9 | 5.2 | 276 |
| 75 | 13273126 | 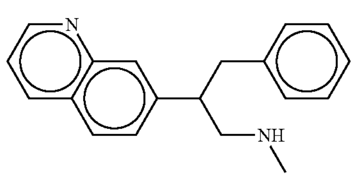 | 10 | 4.8 | 276 |
| 76 | 13303502 | 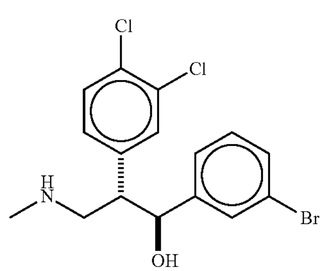 | 9.4 | | 389 |

TABLE 1-continued

| Compound ID No. | Compound Reference No. | Structure | pKa (Base 1) | pKa (Base 2) | M.W. |
|---|---|---|---|---|---|
| 77 | 13373098 | 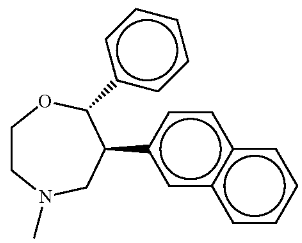 | 8.2 | | 317 |
| 78 | 13332464 | 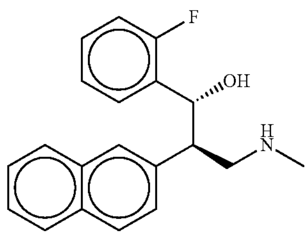 | 9.7 | | 309 |
| 79 | 13370736 | 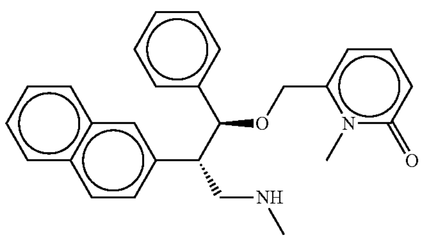 | 9.7 | | 413 |
| 80 | 13287456 | racemic | 9.6 | 5.2 | 295 |
| 81 | 13371279 | 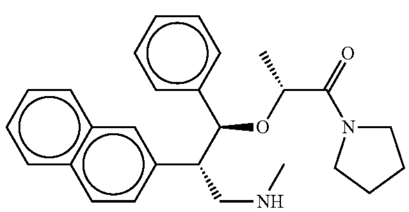 | 9.6 | | 417 |
| 82 | 13228464 | 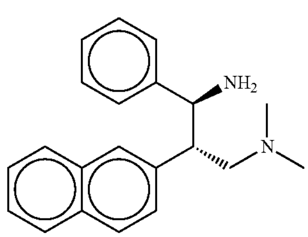 | 9 | 8.3 | 304 |

TABLE 1-continued
Compound Structures.
| Compound ID No. | Compound Reference No. | Structure | pKa (Base 1) | pKa (Base 2) | M.W. |
|---|---|---|---|---|---|
| 83 | 13094210 | 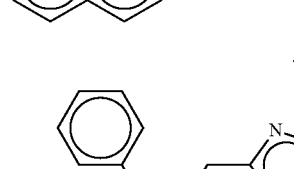 | 9 | | 305 |
| 84 | 13376701 | 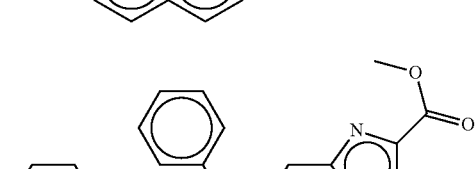 | 9.6 | | 431 |
| 85 | 13326301 | 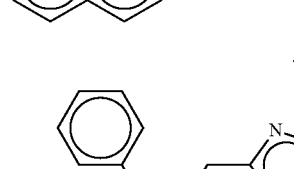 | 10.1 | | 305 |
| 86 | 13228816 | 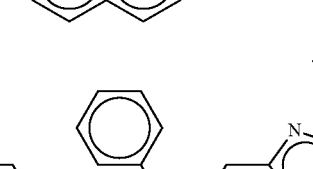 | 9.2 | | 319 |
| 87 | 13242217 | 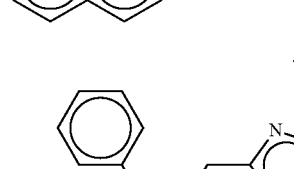 | 9.8 | 8.5 | 290 |
| 88 | 13314785 | 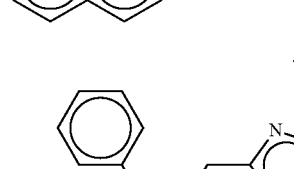 | 8.7 | | 277 |

TABLE 1-continued

Compound Structures.

| Compound ID No. | Compound Reference No. | Structure | pKa (Base 1) | pKa (Base 2) | M.W. |
|---|---|---|---|---|---|
| 89 | 13322895 | 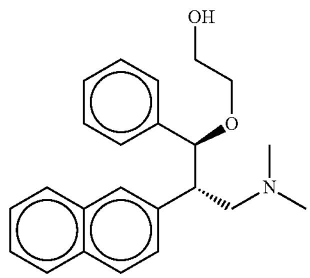 | 8.9 | | 349 |
| 90 | 13338191 | 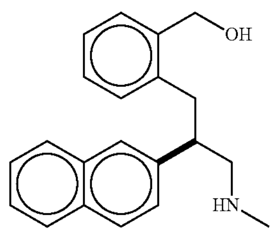 | 10 | | 305 |
| 91 | 13097910 | 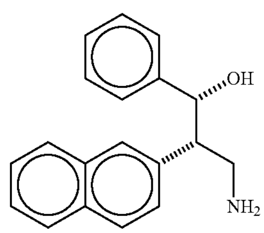 | 8.7 | | 277 |
| 92 | 13331486 | 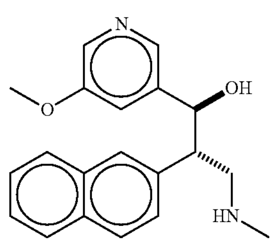 | 9.6 | 4.5 | 322 |
| 93 | 13334801 | 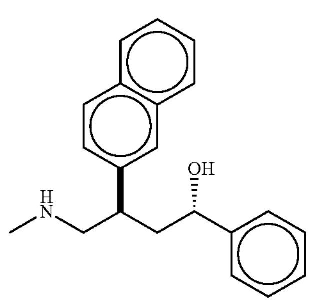 | 10.1 | | 305 |

TABLE 1-continued

Compound Structures.

| Compound ID No. | Compound Reference No. | Structure | pKa (Base 1) | pKa (Base 2) | M.W. |
|---|---|---|---|---|---|
| 94 | 13320573 | 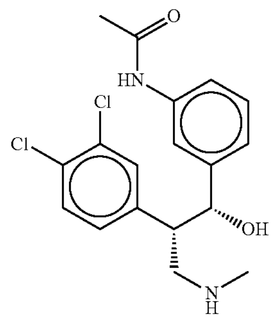 | 9.4 | | 367 |
| 95 | 13364611 | 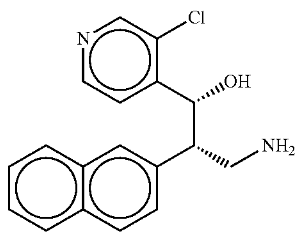 | 8 | | 313 |
| 96 | 13328422 | 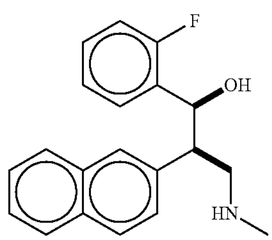 | 9.7 | | 309 |
| 97 | 13322960 | 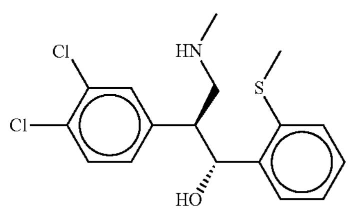 | 9.4 | | 356 |
| 98 | 13320581 | 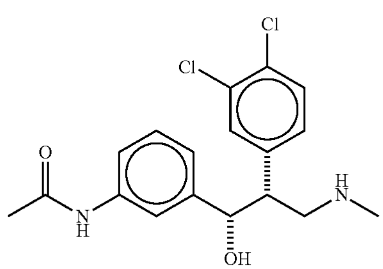 | 9.4 | | 367 |
| 99 | 13324636 | 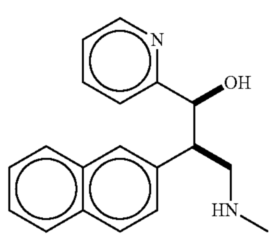 | 9.6 | 4.1 | 292 |

TABLE 1-continued

Compound Structures.

| Compound ID No. | Compound Reference No. | Structure | pKa (Base 1) | pKa (Base 2) | M.W. |
|---|---|---|---|---|---|
| 100 | 13321139 | 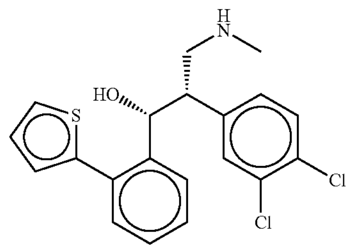 | 9.4 | | 392 |
| 101 | 13332457 | 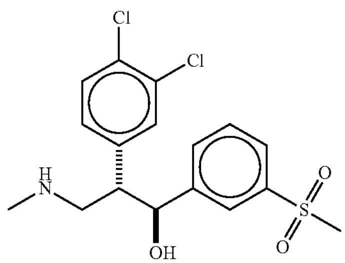 | 9.3 | | 388 |
| 102 | 13303500 | 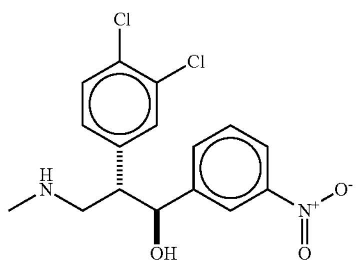 | 9.3 | | 355 |
| 103 | 13305857 | 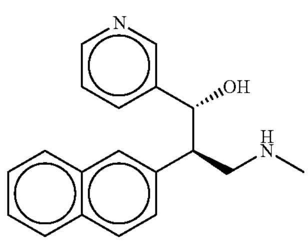 | 9.6 | 5.1 | 292 |
| 104 | 13351506 | 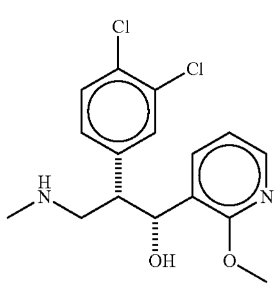 | 9.2 | 3.2 | 341 |

TABLE 1-continued
Compound Structures.
| Compound ID No. | Compound Reference No. | Structure | pKa (Base 1) | pKa (Base 2) | M.W. |
|---|---|---|---|---|---|
| 105 | 13230850 | 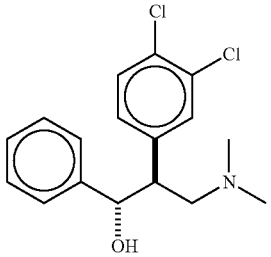 racemic | 8.8 | | 324 |
| 106 | 13308441 | 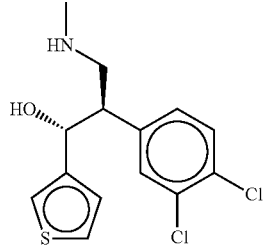 | 9.5 | | 316 |
| 107 | 13305701 | 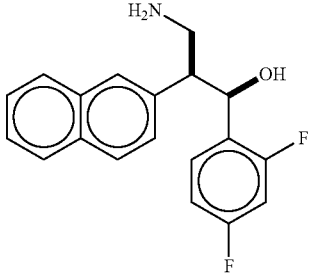 | 8.5 | | 313 |
| 108 | 13305597 | 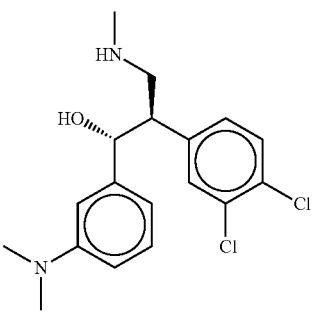 or enantiomeric structure | 9.5 | 4.9 | 353 |
| 109 | 13363016 | 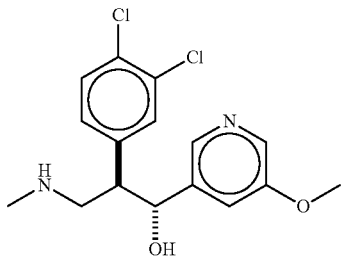 | 9.3 | 4.5 | 341 |

TABLE 1-continued

Compound Structures.

| Compound ID No. | Compound Reference No. | Structure | pKa (Base 1) | pKa (Base 2) | M.W. |
|---|---|---|---|---|---|
| 110 | 13311883 | (structure: methylamino-hydroxy-phenyl-(3-chloro-4-bromophenyl) compound) | 9.4 | | 355 |
| 111 | | Paroxetine | | | |
| 112 | 13320725 | (structure: 3,4-dichlorophenyl, pyridin-3-ylmethyl, aminopropyl compound) | 8.6 | 5.1 | 281 |
| 113 | 13270300 | (structure: biphenyl, phenyl-hydroxy, methylamino compound) racemic | 9.8 | | 317 |
| 114 | 13245752 | (structure: 3,4-dichlorophenyl, phenyl-hydroxy, methylaminomethyl compound) | 9.4 | | 310 |
| 115 | 13328854 | (structure: 3,4-dichlorophenyl, pyridin-3-ylmethyl, methylaminomethyl compound) | 9.6 | 5.2 | 295 |

TABLE 1-continued
Compound Structures.
| Compound ID No. | Compound Reference No. | Structure | pKa (Base 1) | pKa (Base 2) | M.W. |
|---|---|---|---|---|---|
| 116 | 13334197 | 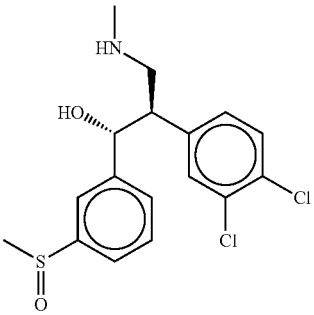 or enantiomeric structure | 9.4 | | 372 |
| 117 | 13322959 | 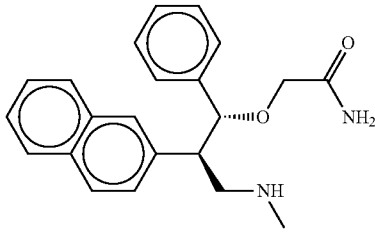 | 9.6 | | 348 |
| 118 | 13366077 | 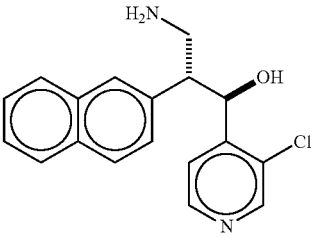 | 8 | | 313 |
| 119 | 13326650 | 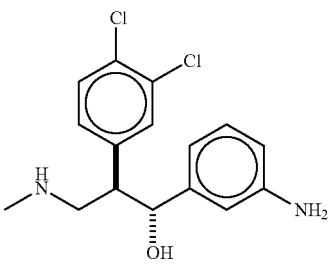 | 9.4 | 4.3 | 325 |
| 120 | 13303494 | 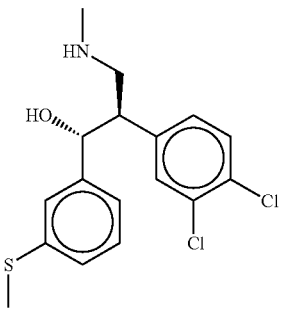 | 9.4 | | 356 |

TABLE 1-continued
Compound Structures.
| Compound ID No. | Compound Reference No. | Structure | pKa (Base 1) | pKa (Base 2) | M.W. |
|---|---|---|---|---|---|
| 121 | 13329271 | 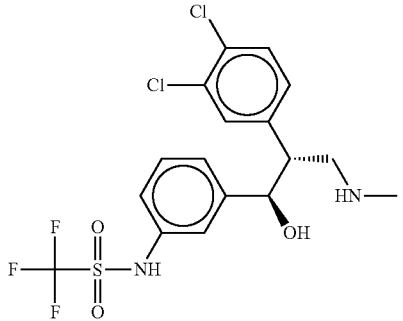 | 9.4 | | 457 |
| 122 | 13328652 | 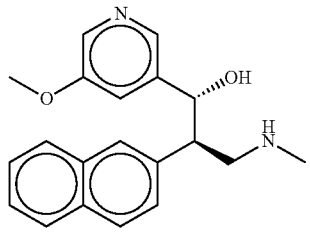 | 9.6 | 4.5 | 322 |
| 123 | 13334795 | 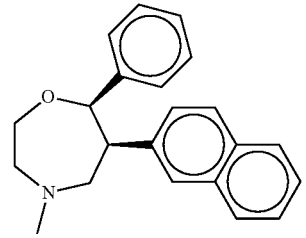 | 8.2 | | 317 |
| 124 | 13334794 | 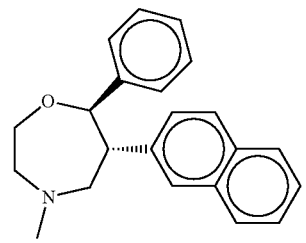 | 8.2 | | 317 |
| 125 | 13303501 | 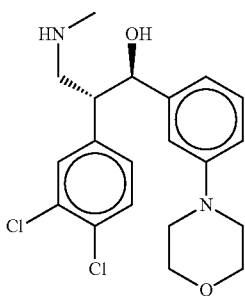 | 9.4 | 5.1 | 395 |

TABLE 1-continued

Compound Structures.

| Compound ID No. | Compound Reference No. | Structure | pKa (Base 1) | pKa (Base 2) | M.W. |
|---|---|---|---|---|---|
| 126 | 13366127 | 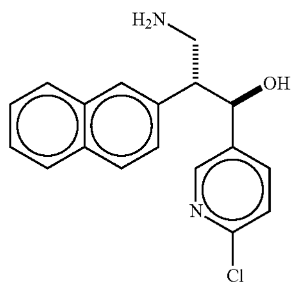 | 8.3 | | 313 |
| 127 | 13328856 | 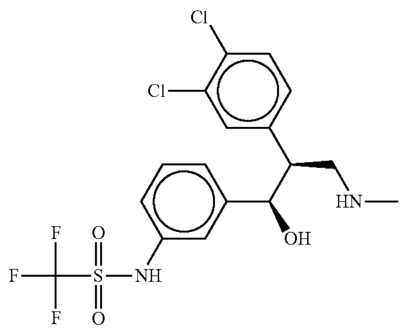 | 9.4 | | 457 |
| 128 | 13332636 | 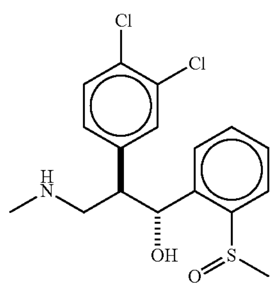 | 9.4 | | 372 |
| 129 | 13366724 | 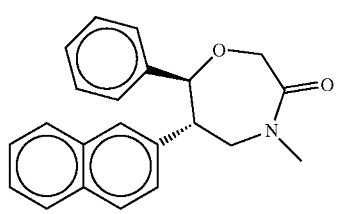 | | | 331 |
| 130 | 13337429 | | 4.6 | | 359 | or enantiomeric structure

TABLE 1-continued

Compound Structures.

| Compound ID No. | Compound Reference No. | Structure | pKa (Base 1) | pKa (Base 2) | M.W. |
|---|---|---|---|---|---|
| 131 | 13381274 | 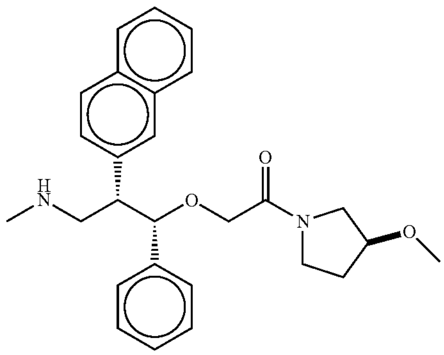 | 9.6 | | 433 |
| 132 | 13279931 | 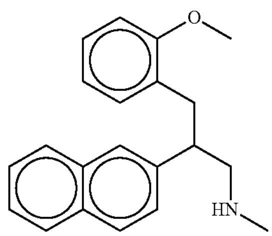 | 10.1 | | 305 |
| 133 | 13297150 | 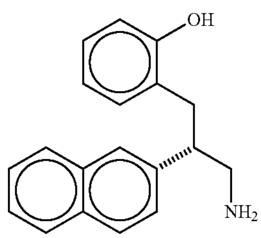 | 9.4 | | 277 |
| 134 | 13259059 | 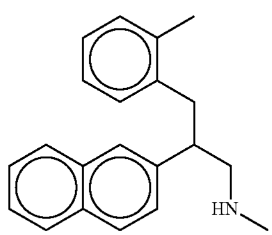 | 10.1 | | 289 |
| 135 | 13270299 | racemic | 8.9 | | 311 |

TABLE 1-continued
Compound Structures.
| Compound ID No. | Compound Reference No. | Structure | pKa (Base 1) | pKa (Base 2) | M.W. |
|---|---|---|---|---|---|
| 136 | 13270719 | 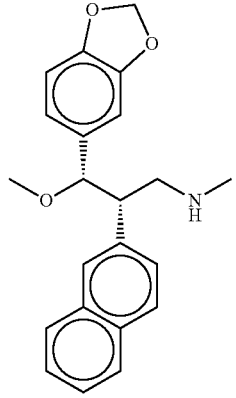 racemic | | 9.7 | 349 |
| 137 | 13273127 | 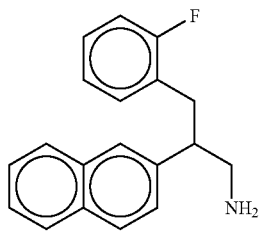 | | 9.3 | 279 |
| 138 | 13320978 | 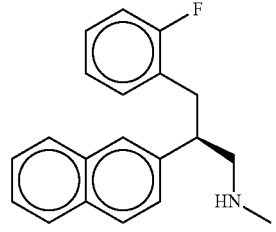 | | 10 | 293 |
| 139 | 13253992 | 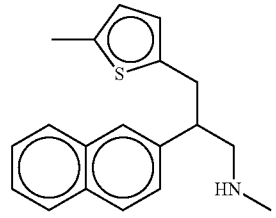 | | 10 | 295 |
| 140 | 13298152 | 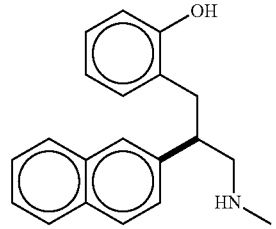 | | 10 | 291 |

TABLE 1-continued

| Compound ID No. | Compound Reference No. | Structure | pKa (Base 1) | pKa (Base 2) | M.W. |
|---|---|---|---|---|---|
| 141 | 13296640 | 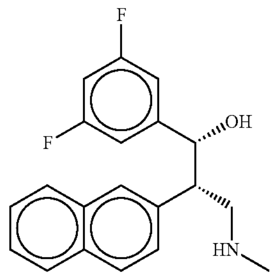 | 9.6 | | 327 |
| 142 | 13298144 | 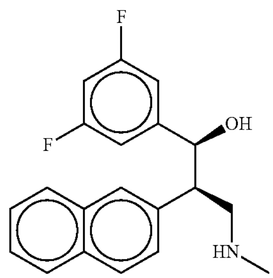 | 9.6 | | 327 |
| 143 | 13283202 | 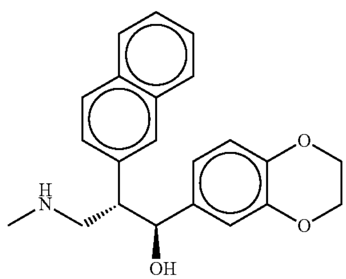 | 9.7 | | 349 |
| 144 | 13283194 | 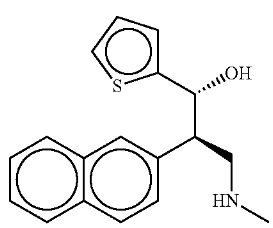 | 9.7 | | 297 |
| 145 | 13270301 | racemic | 9.7 | | 349 |

TABLE 1-continued

Compound Structures.

| Compound ID No. | Compound Reference No. | Structure | pKa (Base 1) | pKa (Base 2) | M.W. |
|---|---|---|---|---|---|
| 146 | 13242221 | (structure) | 9.5 | | 310 |
| 147 | 13267552 | (structure) | 10.1 | | 269 |
| 148 | 13250685 | (structure) racemic | 9.7 | | 276 |
| 149 | 13251189 | (structure) racemic | 9.7 | | 320 |
| 150 | 13267189 | (structure) racemic | 9.4 | | 355 |

TABLE 1-continued

Compound Structures.

| Compound ID No. | Compound Reference No. | Structure | pKa (Base 1) | pKa (Base 2) | M.W. |
|---|---|---|---|---|---|
| 151 | 13320727 | 3,4-dichlorophenyl, 3-iodophenyl, OH, CH2NHMe | 9.4 | | 436 |
| 152 | 13322451 | 3,4-dichlorophenyl, 2-iodophenyl, OH, CH2NHMe | 9.4 | | 436 |
| 153 | 13308428 | 3,4-dichlorophenyl, 3-thienyl, OH, CH2NHMe | 9.5 | | 316 |
| 154 | 13303499 | 3,4-dichlorophenyl, 3-(methylthio)phenyl, OH, CH2NHMe | 9.4 | | 356 |
| 155 | 13270733 | 3,4-dichlorophenyl, 4-pyridyl, OH, CH2NHMe (racemic) | 9.3 | 5.3 | 311 |

TABLE 1-continued

Compound Structures.

| Compound ID No. | Compound Reference No. | Structure | pKa (Base 1) | pKa (Base 2) | M.W. |
|---|---|---|---|---|---|
| 156 | 13320772 | 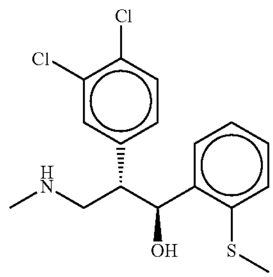 | 9.4 | | 365 |
| 157 | 13328622 | 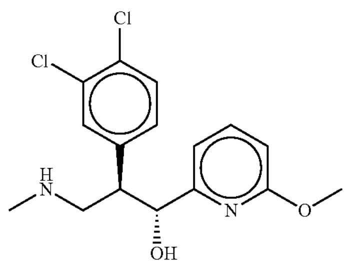 | 9.2 | | 341 |
| 158 | 13320641 | 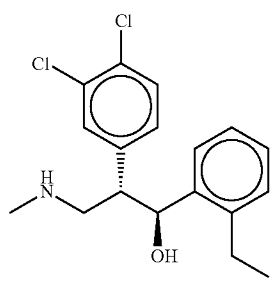 | 9.4 | | 338 |
| 159 | 13320572 | 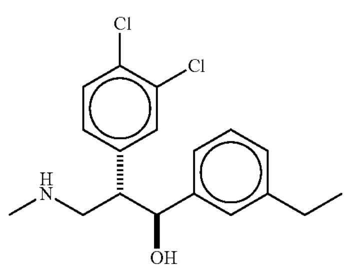 | 9.4 | | 338 |
| 160 | 13312320 | 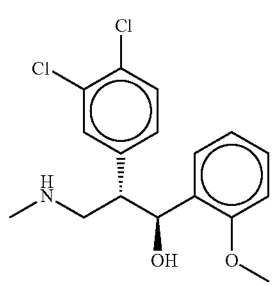 | 9.4 | | 340 |

TABLE 1-continued

Compound Structures.

| Compound ID No. | Compound Reference No. | Structure | pKa (Base 1) | pKa (Base 2) | M.W. |
|---|---|---|---|---|---|
| 161 | 13326651 | 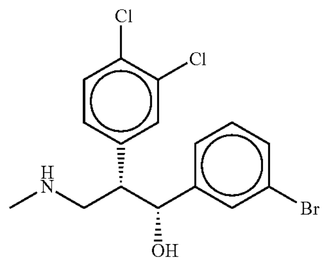 | 9.4 | | 389 |
| 162 | 13303497 | 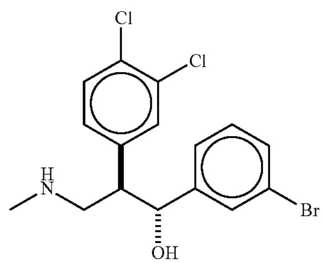 | 9.4 | | 389 |
| 163 | 13320512 | 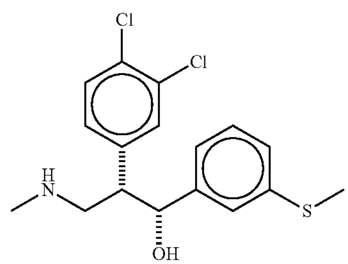 | 9.4 | | 356 |
| 164 | 13322452 | 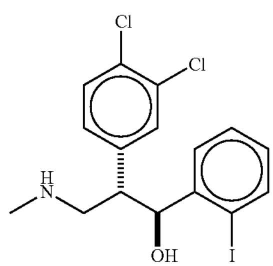 | 9.4 | | 436 |
| 165 | 13321142 | 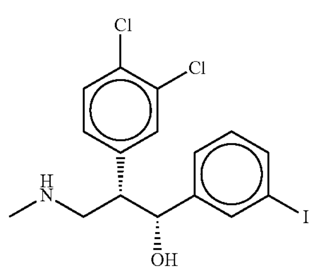 | 9.4 | | 436 |

TABLE 1-continued

Compound Structures.

| Compound ID No. | Compound Reference No. | Structure | pKa (Base 1) | pKa (Base 2) | M.W. |
|---|---|---|---|---|---|
| 166 | 13363017 | 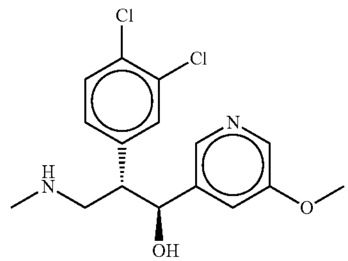 | 9.3 | 4.5 | 341 |
| 167 | 13328653 | 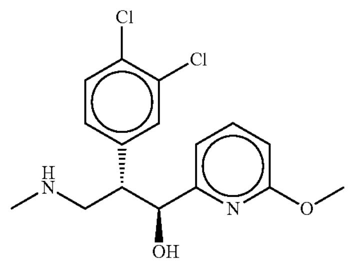 | 9.2 | | 341 |
| 168 | 13305595 | or enantiomer | 9.5 | 4.9 | 353 |
| 169 | 13366126 | 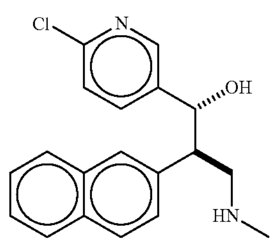 | 9.6 | | 327 |
| 170 | 13329113 | 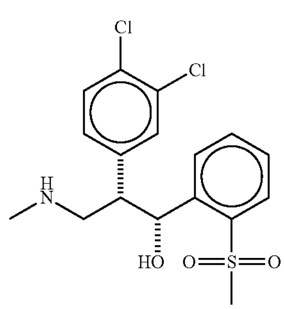 | 9.3 | | 388 |

TABLE 1-continued

Compound Structures.

| Compound ID No. | Compound Reference No. | Structure | pKa (Base 1) | pKa (Base 2) | M.W. |
|---|---|---|---|---|---|
| 171 | 13350716 | 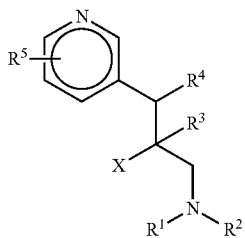 | 9.2 | 3.2 | 341 |
| 172 | 13331217 | 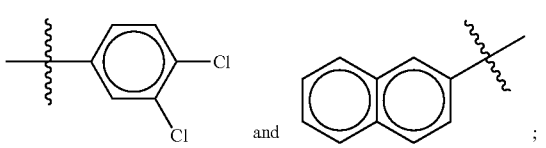 | 9.4 | | 471 | pKa (Base 1) refers to the first base, e.g., an aliphatic primary, secondary, or tertiary amine. pKa (Base 2) refers to the second base in the same molecule (if present). For example, Compound ID Nos. 7, 12, 42, 48, 49, 80, 92, 99, 103, 104, 109, 112, 115, 122, and 125 have a pyridine nucleus as a second base. For Compound ID Nos. 24, 63, 108, and 119, the second base is an aniline. In a few other examples (e.g., Compound ID No. 82 and 87), there are two aliphatic amine moieties in the same molecule where the basicity order is expected to be such that the secondary amine is more basic (PKa1) than the primary amine or tertiary amine. The anilines are less basic (higher pKa) than aliphatic amines. M.W. refers to molecular weight.

In some embodiments, a compound provided herein can be a compound of Formula (I):

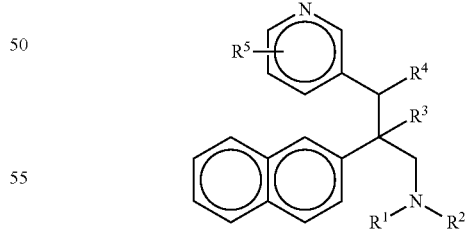

or a pharmaceutically acceptable salt thereof,
wherein:
X is selected from the group consisting of:

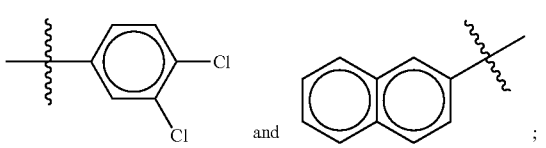

$R^1$, $R^2$, and $R^3$ are independently selected from H and $C_{1-6}$alkyl;
$R^4$ is H, OH, and alkoxy; and
$R^5$ is selected from the group consisting of: H, halo, and alkoxy.

In some embodiments, $R^1$ is H. In some embodiments, $R^2$ is a $C_{1-6}$alkyl. For example, $R^2$ can be methyl. In some embodiments, $R^3$ is H. In some embodiments, $R^4$ can be H or OH. For example, $R^4$ can be OH. In some embodiments, $R^5$ is H. In some embodiments, $R^5$ is chloro. In some embodiments, $R^5$ is an alkoxy. For example, $R^5$ can be methoxy.

In some embodiments, $R^1$, $R^3$, $R^4$ and $R^5$ are H and $R^2$ is methyl.

Also provided herein is a compound of Formula (IA):

or a pharmaceutically acceptable salt thereof,
wherein:
$R^1$, $R^2$, and $R^3$ are independently selected from H and $C_{1-6}$alkyl;
$R^4$ is H, OH, and alkoxy; and
$R^5$ is selected from the group consisting of: H, halo, and alkoxy.

In some embodiments, $R^1$ is H. In some embodiments, $R^2$ is a $C_{1-6}$alkyl. For example, $R^2$ can be methyl. In some embodiments, $R^3$ is H. In some embodiments, $R^4$ can be H or OH. For example, $R^4$ can be OH. In some embodiments, $R^4$ can be alkoxy. In some embodiments, $R^5$ is H. In some embodiments, $R^5$ is chloro. In some embodiments, $R^3$ is an alkoxy. For example, $R^5$ can be methoxy.

In some embodiments, $R^1$, $R^3$, $R^4$ and $R^5$ are H and $R^2$ is methyl.

Non-limiting examples of a compound of Formula (I) and/or Formula (IA): include:

-continued

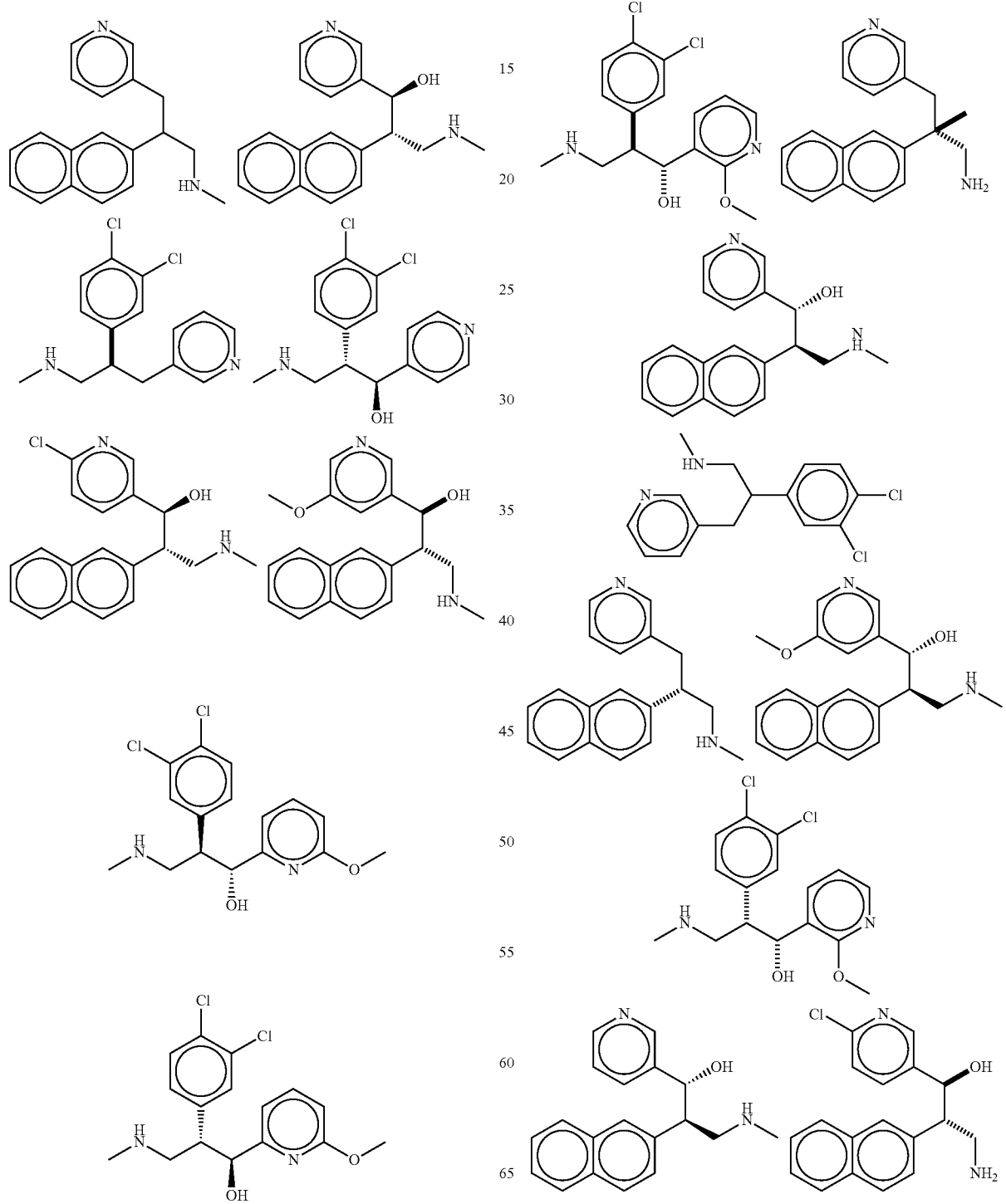

-continued

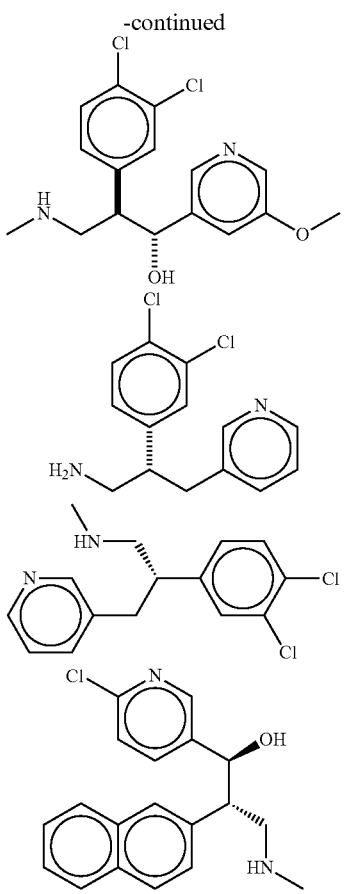

or a pharmaceutically acceptable salt thereof. In some embodiments, a compound of Formula (I) can be:

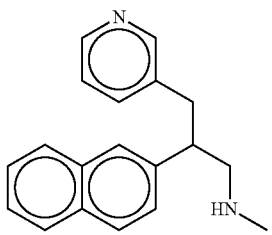

or a pharmaceutically acceptable salt thereof.

In some embodiments, a compound provided herein can be a compound of Formula (II):

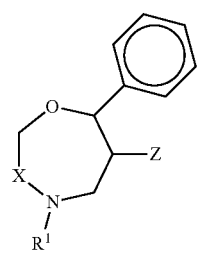

or a pharmaceutically acceptable salt thereof, wherein:
Z is selected from the group consisting of:

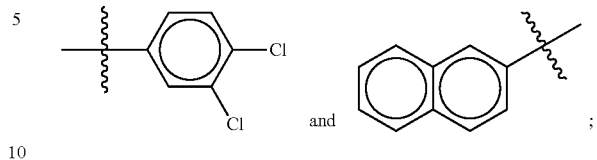

$R^1$ is H or a $C_{1-6}$alkyl; and
X is —$CH_2$ or —C(O)H.

In some embodiments, $R^1$ can be a $C_{1-6}$alkyl. For example, $R^1$ can be methyl. In some embodiments, X is —$CH_2$.

Also provided here is a compound of Formula (IIA):

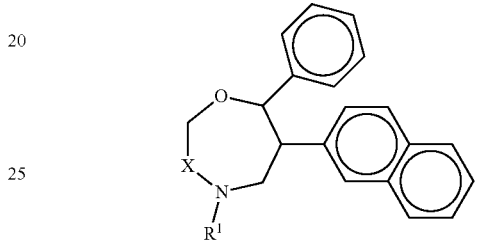

or a pharmaceutically acceptable salt thereof,
wherein:
$R^1$ is H or a $C_{1-6}$alkyl; and
X is —$CH_2$ or —C(O)H.

In some embodiments, $R^1$ can be a $C_{1-6}$alkyl. For example, $R^1$ can be methyl. In some embodiments, X is —$CH_2$.

Non-limiting examples of a compound of Formula (II) and/or Formula (IIA) include:

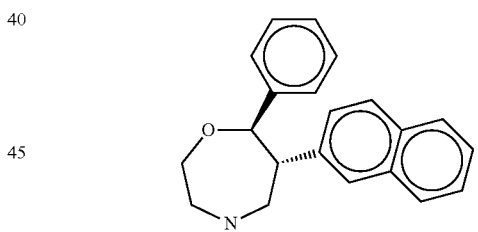

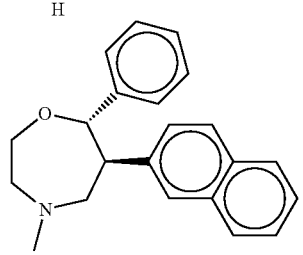

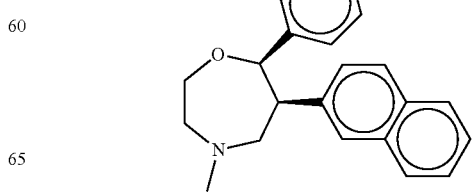

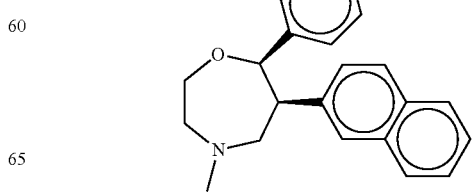

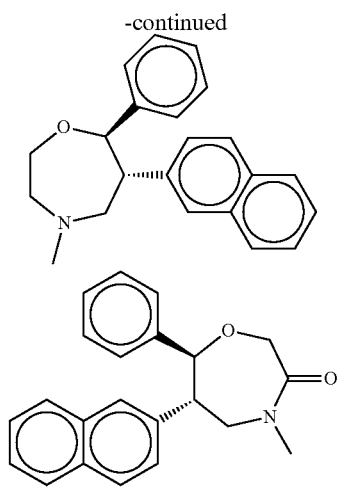

or a pharmaceutically acceptable salt thereof.

The term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc.

The term "alkoxy" refers to an alkyl group having an oxygen attached thereto. Representative alkoxy groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxy.

It is understood that a particular compound provided herein (e.g., a compound having the structure set forth in Table 1) can include any one of that compound's stereoisomers as well as any combination thereof. For example, Compound ID No. 91 can be a 2R,3R-stereoisomer, a 2S,3S-stereoisomer, a 2R,3S-stereoisomer, or a 2S,3R-stereoisomer, or any combination of 2R,3R-, 2S,3S-, 2R,3S-, or 2S,3R-stereoisomers. Examples of particular selected stereoisomers are provided in Table 1 for particular compounds.

This document also provides methods of synthesizing compounds such as amine compounds. For example, in some cases, a compound set forth in Table 1 can be synthesized by any of a variety of appropriate organic chemistry techniques including, without limitation, addition of α-cyanomethylaryl anions to aryl or alkyl aldehydes to give predominantly anti-oriented β-hydroxynitriles, reduction of the resulting nitrile to a primary amine by a strong reducing agent, such as lithium aluminum hydride or borane, conversion of the primary amine to a mono- or dimethylamine through an appropriate carbamate with reducing agents, such as lithium aluminum hydride or borane, or by direct dimethylation of primary amine using formaldehyde and sodium cyanoborohydride, and finally resolving the racemic amines by chiral acid-mediated optical resolution of using a chiral Superfluid Chromatography system. After protection of the secondary amino function, the stereochemistry of the hydroxyl group bearing carbon, if present, can be inverted with appropriate substitution of an azide function, or any other appropriate functional group, such as a fluoride or chloride. In some cases, the hydroxyl group, if present, can be converted to a good leaving group, such as a methanesulfonate or a halide and then displaced with a halide such as chloride or fluoride, and ammonia, or an ammonia derivative. In some cases, a compound can be synthesized to lack the hydroxyl group using, for example, a direct deoxygenation reductive protocol, such as triethylsilane in trifluoroacetic acid, or by using a variation of a Barton deoxygenation procedure, such as conversion to a xanthate followed by tin hydride-mediated reduction.

In some cases, a fluoride or a chloride can be directly introduced using diethylaminosulfur trifluoride (DAST) and thionyl chloride, respectively. In some cases, a C-3 substituted alcohol or amine can be cyclized to a 6-membered 1,3-oxazines or 1,3-diazines through a methylene bridge after condensing with a formaldeyhyde equivalent. Other compounds with cis-stereochemistry can be isolated either as minor products from aldol-type reactions, or through Mitsunobu reactions of their major anti counterparts containing a hydroxyl group at C-3 as described herein. In some cases, a hydroxyl group in an anti-oriented compound can be inverted using triphenylphosphine and a diethyl azodicarboxylate (Mitsunobu protocol) followed by basic hydrolysis to give their syn hydroxyl counterparts. The syn compounds produced can be used for further chemical transformations as described herein.

The compounds set forth in Table 1 can be active in serotonin, norepinephrine, and/or dopamine reuptake inhibition assays, and in some cases, can be resolved by diastereomeric bias on acid-base salt formation with optically pure acids, such as tartaric acid, lactic acid, and camphorsulfonic acid.

Any compound set forth in Table 1 can be a mixture of stereoisomers or can be resolved to form a racemic syn-diastereomer composition, or a racemic anti-diastereomer composition, or these racemates can be optically resolved to furnish pure enantiomers. For example, a compound can be resolved to a pure enantiomer by classical resolution using enantiomerically pure acids including, without limitation, (+)- and (−)-tartaric acid, (+)- and (−)-ditoluyl-tartaric acid, (+)- and (−)-camphorsulfonic acid, or any other optically pure acids.

Any appropriate method can be used to isolate diastereomers and enantiomers such as those described elsewhere (Eliel et al., In: Stereochemistry of Organic Compounds; John Wiley & Sons: New York, 1994). The racemic anti-diastereomeric mixture (50:50 of the 2S,3S and 2R,3R enantiomers) of a compound provided herein can be resolved into the pure enantiomers by classical optical resolution methods. For example, a racemic anti-diastereomer of _(1S,2S)-3-(methylamino)-2-(naphthalen-2-yl)-1-phenylpropan-1-ol (50:50 2R,3R and 2S,3S) (Compound ID No. 124 in Example 124) can be isolated by selective crystallization from a diastereomeric salt mixture with a chiral organic acid, such as tartaric acid, camforsulfonic acid, or a lactic acid etc. After selective crystallization, the optically enriched or pure enantionmeric forms can be obtained by treatment with an aqueous strong base.

Any compound or enantiomer thereof provided herein can be chemically converted from its free base form to a pharmaceutically acceptable salt by reacting the free base with an equivalent amount of any acid that forms a non-toxic salt. Such acids can be either inorganic or organic including, without limitation, hydrochloric acid, hydrobromic acid, fumaric acid, maleic acid, succinic acid, sulfuric acid, phosphoric acid, tartaric acid, acetic acid, citric acid, and oxalic acid. Any compound or pharmaceutically acceptable salt thereof provided herein can be administered to a mammal by itself or in combination with a carrier. Such carriers include, without limitation, sterile aqueous or non-aqueous solutions, suspensions, and emulsions. Examples of non-aqueous solvents include, without limitation, propylene glycol, polyethylene glycol, vegetable oils, and injectable organic esters. Aqueous carriers include, without limitation, water, alcohol, saline, and buffered solutions. Preservatives, flavorings, and other additives such as, for example, antimicrobials, antioxidants, chelating agents, inert gases, and the like can also be present. It will be appreciated that any compound provided herein that is to be administered to a mammal can contain zero, one, or more than one commonly known pharmaceutically acceptable carriers.

The term "pharmaceutically acceptable salt" refers to the relatively non-toxic, inorganic and organic acid addition salts of a compound provided herein. These salts can be prepared in situ during the final isolation and purification of a compound provided herein, or by separately reacting the compound in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. See, for example, Berge et al., "Pharmaceutical Salts", *J. Pharm. Sci.*, 66: 1-19 (1977).

In some embodiments, a compound provided herein may contain one or more acidic functional groups and, thus, is capable of forming pharmaceutically acceptable salts with pharmaceutically acceptable bases. The term "pharmaceutically acceptable salts" in these instances refers to the relatively non-toxic inorganic and organic base addition salts of a compound provided herein. These salts can likewise be prepared in situ during the final isolation and purification of the compound, or by separately reacting the purified compound in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

Inhibiting Neurotransmitter Reuptake

This document provides methods for using the compounds set forth in Table 1 to inhibit neurotransmitter reuptake in a mammal. The term "inhibit" as used herein with respect to neurotransmitter reuptake refers to any reduction in neurotransmitter reuptake. For example, a reduction in neurotransmitter reuptake greater than zero percent (e.g., greater than 0.1, 0.5, 1, 2, 5, 10, 25, 50, 75, or 99 percent) is considered an inhibition of neurotransmitter reuptake. In some embodiments, a compound provided herein can inhibit neurotransmitter reuptake such that the reduction in neurotransmitter reuptake is greater than zero percent (e.g., greater than 0.1, 0.5, 1, 2, 5, 10, 25, 50, 65, 75, 85, 95, or 99 percent) as compared to untreated controls (e.g., untreated mammals or cells). Any appropriate method can be used to assess whether or not neurotransmitter reuptake has been inhibited in a mammal. Such methods can be qualitative or quantitative. An example of a qualitative method includes assessing whether or not a mammal with depression experiences loss of pleasure in daily activities, significant weight loss or gain, changes in mobility (e.g., lethargy, nervousness), feelings of worthlessness, diminished ability to concentrate, or suicidal thoughts to a lesser extent following treatment with a compound provided herein than the extent experienced before treatment. In some cases, such methods can be quantitative. For example, the concentration of serotonin in a platelet sample from a mammal after treatment with a compound can be measured and compared to the concentration of serotonin in a platelet sample from the same mammal before treatment with that compound. If the concentration of serotonin after treatment is reduced compared to the concentration of serotonin before treatment, then that compound inhibited neurotransmitter reuptake in that mammal.

To inhibit neurotransmitter reuptake, an effective amount of any compound provided herein can be administered to a mammal. The term "effective" as used herein refers to any amount that induces a desired level of neurotransmitter reuptake inhibition while not inducing significant toxicity in the mammal. Such an amount can be determined using the methods and materials provided herein. An effective amount of a compound or formulation containing a compound can be any amount that reduces, prevents, or eliminates an anxiety or depressive disorder or relieves pain upon administration to a mammal without producing significant toxicity to that mammal. Some compounds may have a relatively broad concentration range that is effective while others may have a relatively narrow effective concentration range. In addition, the effective amount can vary depending upon the specific mammal or the specific anxiety or depressive disorder to be treated because certain mammals and anxiety or depressive disorders can be more or less responsive to a particular compound. Such effective amounts can be determined for individual compounds using commonly available or easily ascertainable information involving equilibrium dissociation constants, mammal toxicity concentrations, and bioavailability. For example, non-toxic compounds typically can be directly or indirectly administered to a mammal in any amount that reduces, prevents, or eliminates an anxiety or depressive disorder in that mammal.

In some cases, a compound provided herein such as a compound set forth in Table 1 can be used to treat depression (e.g., adjunctive treatment for severe refractory depression), anxiety (e.g., a generalised anxiety disorder), post traumatic stress, social phobia, obsessive-compulsive disorder, impulsivity, attention deficit disorders (e.g., ADD), attention deficit hyperactivity disorder (ADHD), schizophrenia (e.g., schizophrenia with predominantly negative symptoms), movement disorders (e.g., Parkinson's disease or restless leg syndrome), sleep disorder (e.g., narcolepsy), obesity, sexual dysfunction, or substance abuse. In some cases, schizophrenia can be treated with a compound provided herein such as a compound set forth in Table 1 in combination with other typical and atypical antipsychotic agents.

Using the information provided herein, such effective amounts also can be determined by routine experimentation in vitro or in vivo. For example, a patient having an anxiety or depressive disorder can receive direct administration of a compound provided herein in an amount to achieve a blood level close to the equilibrium dissociation constant (i.e., $K_d$) calculated from in vitro analysis sufficient to inhibit the uptake of a particular neurotransmitter. If the patient fails to respond, then the amount can be increased by, for example, two fold. After receiving this higher concentration, the patient can be monitored for both responsiveness to the treatment and toxicity symptoms, as well as blood levels of the drug, and adjustments made accordingly.

To help determine effective amounts of different compounds, it can be useful to refer to an effective amount equivalent based on the effective amount of a common drug used to treat anxiety or depressive disorders. For example, the direct administration of 0.30 mg/kg Prozac® (fluoxetine) daily for three weeks to a mammal can be an effective amount for treating anxiety or depressive disorders. The effects produced by this effective amount can be used as a reference point to compare the effects observed for other compounds used at varying concentrations. Once an equivalent effect is observed, then the specific effective amount for that particular compound can be determined. In this case, that particular amount would be termed a Prozac® effective amount equivalent.

The ability of a compound to inhibit neurotransmitter reuptake also can be assessed in vitro. For example, the level of serotonin reuptake can be determined by measuring the amount of radiolabeled serotonin taken up by synaptosomes ("pinched-off" nerve endings) purified from a tissue source abundant in serotonin transporters (e.g., rat brain cortical tissue). Rat brain cortical tissue can be isolated to produce neuronal membrane fragments such that the membrane fragments close back on themselves to form synaptosomes that retain functional serotonin transporters. The serotonin transporters concentrate serotonin by transporting it from the fluid in which the synaptosomes are suspended to the interior of the synaptosomes. If the serotonin in the suspension fluid is radiolabeled, then the level of serotonin reuptake can be measured by counting the radioactivity in the synaptosomal pellet obtained by rapid filtration or centrifugation. The ability of a compound to inhibit the level of serotonin reuptake can be determined by adding different concentrations to aliquots of the same synaptosomal preparation. For example, the potency of Compound ID No. 71 as an inhibitor of serotonin reuptake can be measured by (1) adding different concentrations of Compound ID No. 71 to aliquots of synaptosomes purified from rat brain cortical tissue, (2) adding the same concentration of radiolabeled serotonin to each aliquot, (3) allowing the serotonin transporters to concentrate the radiolabeled serotonin in the synaptosomes, and (4) counting the radioactivity in the synaptosomal pellet of each aliquot obtained after centrifugation. Compounds with a higher potency will more effectively inhibit reuptake at lower concentrations thus resulting in less detectable radioactivity in the synaptosomal pellet.

In another in vitro example, intact cultured mammalian cells expressing a particular recombinant neurotransmitter transporter can be used to assess the ability of a compound to inhibit neurotransmitter reuptake. For example, the potency of Compound ID No. 87 as an inhibitor of norepinephrine transport can be measured using cultured mammalian cells expressing the norepinephrine transporter. In addition, the potency of a particular compound to inhibit multiple neurotransmitter transporters can be measured. For example, the potency of Compound ID No. 87 as an inhibitor of both serotonin and norepinephrine transport can be measured using separate cultured mammalian cells expressing the serotonin transporter and cultured mammalian cells expressing the norepinephrine transporter. It is understood that measured neurotransmitter transport levels are compared to controls. Controls include, without limitation, vehicle only as well as known inhibitors such as Prozac®, Paxil® (paroxetine), Effexor® (venlafaxine), or Norpramin® (desipramine).

In addition, the potency of a compound to inhibit the reuptake of different neurotransmitters can be assessed by determining the equilibrium dissociation constant (i.e., $K_d$) or the dissociation constant for inhibitor binding (i.e., $K_i$) of that particular compound for a particular neurotransmitter transporter. Typically, the $K_d$ value is determined as described elsewhere (Tatsumi et al, *Eur. J. Pharmacol.*, 340:249-258 (1997)), and the $K_i$ value is determined as described elsewhere (Cheng and Prusoff, *Biochem. Pharmacol.*, 22(23):3099-3108 (1973)). Once determined, the $K_d$ or $K_i$ value for a particular compound can be used to compare that compound's potency with the potency of other compounds or other known inhibitors. For example, if a particular compound has a $K_d$ of 4.1 nM for the serotonin transporter and a $K_d$ of 12.5 nM for the norepinephrine transporter, then that particular compound can be characterized as having a greater ability to inhibit serotonin reuptake compared to norepinephrine reuptake. Likewise, if a first compound has a $K_d$ of 54 nM for the dopamine transporter and a second compound has a $K_d$ of 134 nM for the dopamine transporter, then the first compound can be characterized as having a greater ability to inhibit dopamine reuptake compared to the second compound.

Various factors can influence the actual effective amount used for a particular application. For example, the frequency of administration, duration of treatment, rate of metabolism of the drug, combination of other compounds, and site of administration may require an increase or decrease in the actual effective amount administered.

The frequency of administration can be any frequency that reduces, prevents, or eliminates an anxiety disorder or depression in a mammal without producing significant toxicity to the mammal. For example, the frequency of administration can be from about once a day to about once a month, or more specifically, from about twice a day to about once a week. In addition, the frequency of administration can remain constant or can be variable during the duration of treatment. As with the effective amount, various factors can influence the actual frequency of administration used for a particular application. For example, the effective amount, duration of treatment, rate of metabolism of the drug, combination of other compounds, and site of administration may require an increase or decrease in administration frequency.

An effective duration for amine compound administration can be any duration that reduces, prevents, or eliminates an anxiety or depressive disorder in a mammal without producing significant toxicity to the mammal Thus, the effective duration can vary from several days to several weeks, months, or years. In general, the effective duration for the treatment of an anxiety or depressive disorder can range in duration from several days to several years. Once the compound administrations are stopped, however, the treated anxiety or depressive disorder may return. Thus, the effective duration for the prevention of an anxiety or depressive disorder can last in some cases for as long as the individual is alive.

Multiple factors can influence the actual effective duration used for a particular treatment or prevention regimen. For example, an effective duration can vary with the frequency of compound administration, effective compound amount, combination of multiple compounds, and site of administration. It is noted that diagnostic algorithm methods can be devised to determine or reflect appropriate effective doses, durations, and frequencies.

The level of toxicity, if any, can be determined by assessing a mammal's clinical signs and symptoms before and after administering a known amount of a particular composition. It is noted that the effective amount of a particular composition administered to a mammal can be adjusted according to a desired outcome as well as the mammal's response and level of toxicity. Significant toxicity can vary for each particular mammal and each particular composition.

Any combination of compounds provided herein can be administered to a mammal. For example, two compounds can be administered together to a mammal to inhibit norepinephrine reuptake in that mammal. In another example, one or more compounds that can inhibit serotonin reuptake and one or more compounds that can inhibit dopamine reuptake can be administered together to a mammal to inhibit both serotonin and dopamine reuptake in that mammal. The efficacy of such combinations can be assessed using the methods and materials provided herein.

A compound or combination of compounds provided herein can be administered to any part of a mammal's body. For example, a compound can be delivered to, without limitation, spinal fluid, blood, lungs, intestines, muscle tissues, skin, joints, peritoneal cavity, or brain of a mammal. In addition, a compound or combination of compounds can be administered intravenously, intraperitoneally, intramuscularly, subcutaneously, intrathecally, intracerebroventricularly, or intradermally, orally, by inhalation, or by gradual perfusion over time. The duration of treatment can be any length of time from as short as one day to as long as the life span of the mammal (e.g., many years). For example, a compound provided herein can be administered daily for three months or ten years. It is also noted that the frequency of treatment can be variable. For example, a compound can be administered once (or twice, three times, etc.) daily, weekly, monthly, or yearly.

The invention will be further described in the following examples, which do not limit the scope of the invention described in the claims.

EXAMPLES

Example 1—Synthesis of Compound ID No. 1 (N-methyl-2-((1S,2S)-3-(methylamino)-2-(naphthalen-2-yl)-1-phenylpropoxy)acetamide)

Ethyl 2-((1S,2S)-3-(methylamino)-2-(naphthalen-2-yl)-1-phenylpropoxy)acetate (Example 35) (0.023 g, 0.060 mmol) was dissolved in methanol and methylamine gas was bubbled through the solution for 6 h. The solvent was removed in vacuo, THF (5 mL) added, and 4N HCl (5 mL) in THF were added, and the resulting reaction mixture was stirred for 1 hour at room temperature then heated at 60° C. until the reaction was judged complete by MS. Solvents were evaporated, and residue was transferred to a vial using DCM. The solvent was removed with dry nitrogen and kept under high vacuum for 18 hours, furnishing the product as a white solid (10.00 mg, 38.7%). $^1$H NMR (500 MHz, CD$_3$OD) δ 7.63-7.76 (m, 4H), 7.52 (s, 1H), 7.36-7.46 (m, 2H), 7.06-7.18 (m, 6H), 4.82 (d, 1H, J=10.1 Hz), 4.05 (d, 1H, J=15.3 Hz), 3.93-3.97 (m, 1H), 3.87-3.92 (m, 1H), 3.60 (td, 1H, J=10.2, 3.7 Hz), 3.39-2.82 (s, 3H), 3.39 (dd, 1H, J=12.8, 3.7 Hz), 2.86 (s, 3H). MS m/z (ESI) 363 (MH$^+$).

Example 2—Synthesis of Compound ID No. 2 ((S)-2-(3-(methylamino)-2-(naphthalen-2-yl)propyl) phenyl)methanol)

A 250 mL round bottom was charged 10 mL of dry methanol followed by careful addition of sodium metal (315 mg, 13.7 mmol). Upon solvency, 2-naphthylacetonitrile was added (2.29 g, 13.7 mmol), and the suspension was allowed to stir for 20 minutes. 2-carboxybenzaldehyde (1.88 g, 12.5 mmol) was added followed by additional methanol (2 mL) The flask was equipped with a reflux condenser, and the suspension was heated to reflux for 24 hours. After cooling, the solution was poured into a flask immersed in an ice bath containing 10 mL of 12 M HCl. The voluminous precipitate was filtered and washed with water. After drying in a vacuum oven, the solid was purified via silica gel flash chromatography (3% CH$_3$OH in CH$_2$Cl$_2$ with 1 mL HOAc per 100 mL eluent) to give 1.31 g (4.4 mmol, 35%) of an amorphous white solid. The conjugate reduction was performed in the usual way with a portion of this material (700 mg, 2.34 mmol) to give a crude oil.

The oil was dissolved in 10 mL CH$_2$Cl$_2$ followed by addition of triethylamine (1 mL). The solution was concentrated and dried in vacuo to remove any ammonia. The residue was then dissolved in CH$_2$Cl$_2$ (10 mL), followed by addition of triethylamine (1.0 mL, 2.34 mmol). The solution was chilled to 0° C., and ethyl chloroformate was added (0.27 mL, 2.8 mmol). The solution was allowed to stir at 0° C. for 2 hours and warmed to room temperature. After two days, the volatiles were removed in vacuo, and the residue was acidified with 10 mL of aqueous 1M HCl. 15 mL of Et$_2$O was added, and the contents were poured in a separatory funnel and extracted with EtOAc (3×15 mL) and dried over MgSO$_4$. After filtration, evaporation gave a white foam that was dissolved in 10 mL of dry THF. To this solution was added LiAlH$_4$ (271 mg, 7.14 mmol). The suspension was heated to reflux under nitrogen for 16 hours. Upon cooling, 10 mL of Et$_2$O was added followed by 0.27 mL water, 0.27 mL of a 15% KOH solution, and finally 0.81 mL of water. The white precipitate was filtered, and the filtrate was concentrated and purified via silica gel flash chromatography (5% CH$_3$OH in CH$_2$Cl$_2$ with 1 mL NH$_4$OH per 100 mL eluent) to give 127 mg (0.42 mmol, 18%) of a colorless oil. $^1$H NMR (400 MHz, CD$_3$OD) δ 7.82-7.72 (m, 3H), 7.59 (s, 1H), 7.46-7.36 (m, 3H), 7.29 (d, J=6.9 Hz, 1H), 7.11 (td, J=7.4, 1.4 Hz, 1H), 7.08-7.02 (m, 1H), 7.01-6.95 (m, 1H), 4.55 (dd, J=41.7, 12.6 Hz, 2H), 3.17 (dd, J=13.8, 6.6 Hz, 1H), 3.05-2.89 (m, 3H), 2.29 (s, 3H). HRMS (ESI-TOF) calculated for C$_{21}$H$_{24}$NO (MH$^+$) 306.1852, found 306.1845 (−2.43 ppm, 0.7 mmu).

This racemate was separated into its enantiomers using a chiral stationary phase supercritical fluid chromatography (Multigram III SFC system) on an ADH column (30×250 mm). Isocratic elution using 25% EtOH (containing 1% isopropylamine) at a flow rate of 56 mL/min gave enantiomer retention times of 8.11 and 8.69 minutes, respectively. For large-scale separation, 0.1 g of the sample was diluted in 3 mL of EtOH (containing 0.5% isopropylamine), and stacked injections of 0.3 mL were made. The combined fractions of the first-eluting enantiomer were concentrated in vacuo and converted to an HCl salt which afforded 34 mg of Compound ID No. 2, which was shown by the above described SCF system to have 99% enantiomeric excess. $^1$H NMR (500 MHz, CD$_3$OD) δ 3.12 (dd, J=13.7, 6.4 Hz, 1H), 3.25 (dd, J=14.3, 4.6 Hz, 1H), 3.31 (br. s., 3H), 3.40 (d, J=7.6 Hz, 1H), 3.51-3.62 (m, 2H), 4.51-4.58 (m, 1H), 4.62-4.71 (m, 1H), 7.01 (d, J=7.3 Hz, 1H), 7.10 (t, J=7.3 Hz, 1H), 7.16 (t, J=7.3 Hz, 1H), 7.32 (d, J=7.3 Hz, 1H), 7.41-7.53 (m, 3H), 7.73 (s, 1H), 7.77-7.88 (m, 2H), 7.90 (d, J=8.5 Hz, 1H). Since this compound was more potent at hNET than the second-eluting enantiomer, it was presumed to be (S)-configured.

Example 3—Synthesis of Compound ID No. 3 (2-(1S,2S)-3-(methylamino)-2-(naphthalen-2-yl)-1-phenylpropoxy)acetamide)

Ethyl 2-((1S,2S)-3-(methylamino)-2-(naphthalen-2-yl)-1-phenylpropoxy)acetate (Example 35) (0.254 g, 0.502 mmol)

was dissolved in 15 mL of MeOH in an oven dried round bottom flask with a stirrer, and $NH_3$ gas was passed through it for 15 minutes. The reaction mixture was then stirred at room temperature for 40 hours. The solvents were evaporated using a rotary evaporator. The product was dissolved in MeOH and was purified by reverse phase chromatography HPLC (Vydac column, C-18, 2.2×25 cm, elution with 10% B-100% B in 30 min; B=80% aq. $CH_3CN$ with 0.1% TFA, A=$H_2O$ with 0.1% TFA); FR 8 mL/min, $\lambda_{max}$=254 nm, RT=22.46 minutes). The relevant HPLC fractions were removed using a rotary evaporator. The free amine was converted to a hydrochloride with 1N HCl. The residue was then leached with ether to give a sticky solid that was dried under high vacuum. $^1$H NMR (300 MHz, $CD_3OD$) δ 7.80-7.64 (m, 3H), 7.54 (s, 1H), 7.47-7.38 (m, 2H), 7.21-7.09 (m, 6H), 1H hidden in the $H_2O$ peak, 4.11 (d, 1H, J=15.8 Hz), 4.01-3.89 (m, 2H), 3.67-3.56 (m, 1H), 3.43-3.35 (m, 1H), 2.86 (s, 3H), MS m/z (ESI) 349.08 ($MH^+$). $^1$H NMR (500 MHz, $CD_3OD$) δ 7.61-7.77 (m, 3H) 7.36-7.46 (m, 2H), 7.52 (s, 1H), 6.98-7.18 (m, 6H), 4.84 (d, 1H, J=10.1 Hz), 4.03-4.13 (m, 1H), 3.87-4.01 (m, 2H), 3.61 (td, 1H, J=10.0, 3.8 Hz), 3.33-3.41 (m, 1H), 2.84 (s, 3H).

Example 4—Synthesis of Compound ID No. 4 ((5S,6S)-3-methyl-5-(naphthalen-2-yl)-6-phenyl-1,3-oxazinane)

A solution of 11.6 M 36.5% aq. formaldehyde (0.400 mL) and MeOH (2 mL, 0.343 mmol) was added to (1S,2S)-3-(methylamino)-2-(naphthalen-2-yl)-1-phenylpropan-1-ol hydrochloride (0.100 g, 0.343 mmol) in an oven dried round bottom flask equipped with a stirrer and water condenser. The reaction mixture was then refluxed at 65° C. overnight. The volatiles were evaporated using a rotary evaporator. The residue was dissolved in 5 mL of methanol and 20 mL of ether, and about 18 mL of hexane were added with stirring till permanent turbidity was observed. The turbid suspension was allowed to crystallize overnight at 4° C. White crystals were formed which were filtered and dried (0.098 g, 94%). $^1$H NMR (500 MHz. $CD_3OD$) δ 7.81-7.70 (m, 3H), 7.64 (s, 1H), 7.48-7.41 (m, 2H), 7.23 (d, 1H, J=8.1 Hz), 7.15 (s, 5H), 5.29 (d, 1H, J=8.5 Hz), 5.09 (d, 1H, J=8.6 Hz), 4.92 (d, 1H, J=9.1 Hz), 3.94-3.83 (m, 2H), 3.67-3.53 (m, 1H), 2.97 (s, 3H) MS m/z (ESI) 304.16 ($MH^+$) $[\alpha]_D^{20}$+133.8 (c 0.26, 9:1 EtOH:$H_2O$).

Example 5—Synthesis of Compound ID No. 5 ((S)—N-methyl-2-(naphthalen-2-yl)-3-phenylpropan-1-amine)

To slurry of (1S,2S)-3-(methylamino)-2-(naphthalen-2-yl)-1-phenylpropan-1-ol HCl salt (260 mg, 0.79 mmol) and triethylsilane (5 mL, 31.30 mmol) was added trifluoroacetic acid (5 mL, 64.90 mmol). The reaction was heated for 20 hours at 50° C. and concentrated in vacuo. The residue was mixed with 20 mL 2N NaOH and then extracted with chloroform (3×20 mL) After drying, filtration, and concentration in vacuo, the residue was purified by flash chromatography starting with dichloromethane and moving to 10% 7 M ammonia in dichloromethane. Concentration of the relevant fractions gave an oil which was dissolved in 50 mL ether, to which 4 N HCl in dioxane was added. After stirring for 30 minutes, the accumulated solid was collected by filtration, washed with ether, and then dried under high vacuum to give Compound ID No. 5 as the HCl salt (127 mg, 51.4%). $^1$H NMR (300 MHz, DMSO-$d_6$) δ 8.81 (br. s., 1H), 8.30 (br. s., 0H), 8.07-7.64 (m, 4H), 7.61-7.33 (m, 3H), 7.31-6.96 (m, 5H), 3.70-3.42 (m, 1H), 3.42-3.08 (m, 6H), 3.08-2.88 (m, 1H). MS m/z (ESI) 276.17 ($MH^+$) $[\alpha]_D^{20}$+92.5 (c 2.595, EtOH).

Example 6—Synthesis of Compound ID No. 6 (N-ethyl-2-(1S,2S)-3-(methylamino)-2-(naphthalen-2-yl)-1-phenylpropoxy)acetamide)

This compound was made by dissolving ethyl 2-((1S,2S)-3-(methylamino)-2-(naphthalen-2-yl)-1-phenylpropoxy)acetate (Example 35) in MeOH and passing ethylamine gas through for several hours. The volatiles were removed in vacuo and the product was lyophilized. $^1$H NMR ($CD_3OD$) δ 7.67-7.52 (m, 3H), 7.43 (s, 1H), 7.36-7.27 (m, 2H), 7.09-6.97 (m, 5H), 4.72 (d, 1H, J=9.98 Hz), 4.08-3.99 (M, 1H), 3.95 (d, 1H, J=15.07 Hz), 3.89-3.74 (m, 2H), 3.55-3.42 (m, 1H), 3.32-3.24 (m, 2H) 2.76 (s, 3H), 1.06 (t, 3H, J=7.16 Hz, 7.16 Hz) MS m/z (ESI) 349.10 ($MH^+$).

Example 7—Synthesis of Compound ID No. 7 ((1R,2S)-1-(3-chloropyridin-4-yl)-3-(methylamino)-2-(naphthalen-2-yl)propan-1-ol)

anti- and syn-3-(3-chloropyridin-4-yl)-3-hydroxy-2-(naphthalen-2-yl)propanenitrile: These compounds were made in a standard LDA-mediated reaction of 2-naphthylacetonitrile and 3-chloro-4-pyridine carboxaldehyde at −78° C. in THF. The syn aldol was isolated and identified in the customary way: $^1$H NMR ($CDCl_3$) δ 8.57 (s, 1H), 8.30 (d, 1H, J=5.1 Hz), 7.83-7.76 (m, 1H), 7.75-7.68 (m, 2H), 7.61 (bs, 1H), 7.53-7.49 (m, 2H), 7.12 (dd, 1H, J=8.4, 1.6 Hz), 7.08 (d, 1H, J=4.8 Hz), 5.86 (t, 1H, J=4.5 Hz), 4.46 (d, 1H, J=4.5 Hz), 2.86 (d, 1H, J=4.5 Hz).

syn-3-amino-1-(3-chloropyridin-4-yl)-2-(naphthalen-2-yl)propan-1-ol: A solution of syn-3-(3-chloropyridin-4-yl)-3-hydroxy-2-(naphthalen-2-yl)propanenitrile (1.4 g, 4.53 mmol), in 20 mL of dry THF, was placed in an oven-dried round-bottom flask with a reflux condenser under nitrogen. Next, 1M borane-THF solution (18.14 mL, 18.14 mmol) was added via syringe. This mixture was stirred at 60° C. overnight while monitoring the reaction progress by TLC. After quenching the reaction with cautious addition of saturated $NaHCO_3$, the reaction mixture was poured into a separatory funnel. The layers were separated, and the aqueous layer was extracted with EtOAc (3×50 mL). The combined organic layers were washed with water and brine, dried over $MgSO_4$, and were concentrated using a rotary evaporator. The residue was dissolved in DCM. 4N HCl in dioxane was added, and the mixture was stirred. The solvents were evaporated in vacuo, and the resulting salt was washed with ether, dried, and lyophilized yielding a white solid (1.367 g, 78%). A low J-value (3.4 Hz) of the benzylic proton indicated syn configuration. $^1$H NMR ($CDCl_3$) δ 8.45 (s, 1H), 8.21 (d, 1H, J=5.1 Hz), 7.59-7.88 (m, 4H), 7.39-7.57 (m, 2H), 7.21-7.36 (m, 1H), 7.19 (d, 1H, J=5.1 Hz), 5.64 (d, 1H, J=3.4 Hz), 3.37 (d, 3H, J=4.2 Hz). MS m/z (ESI) 313.11 ($MH^+$).

syn-tert-Butyl 3-(3-chloropyridin-4-yl)-3-hydroxy-2-(naphthalen-2-yl)propylcarbamate: To a solution of syn-3-amino-1-(3-chloropyridin-4-yl)-2-(naphthalen-2-yl)propan-1-ol hydrochloride (1.1 g, 2.85 mmol) in 15 mL dry DCM at −10° C. was added triethylamine (TEA) (1.192 mL, 8.56 mmol) drop-wise, followed by slow addition of Boc anhydride (0.685 g, 3.14 mmol). After stirring for 1 hour at −10° C., the ice bath was removed, and the mixture was allowed to warm to 0° C. TLC showed completion of reaction after 1 hour. The reaction was quenched with saturated $NaHCO_3$, and the reaction mixture was poured into a separatory funnel. The aqueous layer was extracted with DCM (3×25 mL) The combined organic extracts were washed with water, dried over $MgSO_4$, and were evaporated off using a rotary evaporator. The resulting residue was purified by flash chromatography over silica gel (elution with 70% EtOAc in hexanes) to afford a sticky white solid (0.572 g, 48.6%). $^1H$ NMR ($CDCl_3$) δ 8.45 (s, 1H), 7.99 (d, 1H, J=5.1 Hz), 7.75-7.62 (m, 2H), 7.61 (d, 1H, J=8.4 Hz), 7.53 (bs, 1H), 7.49-7.39 (m, 2H), 7.14 (dd, 1H, J=5.4, 1.3 Hz), 6.85 (d, 1H, J=5.1), 5.41 (bs, 1H), 5.04 (bm, 1H), 4.74 (bs, 1H), 4.20-4.10 (m, 1H), 3.33-3.21 (2H). MS m/z (ESI) 412.72 ($MH^+$).

Compound ID No. 7: A solution of syn-tert-butyl 3-(3-chloropyridin-4-yl)-3-hydroxy-2-(naphthalen-2-yl)propyl-carbamate (0.3 g, 0.727 mmol) in 3 mL of dry THF was placed under nitrogen in an oven-dried round-bottom flask fitted with a reflux condenser. Next, 1 M borane-THF solution (2.91 mL, 2.91 mmol) was added via syringe. This mixture was stirred at 60° C. overnight while monitoring the reaction progress by TLC. After quenching the reaction with cautious addition of $NaHCO_3$, the reaction mixture was poured into a separatory funnel, and the layers were separated. The aqueous layer was extracted with EtOAc (3×25 mL). The combined organic layers were washed with water and brine, dried over $MgSO_4$, and were concentrated using a rotary evaporator. The resulting residue was dissolved in DCM, and 4 N HCl in dioxane was added, and the reaction mixture was stirred. The solvents were evaporated in vacuo, and the resulting salt was dried, washed and leached with ether, dried and lyophilized. The residue was purified by reverse phase HPLC (Vydac column, C-18, 2.2×25 cm, elution with 10% B-50% B in 60 min; B=0.1% aq. $CH_3CN$ with 0.1% TFA, A=$H_2O$ with 0.1% TFA); FR 8 mL/min, $\lambda_{max}$=254 nm RT=27.34 min) The fractions containing the compound were pooled and lyophilized to afford the product as a white solid. The racemate was resolved via chiral SFC chromatography. The first eluting enantiomer that had higher potency at the hNET was assigned R,S-configuration. $^1H$ NMR (300 MHz, $CD_3OD$) δ 9.43 (br s, 1H), 8.49 (br s, 1H), 8.07 (br s, 1H), 7.78-7.56 (m, 3H), 7.53 (s, 1H), 7.49-7.41 (m, 2H), 7.17 (d, 1H, J=8.67 Hz), 5.65 (br s, 1H), 4.02-3.83 (m, 2H) 3.44-3.29 (m, 1H) 2.79 (s, 3H). $^1H$ NMR (500 MHz, $CDCl_3$) δ 9.42 (br. s., 1H), 8.48, (br. s., 1H), 8.04 (br. s., 1H), 7.57-7.84 (m, 3H), 7.37-7.57 (m, 3H), 7.15 (d, 1, H, J=8.4 Hz), 5.83 (br. s., 1H), 5.65 (br. s., 1H), 3.76-4.07 (m, 2H), 3.37 (hr. s., 1H), 2.76 (br. s., 3H), 2.04 (s, 1H). MS m/z (ESI) 327.16 ($MH^+$).

Example 8—Synthesis of Compound ID No. 8 (N-cyclobutyl-2-((1S,2S)-3-(methylamino)-2-(naphthalen-2-yl)-1-phenylpropoxy)acetamide)

Synthesis of the titled compound involved formation of two intermediates, Compound Nos. 8a and 8b. These intermediates were also employed in the synthesis of several other compounds.

tert-butyl-(2S,3S)-3-hydroxy-2-(naphthalen-2-yl)-3-phenyl-propyl(methyl)carbamate (Compound No. 8a): (1S,2S)-3-(methylamino)-2-(naphthalen-2-yl)-1-phenylpropan-1-ol (10 g, 34.33 mmol) and triethylamine (11.90 mL, 85.82 mmol) were added in 50 mL of dichloromethane, and to the resulting solution was added di-tert-butyl dicarbonate (8.24 g, 37.76 mmol) at 0° C. The mixture was stirred at 25° C. for 12 hours before the reaction was reduced to 10 mL, diluted with 200 mL of ethyl acetate, and washed with 0.01 N HCl. The organic phase was washed with aqueous sodium bicarbonate, water, brine and dried over sodium sulfate, filtered, and concentrated to give 13 g of an oily product, which was recrystallized from dichloromethane/hexane to afford Compound No. 8a (tert-butyl-(2S,3S)-3-hydroxy-2-(naphthalen-2-yl)-3-phenylpropyl(methyl)carbamate) as a solid (12 g).

Ethyl 2-((1S,2S)-3-(tert-butoxycarbonyl(methyl)amino)-2-(naphthalen-2-yl)-1-phenylpropoxy)acetate (Compound No. 8b): Compound No. 8a (3.4 g, 8.68 mmol) was dissolved in DMF and treated with NaH (0.521 g, 13.03 mmol) at 0° C. for 10 minutes. Thereafter, ethyl 2-bromoacetate (1.922 mL, 17.4 mmol) in DMF was added at 0° C. slowly into the stirring solution. The resulting mixture were warmed to 25° C. and stirred for 12 hours. The reaction was then diluted with 150 mL of dichloromethane and added to 150 mL of water and mixed vigorously to destroy any residual NaH. The organic layer was separated, and the aqueous layer was extracted one more time with 150 mL of dichloromethane. The combine organic layers were dried with magnesium sulfate, filtered, and concentrated first on the rotary evaporator, and then on high vacuum to remove residual. The residue was absorbed onto silica gel and purified using an ISCO automated flash chromatography system (80 gram normal phase column) eluting with 0-100% ramp of EtOAc/Hexane. Compound No. 8b (ethyl 2-((1S, 2S)-3-(tert-butoxycarbonyl(methyl)amino)-2-(naphthalen-2-yl)-1-phenylpropoxy)acetate) was isolated (2.17 g, 52%).

Compound ID No. 8: Compound No. 8b (245 mg, 0.51 mmol) and cyclobutanamine (2 mL, 23.42 mmol) were mixed, and the mixture was heated to 140° C. for six 10 minute intervals in a microwave. Between each heating, the reaction was allowed to cool to room temperature, but was not opened or analyzed. After the sixth heating, LCMS showed one peak with the desired mass. The reaction was concentrated in vacuo and purified using an ISCO automated flash chromatography system (40 gram normal phase column) First the material was washed onto the dry column with dichloromethane, and then the elution started with a 2 minute hexane wash and then ramped from 0-100% EtOAc. The material eluted at about 50% EtOAc. The desired fractions were then evaporated to dryness and subjected to deprotection by dissolving in 15 ml of dichloromethane, to which 2,2,2-trifluoroacetic acid (5 mL, 67.31 mmol) was added in one portion. The reaction was stirred for 30 minutes at 25° C., and concentrated in vacuo. This residue (259 mg) was dissolved in dichloromethane and purified by ISCO automated flash chromatography (40 gram normal phase column) on a ramp from 5% MeOH (3.5N $NH_3$) to 30% MeOH (3.5 N ammonia) in dichloromethane. The largest portion of the product peak that could be collected was concentrated and taken up in diethyl ether, and 2.0 M HCl in ether was added forming a white solid. Concentration and drying overnight in a drying oven at 40° C. afforded Compound ID No. 8 as the HCl salt (0.125 g, 49.0%). $^1H$ NMR (500 MHz, DMSO-$d_6$) δ 9.29 (br. s., 1H) 9.17 (br. s., 1H) 8.42 (d, 1H, J=7.6 Hz) 7.68-7.82 (m, 3H) 7.61 (s, 1H) 7.39-7.48 (m, 2H) 7.21-7.27 (m, 1H) 7.06-7.18 (m, 4H) 4.87 (d, 1H, J=9.8 Hz) 4.25-4.36 (m, 1H) 3.70-3.89 (m, 3H) 3.18-3.31 (m, 1H) 2.68 (t, 3H, J=5.3 Hz) 2.13-2.24 (m, 2H) 1.86-2.01 (m, 2H) 1.59-1.69 (m, 2H).

Example 9—Synthesis of Compound ID No. 9 ((2S,3S)-3-fluoro-N-methyl-2-(naphthalen-2-yl)-3-phenylpropan-1-amine)

(1R,2S)-3-((tert-butoxycarbonyl)(methyl)amino)-2-(naphthalen-2-yl)-1-phenylpropyl 4-chlorobenzoate: 4-Chlorobenzoic acid (0.095 g, 0.607 mmol) was added to a stirred solution of tert-butyl-(2S,3S)-3-hydroxy-2-(naphthalen-2-yl)-3-phenylpropyl(methyl)carbamate (Compound No. 8a) (0.297 g, 0.759 mmol) in 10 mL of dry THF under nitrogen at 0° C. Triphenylphosphine (0.191 g, 0.759 mmol) and diisopropyl azodicarboxylate (DIAD) (0.149 mL, 0.759 mmol) were sequentially added. The cold bath was removed, and the reaction mixture was allowed to warm to room temperature and stirred for 5 hours. The reaction was carefully quenched with 20 mL saturated $NaHCO_3$ and extracted with ether (3×25 mL) in a separatory funnel. The combined organic layers were then washed with water and brine, dried with $MgSO_4$, and evaporated under reduced pressure. The crude product was then chromatographed with 10-20% EtOAc in hexane to afford a white powder (0.250 g, 62.2%). $^1$H NMR ($CDCl_3$) δ 7.98-7.15 (m, 16H), 6.28 (d, 1H, J=6.8 Hz), 1H), 3.84-3.56 (m, 3H), 2.56 (s, 3H), 1.29 (s, 9H). MS m/z (ESI) 551.96 $(MNa)^+$.

tert-Butyl (2S,3R)-3-hydroxy-2-(naphthalen-2-yl)-3-phenylpropyl-(methyl)carbamate: A solution of KOH (0.527 g, 9.397 mmol) prepared in water (3 mL), MeOH (3 mL) and EtOH (3 mL) was added to tert-butyl (2S,3R)-3-hydroxy-2-(naphthalen-2-yl)-3-phenylpropyl(methyl)carbamate (0.250 g, 0.470 mmol) at room temperature. The reaction mixture was heated at 60° C. overnight. The volatiles were evaporated off using a rotary evaporator. Water was added, and the aqueous layer was extracted with ether (3×25 mL). The combined organic layers were washed with water and brine, dried with $MgSO_4$, and evaporated under reduced pressure, yielding the product as a white powder (0.165 g, 90%). $^1$H NMR ($CDCl_3$) δ 7.76-7.63 (m, 5H), 7.45-7.38 (m, 2H), 7.12 (s, 5H), 4.97 (dd, 1H, J=4.3, 4.0 Hz), 4.48-4.26 (m, 1H), 3.73-3.15 (m, 2H), 2.91 (s, 3H), 2.56 (br s, OH), 1.47 (s, 9H). MS m/z (ESI) 414.26 $(MNa)^+$.

(2S,3R)-3-hydroxy-N-methyl-2-(naphthalen-2-yl)-3-phenylpropan-1-amine: To tert-butyl (2S,3R)-3-hydroxy-2-(naphthalen-2-yl)-3-phenylpropyl(methyl) carbamate (0.100 g, 0.255 mmol), 6 mL of 2.9N HCl in dioxane was added and the resulting solution was stirred at room temperature under nitrogen for 1 h. Completion of reaction was determined by MS. The volatiles were removed by evaporation under vacuum. The resulting residue was washed with ether and the residue was dried under high vacuum to afford the product as a white powder (0.083 g, 99%). $^1$H NMR ($CD_3OD$) δ 7.89-7.72 (m, 3H), 7.59 (s, 1H), 7.51-7.41 (m, 2H), 7.37-7.28 (m, 1H), 7.26-7.16 (m, 3H), 7.15-7.06 (m, 2H), 5.08 (d, 1H, J=4.9 Hz), 3.68-3.46 (m, 2H), 3.45-3.35 (m, 1H), 2.65 (s, 3H). MS m/z (ESI) 292.23 $(MH)^+$. A low J-value (4.9 Hz) of the benzylic proton indicated syn configuration.

Compound ID No. 9: To a suspension of the (2S,3R)-3-hydroxy-N-methyl-2-(naphthalen-2-yl)-3-phenylpropan-1-amine hydrochloride (0.1736 g, 0.596 mmol) in 10 mL of DCM was added neat diethylaminosulfur trifluoride (DAST) (0.312 mL, 2.383 mmol). The reaction mixture was stirred overnight at room temperature. The reaction was quenched with $NaHCO_3$ very carefully on ice, and the mixture was stirred at room temperature for 1 hour. The reaction mixture was poured into a separatory funnel, and the aqueous layer was extracted with EtOAc (3×25 mL) The combined organic layers were washed with water and brine, then dried over $MgSO_4$, and were concentrated using a rotary evaporator. The resulting residue was purified twice by flash chromatography over silica gel (elution with 0.1% TEA in 5% MeOH/DCM) to afford the product as a gum that turned into a solid after conversion to a hydrochloride salt. (0.093 g, 53.4%). $^1$H NMR ($CD_3OD$) δ 7.87-7.72 (m, 3H), 7.67 (s, 1H), 7.52-7.40 (m, 2H), 7.32-7.24 (m, 1H), 7.19 (s, 5H), 5.81 (dd, 1H, J=46.9, 8.5 Hz), 3.88-3.62 (m, 3H), 2.72 (s, 3H). MS (ESI) m/z 294.12 $(MH^+)$.

Example 10—Synthesis of Compound ID No. 10 ((1S,2S)-2-(3,4-dichlorophenyl)-3-(methylamino)-1-phenylpropan-1-ol)

(2-(3,4-dichlorophenyl)-3-hydroxy-3-phenylpropanenitrile: A 250 mL round bottom flask equipped with a magnetic stirring bar, nitrogen inlet, and septum was charged with THF (200 mL) and 1.8 M LDA (59.7 mL, 107.50 mmol). After cooling to −78° C., 2-(3,4-dichlorophenyl)acetonitrile (20 g, 107.50 mmol) was added. After 60 minutes, benzaldehyde (10.86 mL, 107.5 mmol) was added via syringe. After stirring at −78° C. for 3 hours, the reaction was quenched at −70° C. by the addition of acetic acid (6.15 mL) Aqueous workup, extraction, and concentration in vacuo afforded the crude aldol (35 g). ISCO purification on silica gel eluting with 0-50% of ethyl acetate in hexane afforded a 1:1 anti:syn mixture of the aldols (19 g).

2-(3,4-dichlorophenyl)-3-(methylamino)-1-phenylpropan-1-ol: A portion of the above material (2-(3,4-dichlorophenyl)-3-hydroxy-3-phenylpropanenitrile, 9 g, 30.81 mmol) was dissolved in THF (100 mL) and heated to reflux, and borane•dimethylsulfide complex (45.0 mL, 90 mmol) was added drop-wise over 5 minutes. Liberated dimethyl sulfide was collected in a Dean-Stark trap, and after 3.5 hours, the mixture was allowed to cool to ambient temperature, quenched with ethanol, and concentrated in vacuo. The residue was dissolved in dioxane (100 mL), and 4N HCl in dioxane (9 mL) was added. After stirring for 30 minutes, the sample was concentrated in vacuo, triturated with ether, washed with ether, ethyl acetate, and hexane, and dried to afford the primary amine hydrochloride (10 g, 98%). These synthetic steps were then repeated to afford another 10 g of the hydrochloride salt of amino-2-(3,4-dichlorophenyl)-1-phenylpropan-1-ol.

Ethyl 2-(3,4-dichlorophenyl)-3-hydroxy-3-phenylpropylcarbamate: The combined samples of 2-(3,4-dichlorophenyl)-3-(methylamino)-1-phenylpropan-1-ol (20 g, 67.52 mmol) were combined with triethylamine (23.53 mL, 168.81 mmol) in dichloromethane (100 mL) and chilled to 0° C. To the chilled solution was added ethyl carbonochloridate (7.78 mL, 81.03 mmol) over 10 minutes, and the reaction was allowed to stir at ambient temperature for 12 hours. The reaction was concentrated in vacuo, diluted with ethyl acetate (300 ml), washed with 0.1 N HCl (2×150 mL), saturated sodium bicarbonate (150 mL) and brine (200 mL), and then dried over magnesium sulfate, filtered, and concentrated in vacuo to give the product as a foam (20 g).

2-(3,4-dichlorophenyl)-3-(methylamino)-1-phenylpropan-1-ol: A portion of the above material, ethyl 2-(3,4-dichlorophenyl)-3-hydroxy-3-phenylpropylcarbamate, 4 g, 10.86 mmol) and 125 mL THF were transferred to a 500 mL 3-neck r.b. flask equipped with a magnetic stirrer, addition funnel, thermometer, and Dean-Stark trap fitted with a condenser and nitrogen inlet. The solution was heated to reflux, and a solution of borane-methyl sulfide complex (27.2 mL, 54.31 mmol) was added drop-wise over 10 minutes. Dimethyl sulfide distillate was collected (bp 38° C.). After 7 hours, the reaction was cooled to ambient temperature, and methanol (10 mL) was added, causing an exotherm and gas evolution. Concentration in vacuo gave the crude product (3 g, 89%). This procedure was repeated on the identical scale.

Compound ID No. 10: The combined samples of 2-(3,4-dichlorophenyl)-3-(methylamino)-1-phenylpropan-1-ol (6.0 g) were then subjected to stereoisomer separation by SFC. The two major stereoisomers were isolated. The first concentrated to a mass of 1 g; and the second concentrated to a mass of 2 g. $^1$H NMR analysis using the TBPTA shift reagent gave coupling constants $J_{12}$ of 10.0 Hz for each, confirming their relative stereochemistry as anti-. The second-eluting anti-enantiomer comprises Compound ID No. 10. $^1$H NMR (500 MHz, DMSO-$d_6$) δ 7.57-7.36 (m, 2H), 7.32-7.02 (m, 6H), 6.04 (d, 1H, J=3.7 Hz), 4.76 (d, 1H, J=4.9 Hz), 3.48 (br. s., 1H), 3.34 (d, 2H, J=6.7 Hz), 2.60-2.51 (m, 3H). Since this compound was more potent at hNET than the first-eluting enantiomer, it was presumed to be (1S,2S)-configured.

Example 11—Synthesis of Compound ID No. 11 ((2S,3R)-3-fluoro-N-methyl-2-(naphthalen-2-yl)-3-phenylpropan-1-amine)

To a suspension of (1S,2S)-3-(methylamino)-2-(naphthalen-2-yl)-1-phenylpropan-1-ol) hydrochloride salt (1.0 g, 3.43 mmol) in 30 mL of DCM was added 4 equivalents of neat diethylaminosulfur trifluoride (DAST) (13.73 mmol, 1.8 mL). The reaction mixture was stirred overnight at room temperature. The reaction was quenched with NaHCO$_3$ very carefully on ice and was stirred at room temperature for 1 hour. The reaction mixture was poured into a separatory funnel, and the aqueous layer was extracted with EtOAc (3×25 mL). The combined organic layers were washed with water and brine, then dried over MgSO$_4$. Concentration of left the solvent in vacuo left a residue that was purified by flash chromatography over silica gel (elution with 0.1% TEA in 5% MeOH/DCM). Evaporation of the solvents from the product containing fractions gave a gum that turned into a brownish solid (0.6662 g, 66.2%) after conversion to a hydrochloride salt. $^1$H NMR (CD$_3$OD) δ 7.84-7.71 (m, 3H), 7.66 (s, 1H), 7.51-7.42 (m, 2H), 7.28 (dd, 1H, J=8.67, 1.7 Hz), 7.19 (s, 5H), 5.82 (dd, 1H, J=46.9, 8.5 Hz), 3.89-3.64 (m, 3H), 2.72 (s, 3H). MS m/z (ESI) 294.12 (MH$^+$).

Example 12—Synthesis of Compound ID No. 12 ((1S,2S)-3-(methylamino)-2-(naphthalen-2-yl)-1-(pyridin-4-yl)propan-1-ol))

anti-3-Hydroxy-2-(naphthalen-2-yl)-3-(pyridin-4-yl)propanenitrile: This compound was synthesized by the standard LDA-mediated aldol reaction between the 2-naphtylcyanide and 4-pyridine carboxaldehyde in THF at −78° C. The anti-isomer was isolated as the major product. $^1$H NMR (DMSO-$d_6$) δ 8.54 (d, 1H, J=5.84 Hz), 7.98-7.89 (m, 4H), 7.61-7.51 (m, 3H), 7.46 (d, 1H, J=5.8 Hz), 6.35 (d, 1H, J=5.09 Hz), 5.08 (t, 1H, J=4.7, 4.7 Hz), 4.78 (d, 1H, J=4.71 Hz). MS m/z (ESI) 275.01 (MH$^+$).

anti-3-Amino-2-(naphthalen-2-yl)-1-(pyridin-4-yl)propan-1-ol hydrochloride: A solution of anti-3-Hydroxy-2-(naphthalen-2-yl)-3-(pyridin-4-yl)propanenitrile (10.2 g, 0.729 mmol) in 5 mL of dry THF was placed in an oven-dried round-bottom flask under nitrogen. Next, 1M borane-THF solution (2.92 mL, 2.92 mmol) was added via syringe. The reaction mixture was stirred at 60° C. overnight while monitoring the reaction progress by TLC. After quenching the reaction with cautious addition of NaHCO$_3$, the reaction mixture was poured into a separatory funnel. The aqueous layer was extracted with EtOAc (3×50 mL). The combined organic layers were washed with water and brine, dried over MgSO$_4$ and concentrated using a rotary evaporator. The residue was dissolved in DCM, 1N HCl was added, and the mixture was stirred for 10 minutes. The solvents were evaporated in vacuo, and the resulting salt was washed and leached with DCM, dried, and lyophilized, yielding a white solid (0.206 g, 89.6%). $^1$H NMR (CD$_3$OD) δ 8.64 (d, 2H, J=6.40 Hz), 7.92-7.78 (m, 5H), 7.72 (s, 1H), 7.55-7.47 (m, 2H), 7.44-7.37 (m, 1H), 5.39 (d, 1H, J=8.85 Hz), 3.96-3.85 (m, 1H), 3.63-3.41 (m, 2H) MS m/z (ESI) 279.36 (MH$^+$).

tert-Butyl anti-3-hydroxy-2-(naphthalen-2-yl)-3-(pyridin-4-yl)propylcarbamate: To a solution of anti-3-amino-2-(naphthalen-2-yl)-1-(pyridin-4-yl)propan-1-ol hydrochloride (0.45 g, 1.281 mmol) in 10 mL dry DCM at −10° C. in an oven dried round bottom flask was added triethylamine (TEA) (0.536 mL, 3.84 mmol) drop-wise, followed by slow addition of Boc anhydride (0.308 g, 1.409 mmol). After stirring for 1 hour at −10° C., the ice bath was removed, and the mixture was allowed to warm to 0° C. TLC showed completion or reaction after 1 hour. The reaction was quenched with saturated NaHCO$_3$, and the mixture was poured into a separatory funnel. The aqueous layer was extracted with DCM (3×25 mL) The combined organic extracts were washed with water and dried over MgSO$_4$, and the solvents were evaporated off using a rotary evaporator. The resulting residue was purified by flash chromatography over silica gel (elution with 70% EtOAc in hexanes) to afford a sticky white solid (0.4 g, 83%). $^1$H NMR (CDCl$_3$) δ 8.38 (d, 2H, J=5.09 Hz), 7.83-7.55 (m, 3H), 7.52 (s, 1H), 7.49-7.33 (m, 2H), 7.24-7.23 (m, 1H), 7.09 (d, 1H, J=5.09 Hz), 4.99 (dd, 1H, J=8.29, 1.88 Hz), 4.72 (br s, 1H), 4.34 (br s, 1H), 3.94-3.90 (m, 1H), 3.54-3.38 (m, 1H), 3.28-3.16 (s, 1H), 1.44 (s, 9H). MS m/z (ESI) 393.03 (MH$^+$)

anti-3-(methylamino)-2-(naphthalen-2-yl)-1-(pyridin-4-yl)propan-1-ol: tert-Butyl anti-3-hydroxy-2-(naphthalen-2-yl)-3-(pyridin-4-yl)propylcarbamate (0.4 g, 1.057 mmol), dissolved in 5 mL of dry THF, was placed in an oven-dried round-bottom flask under nitrogen. Next, 1M borane-THF solution (2.85 mL, 2.85 mmol) was added via syringe. This mixture was stirred at 60° C. overnight while monitoring the reaction progress by TLC. After quenching the reaction with cautious addition of NaHCO$_3$, the reaction mixture was poured into a separatory funnel. The aqueous layer was extracted with EtOAc (3×25 mL). The combined organic layers were washed with water and brine, dried over MgSO$_4$, and were concentrated using a rotary evaporator. The resulting residue was dissolved in DCM, 1N HCl was added, and the mixture was stirred for several minutes. The solvents were evaporated in vacuo, and the resulting salt was washed and leached with DCM, dried, and lyophilized, yielding a white solid (0.245 g, 63.5%). A high J-value (9.04 Hz) of the benzylic proton signal indicated anti-configuration. $^1$H NMR (CD$_3$OD) δ 8.63 (d, 2H, J=6.59 Hz), 7.96-7.75 (m, 5H), 7.71 (s, 1H), 7.56-7.45 (m, 2H), 7.42-7.34 (m, 1H), 5.37 (d, 1H, J=9.04 Hz), 4.01-3.89 (m, 1H), 3.67-3.46 (m, 2H), 2.77 (s, 3H). $^1$H NMR (500 MHz, CDCl$_3$) δ 8.34 (d, 2 h, J=6.1 Hz), 7.77 (d, 1H, J=9.2 Hz), 7.66-7.74 (m, 2H), 7.52 (s, 1H), 7.45 (d, 2H, J=4.0 Hz), 7.11 (dd, 1H, J=8.4, 1.4 Hz), 7.01 (d, 2H, J=6.1 Hz), 5.16 (d, 1H, J=8.2 Hz, 3.39 (dd, 1H, J=11.9, 10.1 Hz), 3.12 (dd, 1H, J=12.2, 2.7 Hz), 3.02 (br. s., 1H), 2.53 (s, 3H). MS m/z (ESI) 293.3 (MH$^+$).

Compound ID No. 12: The above compound, which was a racemate, was resolved into the S,S and R,R enantiomers by SFC chiral chromatography. The second eluting enantiomer comprises Compound 12. Since this compound was more potent at hNET than the first-eluting enantiomer, it was presumed to be (1S,2S)-configured. $^1$H NMR (500 MHz, CDCl$_3$) δ 8.34 (d, 2 h, J=6.1 Hz), 7.77 (d, 1H, J=9.2 Hz), 7.66-7.74 (m, 2H), 7.52 (s, 1H), 7.45 (d, 2H, J=4.0 Hz), 7.11 (dd, 1H, J=8.4, 1.4 Hz), 7.01 (d, 2H, J=6.1 Hz), 5.16 (d, 1H, J=8.2 Hz, 3.39 (dd, 1H, J=11.9, 10.1 Hz), 3.12 (dd, 1H, J=12.2, 2.7 Hz), 3.02 (br. s., 1H), 2.53 (s, 3H). MS m/z (ESI) 293.3 (MH$^+$).

Example 13—Synthesis of Compound ID No. 13 (N-cyclopropyl-2-((1S,2S)-3-(methylamino)-2-(naphthalen-2-yl)-1-phenylpropoxy)acetamide)

Ethyl 2-((1S,2S)-3-(tert-butoxycarbonyl(methyl)amino)-2-(naphthalen-2-yl)-1-phenylpropoxy)acetate (Compound No. 8b) (156 mg, 0.33 mmol) and cyclopropanamine (1 mL, 14.43 mmol) were mixed, and the mixture was heated to 150° C. for 45 minutes in a microwave and then at 150° C. for two 20 minute portions. The reaction was then concentrated to a clear yellow oil, dissolved in chloroform with a few drops of MeOH, and purified using an ISCO automated flash chromatography system (40 g normal phase column) with a ramp of 0-100% ethyl acetate/hexane. The major peak was desired material with no starting material present and concentrated in vacuo to give a residue of 147 mg. This material was dissolved in 8 mL of dichloromethane, to which trifluoroacetic acid (2 mL, 26.92 mmol) was added in one portion, and stirred for 45 minutes at 25° C. Aqueous sodium bicarbonate was then added to neutralize the trifluoroacetic acid, and the reaction was extracted with dichloromethane. The combined organic layers were dried with magnesium sulfate and concentrated in vacuo. The residue was dissolved in dichloromethane and purified by ISCO automated flash chromatography (40 g normal phase column) with a ramp of 0-30% MeOH (with 10% 7 N ammonia in MeOH) in dichloromethane. The purified product was dissolved in dichloromethane, washed with 0.1 N NaOH, dried over magnesium sulfate, and concentrated in vacuo. This residue was dissolved in chloroform/diethyl ether, and HCl etherate was added. The solvent was removed in vacuo to form Compound ID No. 13 as the HCl salt (0.123 g, 86%, off-white solid). $^1$H NMR data were consistent with the desired structure.

Example 14—Synthesis of Compound ID No. 14 (N-(2-hydroxyethyl)-2-((1S,2S)-3-(methylamino)-2-(naphthalen-2-yl)-1-phenylpropoxy)acetamide)

Compound No. 8b (180 mg, 0.38 mmol) and 2-aminoethanol (120 mg, 1.96 mmol) in EtOH were subjected to microwave conditions at 130° C. for 4 hours. The amber solution was concentrated, and the crude product was subjected to ISCO automated flash chromatography, eluting with a 0-100% EtOAc/hexanes gradient followed by 2% MeOH/EtOAc to give purified tert-butyl (2S,3S)-3-(2-(2-hydroxyethylamino)-2-oxoethoxy)-2-(naphthalen-2-yl)-3-phenylpropyl(methyl)-carbamate (180 mg, 97%). This material was combined with 4M HCl in dioxane (2 mL) and was allowed to stand at 25° C. for 15 minutes, concentrated to near dryness, and triturated with ether (2×). The resulting white solid was collected and dried in vacuo to give Compound ID No. 14 as the HCl salt (135 mg, 86%). $^1$H NMR data were consistent with the desired structure.

Example 15—Synthesis of Compound ID No. 15 ((S,S)-1-(2-fluorophenyl)-3-(methylamino)-2-(naphthalen-2-yl)propan-1-ol)

An oven dried 2 neck 100 mL round bottom flask was charged with Compound No. 15a (616 mg, 2.12 mmol) and dry THF (10 mL) While stirring at room temperature, BH$_3$/THF (1M in THF, 10.6 mL, 10.6 mmol) was added from a syringe. Upon addition of borane, the system was fitted with a reflux condenser and heated to reflux for 6 hours. After cooling to room temperature, 5 mL of methanol was carefully added. Upon cessation of bubbles, the system was heated to reflux for 1 hour. The volatiles were then removed in vacuo, and to the residue was added 10 mL of methanol and 1 mL of a 4 M HCl solution in dioxane. The homogenous solution was concentrated to give a white amorphous solid that was triturated with diethyl ether to give 648 mg of a white powder. A portion of this solid (634 mg, 1.91 mmol) was dissolved in CH$_2$Cl$_2$ (15 mL) followed by addition of triethyl amine (1.3 mL, 9.55 mmol) and cooled to 0° C. Ethyl chloroformate (0.26 mL, 2.7 mmol) was then added at 0° C. Solution was allowed to warm to room temperature overnight. In the morning, the solution was concentrated, and the residue was purified via silica gel flash chromatography (35% EtOAc in hexanes) to give 530 mg (1.44 mmol, 76%) of a colorless gum. A portion of this material (495 mg, 1.35 mmol) was dissolved in dry THF (10 mL) followed by addition of LiAlH$_4$ (204 mg, 5.4 mmol). This suspension was heated to reflux under nitrogen for 16 hours. Upon cooling, 10 mL of Et$_2$O was added followed by 0.2 mL water, 0.2 mL of a 15% KOH solution, and finally 0.60 mL of water. The white precipitate was filtered, and the filtrate was concentrated and purified via silica gel flash chromatography (5% CH$_3$OH in CH$_2$Cl$_2$ with 1 mL NH$_4$OH per 100 mL eluent) to give 159 mg (0.51 mmol, 38%) of a colorless oil. $^1$H NMR (300 MHz, CDCl$_3$) δ 7.60-7.78 (m, 4H), 7.50 (td, J=7.2, 2.5 Hz, 1H), 7.35-7.46 (m, 1H), 7.35-7.46 (m, 1H), 7.19-7.24 (m, 1H), 7.00-7.13 (m, 2H), 6.77 (dd, J=10.7, 2.3 Hz, 1H), 5.53 (d, J=7.2 Hz, 1H), 3.21-3.42 (m, 2H), 3.05-3.21 (m, 1H), 2.51 (s, 3H). HRMS (ESI-TOF) calculated for C$_{20}$H$_{21}$FNO (MH$^+$) 310.1602, found 310.1619 (5.43 ppm, 1.7 mmu).

This racemate was separated into its enantiomers using a chiral stationary phase supercritical fluid chromatography. The combined fractions of the first-eluting enantiomer were concentrated in vacuo and converted to an HCl salt, which afforded 58 mg of Compound ID No. 15, which was shown by the previously described SCF system to have 99% enantiomeric excess. $^1$H NMR (300 MHz, CD$_3$OD) δ 7.68-7.81 (m, 3H), 7.62 (s, 1H), 7.39-7.53 (m, 3H), 7.26 (dd, J=8.5, 1.3 Hz, 1H), 7.04-7.20 (m, 2H), 6.78 (ddd, J=10.6, 8.2, 1.1 Hz, 1H), 5.36 (d, J=9.0 Hz, 1H), 3.78-3.91 (m, 1H), 3.46-3.61 (m, 2H), 2.75 (s, 3H). Since this enantiomer is more potent at hNET than the second-eluting enantiomer, it was presumed to be (S,S)-configured.

Example 15a—Synthesis of Compound No. 15a (anti-3-(2-fluorophenyl)-3-hydroxy-2-(naphthalen-2-yl)propanenitrile)

A 150 mL 2 necked round bottom flask was purged with N$_2$ and was charged with 2-naphthylacetonitrile (3.34 g, 20 mmol) and dry THF (75 mL) The solution was cooled to −78° C. followed by drop-wise addition of NaHMDS (2 M in THF, 10.5 mL, 21 mmol). The solution was allowed to stir at −78° C. for 20 minutes before the addition of 2-fluorobenzaldehyde (2.5 mL, 24 mmol). This solution was allowed to stir for 45 minutes at −78° C. While at −78° C., saturated aqueous NH$_4$Cl was added, and the cooling bath was removed. When the solution reached room temperature, 5 mL of 1 M HCl was added followed by 10 mL of Et$_2$O, and the contents were poured in a separatory funnel, extracted with Et$_2$O (3×15 mL), and dried over MgSO$_4$. The suspension was filtered and concentrated to give a pale yellow oil. The crude oil was purified by silica gel column chromatography (10% EtOAc in hexanes) to give 598 mg of the syn diastereomer Compound No. 60a, 4.18 g of a mixture of both the anti and syn diastereomers, and 365 mg of the anti diastereomer Compound No. 15a for a combined mass of 5.14 g (88%). The anti/syn mixture was ran through a subsequent chromatographic separation to obtain an additional 654 mg of the anti diastereomer Compound No. 15a. $^1$H NMR (400 MHz, CDCl$_3$) δ 7.96-7.81 (m, 4H), 7.70 (td, J=7.2, 1.5 Hz, 1H), 7.58-7.51 (m, 2H), 7.45 (dd, J=8.5, 1.9 Hz, 1H), 7.34 (tdd, J 7.3, 5.4, 1.8 Hz, 1H), 7.27-7.21 (m, 1H), 7.05 (ddd, J=10.5, 8.2, 1.1 Hz, 1H), 5.39 (t, J=4.2 Hz, 1H), 4.39 (d, J=4.1 Hz, 1H), 2.39 (d, J=4.4 Hz, 1H).

Example 16—Synthesis of Compound ID No. 16 ((1S,2S)-2-(4-bromo-3-chlorophenyl)-3-(methylamino)-1-phenylpropan-1-ol)

Compound No. 16a: A 250 mL round bottom flask equipped with a magnetic stirring bar, nitrogen inlet, and septum was charged with THF (200 mL) and 2.0 M LDA (27.6 mL, 55.10 mmol). After cooling to −78° C., 2-(4-bromo-3-chlorophenyl)acetonitrile (12.7 g, 55.10 mmol) was added. After 60 minutes, benzaldehyde (5.57 mL, 55.10 mmol) was added via syringe. After stirring at −78° C. for 3 hours, the reaction was quenched by the addition of acetic acid (20 mL) while stirring at −70° C. The aqueous layer was extracted with ether (2×50 mL), and the combined organic extracts were washed with brine (50 mL) and dried over magnesium sulfate. Concentration in vacuo afforded the crude aldol as a mixture of anti- and syn-diastereomers (21 g). ISCO automated flash chromatography on silica gel, eluting with 0-30% ethyl acetate in hexane, afforded the product as 3:1 anti-:syn-mixture (16 g, ratio measured by $^1$H NMR). This material (2-(4-bromo-3-chlorophenyl)-3-hydroxy-3-phenylpropanenitrile, 16 g, 47.53 mmol), dissolved in THF (150 mL), was heated to reflux at 76° C., and borane•dimethyl sulfide (93 mL, 186 mmol) was added drop-wise over 15 minutes. The liberated dimethyl sulfide was collected in a Dean-Stark trap. After 3.5 hours, the mixture was cooled to ambient temperature and treated with 4N HCl in dioxane (12 mL) and then MeOH (12 mL) slowly to quench excess borane, maintaining the temperature under 25° C. The reaction mixture was heated to 64° C. for 15 minutes to ensure quench, and then concentrated in vacuo to remove all the trimethyl borate to afford a yellow oil.

The residue was diluted with methanol (15 mL), concentrated in vacuo, and triturated with ether to give a white precipitate that was collected, washed with ether, and dried to give 17 g of the desired 3-amino-2-(4-bromo-3-chlorophenyl)-1-phenylpropan-1-ol hydrochloride salt (97%). A portion of this material (15 g, 44.03 mmol) was combined with triethylamine (15.34 mL, 110.09 mmol) in dichloromethane (100 mL) and cooled to 0° C. To the chilled solution was added ethyl carbonochloridate (5.07 mL, 52.84 mmol) over 10 minutes and then stirred for 2 hours at room temperature. The reaction was then concentrated to near dryness, diluted with ethyl acetate (200 mL), washed with 0.1 N HCl (2×150 mL), saturated sodium bicarbonate (150 mL), and brine (200 mL), and then dried over magnesium sulfate, filtered, and concentrated in vacuo to give a foam (14 g). This mixture was purified by ISCO automated flash chromatography, eluting with 0-40% of ethyl acetate in hexane over 15 minutes. Two fractions were collected, that totaled 11 g of Compound No. 16a (ethyl-2-(4-bromo-3-chlorophenyl)-3-hydroxy-3-phenylpropylcarbamate) as a mixture of all four stereoisomers.

This mixture was subjected to SFC to separate all four stereoisomers (two anti-enantiomers and two syn-enantiomers). The Multigram III SFC system was used with a 30 mm×250 mm Phenomenex Lux CE-2 column. The 11 g sample of Compound No. 16a was diluted to 50 mL with EtOH (0.5% isopropylamine), and stacked injections of 0.5 mL each were run using 25% of EtOH (0.5% isopropylamine) isocratic at 110 mL/minute. The four stereoisomer peaks were very well separated with little tailing affording 2.4 grams of each anti-enantiomer (peaks 3 and 4). The anti-stereochemistry of each compound was confirmed by $^1$H NMR spectroscopy with the TBPTA shift reagent (J$_{12}$=8.1-8.3 Hz for both). A portion of the second-eluting enantiomer (ethyl (2S,3S)-2-(4-bromo-3-chlorophenyl)-3-hydroxy-3-phenylpropylcarbamate, 1.6 g, 3.88 mmol) was dissolved in THF (50 mL) and heated to reflux. Borane•THF complex (38.8 mL, 38.77 mmol) was added drop-wise over 15 minutes, and the reaction kept at reflux for 20 hours. The reaction mixture was cooled to 0° C., and 4 N HCl in dioxane (5 mL) was added, followed by slow addition of methanol (10 mL) to quench excess borane, maintaining the temperature under 25° C. The reaction mixture was heated to 64° C. to ensure quenching, and concentrated in vacuo to afford a yellow oil. Ethanol (5 mL) was added, the solution concentrated in vacuo, and the residual gum triturated with ether to give a white precipitate that was collected, washed with ether, and dried to give Compound ID No. 16 as the HCl salt (1.3 g, 86%). $^1$H NMR (500 MHz, DMSO-d6) δ 2.50 (d, J=3.7 Hz, 3H), 3.32-3.44 (m, 2H), 3.47 (dd, J=11.3, 4.0 Hz, 1H), 4.76 (d, J=7.6 Hz, 1H), 7.06 (dd, J=8.2, 1.8 Hz, 0H), 7.10-7.30 (m, 5H), 7.45 (d, J=1.8 Hz, 0H), 7.60 (d, J=8.2 Hz, 0H). Since this compound was more potent at hNET than the reduction product of the first-eluting anti-enantiomer, it was presumed to be (1S,2S)-configured.

Example 17—Synthesis of Compound ID No. 17 ((S)-3-(2-fluorophenyl)-N-methyl-2-(naphthalen-2-yl)propan-1-amine)

A 50 mL round bottom flask equipped with a stir bar was charged with Compound No. 17a (858 mg, 0.59 mmol), dry THF (20 mL), and lithium aluminum hydride (325 mg, 8.54 mmol). A reflux condenser was added, and the system was purged with nitrogen and heated to reflux for 16 hours. Upon cooling, diethyl ether (20 mL) was added followed by water (0.33 mL), 15% KOH solution (0.33 mL), and water again (1.0 mL). After 30 minutes of stirring, the white suspension was filtered, and the filter cake was washed with ether. The filtrate was dried over MgSO$_4$ and evaporated. The residue was purified via silica gel flash chromatography to give a yellow oil, which was taken up in diethyl ether (10 mL) and treated with 4N HCl in dioxane (1 mL). Toluene (20 mL) was then added, and the solution was concentrated to afford 574 mg (1.74 mmol, 71%) of a white powder. $^1$H NMR (400 MHz, CD$_3$OD) δ 7.89 (d, J=8.5 Hz, 1H), 7.87-7.78 (m, 2H), 7.69 (s, 1H), 7.51-7.46 (m, 2H), 7.44 (dd, J=8.5, 1.9 Hz, 1H), 7.16 (ddd, J=15.5, 5.4, 1.8 Hz, 1H), 7.04-6.96 (m, 2H), 6.93 (td, J=7.4, 1.1 Hz, 1H), 3.64-3.55 (m, 1H), 3.48 (s, 1H), 3.40 (dd, J=11.8, 4.3 Hz, 1H), 3.22 (dd, J=13.7, 6.1 Hz, 1H), 3.05 (dd, J=13.7, 8.8 Hz, 1H), 2.64 (s, 3H). HRMS (ESI-TOF) calculated for C$_{20}$H$_{21}$FN (MH$^+$) 295.1685, found 295.1690 (+1.41 ppm, 0.5 mmu).

The solid was mixed with 5 N NaOH and extracted with chloroform (3×3 mL) The organic layers were dried over anhydrous sodium sulfate, filtered, and concentrated to give an oil. This racemate was separated into its enantiomers using a chiral stationary phase supercritical fluid chromatography (Multigram III SFC system) on an ADH column (30×250 mm). Isocratic elution using 12% EtOH (containing 0.5% isopropylamine) at a flow rate of 50 mL/minute gave enantiomer retention times of 8.75 and 10.6 minutes, respectively. For large-scale separation, 0.5 g of the sample was diluted in 3 mL of EtOH (containing 0.5% isopropylamine), and stacked injections of 0.2-0.25 mL were made. The combined fractions of the second-eluting enantiomer were concentrated in vacuo, yielding 183 mg of Compound ID No. 17, which was shown by the above described SCF system to have 98% enantiomeric excess. $^1$H NMR (300 MHz, CD$_3$OD) δ 1.45 (s, 3H), 1.78-1.93 (m, 1H), 1.96-2.08 (m, 1H), 2.16-2.50 (m, 3H), 5.63-5.88 (m, 3H), 5.89-6.06 (m, 1H), 6.15-6.34 (m, 3H), 6.50 (s, 1H), 6.55-6.77 (m, 3H). Since this enantiomer was more potent at hNET than the first-eluting enantiomer, it was presumed to be (S)-configured.

Example 17a—Synthesis of Compound No. 17a (ethyl (3-(2-fluorophenyl)-2-(naphthalen-2-yl)propyl)carbamate)

To a stirred solution of 2-naphthylacetonitrile (917 mg, 5.48 mmol) in absolute ethanol (15 mL) was added 2-fluorobenzaldehyde (687 mg, 5.54 mmol). A solution of sodium ethoxide (37 mg, 0.55 mmol) in absolute ethanol (2 mL) was added. Within 15 minutes, a solid was formed, and to the suspension was added 15 mL of hot THF. The solution was then concentrated to afford 1.37 g (5.02 mmol, 92%) of a pale yellow solid that was used without further purification. A reduction of the α-β unsaturated nitrile was performed by adding a slurry of Raney nickel 2800 (approximately 1 g) to an air-free Schlenk flask under N$_2$. The slurry was washed with absolute ethanol and decanted. To this ethanolic slurry was added 10 mL of 4M NH$_4$OH in ethanol. The N$_2$ was carefully evacuated and backfilled with H$_2$. While maintaining a H$_2$ atmosphere, a solution of the α-β unsaturated nitrile (843 mg, 3.08 mmol) in THF (10 mL) was then added, and the flask was then equipped with a stir bar and hydrogen gas balloon. The suspension was stirred at room temperature for 1 hour and was then filtered through celite. The celite was washed with CH$_2$Cl$_2$, and the filtrate was evaporated to give a residue that was purified via silica gel flash chromatography (8% CH$_3$OH in CH$_2$Cl$_2$ with 1 mL NH$_4$OH per 100 mL of eluent) to give 714 mg (2.56 mmol, 83%) of a yellow oil. The oil was then dissolved in 20 mL of CH$_2$Cl$_2$ and cooled to 0° C. followed by addition of TEA (0.86 mL, 6.1 mmol) and ethyl chloroformate (0.29 mL, 3.1 mmol). The solution was allowed to warm to room temperature overnight. In the morning, 1 mL of water was added. The contents were poured into a separatory funnel and extracted with CH$_2$Cl$_2$ (2×15 mL) The organics were dried over Na$_2$SO$_4$, filtered, and concentrated. The residue was purified via silica gel flash chromatography (10% EtOAc in hexanes) to give 858 mg (2.44 mmol, 95%) of Compound No. 17a as a colorless gum. A portion of this compound was used directly in the preparation of Compound ID No. 17.

Example 18—Synthesis of Compound ID No. 18 ((2S,3S)—N-methyl-3-((5-methylisoxazol-3-yl)methoxy)-2-(naphthalen-2-yl)-3-phenylpropan-1-amine)

Compound No. 8a (200 mg, 0.51 mmol) was dissolved in DMF and treated with NaH (61.3 mg, 1.53 mmol) at 0° C. for 20 minutes, to which was added 3-(bromomethyl)-5-methylisoxazole (180 mg, 1.02 mmol) in DMF (2 mL). The resulting mixture was warmed to room temperature and stirred for 12 hours, at which time LC/MS indicated the reaction was complete. The reaction was diluted with ethyl acetate (100 mL), washed with water and brine, and dried with sodium sulfate. Concentration under reduced pressure and purification using ISCO automated flash chromatography (0-60% ethyl acetate in hexane) afforded the desired product (158 mg). This material was dissolved in 4 M HCl in dioxane (1.6 mL) and stirred at 25° C. for 12 hours, at which time LC/MS indicated reaction was complete. The solvent was evaporated, and the resulting solid was washed with ether, then hexane, and dried under vacuum affording Compound ID No. 18 as the HCl salt (140 mg, white solid). $^1$H NMR (500 MHz, CHLOROFORM-d) δ 2.46 (s, 3H), 2.85 (br. s., 3H), 3.46 (s, 0H), 3.57-3.85 (m, 2H), 4.17 (s, 1H), 4.37 (d, J=15.0 Hz, 1H), 4.61 (d, J=14.6 Hz, 1H), 4.83 (d, J=10.1 Hz, 1H), 5.83 (s, 1H), 6.95-7.75 (m, 12H).

Example 19—Synthesis of Compound ID No. 19 (1-((S)-3-hydroxypyrrolidin-1-yl)-2-((1S,2S)-3-(methylamino)-2-(naphthalen-2-yl)-1-phenyl-propoxy)ethanone)

Compound No. 8b (160 mg, 0.34 mmol) and (S)-pyrrolidin-3-ol (110 mg, 1.26 mmol) in EtOH was subjected to microwave conditions at 125° C. for 7 hours. The amber solution was concentrated and subjected to ISCO automated flash chromatography, eluting with a 0-100% ethyl acetate/hexanes gradient followed by 2% MeOH/ethyl acetate to give purified tert-butyl (2S,3S)-3-(2-((S)-3-hydroxypyrrolidin-1-yl)-2-oxoethoxy)-2-(naphthalen-2-yl)-3-phenylpropyl (methyl)carbamate (132 mg, 76%) as a pale yellow amorphous solid. This material was dissolved in 4 M HCl in dioxane (3 mL), allowed to stand at 25° C. for 0.5 hours, and concentrated to dryness. The resulting solid was triturated with ether and dried in vacuo to give Compound ID No. 19 as the HCl salt (94 mg, 83%). $^1$H NMR data were consistent with the desired structure.

Example 20—Synthesis of Compound ID No. 20 ((2S,3S)—N-methyl-3-((3-methylisoxazol-5-yl)methoxy)-2-(naphthalen-2-yl)-3-phenylpropan-1-amine)

Compound No. 8a (205 mg, 0.52 mmol) was dissolved in DMF (4.5 mL) and cooled to 0° C., and NaH (75 mg, 1.88 mmol) was added in one portion. The mixture was stirred for 10 minutes, and then 5-(chloromethyl)-3-methylisoxazole (110 mg, 0.84 mmol) was added as a solution in DMF (0.5 mL) After stirring for 1 hour, the reaction was diluted with ether (30 mL) and washed with water and brine. The combined aqueous layers were back-extracted with ether, and the combined organic layers dried and concentrated to give the crude product.

Purification was performed using an ISCO automated flash chromatography system, eluting with a 0-50% EtOAc/hexanes gradient to give purified tert-butyl methyl((2S,3S)-3-((3-methylisoxazol-5-yl)methoxy)-2-(naphthalen-2-yl)-3-phenylpropyl)carbamate (230 mg, 90%). This compound was dissolved in 4 M HCl in dioxane for 0.5 hours, then concentrated to dryness, and triturated with ether (3×), and the resulting white solid dried in vacuo to give Compound ID No. 20 as the HCl salt (177 mg, 89%). $^1$H NMR data were consistent with the desired structure.

Example 21—Synthesis of Compound ID No. 21 ((1R,2S)-2-(4-bromo-3-chlorophenyl)-3-(methylamino)-1-phenylpropan-1-ol)

As described in Example 16, Compound No. 16a included four stereoisomers, which were separated by SFC. Peaks 1 and 2 included the syn-enantiomers and were concentrated to masses of 2.2 and 2.3 g, respectively. Syn-stereochemistry was determined by $^1$H NMR analysis in the presence of the TBPTA shift reagent, which demonstrated coupling constants J12=4.5 Hz for both samples. The second-eluting enantiomer of syn-ethyl-2-(4-bromo-3-chlorophenyl)-3-hydroxy-3-phenylpropylcarbamate (2.3 g, 5.57 mmol) was dissolved in THF (50 mL) and heated to reflux, borane•THF complex (44.6 mL, 44.58 mmol) was added drop-wise over 15 minutes, and the reaction was kept at reflux for 14 hours. After cooling to ambient temperature, the reaction was treated with 4N HCl in dioxane (5 mL), and then methanol (10 mL) was slowly added to quench excess borane, maintaining the temperature under 25° C. The reaction mixture was heated to 64° C. for 15 minutes to ensure complete quench and concentrated in vacuo to afford a yellow oil. Methanol (5 mL) was added, and the solution concentrated in vacuo. The residue was triturated with ether to give a white precipitate that was collected, washed with ether and ethyl acetate/hexane 50% mixture, and dried to give Compound ID No. 21 as the HCl salt (1.2 g, 95%). $^1$H NMR (500 MHz, DMSO-d$_6$) δ 2.50 (d, J=1.8 Hz, 3H), 3.20 (br. s., 0H), 3.35 (d, J=3.4 Hz, 2H), 4.98 (br. s., 1H), 5.73 (d, J=4.3 Hz, 1H), 6.99 (dd, J=8.2, 1.8 Hz, 0H), 7.09-7.31 (m, 2H), 7.38 (d, J=2.1 Hz, 0H), 7.60 (d, J=8.2 Hz, 0H). Because this compound is more potent at hNET than the reduction product of the first-eluting syn-enantiomer, it was presumed to be (1R,2S)-configured.

Example 22—Synthesis of Compound ID No. 22 ((2S,3S)—N-methyl-3-((5-methyl-1,2,4-oxadiazol-3-yl)methoxy)-2-(naphthalen-2-yl)-3-phenylpropan-1-amine)

To an ice-cooled stirred suspension of the sodium hydride (75 mg, 1.88 mmol) in 2.5 mL DMF was added drop-wise a solution of Compound No. 8a (210 mg, 0.54 mmol) in 0.75 mL DMF. After stirring for 30 minutes at 0° C., a solution of 3-(chloromethyl)-5-methyl-1,2,4-oxadiazole (140 mg, 1.06 mmol) in DMF (0.5 mL)) was added. The resulting mixture was allowed to gradually warm to 25° C. over 4 hours, was diluted with ether (30 mL), was washed with water and brine, was aqueous back-extracted with ether. The organics were combined, dried, and concentrated to give crude product. This product was subjected to ISCO automated flash chromatography, eluting with a 0-50% EtOAc/hexanes gradient to give purified tert-butyl methyl((2S,3S)-3-((5-methyl-1,2,4-oxadiazol-3-yl)methoxy)-2-(naphthalen-2-yl)-3-phenylpropyl)carbamate (70.0 mg, 26.8%). This material was dissolved in 4M HCl in dioxane (1 mL) for 1 hour, concentrated to dryness, and triturated with ether (3×). The resulting white solid was dried in vacuo at 60 degrees overnight to give Compound ID No. 22 as the HCl salt (54.2 mg, 91%). $^1$H NMR data were consistent with the desired structure.

Example 23—Synthesis of Compound ID No. 23 (2-((1S,2S)-3-(methylamino)-2-(naphthalen-2-yl)-1-phenylpropoxy)-1-morpholinoethanone)

Compound No. 23a was prepared by dissolving 2-bromoacetyl bromide (0.861 mL, 9.91 mmol) in dichloromethane (100 mL) at 0° C., at which point morpholine (1.726 g, 19.82 mmol) in dichloromethane (12 mL) was added slowly at 0° C. and stirred for 90 minutes. The reaction mixture was washed with water twice, dried through magnesium sulfate, and concentrated to give 2-bromo-1-morpholinoethanone as a pale-yellow liquid as the desired product. $^1$H NMR spectroscopy was consistent with the proposed structure.

Compound No. 8a (0.538 g, 1.37 mmol) was dissolved in DMF (30 mL) at 0° C., and sodium hydride (0.165 g, 4.12 mmol) was added. The reaction was stirred at 0° C. for 0.5 hours, warmed to room temperature for 15 minutes, and then cooled again to 0° C. Compound No. 23a (1 g, 4.81 mmol) was added in one portion and allowed to stir at room temperature for 2 hours. The reaction was diluted with dichloromethane (50 mL), and a few chunks of ice were added causing a vigorous reaction. A total of 50 mL of water was then added, and this mixture was mixed to destroy all remaining NaH. The dichloromethane layer was separated, and the aqueous phase was extracted two more times with dichloromethane. The combined organic layers were combined, dried with magnesium sulfate, filtered, and evaporated in vacuo.

This material was purified by automated ISCO flash chromatography using an ethyl acetate/hexane 0 to 100% ramp. The desired compound tert-butyl methyl((2S,3S)-3-(2-morpholino-2-oxoethoxy)-2-(naphthalen-2-yl)-3-phenylpropyl)carbamate was isolated in quantitative yield (0.711 g, 100%). A portion of this compound (0.20 g, 0.39 mmol) was taken up in 40 mL of dichloromethane, and trifluoroacetic acid (5 mL, 67.31 mmol) was added in one portion. After stirring for 45 minutes at 25° C., the reaction was concentrated in vacuo, absorbed onto silica gel, and purified by ISCO automated flash chromatography (40 gram normal phase column), eluting 0-50% 3.5 N ammonia in MeOH/dichloromethane. After concentration of the desired fractions, the residue was dissolved in dichloromethane and washed with aqueous NaOH (0.1 N, 50 mL) The organic fraction was dried, filtered, and concentrated in vacuo. The residue was then dissolved in a minimal amount of CHCl$_3$ and diluted with ether, and 2.0 M HCl in ether (3 mL) was added, forming a solid, which was collected by filtration and washed with a minimal amount of ether, and dried overnight under high vacuum to afford Compound ID No. 23 as the HCl salt (0.058 g, 28%, white solid). $^1$H NMR data were consistent with the desired structure.

Example 24—Synthesis of Compound ID No. 24 ((1S,2S)-1-(3-aminophenyl)-2-(3,4-dichlorophenyl)-3-(methylamino)propan-1-ol)

2-(3,4-dichlorophenyl)acetonitrile (6 g, 32.25 mmol) was dissolved in THF (70 mL) and cooled to −75° C. n-Butyllithium (1.6 M in hexanes, 22.17 mL, 35.48 mmol) was added slowly, and the reaction was stirred at −75° C. for 20 minutes. 3-Nitrobenzaldehyde (5.36 g, 35.48 mmol) in tetrahydrofuran (20 mL) was added drop-wise, maintaining the temperature under −70° C. After the addition, the reaction was stirred at −75° C. for another hour. Then, acetic acid (2.77 mL, 48.38 mmol) was added at −75° C. to quench the reaction. The reaction mixture was warmed to room temperature and diluted with saturated sodium bicarbonate (50 mL), and the organic layer was separated from the aqueous layer. The aqueous layer was extracted with ether (100 mL×2), and the combined organic layers were dried over magnesium sulfate and concentrated in vacuo. The residue was purified by ISCO automated flash chromatography, eluting with 0-100% EtOAc in hexane to give a mixture of the aldol diastereomers as yellow oil (11.1 g, 87% yield). This material (2-(3,4-dichlorophenyl)-3-hydroxy-3-(3-nitrophenyl)propanenitrile, 11 g, 27.83 mmol) was dissolved in THF (100 mL) and heated to reflux, and a solution of borane-dimethyl sulfide complex (34.8 mL, 69.57 mmol) in THF was added drop-wise over 15 minutes.

A Dean-Stark trap was set up to collect liberated dimethylsulfide, and after 4 hours, the reaction was cooled to ambient temperature. Excess borane was quenched with methanol (20 mL), added slowly to maintain the temperature under 25° C. The reaction mixture was heated to 64° C. for 15 minutes to ensure full quench and to collect the B(OMe)$_3$-MeOH azeotrope in the Dean-Stark trap. The reaction mixture was then concentrated to give a yellow foam. This material was dissolved in dichloromethane (100 mL), and then 4 M HCl in dioxane (10 mL) was added. A white solid precipitated, which was filtered and washed with dichloromethane (30 mL×2). The collected white solid was suspended in 500 mL of dichloromethane and free-based by treatment with aqueous sodium bicarbonate. The organic layer was separated, and insoluble material was removed by filtration. The aqueous layer was extracted with dichloromethane (10×100 mL), and the combined organic extracts dried over magnesium sulfate and concentrated in vacuo to give the desired intermediate as an off-white foam (7.45 g, 78% yield). A portion of this material (3-amino-2-(3,4-dichlorophenyl)-1-(3-nitrophenyl)propan-1-ol, 7.3 g, 20.33 mmol) was dissolved in dichloromethane (100 mL), and triethylamine (4.25 mL, 30.49 mmol) was added. The reaction mixture was cooled to 0° C., and ethyl carbonochloridate (2.342 mL, 24.39 mmol) was added slowly at 0° C. After 15 minutes, the reaction was allowed to stir at room temperature for 3 hours. The reaction was washed with 0.5 N HCl (100 mL), saturated sodium bicarbonate (50 mL) and water (100 mL), dried over magnesium sulfate, and concentrated in vacuo to give a yellow oil. The oil was purified by ISCO automated flash chromatography, eluting with 0-100% EtOAc in hexane, which allowed the anti- and syn-diastereomers to be separated. The anti-diastereomer eluted first and was concentrated to 1.58 g (19% yield). The syn-diastereomer eluted second and was concentrated to 4.57 g (55% yield). A portion of the anti-diastereomer (anti-2-(3,4-dichlorophenyl)-3-hydroxy-3-(3-nitrophenyl)propylcarbamate, 1.57 g, 3.72 mmol) was dissolved in THF (50 mL) and heated to reflux, and borane-methyl sulfide complex (6.52 mL, 13.03 mmol) was added drop-wise over 15 minutes.

A Dean-Stark trap was set up to collect liberated dimethylsulfide, and after 7 hours at reflux, the reaction was stirred overnight at room temperature. The excess borane was quenched by adding 4 M HCl in Dioxane (1.5 mL), and methanol (10 mL) was added slowly, maintaining the temperature under 25° C. The reaction mixture was heated to 64° C. for 15 minutes to ensure quench was complete and to collect the B(OMe)$_3$-MeOH azeotrope in the Dean-Stark trap. The reaction mixture was concentrated in vacuo, dissolved in chloroform (100 mL), and stirred with aqueous sodium bicarbonate for 10 minutes. The aqueous layer was extracted with chloroform, and the combined extracts dried over magnesium sulfate. After concentration in vacuo, the resulting yellow oil was purified by ISCO automated flash chromatography, eluting with 0-10% MeOH in dichloromethane. The relevant fractions were concentrated in vacuo to give the desired intermediate as a colorless gel (900 mg, 68% yield). A portion of this compound (anti-2-(3,4-dichlorophenyl)-3-(methylamino)-1-(3-nitrophenyl)propan-1-ol, 630 mg, 1.77 mmol) was combined with iron (396 mg, 7.09 mmol) in acetic acid (1.5 mL) and ethanol (1.5 mL) and heated to reflux. The reaction mixture was neutralized with saturated aqueous sodium carbonate and extracted with chloroform (3×50 mL). The combined organic layers were dried over magnesium sulfate, filtered, and concentrated. The resulting brown oil was added to a silica gel column and was eluted with 0-10% 7 M ammonia in MeOH/dichloromethane to give a dark yellow oil (439 mg, 76% yield). A portion of this racemic sample (127 mg, 0.39 mmol) was separated into its enantiomers using SFC (ADH column, 30% iPrOH with 0.5% isopropylamine) Following separation, each enantiomer was converted into the corresponding hydrochloride salt. The first-eluting enantiomer gave 33.9 mg, (22% yield), and the second-eluting enantiomer gave 37.7 mg (24%). Compound ID No. 24 was composed of the HCl salt of the second-eluting enantiomer. $^1$H NMR (300 MHz, CHLOROFORM-d) δ ppm 7.24 (d, J=8.9 Hz, 1H) partially covered under the solvent—CHCl3) 7.18 (d, J=2.1 Hz, 1H) 6.96 (t, J=7.8 Hz, 1H) 6.88 (dd, J=8.2, 1.9 Hz, 1H) 6.55 (s, 1H) 6.49 (dd, J=8.0, 2.1 Hz, 1H) 6.43 (d, J=7.6 Hz, 1H) 4.86 (d, J=7.6 Hz, 1H) 3.56 (br. s., 2H) 3.11-3.22 (m, 1H) 2.97-3.05 (m, 1H) 2.90 (td, J=8.4, 3.4 Hz, 1H) 2.47 (s, 3H). Since this compound was more potent at hNET than the first-eluting anti-enantiomer, it was presumed to be (1S,2S)-configured.

Example 25—Synthesis of Compound ID No. 25 ((2S,3RS)-4-(methylamino)-3-(naphthalen-2-yl)-2-phenylbutan-1-ol)

To a solution of n-BuLi (2.5 M in hexane, 8.66 mL, 21.64 mmol) in THF (40 mL) at 0° C. was added diisopropylamine (3.08 mL, 21.64 mmol), and the mixture was stirred for 15 minutes. A solution of 2-(naphthalen-2-yl)acetonitrile (3.62 g, 21.64 mmol) and TMEDA (3.27 mL, 21.64 mmol) in THF (20 mL) was added. This solution was stirred at 0° C. for 30 minutes before (R)-2-phenyloxirane (1.903 mL, 16.65 mmol) was added neat. The reaction was stirred at 0° C. and allowed to warm to room temperature overnight. LC/MS indicated product formation plus unreacted nitrile (in excess). The reaction mixture was diluted with 1 N HCl, and the organic layer was isolated. The organic layer was washed twice more with 1 N HCl, once with saturated sodium bicarbonate, washed with brine, dried over sodium sulfate, filtered, and concentrated. This residue was purified by ISCO automated flash chromatography (80 g normal phase column) using a 0-80% ethyl acetate/hexane ramp over 20 minutes. The relevant fractions were concentrated to give the desired intermediate as a mixture of diastereomers (614 mg). A portion of this material ((3S')-4-hydroxy-2-(naphthalen-2-yl)-3-phenylbutanenitrile, 600 mg, 2.09 mmol) was dissolved in tetrahydrofuran (15 mL) and heated to reflux, and borane•dimethylsulfide complex (2.61 mL, 5.22 mmol) was added drop-wise via syringe. After 3 hours, the reaction mixture was cooled to room temperature, and excess borane was quenched by the careful addition of MeOH and then 1N HCl. The reaction was concentrated in vacuo, then diluted with water and 1N HCl, and extracted three times with dichloromethane. The aqueous layer was made basic with 1 N NaOH and extracted three times with dichloromethane. The combined dichloromethane layers were washed with brine, dried over sodium sulfate, filtered, and concentrated to give the desired primary amine intermediate as a white solid (593 mg). This compound ((2S)-4-amino-3-(naphthalen-2-yl)-2-phenylbutan-1-ol, 593 mg, 2.04 mmol) was dissolved in dichloromethane (10 mL), and triethylamine (1.135 mL, 8.14 mmol) was added. After cooling to 0° C., ethyl carbonochloridate (0.234 mL, 2.44 mmol) was added drop-wise via syringe. The reaction mixture was then stirred at 0° C. for several minutes and allowed to warm to ambient temperature for 1 hour. The reaction mixture was diluted with dichloromethane, washed with 1N HCl, saturated sodium bicarbonate, and brine, dried over sodium sulfate, filtered, and concentrated to afford a residue (687 mg). This mixture was purified by prep TLC, and the lower band isolated (203 mg, Rf=0.33 in 50% ethyl acetate/hexane). A portion of this compound (ethyl (3S)-4-hydroxy-2-(naphthalen-2-yl)-3-phenylbutylcarbamate, 84 mg, 0.23 mmol) dissolved in THF (1 mL) was added drop-wise to LiAlH$_4$ (1 M in THF, 0.46 mL, 0.46 mmol) solution in THF (2 mL) at 55° C. under nitrogen. After 2.5 hours reflux, the reaction mixture was quenched carefully with saturated aqueous sodium sulfate and diluted with saturated sodium bicarbonate. The mixture was extracted several times with ether, and the ether extracts were washed with saturated sodium bicarbonate and brine, dried over magnesium sulfate, filtered, and concentrated to a white solid (47 mg). This material was converted to the HCl salt by addition of 4 M HCl in dioxane, concentrated in vacuo, triturated with ether, and collected as a white solid to afford Compound ID No. 25 as the HCl salt (40 mg). $^1$H NMR spectroscopy indicated that this compound was a single diastereomer. The configuration at C2 is known to be (S), given the (R)-configuration of the phenyloxirane starting material. The configuration at C3 was either (R) or (S). $^1$H NMR (500 MHz, CHLOROFORM-d) δ 2.49 (s, 3H) 3.01 (dd, J=12.0, 3.6 Hz, 1H) 3.13 (d, J=7.8 Hz, 1H) 3.24-3.32 (m, 2H) 3.88 (d, J=3.8 Hz, 1H) 3.93 (d, J=6.7 Hz, 1H) 6.94-7.02 (m, 3H) 7.04 (d, J=7.2 Hz, 2H) 7.12 (dd, J=8.5, 1.7 Hz, 1H) 7.37 (ddd, J=7.4, 6.4, 1.5 Hz, 3H) 7.61 (d, J=8.5 Hz, 1H) 7.65 (d, J=7.3 Hz, 1H) 7.69 (d, J=1.5 Hz, 1H).

Example 26—Synthesis of Compound ID No. 26 ((1S,2S)-1-(6-chloropyridin-3-yl)-3-(methylamino)-2-(naphthalen-2-yl)propan-1-ol)

tert-butyl (2S,3S and 2R,3R)-3-(6-chloropyridin-3-yl)-3-hydroxy-2-(naphthalen-2-yl)propylcarbamate: To a solution of anti-3-amino-1-(6-chloropyridin-3-yl)-2-(naphthalen-2-yl)propan-1-ol dihydrochloride (Example 126) (2.06 g, 5.34 mmol) in 25 mL dry DCM at −10° C. was added triethylamine (TEA) (2.233 mL, 16.02 mmol) drop-wise. This was followed by slow addition of Boc anhydride (1.282 g, 5.87 mmol). After stirring the reaction mixture for 1 hour at −10° C., the ice bath was removed, and the mixture was allowed to warm to 0° C. TLC showed completion of reaction after 1 hour. The reaction was quenched with saturated NaHCO$_3$, and the aqueous layer was extracted with DCM (3×25 mL). The combined DCM extracts were washed with water, dried over MgSO$_4$, and concentrated using a rotary evaporator. The resulting residue was purified by flash chromatography over silica gel (elution with 70% EtOAc in hexane) to afford a sticky white solid (0.755 g, 34.2%). $^1$H NMR (CDCl$_3$) δ 8.07 (d, 1H, J=2.1 Hz), 7.80-7.70 (m, 3H), 7.46-7.25 (m, 4H), 7.15 (dd, 1H, J=7.4, 1.2 Hz), 7.07 (d, 1H, J=7.4 Hz), 4.97 (d, 1H, J=9.4 Hz), 4.84 (t, 1H, J=6.2 Hz), 3.92-3.88 (m, 1H), 3.56-3.49 (m, 1H), 3.18-3.12 (m, 1H), 1.45 (s, 9H). MS m/z (ESI) 412.16 (MH$^+$).

(1S,2S and 2R,3R)-1-(6-chloropyridin-3-yl)-3-(methylamino)-2-(naphthalen-2-yl)propan-1-ol: To a solution of tert-butyl (2S,3S and 2R,3R)-3-(6-chloropyridin-3-yl)-3-hydroxy-2-(naphthalen-2-yl)propylcarbamate (0.500 g, 1.211 mmol) in 5 mL of dry THF was added a 1M borane-THF solution (4.84 mL, 4.84 mmol) via syringe under nitrogen. The resulting mixture was stirred at 60° C. overnight. After cooling to ambient temperature, the reaction was quenched by cautious addition of NaHCO$_3$, and the reaction mixture was poured into a separatory funnel. The layers were separated, and the aqueous layer was extracted with EtOAc (3×25 mL). The combined organic layers were washed with water and brine, dried over MgSO$_4$, and concentrated using a rotary evaporator. The residue was dissolved in DCM, 4N HCl in dioxane was added, and the mixture was stirred for a few minutes. The volatiles were evaporated in vacuo, and the resulting salt was leached with ether and dried. The product was then purified by reverse phase HPLC (Vydac column, C-18, 2.2×25 cm, elution with 10% B-100% B in 30 min; B=80% aq. CH$_3$CN with 0.1% TFA, A=H$_2$O with 0.1% TFA); FR 8 mL/min, l$_{max}$=254 nm. RT=20.833 min). The fractions containing the product were pooled and lyophilized. A sticky solid was obtained (0.350 g, 88%). $^1$H NMR (CDCl$_3$) δ 9.93 (br s, 1H), 8.78 (br s, 1H), 8.24 (s, 1H), 7.80-7.65 (m, 2H), 7.51-7.39 (m, 2H), 7.35-7.29 (m, 1H), 7.03 (d, 1H, J=8.10 Hz), 5.19 (d, 1H, J 9.98 Hz), 3.94-3.79 (m, 1H), 3.69-3.58 (m, 1H), 3.39-3.25 (m, 1H), 2.81 (s, 3H). $^1$H NMR (500 MHz, CD$_3$OD) δ 7.98 (d, 1H, J=2.14 Hz), 7.74-7.84 (m, 3H), 7.56-7.63 (m, 2H), 7.37-7.52 (m, 2H), 7.16-7.28 (m, 2H), 5.09 (d, 1H, J=9.77 Hz), 3.92 (dd, 1H, J=12.82, 7.93 Hz), 3.50 (dd, 1H, J=12.82, 6.10 Hz), 3.38 (ddd, 1H, J=9.61, 8.09, 6.10 Hz), 2.77 (s, 3H). A high J-value of the benzylic proton (9.77 Hz) indicated anti-configuration. MS m/z (ESI) 327.09 (MH$^+$).

Compound ID No. 26: The above compound, which was a racemate, was resolved into S,S and R,R enantiomers. The Multigram III SFC system was used with a 30 mm×250 mm ChiralPak ADH column. The 0.35 g of sample was diluted in 4 mL of EtOH, and stacked injections of 0.4 mL each were run using 25% EtOH/1% IsoPropylAmine isocratic at 100 mL/minute. Second eluting enantiomer: $^1$H NMR (500 MHz, CD$_3$OD) δ 7.98 (d, 1H, J=2.29 Hz), 7.73-7.84 (m, 3H), 7.58-7.66 (m, 2H), 7.42-7.52 (m, 2H), 7.20-7.28 (m, 1H), 5.10 (d, 1H, J=9.61 Hz), 3.92 (dd, 1H, J=12.66, 7.93 Hz), 3.47-3.55 (m, 1H), 3.36-3.45 (m, 1H), 2.77 (s, 3H). Compound ID No. 26 recovered from the second eluting enantiomer was assigned (1S,2S)-configuration based on its higher inhibitory activity on the hNET compared to the first eluting enantiomer isolated from this SFC separation.

Example 27—Synthesis of Compound ID No. 27 ((1R,2S)-2-((methylamino)methyl)-1,4-diphenylbutan-1-ol)

To a 500 mL oven-dried round bottom flask charged with THF (95 mL) was added diisopropylamine (2.454 mL, 17.22 mmol), and the reaction flask was cooled to 0° C. n-BuLi (1.6 M in hexanes, 9.47 mL, 15.15 mmol) was then added drop-wise via syringe, and the resulting LDA solution was stirred for 30 minutes at 0° C. The reaction mixture was then further cooled to −78° C., and the 4-phenylbutanenitrile (2.055 mL, 13.77 mmol) was added neat via syringe. The reaction was stirred for 20 minutes before benzaldehyde (1.392 mL, 13.77 mmol) was added in THF (10 mL) via syringe over 5 minutes. The reaction mixture was then stirred at −78° C. for 60 minutes, quenched with saturated sodium bicarbonate, and warmed to room temperature. The organic layer was separated, and the aqueous layer extracted twice with dichloromethane. The combined organics were washed with brine, dried over sodium sulfate, filtered, and concentrated in vacuo. The residue was purified by ISCO automated flash chromatography (40 g normal phase column) using a 0-40% ethyl acetate/hexane ramp over 16 minutes. The desired intermediate was obtained as a mixture of diastereomers (1.78 g, 51%). This material (2-(hydroxy(phenyl)methyl)-4-phenylbutanenitrile, 1.78 g, 7.08 mmol) was dissolved in tetrahydrofuran (25 mL) and heated to reflux, and borane-dimethyl sulfide complex (8.85 mL, 17.71 mmol) was added drop-wise via syringe. After heating for 3.5 hours, the reaction was cooled to room temperature, quenched with methanol, and concentrated in vacuo. The residue was dissolved in ethyl acetate and washed twice with saturated sodium bicarbonate, brine, filtered, and concentrated in vacuo (1.73 g, 98%). This material (2-(aminomethyl)-1,4-diphenylbutan-1-ol, 1.73 g, 6.77 mmol) was suspended in dichloromethane (30 mL), and after triethylamine was added (3.78 mL, 27.10 mmol), a clear solution formed. The reaction mixture was cooled to 0° C., and ethyl carbonochloridate (0.777 mL, 8.13 mmol) was added drop-wise via syringe. The reaction mixture was then stirred at 0° C. for several minutes and allowed to warm to room temperature for 90 minutes. The reaction mixture was diluted with dichloromethane, washed with 1 N HCl, saturated sodium bicarbonate, and brine, dried over sodium sulfate, filtered, and concentrated (900 mg). This crude product was purified via automated flash chromatography (12 g normal phase column), eluting with 0 to 30% ethyl acetate/hexane over 15 minutes. The major component was concentrated to afford a 3:1 mixture of diastereomers (ratio determined by $^1$H NMR, 755 mg).

This mixture of four stereoisomers (two anti-enantiomers, two syn-enantiomers) was separated by SFC. Peaks 1 and 2 were the anti-enantiomers (72 and 55 mg respectively), and peaks 3 and 4 were the syn-enantiomers (220 and 225 mg, respectively). The second-eluting syn-enantiomer (peak 4, ethyl 2-(hydroxy(phenyl)methyl)-4-phenylbutylcarbamate, 225 mg, 0.69 mmol)) was dissolved in THF (3 mL) and added to lithium aluminum hydride (1 M in THF, 1.890 mL, 1.89 mmol) solution in THF (3 mL) at 55° C. under nitrogen over 5 minutes. After reflux for 90 minutes, the reaction was quenched with saturated aqueous sodium sulfate and then saturated aqueous sodium bicarbonate. This mixture was extracted three times with ether, the ethereal layers combined, washed with saturated sodium bicarbonate and brine, dried over sodium sulfate, filtered, and concentrated to give an oil (168 mg). $^1$H NMR analysis using the TBPTA indicated syn-stereochemistry ($J_{12}$=2.6 Hz). This material was dissolved in dichloromethane, to which 4 M HCl in dioxane (0.40 mL) was added drop-wise, affording a solid. The mixture was concentrated in vacuo, triturated with ether, collected by filtration, washed with ether, and dried affording Compound ID No. 27 as the HCl salt (135 mg, white solid). $^1$H NMR (500 MHz, DMSO-d$_6$) δ 1.38-1.55 (m, 2H) 1.76 (d, J=3.1 Hz, 1H) 1.92-1.92 (m, 1H) 2.27 (s, 3H) 2.30-2.39 (m, 1H) 2.43 (dd, J=11.7, 4.7 Hz, 1H) 2.60 (d, J=7.0 Hz, 2H) 4.79 (d, J=4.3 Hz, 1H) 7.05 (d, J=6.7 Hz, 2H) 7.12 (d, J=7.3 Hz, 1H) 7.16-7.24 (m, 3H) 7.25-7.33 (m, 5H). Since this compound is more potent at hNET than the reduction product of the first-eluting syn-enantiomer, the stereochemistry of this compound was presumed to be (1R,2S).

Example 28—Synthesis of Compound ID No. 28 ((2S,3S)-3-(methylamino)-2-(naphthalen-2-yl)-1-(o-tolyl)propan-1-ol)

An air-free Schlenk flask under N$_2$ was charged with a slurry of Raney nickel 2800 (approximately 2.2 g). The slurry was washed with absolute ethanol and decanted. To this ethanolic slurry was added 5 mL of a 1:1 saturated aqueous NH$_4$Cl solution and ethanol mixture. The N$_2$ was carefully evacuated and backfilled with H$_2$. While maintaining a H$_2$ atmosphere, a solution of racemic anti-3-hydroxy-2-(naphthalen-2-yl)-3-(o-tolyl)propanenitrile (531 mg, 1.85 mmol) in THF (5 mL) was then added, and the flask was then equipped with a stir bar and hydrogen gas balloon. The suspension was stirred at room temperature for 0.5 hour and was then filtered through celite. The celite was washed with CH$_2$Cl$_2$, and the filtrate was evaporated to give a residue that was purified via silica gel flash chromatography (8% CH$_3$OH in CH$_2$Cl$_2$ with 1 mL NH$_4$OH per 100 mL of eluent) to give 269 mg (0.92 mmol, 50%) of a yellow oil. A portion of this material (253 mg, 0.87 mmol) was dissolved in CH$_2$Cl$_2$ and cooled to 0° C. DIEA (0.36 mL, 2.08 mmol) was then added followed by addition of ethyl chloroformate (0.1 mL, 1.04 mmol). The solution was allowed to stir at 0° C. for 2 hours. The work up and purification was performed in the usual way (see, e.g., Example 17) to give 287 mg (0.79 mmol, 91%) of a colorless gum. A portion of this material (272 mg, 0.75 mmol) was treated with LiAlH$_4$ and acidified in the usual way (see, e.g., Example 17) to give 231 mg of the HCl salt (0.68 mmol, 90%). $^1$H NMR (500 MHz, CD$_3$OD) δ 7.82-7.66 (m, 3H), 7.57 (d, J=8.0 Hz, 2H), 7.49-7.37 (m, 2H), 7.24-7.13 (m, 2H), 7.05-7.01 (m, 1H), 6.84 (d, J=7.6 Hz, 1H), 5.28 (d, J=8.8 Hz, 1H), 3.92 (dd, J=11.8, 7.6 Hz, 1H), 3.54-3.45 (m, 3H), 2.76 (s, 3H), 1.88 (s, 3H). HRMS (ESI-TOF) calculated for C$_{21}$H$_{24}$NO (MH$^+$) 306.1852 found 306.1854 (0.53 ppm, 0.2 mmu) This racemate was separated into its enantiomers using a chiral stationary phase supercritical fluid chromatography (Multigram III SFC system) on a CE-2 column (30×250 mm). Isocratic elution using 18% MeOH (containing 0.5% isopropylamine) at a flow rate of 130 mL/minute gave enantiomer retention times of 12.38 and 14.23 minutes, respectively. The combined fractions of the second-eluting enantiomer were concentrated in vacuo and converted to an HCl salt, which afforded 15 mg of Compound ID No. 28, which was shown by the previously described SCF system to have 95% enantiomeric excess. $^1$H NMR (500 MHz, DMSO-d6) δ 7.73-7.89 (m, 3H), 7.70 (s, 1H), 7.42-7.52 (m, 3 FI), 7.31 (dd, J=8.39, 1.68 Hz, 1H), 7.16 (d, J=7.48 Hz, 1H), 7.02 (d, J=6.71 Hz, 1H), 6.89 (d, J=7.63 Hz, 1H), 5.95 (br. s., 1H), 5.10 (d, J=7.93 Hz, 1H), 3.61-3.72 (m, 1H), 3.43-3.58 (m, 2H) 2.55 (t, J=5.34 Hz, 3H), 2.01 (s, 3H). Since this enantiomer was more potent at hNET than the first-eluting enantiomer, it was presumed to be (S,S)-configured.

Example 29—Synthesis of Compound ID No. 29 (2-(((1S,2S)-3-(methylamino)-2-(naphthalen-2-yl)-1-phenylpropoxy)-N-propylacetamide)

Compound No. 29a was prepared by dissolving 2-bromoacetyl bromide (0.430 mL, 4.95 mmol) in dichloromethane (1.5 mL) at 0° C., to which was added propan-1-amine (0.815 mL, 9.91 mmol) in dichloromethane (0.5 mL), and the mixture was stirred for 30 minutes at 0° C. The reaction mixture was washed with water twice, dried over magnesium sulfate, and concentrated to give 2-bromo-N-propylacetamide as a pale-yellow liquid (870 mg, 98% yield).

Compound No. 8a (200 mg, 0.51 mmol) was dissolved in DMF (5 mL) and cooled to 0° C., and sodium hydride (61.3 mg, 1.53 mmol) was added. The reaction was stirred at 0° C. for 2.5 hours, after which Compound No. 29a (322 mg, 1.79 mmol) was added, stirred at 0° C. for 60 minutes, and stirred at 25° C. for several hours. LC/MS analysis at this point showed 60% of undesired self-cyclized product and 40% of the desired product. The reaction mixture was diluted with dichloromethane (100 mL), washed with water (100 mL×3), and dried over magnesium sulfate to give an orange oil that was purified via ISCO automated flash chromatography, eluting with 0-100% ethyl acetate/hexane. The relevant fractions were collected to give the desired product as a yellow gum (71.9 mg, 29% yield). A portion of this compound (68.8 mg, 0.14 mmol) was dissolved in 33% trifluoroacetic acid in dichloromethane (~1.5 mL) at 25° C. for three hours. The reaction mixture was made basic with saturated sodium bicarbonate (6 mL; as little as possible) and extracted with chloroform (10 mL×4). The organic layer was dried over magnesium sulfate, concentrated in vacuo, and purified via ISCO automated flash chromatography, eluting with 0-5% 3.5 M ammonia in MeOH/dichloromethane. The relevant fractions were concentrated to afford a yellow oil. This oil was dissolved in dichloromethane (1 mL), and 2 N HCl in ether (1 mL) was added, forming white solid. Concentration in vacuo afforded Compound ID No. 29 as the HCl salt (35 mg, 59% yield). $^1$H NMR (300 MHz, CHLOROFORM-d) δ 7.75 (dd, J=8.6, 4.4 Hz, 1H) 7.71 (d, J=8.0 Hz, 2H) 7.52 (s, 1H) 7.37-7.48 (m, J=5.2, 5.2, 5.1, 4.8 Hz, 2H) 7.05-7.24 (m, 6H) 4.68 (d, J=7.6 Hz, 1H) 3.90 (d, J=15.7 Hz, 1H) 3.74 (d, J=15.7 Hz, 1H) 3.44 (td, J=7.8, 5.1 Hz, 1H) 3.04-3.26 (m, 4H) 2.39 (s, 3H) 1.40 (sxt, J=7.3 Hz, 2H) 0.86 (t, J=7.4 Hz, 3H).

Example 30—Synthesis of Compound ID No. 30 (1-(azetidin-1-yl)-2-((1S,2S)-3-(methylamino)-2-(naphthalen-2-yl)-1-phenylpropoxy)ethanone)

Compound No. 8b (235 mg, 0.49 mmol) and azetidine (1 mL, 14.78 mmol) free base were mixed with 1 mL of ethanol in a rounded bottom smaller size microwave vial. This mixture was heated at 120° C. for 16 minutes. The reaction was cooled to 25° C. and analyzed by LCMS, which indicated complete conversion. Following concentration, the residue was purified by ISCO automated flash chromatography (40 g normal phase column), eluting with 0-100% EtOAc/hexane. This material was analyzed and then mixed with that of a parallel identical reaction for the next step. This combined sample (0.329 g, 0.67 mmol) was dissolved in dichloromethane (15 mL), and trifluoroacetic acid (5 mL, 67.31 mmol) was added in one portion. After stilling for 30 minutes at room temperature, the reaction was concentrated in vacuo and purified via ISCO automated flash chromatography (40 gram normal phase) with a ramp of 0-30% 7 N ammonia in MeOH/dichloromethane. The relevant fractions were concentrated in vacuo, dissolved in a minimal amount of chloroform, and diluted with diethyl ether (1 mL), two which 2.0 N HCl in ether (1 mL) was added. Concentration afforded Compound ID No. 30 as the HCl salt (0.051 g, 15.18%). $^1$H NMR (500 MHz, DMSO-d$_6$) δ 9.42 (br. s., 1H), 9.03 (br. s., 1H), 7.76-7.82 (m, 1H), 7.67-7.76 (m, 2H), 7.58 (s, 1H), 7.40-7.48 (m, 2H), 7.19-7.24 (m, 1H), 7.07-7.16 (m, 5H), 4.84-4.93 (m, 1H), 3.94-4.07 (m, 4H), 3.74-3.88 (m, 2H), 3.67 (td, J=9.9, 3.4 Hz, 1H), 3.19-3.30 (m, 1H), 2.69 (t, J=5.3 Hz, 3H). 2.25 (quin, J=7.7 Hz, 2H).

Example 31—Synthesis of Compound ID No. 31 (1-methyl-3-(((1S,2S)-3-(methylamino)-2-(naphthalen-2-yl)-1-phenylpropoxy)methyl)pyridin-2(1H)-one)

Compound No. 8a (205 mg, 0.52 mmol) was dissolved in 4.5 ml DMF and cooled to 0° C., and sodium hydride (75 mg, 1.88 mmol) was added in one portion. The mixture was stirred for 10 minutes, and 3-(chloromethyl)-1-methylpyridin-2(1H)-one (110 mg, 0.70 mmol) in DMF (0.5 mL) was added drop-wise. After stirring for 1 hour, the reaction was diluted with ether (30 mL) and washed with water and brine, and the aqueous layer was washed with ether. The combined organic layers were dried, filtered, and concentrated in vacuo. The residue was subjected to ISCO automated flash chromatography, eluting with a 0-100% EtOAc/hexanes gradient to give purified tert-butyl methyl((2S,3S)-3-((1-methyl-2-oxo-1,2-dihydropyridin-3-yl)methoxy)-2-(naphthalen-2-yl)-3-phenylpropyl)carbamate (65.0 mg, 24.2%). This material was dissolved in 4M HCl in dioxane, and after 30 minutes, concentrated in vacuo and triturated with ether (3×). The resulting white solid was dried in vacuo to give Compound ID No. 31 as the HCl salt (36.1 mg, 62%). $^1$H NMR data were consistent with the desired structure.

Example 32—Synthesis of Compound ID No. 32 (2-((1S,2S)-3-(methylamino)-2-(naphthalen-2-yl)-1-phenylpropoxy)ethanol)

tert-Butyl 2-((1S,2S)-3-(tert-butoxycarbonyl(methyl)amino)-2-(naphthalen-2-yl)-1-phenylpropoxy)acetate: tert-butyl-(2S,3S)-3-hydroxy-2-(naphthalen-2-yl)-3-phenylpropyl(methyl)carbamate (Example 35) (0.7 g, 1.788 mmol) in 15 mL of anhydrous DMF at 0° C. was added to the flask containing NaH with the help of a syringe, and contents stirred for 10 minutes. tert-Butyl bromoacetate (0.391 mL, 2.68 mmol) was added to it, and the reaction mixture was stirred for one half hour. It was quenched with 3 mL of saturated NH$_4$Cl cautiously. The reaction mixture was poured into a separatory funnel containing water. The aqueous layer was extracted with EtOAc (3×25 mL), and the combined organic layers were washed with water and brine and dried over MgSO$_4$. The combined organic layers were concentrated using a rotary evaporator. The resulting residue was purified by flash chromatography over silica gel (elution with 10% EtOAc in hexanes) to afford the product as a colorless oil (0.654 g, 72.3%). 1H NMR (CDCl$_3$) δ 7.70-7.64 (m, 3H), 7.60-7.36 (m, 3H), 7.26 (s, 1H), 7.10-6.91 (m, 5H), 4.92 (d, 1H, J=8.5 Hz), 3.96 (d, 1H, J=8.5 Hz), 3.92 (d, 1H, J=16.2 Hz), 3.68 (t, 1H, J=16.2 Hz), 3.41 (m, 1H), 2.62-2.51 (m, 3H), 1.48 and 1.44 (two s, 9H), 1.50 and 1.21 (two s, 9H). MS m/z (ESI) 506.03 (MH$^+$) and 528.16 (M+Na$^+$).

2-((1S,2S)-3-(methylamino)-2-(naphthalen-2-yl)-1-phenylpropoxy)acetic acid: tert-Butyl 2-((1S,2S)-3-(tert-butoxycarbonyl(methyl)amino)-2-(naphthalen-2-yl)-1-phenylpropoxy)acetate (0.5 g, 1.047 mmol) was mixed with 10 mL of 1:1 TFA:DCM, and the reaction mixture was stirred at room temperature for 1 hour. The solvents were evaporated off using a rotary evaporator. The residue was washed, leached with ether, and dried, yielding a white solid (0.355 g, 86%). 1H NMR (CDCl$_3$) δ 7.80-7.70 (m, 3H), 7.67 (s, 1H), 7.52-7.45 (m, 2H), 7.16-7.13 (m, 6H), 4.91 (d, 1H, J=8.5 Hz), 4.12 (d, 1H, J=16.8 Hz), 4.03 (m, 1H), 3.93 (d, 1H, J=16.8 Hz), 3.59 (t, 1H, J=9.0 Hz), 3.41 (dd, 1H, J=12.3, 2.8 Hz), 2.87 (s, 3H). MS m/z (ESI) 350.08 (MH$^+$).

2-((1S,2S)-3-(methylamino)-2-(naphthalen-2-yl)-1-phenylpropoxy)ethanol (Compound ID No. 32): 2-((1S,2S)-3-(methylamino)-2-(naphthalen-2-yl)-1-phenylpropoxy)acetic acid (0.355 g, 1.016 mmol) dissolved in 5 mL of dry THF was placed in an oven-dried round-bottom flask under nitrogen. Next, 1M borane-THF solution (4.06 mL, 4.06 mmol) was added via syringe. This mixture was stirred at 60° C. overnight while monitoring the reaction progress by TLC. After quenching the reaction with cautious addition of NaHCO$_3$, the reaction mixture was poured into a separatory funnel. The layers were separated, and the aqueous layer was extracted with EtOAc (3×25 mL) Combined organic layers were washed with water and brine, dried over MgSO$_4$, and were concentrated using a rotary evaporator. The residue was then dissolved in DCM, and 1N HCl was added. The mixture was stirred, and the solvents were then evaporated off in vacuo. The resulting salt was washed and leached with DCM, dried, and lyophilized, yielding a white solid. $^1$H NMR (CD$_3$OD)) δ 7.70-7.53 (m, 3H), 7.44 (s, 1H), 7.37-7.27 (m, 2H), 7.12-7.05 (m, 1H), 7.02 (s, 5H), 4.72 (d, 1H, J=9.42 Hz), 3.85 (dd, 1H, J=12.24, 9.23 Hz), 3.76-3.57 (m, 2H), 3.47-3.26 (m, 4H), 2.68 (s, 3H) MS m/z (ESI) 336.11 (MH$^+$).

Example 33—Synthesis of Compound ID No. 33 (N,N-dimethyl-2-((1S,2S)-3-(methylamino)-2-(naphthalen-2-yl)-1-phenylpropoxy)acetamide)

As in the case of Compound No. 23a, bromoacetyl bromide was combined with dimethylamine to yield 2-bromo-N,N-dimethylacetamide. This compound was reacted with Compound No. 8a as in Example 23 to yield tert-butyl (2S,3S)-3-(2-(dimethylamino)-2-oxoethoxy)-2-(naphthalen-2-yl)-3-phenylpropyl(methyl)-carbamate (70 mg, 0.15 mmol). This compound was dissolved in dichloromethane (5 mL), and trifluoroacetic acid (2 mL) was added. After stirring for 1 hour, the reaction was concentrated in vacuo, and the residue was mixed with 5 mL 20% aqueous potassium carbonate and extracted with dichloromethane (4×5 mL). Extracts were dried over sodium sulfate, filtered, and concentrated in vacuo. The resulting oil was dissolved in ether (5 mL) to which 400 µL of 4 N HCl in dioxane was added. A solid formed and was collected by filtration, washed with ether, and dried under vacuum, affording Compound ID No. 33 as the HCl salt (30 mg, 50%). $^1$H NMR (500 MHz, MeOD) δ 2.84 (s, 3H), 2.86 (s, 3H), 3.03 (s, 3H), 3.34 (d, 1H), 3.59 (td, J=10.6, 2.6 Hz, 1H), 3.93 (t, J=11.9 Hz, 1H), 4.11 (d, J=15.9 Hz, 1H), 4.33 (d, J=15.9 Hz, 1H), 4.88 (d, J=10.1 Hz, 1H), 7.07-7.16 (m, 6H), 7.37-7.44 (m, 2H), 7.50 (s, 1H), 7.62-7.76 (m, 3H).

Example 34—Synthesis of Compound ID No. 34 (1-((R)-3-hydroxypyrrolidin-1-yl)-2-((1S,2S)-3-(methylamino)-2-(naphthalen-2-yl)-1-phenylpropoxy)ethanone)

Compound No. 8b (160 mg, 0.34 mmol) was combined with (R)-pyrrolidin-3-ol hydrochloride (110 mg, 0.89 mmol) and triethylamine (0.248 mL, 1.78 mmol) in ethanol, and subjected to microwave conditions at 125° C. for 7 hours. The reaction was concentrated in vacuo and purified using ISCO automated flash chromatography, eluting with a 0-100% EtOAc/hexanes gradient followed by 2% MeOH/EtOAc, to give purified tert-butyl (2S,3S)-3-(2-((R)-3-hydroxypyrrolidin-1-yl)-2-oxoethoxy)-2-(naphthalen-2-yl)-3-phenylpropyl(methyl)carbamate (53.0 mg, 30.5%). This compound was dissolved in 4 M HCl in dioxane (2 mL), and after 1 hour, was concentrated to near dryness. The solid was washed with ether (2×) and dried in vacuo to give Compound ID No. 34 as the hydrochloride salt (35.3 mg, 78%). $^1$H NMR data were consistent with the desired structure.

Example 35—Synthesis of Compound ID No. 35 (ethyl 2-((1S,2S)-3-(methylamino)-2-(naphthalen-2-yl)-1-phenylpropoxy)acetate)

Ethyl 2-((1S,2S)-3-(tert-butoxycarbonyl(methyl)amino)-2-(naphthalen-2-yl)-1-phenylpropoxy)acetate: Sodium hydride (60% in oil) (0.300 g, 6.24 mmol) was washed with pentane (5 mL) in an oven dried round bottom flask and covered with dry DMF (10 mL) A solution of tert-butyl-(2S,3S)-3-hydroxy-2-(naphthalen-2-yl)-3-phenylpropyl (methyl)carbamate (Compound No. 8a) (1.88 g, 4.80 mmol) in 20 mL of anhydrous DMF was added to the flask containing NaH with the help of a syringe and stirring was allowed to continue for 10 minutes. Ethyl bromoacetate (0.797 mL, 7.20 mmol) was then added drop-wise to it, and the reaction mixture was stirred for one half hour. The reaction progress was monitored by TLC. After cautious quenching of the reaction with 5 mL of saturated NH$_4$Cl, the reaction mixture was poured into a separatory funnel containing water. The aqueous layer was extracted with EtOAc (3×25 mL), and the combined organic layers were washed with water and brine, dried over MgSO$_4$, and concentrated using a rotary evaporator. The resulting residue was purified by flash chromatography over silica gel (elution with 10% EtOAc in hexanes) to afford the product as a colorless oil (0.500 g, 21.8%). $^1$H NMR (CDCl$_3$): δ 7.76-7.60 (m, 3H), 7.47-7.38 (m, 3H), 7.22 (m, 1H), 7.18-7.01 (m, 5H), 4.7 (d, 1H, J=8.3 Hz), 4.21-3.80 (m, 7H), 2.17 (s, 3H), 1.31-1.18 (m, 12H). MS m/z (ESI) 478.09 (MH$^+$). MS m/z (ESI) 478.09 (MH$^+$) and 500.22 (M+Na$^+$).

Compound ID No. 35: Ethyl 2-((1S,2S)-3-(tert-butoxycarbonyl(methyl)-amino)-2-(naphthalen-2-yl)-1-phenylpropoxy)acetate (0.5 g, 1.047 mmol) was mixed with 10 mL of 1:1 TFA:DCM, and the reaction mixture was stirred at room temperature for 1 hour. The reaction mixture was poured into a separatory funnel containing water, and the aqueous layer was extracted with EtOAc (3×25 mL) The combined organic layers were washed with water and brine, dried over MgSO$_4$, and concentrated under reduced pressure. The resulting residue was purified by flash chromatography over silica gel (elution with 10% EtOAc in hexanes) to afford a colorless sticky solid (0.254 g, 64.3%). $^1$H NMR (CDCl$_3$) δ 11.43 (br s, NH), 8.62 (br s, NH), 7.77-7.55 (m, 3H), 7.49-7.35 (m, 3H), 7.19-6.97 (m, 6H), 4.71 (d, 1H, J=10.17 Hz), 4.36-4.22 (M, 2H), 4.20-4.07 (m, 2H), 3.87 (d, 1H, J=16.8 Hz), 3.74-3.60 (m, 1H), 3.51-3.39 (m, 1H) 2.87 (s, 3H), 1.32 (t, J=7.2 Hz, 7.2 Hz, 3H) MS m/z (ESI) 378.03 (MH$^+$). $^1$H NMR (500 MHz, CD$_3$OD) δ 7.64-7.79 (m, 3H), 7.51 (s, 1H), 7.39-7.47 (m, 2H), 7.05-7.19 (m, 6H), 4.91 (d, J=10.1 Hz, 1H), 4.31 (q, J=7.1 Hz, 2H), 4.14 (d, J=16.8 Hz, 1H), 4.05 (dd, J=12.4, 10.2 Hz, 1H), 3.97 (d, J=16.8 Hz, 1H), 3.58 (td, J=9.9, 3.4 Hz, 1H), 3.43 (dd, J=12.7, 3.2 Hz, 1H), 2.81-2.91 (m, 3H), 1.31 (t, J=7.2 Hz, 3H).

Example 36—Synthesis of Compound ID No. 36 (3-(2-fluorophenyl)-N-methyl-2-(naphthalen-2-yl) propan-1-amine)

Compound ID No. 36 is the racemate of Compound ID No. 17, and was prepared using the methods set forth in Example 17, except that the enantiomer separation step was omitted.

Example 37—Synthesis of Compound ID No. 37 ((1S,2S)-1-(3,5-difluorophenyl)-3-(methylamino)-2-(naphthalen-2-yl)propan-1-ol)

3-(3,5-difluorophenyl)-3-hydroxy-2-(naphthalen-2-yl) propanenitrile: To a solution of 2-naphthylacetonitrile (2 g, 11.96 mmol) in 170 mL of dry THF placed in an oven-dried round bottom flask containing a stir bar was added diisopropylamine (2 mL, 14.35 mmol) under nitrogen. The mixture was stirred and cooled to −78° C. for 20 minutes. 2.5M Butyllithium (5.74 mL, 14.35 mmol) was then added slowly via a syringe. After 30 minutes, 3,5-difluoro-benzaldehyde (2 mL, 14.35 mmol) was added drop-wise via syringe, and the reaction was monitored by TLC for completion. After 20 minutes, the reaction was quenched quickly with 10 mL 2:1 THF/acetic acid (added all at once). Cold bath was removed, and the reaction was allowed to reach room temperature. Water was added, and the aqueous layer was extracted with EtOAc (3×25 mL). The combined organic layers were washed with water and brine, dried over MgSO$_4$, and concentrated under reduced pressure. The two diastereomeric adducts in the residue were effectively separated by silica gel flash chromatography (elution with 15% to 40% EtOAc in hexanes). Tentative stereochemistry for each diastereomer was assigned on the basis of polarity (TLC mobility) and the J-values of the proton on the benzylic position in the $^1$H NMR. anti-isomer: (1.2 g, 32%)$^1$H NMR (CDCl$_3$) δ 7.89-7.79 (m, 4H), 7.60-7.49 (m, 2H), 7.31 (dd, 1H, J=8.5, 1.70 Hz), 6.95-6.84 (m, 2H), 6.81-6.71 (m, 1H), 5.06 (d, 1H, J=4.9 Hz), 4.22 (d, 1H, J=5.0 Hz). syn-isomer (2.5 g, 67.6%). (1.7 g, 47%). $^1$H NMR (CDCl$_3$) δ 7.92-7.79 (m, 3H), 7.75 (s, 1H), 7.59-7.50 (m, 2H), 7.32 (dd, 1H, J=8.48, 1.7 Hz), 6.92-6.73 (m, 3H), 5.08 (d, 1H, J=6.6 Hz), 4.24 (dd, 1H, J=6.8 Hz).

anti-3-amino-1-(3,5-difluorophenyl)-2-(naphthalen-2-yl)propan-1-ol: A 1M borane-THF solution (20 mL, 20 mmol) was added under nitrogen via syringe to a solution of anti-3-(3,5-difluorophenyl)-3-hydroxy-2-(naphthalen-2-yl)propanenitrile (1.6 g, 5.17 mmol) in 15 mL of dry THF. This mixture was stirred at 60° C. overnight while monitoring the reaction progress by TLC. After quenching the reaction with cautious addition of NaHCO$_3$, the reaction mixture was poured into a separatory funnel. The layers were separated, and the aqueous layer was extracted with EtOAc (3×25 mL). The combined organic layers were washed with water and brine, dried over MgSO$_4$, and concentrated using a rotary evaporator. The residue was dissolved in DCM, and 1N HCl was added under stirring. The solvents were evaporated in vacuo, and the resulting salt was washed with ether and lyophilized yielding a white solid (yield 1.7 g, 94%). MS m/z (ESI) 314.34 (MH). $^1$H NMR (500 MHz, CDCl$_3$) δ 7.73-7.87 (m, 3H), 7.68 (s, 1H), 7.46, (dd, 2H, J=6.7, 2.7 Hz), 7.36 (d, 2H, J=8.2 Hz), 6.64-6.83 (m, 2H), 5.45 (d, 1H, J=5.2 Hz), 3.25 (d, 2H, J=3.4 Hz), 3.11 (br. S, 1H).

anti-tert-Butyl-3-(3,5-difluorophenyl)-3-hydroxy-2-(naphthalen-2-yl)propylcarbamate: To a solution of anti-3-amino-1-(3,5-difluorophenyl)-2-(naphthalen-2-yl)propan-1-ol hydrochloride (1.6 g, 5.11 mmol) in 20 mL dry DCM at −10° C. was added triethylamine (TEA) (15.32 mL, 2.1 mmol) drop-wise, followed by slow addition of Boc anhydride (1.4 g, 6.38 mmol). After stirring for 1 hour at −10° C., the ice bath was removed, and the mixture was allowed to warm to 0° C. TLC showed completion of reaction after 1 hour. The reaction was quenched with saturated NaHCO$_3$. The layers were separated, and the aqueous layer was extracted with DCM (3×25 mL) The combined DCM extracts were washed with water and dried over MgSO$_4$. The resulting residue was purified by silica gel flash chromatography (elution with 15-30% EtOAc in hexanes) to afford a white solid (1.75 g, 83%). $^1$H NMR (CDCl$_3$) δ 7.84-7.71 (m, 3H), 7.54 (s, 1H), 7.51-7.42 (m, 2H), 7.23-7.20 (m, 1H), 6.75 (d, 1H, J=6.42 Hz), 6.55 (t, 1H, J=8.5 Hz), 4.96 (dd, 1H, J=9.0, 4.0 Hz), 4.69 (br s, 1H), 4.14 (br s, 1H), 3.98-3.83 (m, 1H), 3.57-3.43 (m, 1H), 3.25-3.15 (m, 1H), 1.44 (s, 9H). MS m/z (ESI) 436.16 (M+Na$^+$).

anti-1-(3,5-difluorophenyl)-3-(methylamino)-2-(naphthalen-2-yl)propan-1-ol: 1M borane-THF solution (9.58 mL, 9.58 mmol) was added in a drop-wise fashion under nitrogen via syringe to a solution of anti-tert-butyl-3-(3,5-difluorophenyl)-3-hydroxy-2-(naphthalen-2-yl)propylcarbamate (0.99 g, 2.394 mmol) in 15 mL of dry THF. The resulting mixture was stirred at 60° C. overnight while monitoring the reaction progress by TLC. After quenching the reaction with cautious addition of NaHCO$_3$, the reaction mixture was poured into a separatory funnel. The layers were separated, and the aqueous layer was extracted with EtOAc (3×25 mL). The combined organic layers were washed with water and brine, and dried over MgSO$_4$. The volatiles were concentrated using a rotary evaporator. 1N HCl was added, and the mixture was stirred for a few minutes. The solvent was evaporated in vacuo. The resulting salt was taken up in MeOH, ether was added to a state of fine turbidity, and the suspension was stored at 4° C. White crystals were isolated and dried (yield 0.658 g, 76%). $^1$H NMR (CD$_3$OD) δ 7.86-7.73 (m, 3H), 7.61 (s, 1H), 7.51-7.42 (m, 2H), 7.30-7.22 (m, 1H), 6.78-6.62 (m, 3H), 5.02 (dd, 1H, J=9.04 Hz), 3.89-3.79 (m, 1H), 3.53-3.40 (m, 2H), 2.74 (s, 3H). MS m/z (ESI) 328.34 (MH$^+$). This compound was confirmed to have the anti-configuration due to the high J-value (9.04 Hz) of the benzylic proton.

(1S,2S)-1-(3,5-difluorophenyl)-3-(methylamino)-2-(naphthalen-2-yl)propan-1-ol (Compound ID No. 37): The above compound, which is a racemate, was purified by SFC into a single chiral isomer, (1S,2S)-1-(3,5-difluorophenyl)-3-(methylamino)-2-(naphthalen-2-yl)propan-1-ol. (0.017 g, 43%). $^1$H NMR (500 MHz, DMSO-d6) δ 7.79-7.89 (m, 3H), 7.71 (s, 1H) 7.44-7.53 (m, 2H), 7.39 (dd, J=8.39, 1.68 Hz, 1H), 6.92-7.00 (m, 1H), 6.81-6.90 (m, 2H), 6.30 (d, J=3.66 Hz, 1H), 4.93 (d, J=4.27 Hz, 1H), 3.48-3.60 (m, 1H) 3.39-3.48 (m, 2H), 2.54 (t, J=5.34 Hz, 3H). Since this second-eluting enantiomer was more potent at hNET than the first-eluting enantiomer, it was assigned the (1S,2S)-configuration.

Example 38—Synthesis of Compound ID No. 38 (3-methoxy-N-methyl-2 (naphthalen-2-yl)-3-phenyl-propan-1-amine)

Compound ID No. 38 was a preparation of Compound ID No. 46 synthesized as set forth below.

Example 39—Synthesis of Compound ID No. 39 ((S)—N-methyl-2-(naphthalen-2-yl)-3-(o-tolyl)propan-1-amine)

A 50 mL round bottom flask was charged with Compound No. 39b (371 mg, 1.35 mmol), DIPEA (0.58 mL, 3.25 mmol), and 15 mL CH$_2$Cl$_2$. The solution was chilled to 0° C., and ethyl chloroformate was added (0.16 mL, 1.6 mmol). The solution was allowed to stir at 0° C. for 2 hours and warmed to room temperature overnight. In the morning, the contents were poured into a separatory funnel and extracted with ether (3×15 mL) Organics were dried over MgSO$_4$, filtered, and concentrated to give a residue that was purified via silica gel flash chromatography (10% EtOAc in hexanes) to give 391 mg (1.13 mmol, 84%) of a colorless gum. A portion of this material (391 mg, 0.1.13 mmol) was added to a 50 mL round bottom flask and dissolved in dry THF (10 mL) Lithium aluminum hydride was added (129 mg, 3.4 mmol), and the flask was fitted with reflux condenser. The stirred suspension was heated to reflux for 16 hours. Upon cooling, 15 mL of diethyl ether was added followed by 130 μL of water, 130 μL of a 15% KOH solution, and 390 μL of water. After 30 minutes of stirring, the white suspension was removed by filtration, and the filter cake was washed with ether. Filtrate was dried over MgSO₄ and evaporated. The residue was purified via silica gel flash chromatography to give a yellow oil, which was acidified in the usual way to give 240 mg (0.89 mmol, 79%) of a white powder. ¹H NMR (500 MHz, CD₃OD) δ 7.89 (d, J=8.5 Hz, 1H), 7.86-7.78 (m, 2H), 7.70 (s, 1H), 7.53-7.45 (m, 2H), 7.44 (dd, J=8.5, 1.8 Hz, 1H), 7.08 (d, J=7.5 Hz, 1H), 7.06-7.02 (m, 1H), 7.00-6.93 (m, 2H), 3.62 (dd, J=11.8, 10.3 Hz, 1H), 3.40 (ddd, J=16.0, 12.1, 6.2 Hz, 2H), 3.14-3.00 (m, 2H), 2.62 (s, 3H), 2.24 (s, 3H).

This racemate was separated into its enantiomers using a chiral stationary phase supercritical fluid chromatography (Multigram III SFC system) on an ASH column (21.1×250 mm). Isocratic elution using 10% EtOH (containing 0.5% isopropylamine) at a flow rate of 50 mL/minute gave enantiomer retention times of 8.76 and 10.88 minutes, respectively. The combined fractions of the second-eluting enantiomer were concentrated in vacuo and converted to an HCl salt, which afforded 13 mg of Compound ID No. 39, which was shown by the previously described SCF system to have >99% enantiomeric excess. ¹H NMR (500 MHz, DMSO-d6) δ 7.85-7.92 (m, 2H), 7.79-7.85 (m, 1H), 7.73 (s, 1H), 7.43-7.53 (m, 3H), 7.04-7.11 (m, 1H), 6.91-7.04 (m, 3H), 3.49 (dt, J=8.85, 5.65 Hz, 1H), 3.42 (t, J=10.83 Hz, 1H), 3.23-3.28 (m, 1H), 3.13 (dd, J=14.04, 6.10 Hz, 1H), 2.95 (dd, J=14.04, 8.85 Hz, 1H), 2.50 (s, 3H), 2.22 (s, 3H). Since this enantiomer was more potent than the first-eluting enantiomer at hNET, it was presumed to be (S)-configured.

Example 39a—Synthesis of Compound No. 39a
(2-(naphthalen-2-yl)-3-(o-tolyl)acrylonitrile)

To a stirred solution of 2-napthtlyacetonitrile (1.72 g, 10.3 mmol) in absolute ethanol (15 mL) was added o-tolylbenzaldehyde (1.2 mL, 10.3 mmol). A solution of sodium ethoxide (68 mg, 1.03 mmol) in absolute ethanol (2 mL) was added. Within 15 minutes, a solid was formed, and to this suspension was added 15 mL of hot THF. The solution was then concentrated, and the solid was purified via silica gel flash chromatography (50% EtOAc in hexanes) to give 2.05 g (7.5 mmol, 74%) of a white amorphous solid. ¹H NMR (400 MHz, CDCl₃) δ 8.19 (d, J=1.8 Hz, 1H), 8.03-7.84 (m, 5H), 7.78 (dd, J=8.7, 2.0 Hz, 1H), 7.63-7.49 (m, 2H), 7.43-7.25 (m, 3H), 2.44 (s, 3H).

Example 39b—Synthesis of Compound No. 39b
(2-(napthalen-2-yl)-3-(o-tolyl)propan-1-amine
hydrochloride)

The conjugate reduction of Compound No. 39a with Raney nickel and acidification was done in the usual way to give 236 mg (0.76 mmol, 61%) of a white powder. ¹H NMR (500 MHz, CD₃OD) δ 7.88 (d, J=8.5 Hz, 1H), 7.85-7.76 (m, 2H), 7.69 (s, 1H), 7.51-7.44 (m, 2H), 7.43 (dd, J=8.5, 1.8 Hz, 1H), 7.09 (d, J=7.6 Hz, 1H), 7.07-7.01 (m, 1H), 6.98 (dd, J=4.9, 1.2 Hz, 2H), 3.46 (dd, J=14.1, 12.2 Hz, 1H), 3.38-3.31 (m, 2H), 3.15-2.99 (m, 2H), 2.25 (s, 3H). HRMS (ESI-TOF) calculated for C₂₀H₂₂N (MH⁺) 276.1747, found 276.1749 (+0.80 ppm, 0.2 mmu).

Example 40—Synthesis of Compound ID No. 40
((RS)—N-methyl-2-(naphthalen-2-yl)-3-(thiophen-
2-yl)propan-1-amine)

anti-3-hydroxy-2-(naphthalen-2-yl)-3-(thiophen-2-yl) propanenitrile: A solution of 2-naphthylacetonitrile (6.0 g, 35.9 mmol) in 150 mL of dry THF was placed in an oven-dried round bottom flask with stirred under nitrogen. Diisopropylamine (6.04 mL, 43.1 mmol) was added, and the mixture was stirred and cooled to −78° C. for 20 minutes. 2.5 M butyllithium (17.22 mL, 43.1 mmol) was then added slowly with a syringe. After 30 minutes of stirring at −78° C., thiophene-2-carboxaldehyde (3.96 mL, 43.1 mmol) was added drop-wise via syringe. After 10 minutes, the reaction was quenched quickly with 25 mL 2:1 THF/acetic acid. Cold bath was removed, and the reaction was allowed to reach room temperature slowly. Water was added, and the aqueous layer was extracted with EtOAc (3×25 mL) The combined organic layers were washed with water and brine, dried over MgSO₄, and concentrated using a rotary evaporator. The anti-product in the residue was purified by silica gel flash chromatography (eluting with 15% to 20% EtOAc in hexanes) to afford the product as a light yellow solid (8.1 g, 81%). ¹H NMR (CDCl₃) δ 7.89-7.75 (m, 4H), 7.56-7.47 (m, 2H), 7.35-7.26 (m, 2H), 6.94-6.86 (m, 2H), 5.34 (d, 1H, J=6.0 Hz), 4.31 (d, 1H, J=5.7 Hz). MS m/z (ESI) 302.20 (MNa⁺).

anti-3-amino-2-(naphthalen-2-yl)-1-(thiophen-2-yl)propan-1-ol: A solution of anti-3-hydroxy-2-(naphthalen-2-yl)-3-(thiophen-2-yl) propanenitrile (4 g, 14.32 mmol) in 50 mL of dry THF was placed in an oven-dried round-bottom flask under nitrogen. To this, 1M borane. THF solution (57.3 mL, 57.3 mmol) was added via syringe. The resulting mixture was stirred at 60° C. overnight while monitoring the reaction progress by TLC. After quenching the reaction with cautious addition of NaHCO₃, the reaction mixture was poured into a separatory funnel, and the aqueous layer was extracted with EtOAc (3×50 mL). The combined organic layers were washed with water and brine, and dried over MgSO₄. Concentration of the extracts under reduced pressure left a residue that was dissolved in DCM. 1N HCl was added, and the mixture was stirred for a few minutes. The solvents were evaporated in vacuo, and the resulting salt was leached with DCM and lyophilized, affording the product as a light yellow solid with a very pungent odor (4.2 g, 92%). ¹H NMR (CD₃OD) δ 7.84-7.72 (m, 3H), 7.65 (s, 1H), 7.49-7.39 (m, 2H), 7.30 (d, 1H, J=8.3 Hz), 7.18 (d, 1H, J=5.1 Hz), 6.69 (t, 1H, J=4.3 Hz), 6.63-6.56 (m, 1H), 5.33 (d, 1H, J=8.7 Hz), 3.85-3.71 (m, 1H), 3.45-3.34 (m, 2H). MS m/z (ESI) 284.0 (MH⁺).

anti-tert-Butyl-3-hydroxy-2-(naphthalen-2-yl)-3-(thiophen-2-yl)propylcarbamate: To a solution of anti-3-amino-2-(naphthalen-2-yl)-1-(thiophen-2-yl)propan-1-ol hydrochloride (3.27 g, 11.54 mmol) in 30 mL dry DCM at −10° C. was added (TEA) (4.82 mL, 34.6 mmol) drop-wise, followed by slow addition of Boc anhydride (2.77 g, 12.69 mmol). The resulting reaction mixture was stirred at room temperature for 2 hours when the TLC showed completion of reaction. After quenching the reaction with cautious addition of NaHCO₃, the reaction mixture was poured into a separatory funnel, and the aqueous layer was extracted with DCM (3×25 mL). The combined organic layers were washed with water and brine, dried over MgSO₄, and were concentrated using a rotary evaporator. The resulting residue was purified by flash chromatography (40% EtOAc in hexanes as eluent) to afford the product as a sticky white solid (2.452 g, 55.4%). ¹H NMR (CDCl₃) δ 7.83-7.70 (m, 3H), 7.59 (s, 1H), 7.51-7.39 (m, 2H), 7.31-7.23 (m, 1H), 7.08 (d, 1H, J=4.7 Hz), 6.77-6.63 (m, 2H), 5.30 (d, 1H, J=8.9 Hz), 4.77 (br s, 1H), 3.99-3.84 (m, 1H), 3.63-3.48 (m, 1H), 3.37-3.26 (m, 1H), 1.44 (s, 9H). A significant amount of tert-butyl-3-(tert-butoxycarbonyloxy)-2-(naphthalen-2-yl)-

3-(thiophen-2-yl)propylcarbamate was also isolated as indicated by mass measurement. This was also taken to the next step (borane reduction).

N-methyl-2-(naphthalen-2-yl)-3-(thiophen-2-yl)propan-1-amine: The mixture of the tert-butyl-3-hydroxy-2-(naphthalen-2-yl)-3-(thiophen-2-yl)propylcarbamate and tert-butyl-3-(tert-butoxycarbonyloxy)-2-(naphthalen-2-yl)-3-(thiophen-2-yl)propylcarbamate (4.2 g, 10.95 mmol) was dissolved in 50 mL of dry THF under inert atmosphere. Next, 1M borane-THF solution (43.8 mL, 43.8 mmol) was added via syringe, and the resulting mixture was stirred at 60° C. overnight while monitoring the reaction progress by TLC. After quenching the reaction with cautious addition of NaHCO$_3$, the reaction mixture was poured into a separatory funnel, and the aqueous layer was extracted with EtOAc (3×50 mL). The combined organic layers were washed with water and brine, dried over MgSO$_4$, and concentrated using a rotary evaporator. The resulting residue was purified by flash chromatography (elution with 5% MeOH in EtOAc). The resulting residue was dissolved in DCM, 1N HCl was added, and the mixture was stirred for a few minutes. The solvents were removed in vacuo. The product was then leached with DCM and lyophilized yielding the product as an off-white powder (2.2 g, 63.2%). $^1$H NMR (CDCl$_3$) δ 7.96-7.79 (m, 3H), 7.76 (s, 1H), 7.53-7.41 (m, 3H), 7.11 (d, 1H, J=5.1 Hz), 6.84-6.76 (m, 1H), 6.74-6.68 (m, 1H), 3.57-3.32 (m, 5H), 2.63 (3H). MS m/z (ESI) 282.30 (MH$^+$). $^1$H NMR (500 MHz, CD$_3$OD) δ 7.96-7.79 (m, 3H), 7.76 (s, 1H), 7.53-7.41 (m, 2H), 7.11 (d, 1H, J=5.09 Hz), 6.84-6.76 (m, 1H), 6.74-6.68 (m, 1H), 3.57-3.32 (m, 5H), 2.63 (s, 3H).

Example 41—Synthesis of Compound ID No. 41 ((1RS,2RS)-1-(3,5-difluorophenyl)-3-(methylamino)-2-(naphthalen-2-yl)propan-1-ol)

Compound ID No. 41 is the racemic version of Compound ID No. 37. This material was prepared as in Example 37, except that the enantiomer separation step was removed.

Example 42—Synthesis of Compound ID No. 42 ((S)-2-methyl-2-(naphthalen-2-yl)-3-(pyridin-3-yl)propan-1-amine dihydrochloride)

An oven dried 2 neck 100 mL round bottom flask was charged with nitrogen, Compound No. 42a (715 mg, 2.03 mmol), and 10 mL of dry THF. With stirring was added BH$_3$/SMe$_2$ (5.1 mL, 10.1 mmol) Upon addition of borane, the system was fitted with a reflux condenser and heated to reflux for 6 hours. After cooling to room temperature, 5 mL of methanol was carefully added. Upon cessation of bubbles, the system was heated to reflux for 1 hour. The volatiles were then removed in vacuo, and to the residue was added 10 mL of methanol and 1 mL of a 4M HCl solution in dioxane. The homogenous solution was concentrated to give a white amorphous solid that was triturated with diethyl ether. This solid was dissolved in THF (15 mL) and triethyl amine (1.4 mL, 10 mmol) and cooled to 0° C. DMAP (ca. 5 mg) and Boc$_2$O (532 mg, 2.4 mmol) were then added at 0° C. The solution was allowed to warm to room temperature overnight. In the morning, the solution was concentrated, and the residue was purified via silica gel flash chromatography (75% EtOAc in hexanes) to give 372 mg (0.99 mmol, 49%) of a colorless gum. The Boc group was removed by dissolving a portion of this material (143 mg, 0.38 mmol) in 4 mL of CH$_3$OH and adding 8 mL of 4N HCl in dioxane at 0° C. After 1 hour at 0° C., the cooling bath was removed, and the solution was allowed to warm to room temperature overnight. In the morning, diethyl ether was added (4 mL), and the solvents were removed in vacuo to give 107 mg (0.31 mmol, 81%) of a white powder. $^1$H NMR (400 MHz, CD$_3$OD) δ 8.60 (d, J=5.7 Hz, 1H), 8.05 (dd, J=8.5, 6.5 Hz, 3H), 7.99-7.90 (m, 2H), 7.87-7.76 (m, 3H), 7.72 (dd, J=8.6, 2.1 Hz, 1H), 7.69 (s, 114), 7.58-7.50 (m, 3H), 3.82 (d, J=13.2 Hz, 1H), 3.46 (dd, J=36.5, 13.3 Hz, 2H), 3.27 (d, J=13.4 Hz, 1H), 1.59 (s, 3H). HRMS (ESI-TOF) calculated for C$_{18}$H$_{21}$N$_2$ (MH$^+$) 277.1699 found 277.1707 (+2.91 ppm, 0.8 mmu).

This racemate was converted to its free base and separated into its enantiomers using a chiral stationary phase supercritical fluid chromatography (Multigram III SFC system) on an ADH column (21.1×250 mm). Isocratic elution using 20% i-PrOH (containing 0.05% dimethylethanamine) at a flow rate of 60 mL/minute gave enantiomer retention times of 8.61 and 9.17 minutes, respectively. The combined fractions of the first-eluting enantiomer were concentrated in vacuo and converted to an HCl salt to afford 22.9 mg of Compound ID No. 42, which was shown by the previously described SCF system to have 99% enantiomeric excess. Since this enantiomer is more potent than the second-eluting enantiomer at hNET, it was presumed to be (S)-configured.

Example 42a—Synthesis of Compound No. 42a (2-methyl-2-(naphthalen-2-yl)-3-(pyridin-3-yl)propanenitrile)

To a stirred suspension of NaH (60% dispersion in oil, 384 mg, 9.6 mmol) in dry DMF (10 mL) was added 2-(naphthalen-2-yl)propanenitrile (724 mg, 4.0 mmol). The resulting orange solution was allowed to stir at room temperature for 0.5 hours. 3-(bromomethyl)pyridine hydrobromide (1.01 g, 4.0 mmol) was added in one portion followed by an additional 10 mL of dry DMF. After 20 minutes, the red solution was quenched by the addition of a saturated ammonium chloride solution (10 mL). The contents of the flask were poured into a separatory funnel, extracted with EtOAc (3×20 mL), dried over MgSO$_4$, and evaporated onto celite. The celite was placed onto a silica gel column and was eluted with a 35% EtOAc in hexane solution to give 1.17 g (3.31 mmol, 83%) of a yellow oil. $^1$H NMR (400 MHz, CDCl$_3$) δ 8.46 (dd, J=4.8, 1.6 Hz, 1H), 8.21 (d, J=2.2 Hz, 1H), 7.89 (d, J=8.7 Hz, 1H), 7.84 (dd, J=5.4, 4.1 Hz, 1H), 7.82-7.76 (m, 2H), 7.53-7.50 (m, 2H), 7.48 (dd, J=8.6, 2.0 Hz, 1H), 7.39 (dt, J=7.8, 2.0 Hz, 1H), 7.14 (dd, J=7.8, 4.8 Hz, 1H), 3.26 (s, 2H), 1.88 (s, 3H).

Example 43—Synthesis of Compound ID No. 43 ((1RS,2RS)-2-(4-bromo-3-chlorophenyl)-3-(methylamino)-1-phenylpropan-1-ol)

A 250 mL round bottom flask equipped with a magnetic stirring bar, nitrogen inlet, and septum was charged with THF (200 mL) and 1.8 M LDA (1.8 M in THF, 12.34 mL, 22.21 mmol). After cooling to −78° C., 2-(4-bromo-3-chlorophenyl)acetonitrile (5.12 g, 22.21 mmol) was added, and after 60 minutes, benzaldehyde (2.245 mL, 22.21 mmol) was added via syringe. After stirring at −78° C. for 3 hours, the reaction was quenched by the addition of water (20 mL) while stirring at −70° C. The aqueous layer was extracted with ether (2×50 mL), and the combined organic extracts were washed with brine (50 mL) and dried over magnesium sulfate. Concentration in vacuo gave the crude aldol, which was purified by ISCO automated flash chromatography on silica gel, eluting with 0-30% of ethyl acetate in hexane to afford the product as 3:1 anti-:syn-mixture (3 g, 40%). This material (2-(4-bromo-3-chlorophenyl)-3-hydroxy-3-phenyl-propanenitrile, 3 g, 8.91 mmol) was dissolved in THF (150 mL) and heated to reflux, and borane-dimethyl sulfide complex (13.50 mL, 27 mmol) added drop-wise over 5 minutes. The liberated dimethyl sulfide was collected in a Dean-Stark trap, and after 3.5 hours, the mixture was allowed to cool to ambient temperature, quenched with 10 ml of ethanol, and concentrated in vacuo. The residue was dissolved in ethyl acetate (100 mL), washed with saturated aqueous sodium bicarbonate and brine, dried over magnesium sulfate, filtered, and concentrated in vacuo. The residue was dissolved in dichloromethane, filtered, and concentrated in vacuo to afford the primary amine intermediate as a mixture of diastereomers (2.5 g, 82%). This material (HCl salt of 3-amino-2-(4-bromo-3-chlorophenyl)-1-phenylpropan-1-ol, 2.5 g, 7.34 mmol) was combined with triethylamine (2.56 mL, 18.35 mmol) in dichloromethane (100 mL) and chilled to 0° C. To the chilled solution was added ethyl carbonochloridate (0.846 mL, 8.81 mmol) over 10 minutes and then stirred at room temperature for 12 hours. The reaction was concentrated in vacuo, dissolved in ethyl acetate (200 mL), washed with 0.1 N HCl (2×150 mL), saturated sodium bicarbonate (150 mL), and brine (200 mL), dried over magnesium sulfate, and concentrated in vacuo to give a foam (2.6 g). The mixture was purified by ISCO automated flash chromatography, eluting with 0-40% of ethyl acetate in hexane over 15 minutes. The two diastereomers were well separated. The first eluting diasteromer (750 mg) was shown to be syn-, by $^1$H NMR analysis with the TBPTA shift reagent ($J_{12}$=3 Hz). The second-eluting diastereomer (800 mg) was shown to be anti-, by $^1$H NMR analysis with the TBPTA shift reagent ($J_{12}$=9.3 Hz). This anti-diastereomer (ethyl (2RS,3RS)-2-(4-bromo-3-chlorophenyl)-3-hydroxy-3-phenylpropylcarbamate, 800 mg, 1.94 mmol) was dissolved in THF (25 mL) and transferred to a 100 mL 3-neck round bottom flask equipped with a magnetic stirrer, addition funnel, thermometer, and Dean-Stark trap fitted with a condenser and nitrogen inlet. The solution was heated to reflux, and a solution of borane-methyl sulfide complex (4.85 mL, 9.69 mmol) was added drop-wise over 10 minutes. Dimethyl sulfide distillate was collected (bp 38° C.). After 4 hours, the reaction was cooled to room temperature, and methanol was carefully added. After stirring for one hour, the reaction was concentrated in vacuo and dissolved in dioxane, and 4 N HCl in dioxane (0.5 ml) was added and stirred for 20 minutes before concentration in vacuo. The residue was triturated with ether, and the solid collected by filtration, washed with ether, ethyl acetate in hexane (1:1), and hexane. Drying in vacuo afforded Compound ID No. 43 as the HCl salt (400 mg, 53%). $^1$H NMR (500 MHz, DMSO-$d_6$) δ 2.50 (d, J=2.1 Hz, 3H), 3.32-3.44 (m, 2H), 3.43-3.58 (m, 1H), 4.76 (d, J=7.6 Hz, 1H), 6.04 (br. s., 1H), 7.06 (dd, J=8.2, 1.8 Hz, 1H), 7.11-7.31 (m, 5H), 7.45 (d, J=1.8 Hz, 1H), 7.60 (d, J=8.2 Hz, 1H). This compound is racemic.

Example 44—Synthesis of Compound ID No. 44 ((S)—N-methyl-3-(5-methylthiophen-2-yl)-2-(naphthalen-2-yl)propan-1-amine)

Anti-3-hydroxy-3-(5-methylthiophen-2-yl)-2-(naphthalen-2-yl)propanenitrile: Diisopropylamine (4.02 mL, 28.7 mmol) was added to a solution of 2-naphthylacetonitrile (4 g, 23.92 mmol) in 150 mL of dry THF under nitrogen. The mixture was stirred and cooled to −78° C. for 20 minutes before adding 2.5M n-butyllithium (11.48 mL, 28.7 mmol) in a dropwise fashion via a syringe. After 30 minutes of stirring at −78° C., 5-methylthiophene-2-carboxaldehyde (3.07 mL, 28.7 mmol) was added slowly via a cannula. After 10 minutes, the reaction was quickly quenched with 25 mL 2:1 THF/acetic acid. Cold bath was removed and the reaction was allowed to reach r.t slowly. Water was added and the aqueous layer was extracted with EtOAc (3×25 mL). The combined organic layers were washed with water and brine, dried over MgSO4, and concentrated using a rotary evaporator. The resulting residue was dissolved in 5 mL of DCM. Hexane was slowly added till the solution turned turbid. This product was allowed to crystallize overnight at room temperature. Light brown crystals of the anti-adduct were filtered and washed with hexane and dried (2.5 g, 31.6%). 1H NMR (CDCl$_3$) δ 7.86-7.79 (m, 4H), 7.56-7.46 (m, 2H), 7.34 (dd, 1H, J=8.7, 1.5 Hz), 6.68 (d, 1H, J=3.6 Hz), 6.55 (m, 1H), 5.27 (dd, 1H, 5.4, 5.4 Hz), 4.29 (d, 1H, J=6.0 Hz), 2.55 (d, 1H, J=5.4 Hz), 2.48 (s, 3H). MS m/z (ESI) 316.08 (MNa$^+$). The relative anti configuration of this compound was confirmed after borane reduction.

anti-3-Amino-1-(5-methylthiophen-2-yl)-2-(naphthalen-2-yl)propan-1-ol and 3-(5-methylthiophen-2-yl)-2-(naphthalen-2-yl)propan-1-amine: anti-3-Hydroxy-3-(5-methylthiophen-2-yl)-2-(naphthalen-2-yl) propanenitrile (3.0 g, 10.23 mmol), dissolved in 30 mL of dry THF was placed in an oven-dried round-bottom flask under nitrogen. Next, 1M borane-THF solution (40.9 mL, 40.9 mmol) was added via syringe. This mixture was stirred and heated to 60° C. overnight. The progress of the reaction was monitored by TLC. After quenching the reaction with cautious addition of NaHCO3, the reaction mixture was poured into a separatory funnel. The organic phase was separated and the aqueous layer was extracted with EtOAc (3×50 mL). The combined organic layers were washed with water and brine, dried over MgSO4, and concentrated under reduced pressure. The residue was dissolved in DCM. 1N HCl was added and the mixture was stirred for a few min. The solvents were evaporated in vacuo and the resulting salt was leached with DCM and dried under high vacuum to yield the products (mixture of deoxy- and oxygenated 5-methylthiophene in 1:2 ratio) as a white solid (2.87 g, 84%). The two compounds could not be separated at this stage completely. A small amount of the anti-3-amino-1-(5-methylthiophen-2-yl)-2-(naphthalen-2-yl)propan-1-ol was isolated and was assigned anti-configuration because of the high J-value (8.7 Hz) of its benzylic proton. $^1$H NMR (CD$_3$OD) δ 7.80-7.61 (m, 6H), 7.56 (s, 1H), 7.40-7.30 (m, 4H), 7.20 (dd, 1H, J=8.4, 1.6 Hz), 6.40-6.33 (m, 1.2H), 6.28-6.22 (m, 1.8 H), 5.12 (d, 1H, J=8.7 Hz), 3.62 (m, 1H), 3.29-3.10 (m, 4H), 2.22 (s, 3H). MS m/z (ESI) 297.98 (MH$^+$) and 282.17 (MH$^+$).

anti-Ethyl-3-hydroxy-3-(5-methylthiophen-2-yl)-2-(naphthalen-2-yl)propyl)carbamate and ethyl (3-(5-methylthiophen-2-yl)-2-(naphthalen-2-yl)propyl)carbamate: To a solution of a mixture of anti-3-amino-1-(5-methylthiophen-2-yl)-2-(naphthalen-2-yl)propan-1-ol hydrochloride and anti-3-(5-methylthiophen-2-yl)-2-(naphthalen-2-yl)propan-1-amine hydrochloride (1.8 g, 5.39 mmol) in 20 mL dry DCM at −10° C. was added triethylamine (TEA) (2.254 mL, 16.17 mmol) dropwise. This was followed by slow addition of ethyl chloroformate (0.619 mL, 6.47 mmol), and the reaction mixture was stirred at −10° C. for 10 minutes. At this point, the cold bath was removed, and the mixture was allowed to reach 0° C. and poured into a separatory funnel containing DCM and water. The organic layer was separated, and the aqueous phase was extracted with DCM (3×25 mL). The combined DCM extracts were washed with water, dried over MgSO$_4$, and concentrated under reduced pressure. The crude product was purified by flash chromatography (eluting with 15% to 40% EtOAc in hexanes) to afford the two products, anti-ethyl (3-hydroxy-3-(5-methylthiophen-2-yl)-2-(naphthalen-2-yl)propylcarbamate (0.648 g, 32.5%): $^1$H NMR (CDCl$_3$) δ 7.81-7.70 (t, 3H), 7.60 (s, 1H), 7.49-7.36 (m, 2H), 7.28 (dd, 1H, J=8.7, 1.4 Hz), 6.49 (bs, 1H), 6.36 (d, 1H, J=2.4 Hz), 5.20 (dd, 1H, J=8.7, 4.2 Hz), 4.88 (bs, 1H), 4.12-4.01 (m, 2H), 3.89 (m, 1H), 3.71-3.55 (m, 2H), 3.31 (m, 1H), 2.33 (s, 3H), 1.20 (s, 3H); MS m/z (ESI) 391.83 (MNa$^+$), and ethyl 3-(5-methylthiophen-2-yl)-2-(naphthalen-2-yl)propylcarbamate (0.7438 g, 39%): $^1$H NMR (CDCl$_3$) δ 7.83-7.72 (t, 3H), 7.73-7.62 (s, 1H), 7.49-7.40 (m, 2H), 7.33 (dd, 1H, J=8.3, 1.4 Hz), 6.45 (bs, 2H), 4.46 (bs, 1H), 4.04 (t, 2H, J=8.4 Hz), 3.69 (m, 1H), 3.41-3.31 (m, 1H), 3.29-3.08 (m, 3H), 2.35 (s, 3H), 1.16 (s, 3H). MS m/z (ESI) 354.17 (MH$^+$), MS m/z (ESI) 375.86 (MNa$^+$).

anti-N-methyl-3-(5-methylthiophen-2-yl)-2-(naphthalen-2-yl)propan-1-amine: To a solution of ethyl 3-(5-methylthiophen-2-yl)-2-(naphthalen-2-yl)propylcarbamate (0.35 g, 1.031 mmol) in 5 mL of dry THF was added via syringe a 1M borane-THF solution (4.12 mL, 4.12 mmol). This mixture was stirred at 60° C. overnight under nitrogen while monitoring the reaction progress by TLC. After quenching the reaction with cautious addition of NaHCO3, the reaction mixture was poured into a separatory funnel and the aqueous layer was extracted with EtOAc (3×50 mL) The combined organic layers were washed with water and brine, dried over MgSO4, and were concentrated using a rotary evaporator. The resulting residue was purified by silica gel chromatography (eluent: 5-10% MeOH in EtOAc). The resulting residue was dissolved in DCM, 1N HCl was added to it and the mixture was stirred for a few min. The volatiles were then evaporated off using a rotary evaporator. The product was leached with DCM and the product dried under high vacuum furnishing an off-white powder (0.240 g, 69.9%).

Compound ID No. 44: The above racemic compound was resolved and purified by Multigram II SFC chiral chromatography to afford two enantiomers. The first eluting was assigned as S-configuration based on its higher potency on the hNET than its R-antipode. $^1$H NMR (500 MHz, DMSO-d6) δ 7.83-7.95 (m, 3H), 7.79 (s, 1H), 7.45-7.55 (m, 3H), 6.48 (s, 2H), 3.35-3.50 (m, 1H), 3.29 (s, 3H), 3.11-3.21 (m, 1H), 2.49 (s, 3H), 2.27 (s, 3H).

Example 45—Synthesis of Compound ID No. 45 (2-((1S,2S)-3-(methylamino)-2-(naphthalen-2-yl)-1-phenylpropoxy)-N-phenylacetamide)

Compound No. 8a (200 mg, 0.51 mmol) in DMF was treated with NaH (61.3 mg, 1.53 mmol) at 0° C. for 20 minutes. 2-bromo-N-phenylacetamide (164 mg, 0.77 mmol) in DMF was then added slowly at this temperature, and the reaction was allowed to stir at room temperature over 48 hours. The mixture was diluted with ethyl acetate (100 mL), washed with water and brine, and dried with sodium sulfate. After filtration and concentration in vacuo, the crude product was purified by ISCO automated flash chromatography, eluting with ethyl acetate in hexane (0-80%) to afford the desired intermediate (120 mg). This material was dissolved in dichloromethane, and trifluoroacetic acid (0.088 mL, 1.14 mmol) was added. After 6 hours at room temperature, the reaction was concentrated in vacuo and diluted with ethyl acetate, and the resulting mixture was washed with aqueous sodium bicarbonate and brine. The organic phase was separated, dried with sodium sulfate, and concentrated in vacuo. The resulting crude amine was purified by ISCO automated flash chromatography (alumina column), eluting with 0-10% of methanol in DCM to afford Compound ID No. 45 as the free base (25 mg, 26%). $^1$H NMR (500 MHz, CHLOROFORM-d) δ 2.42 (s, 3H) 3.22 (d, J=6.6 Hz, 2H) 3.46-3.54 (m, 1H) 3.90-3.93 (m, 1H) 4.01 (s, 1H) 4.82 (d, J=8.1 Hz, 1H) 7.08-7.13 (m, 3H) 7.14-7.23 (m, 4H) 7.26-7.32 (m, 2H) 7.39-7.45 (m, 4H) 7.52 (s, 1H) 7.68-7.73 (m, 2H) 7.74-7.79 (m, 1H) 9.13 (br. s., 1H).

Example 46—Synthesis of Compound ID No. 46 (2S,3S)-3-methoxy-N-methyl-2-(naphthalen-2-yl)-3-phenylpropan-1-amine)

tert-Butyl ((2S,3S)-3-methoxy-2-(naphthalen-2-yl)-3-phenylpropyl)-(methyl)carbamate: A solution of tert-butyl-(2S,3S)-3-hydroxy-2-(naphthalen-2-yl)-3-phenylpropyl(methyl)carbamate (Compound No. 8a) (0.200 g, 0.511 mmol) in 5 mL DMF was placed in an oven dried round bottom flask under nitrogen. NaH (in 50% oil) (0.037 g, 0.766 mmol) was added portion wise, and the resulting suspension was stirred at 0° C. for 5 minutes. MeI (0.064 mL, 1.022 mmol) was then added, and the mixture was stirred for 2 hours. Completion of reaction was determined by TLC. The reaction mixture was poured into a separatory funnel containing water, and the phases were separated. The aqueous layer was extracted with EtOAc (3×25 mL). The combined organic layers were washed with water and brine, and dried over MgSO$_4$. Concentration of the extracts under reduced pressure left a residue that was purified by flash chromatography (elution with 15% to 40% EtOAc in hexanes) to afford a clear viscous solid (0.157 g, 76%). $^1$H NMR (CDCl$_3$) δ 7.86-6.93 (m, 12H), 5.83 (d, J=8.10 Hz, 1H), 4.40 (d, J=6.0 Hz, 1H), 3.63-3.41 (m, 3H), 3.25 (s, 3H), 2.55 (s, 3H), 1.35-1.03 (m, 9H). MS m/z (ESI) 406.32 (MH$^+$).

Compound ID No. 46: A 2.5 N HCl in dioxane (6 mL) was added to tert-butyl (2S,3S)-3-methoxy-2-(naphthalen-2-yl)-3-phenylpropyl(methyl)carbamate, and the mixture was stirred at room temperature for 1 hour under nitrogen. The reaction was monitored by MS. The solvents were evaporated in vacuo, and the resulting salt was leached with ether and lyophilized furnishing the product as a white solid (0.206 g, 89.6%). $^1$H NMR (CD$_3$OD) δ 7.83-7.66 (m, 3H), 7.53 (s, 1H), 7.47-7.39 (m, 2H), 7.26 (m, 6H), 4.60 (d, J=9.5 Hz, 1H), 3.95-3.82 (m, 1H), 3.50-3.38 (m, 2H), 3.26 (s, 3H), 2.74 (s, 3H). MS m/z (ESI) 306.32 (MH)$^+$[α]$_D^{20}$105.1 (c 0.35, 9:1 EtOH:H$_2$O).

Example 47—Synthesis of Compound ID No. 47 ((1S,2S)-3-(methylamino)-2-(naphthalen-2-yl)-1-(thiophen-2-yl)propan-1-ol)

anti-3-hydroxy-2-(naphthalen-2-yl)-3-(thiophen-2-yl) propanenitrile: A solution of 2-naphthylacetonitrile (6.0 g, 35.9 mmol) in 150 mL of dry THF was placed in an oven-dried round bottom flask with stirrer under nitrogen. Diisopropylamine (6.04 mL, 43.1 mmol) was added, and the mixture was stirred and cooled to −78° C. for 20 minutes. 2.5 M butyllithium (17.22 mL, 43.1 mmol) was then added slowly with a syringe. After 30 minutes of stirring at −78° C., thiophene-2-carboxaldehyde (3.96 mL, 43.1 mmol) was added drop-wise via syringe. After 10 minutes, the reaction was quenched quickly with 25 mL 2:1 THF/acetic acid. Cold bath was removed, and the reaction was allowed to reach room temperature slowly. Water was added, and the aqueous layer was extracted with EtOAc (3×25 mL) The combined organic layers were washed with water and brine, dried over MgSO$_4$, and concentrated using a rotary evaporator. The product in the residue was purified by silica gel flash chromatography (eluting with 15% to 20% EtOAc in hexanes) to afford the anti-product as a light yellow solid (8.1 g, 81%). $^1$H NMR (CDCl$_3$) δ 7.89-7.75 (m, 4H), 7.56-7.47 (m, 2H), 7.35-7.26 (m, 2H), 6.94-6.86 (m, 2H), 5.34 (d, 1H, J=6.0 Hz), 4.31 (d, 1H, J=5.7 Hz). MS m/z (ESI) 302.20 (MNa$^+$).

anti-3-amino-2-(naphthalen-2-yl)-1-(thiophen-2-yl)propan-1-ol: A solution of anti-3-hydroxy-2-(naphthalen-2-yl)-3-(thiophen-2-yl) propanenitrile (4 g, 14.32 mmol) in 50 mL of dry THF was placed in an oven-dried round-bottom flask under nitrogen. To this, 1M borane. THF solution (57.3 mL, 57.3 mmol) was added via syringe. The resulting mixture was stirred at 60° C. overnight while monitoring the reaction progress by TLC. After quenching the reaction with cautious addition of NaHCO$_3$, the reaction mixture was poured into a separatory funnel, and the aqueous layer was extracted with EtOAc (3×50 mL) The combined organic layers were washed with water and brine, and dried over MgSO$_4$. Concentration of the extracts under reduced pressure left a residue that was dissolved in DCM. 1N HCl was added, and the mixture was stirred for a few minutes. The solvents were evaporated in vacuo, and the resulting salt was leached with DCM and lyophilized affording the product as a light yellow solid with a very pungent odor (4.2 g, 92%). $^1$H NMR (CD$_3$OD) δ 7.84-7.72 (m, 3H), 7.65 (s, 1H), 7.49-7.39 (m, 2H), 7.30 (d, 1H, J=8.3 Hz), 7.18 (d, 1H, J=5.1 Hz), 6.69 (t, 1H, J=4.3 Hz), 6.63-6.56 (m, 1H), 5.33 (d, 1H, J=8.7 Hz), 3.85-3.71 (m, 1H), 3.45-3.34 (m, 2H). This compound was assigned anti-configuration based on its high J-value (8.7 Hz) of its benzylic proton. MS m/z (ESI) 284.0 (MH$^+$).

tert-Butyl (2S,3S)-3-hydroxy-2-(naphthalen-2-yl)-3-(thiophen-2-yl)propylcarbamate: To a solution of anti-3-amino-2-(naphthalen-2-yl)-1-(thiophen-2-yl)propan-1-ol hydrochloride (3.27 g, 11.54 mmol) in 30 mL dry DCM at −10° C. was added (TEA) (4.82 mL, 34.6 mmol) drop-wise, followed by slow addition of Boc anhydride (2.77 g, 12.69 mmol). The resulting reaction mixture was stirred at room temperature for 2 hours when the TLC showed completion of reaction. After quenching the reaction with cautious addition of NaHCO$_3$, the reaction mixture was poured into a separatory funnel, and the aqueous layer was extracted with DCM (3×25 mL). The combined organic layers were washed with water and brine, dried over MgSO$_4$, and concentrated using a rotary evaporator. The resulting residue was purified by flash chromatography (40% EtOAc in hexanes as eluent) to afford the product as a sticky white solid (2.452 g, 55.4%). $^1$H NMR (CDCl$_3$) δ 7.83-7.70 (m, 3H), 7.59 (s, 1H), 7.51-7.39 (m, 2H), 7.31-7.23 (m, 1H), 7.08 (d, 1H, J=4.7 Hz), 6.77-6.63 (m, 2H), 5.30 (d, 1H, J=8.9 Hz), 4.77 (br s, 1H), 3.99-3.84 (m, 1H), 3.63-3.48 (m, 1H), 3.37-3.26 (m, 1H), 1.44 (s, 9H).

anti-3-(methylamino)-2-(naphthalen-2-yl)-1-(thiophen-2-yl)propan-1-ol: To a solution of tert-butyl anti-3-hydroxy-2-(naphthalen-2-yl)-3-(thiophen-2-yl)propylcarbamate (2.45 g, 6.39 mmol) in 50 mL of dry THF was added 1M Borane-THF solution (25.6 mL, 25.6 mmol) via syringe under nitrogen. This mixture was stirred at 60° C. overnight while monitoring the reaction progress by TLC. After quenching the reaction with cautious addition of NaHCO$_3$, the reaction mixture was poured into a separatory funnel, and the aqueous layer was extracted with EtOAc (3×50 mL) The combined organic layers were washed with water and brine, and dried over MgSO$_4$. Concentration using a rotary evaporator resulted in an oily residue that was purified by flash chromatography over silica gel (elution with 5% MeOH in EtOAc). The resulting residue was dissolved in DCM. 1N HCl was added to the solution, and the mixture was stirred for a few minutes. The volatiles were evaporated off in vacuo. The product was then leached with DCM and lyophilized affording the product as an off-white powder (1.994 g, 93%). $^1$H NMR (CD$_3$OD) δ 7.82-7.71 (m, 3H), 7.65 (s, 1H), 7.51-7.39 (m, 2H), 7.33-7.25 (m, 1H), 7.19-7.15 (m, 1H), 6.73-6.66 (m, 1H), 6.61-6.55 (m, 1H), 5.33 (d, 1H, J=8.7 Hz), 3.91-3.79 (m, 1H), 3.50-3.38 (m, 2H), 2.73 (s, 3H). MS m/z (ESI) 298.36 (MH$^+$).

Compound ID No. 47: The above racemic mixture was resolved by chiral SCF into enantiomers, and the second-eluting enantiomer was assigned 1S,2S-configuration based on its higher potency at hNET than the first-eluting enantiomer. 1H NMR (DMSO-d6) δ 8.73 (br. s., 1H), 7.68-8.20 (m, 4H), 7.36-7.66 (m, 2H), 7.15-7.32 (m, 1H), 6.61-7.12 (m, 3H), 4.05 (br. s., 2H), 3.45-3.76 (m, 1H), 2.32-2.69 (m, 6H).

Example 48—Synthesis of Compound ID No. 48 ((S)—N-methyl-2-(naphthalen-2-yl)-3-(pyridin-3-yl)propan-1-amine)

The aldol condensation using sodium ethoxide, ethanol, 3-pyridine-carboxaldehyde (590 mg, 5.05 mmol) and 2-naphthylacetonitrile (836 mg, 5.0 mmol) was performed in the usual way to give 1.21 g (4.72 mmol, 95%) of a yellow solid. The conjugate reduction was performed in the usual way with a portion of the above material (554 mg, 2.16 mmol) to give 179 mg (0.68 mmol, 32%) of a crude yellow oil. This oil was then dissolved in CH$_2$Cl$_2$ (10 mL), followed by addition of triethylamine (0.23 mL, 1.64 mmol). The solution was chilled to 0° C., and ethyl chloroformate was added (0.08 mL, 0.82 mmol). The solution was allowed to stir at 0° C. for 2 hours and to warm to room temperature overnight. In the morning, the contents were poured into a separatory funnel and extracted with ether (3×15 mL).

Organics were dried over MgSO$_4$, filtered, and concentrated to give a residue that was purified via silica gel flash chromatography (50% EtOAc in hexanes) to give 103 mg (0.55 mmol, 81%) of a colorless gum. A portion of this material (180 mg, 0.54 mmol) was carbamylated with ethyl chloroformate and reduced with LiAlH$_4$ in the usual way to give 186 mg (0.53 mmol, 99%) of colorless oil. $^1$H NMR (400 MHz, CD$_3$OD) δ 8.60 (d, J=5.6 Hz, 1H), 8.51 (s, 1H), 8.35 (d, J=8.1 Hz, 1H), 7.94 (d, J=8.5 Hz, 1H), 7.92-7.78 (m, 3H), 7.72 (s, 1H), 7.54-7.45 (m, 3H), 3.68-3.48 (m, 5H), 2.70 (s, 3H). HRMS (ESI-TOF) calculated for C$_{18}$H$_{21}$N$_2$ (MH$^+$) 277.1699 found 277.1705 (+2.14 ppm, 0.6 mmu). This racemate (Compound ID No. 74) was separated into its enantiomers using a chiral stationary phase supercritical fluid chromatography (Multigram III SFC system). The first eluting enantiomer was concentrated to provide the desired compound. $^1$H NMR (500 MHz, CDCl$_3$) δ 2.80 (s, 3H), 3.10-3.40 (m, 2H), 3.76-3.94 (m, 1H), 4.02 (dd, J=12.1, 6.0 Hz, 1H), 4.13 (d, J=12.8 Hz, 1H), 7.27-7.95 (m, 9H), 8.51 (d, J=4.0 Hz, 1H), 9.28 (br. s., 1H). Since this compound was more potent at hNET than the second-eluting enantiomer, it was presumed to be (S)-configured.

Example 49—Synthesis of Compound ID No. 49 ((1S,2S)-3-(methylamino)-2-(naphthalen-2-yl)-1-(pyridin-3-yl)propan-1-ol)

(1R,2R and 1S,2S)-3-(methylamino)-2-(naphthalen-2-yl)-1-(pyridin-3-yl)propan-1-ol (Compound ID No. 62) was a pair of enantiomers: S,S (Compound ID No. 49) and R,R (Compound ID No. 103) enantiomers. The enantiomers were separated using chiral Multigram II SFC system. The first-eluting enantiomer was Compound ID No. 49 and assigned the (S,S) configuration since it is more potent at hNET than the second-eluting enantiomer (Compound ID No. 103). $^1$H NMR (500 MHz, DMSO-d6) δ 8.53-8.57 (m, 1H), 8.48-8.52 (m, 1H), 7.99-8.09 (m, 1H), 7.82 (d, 3H, J=8.5 Hz), 7.71 (s, 1H), 7.60-7.67 (m, 1H), 7.48 (d, 2H, J=9.2 Hz), 7.34-7.40 (m, 1H), 5.07-5.15 (m, 1H), 3.54-3.67 (m, 2H), 3.43-3.52 (m, 1H), 2.54 (t, 3H, J=5.3 Hz).

Example 50—Compound ID No. 50 (Compound Reference No. 13341669) 2-((1S,2S)-3-(methylamino)-2-(naphthalen-2-yl)-1-phenylpropoxy)-1-(pyrrolidin-1-yl)ethanone As in the case of Compound No. 23a, bromoacetyl bromide was combined with pyrrolidine to yield 2-bromo-1-(pyrrolidin-1-yl)ethanone. This compound was reacted with Compound No. 8a as in Example 23 to yield tert-butyl methyl((2S,3S)-2-(naphthalen-2-yl)-3-(2-oxo-2-(pyrrolidin-1-yl)ethoxy)-3-phenylpropyl)carbamate (11 mg). This compound was dissolved in tetrahydrofuran (4 mL) to which 4 N HCl (5 mL) was added. After stirring for 1 hour, the mixture was heated to reflux for 1 minute with a heat gun. This heating process was repeated twice more, and the reaction was concentrated in vacuo, affording Compound ID No. 50 as the HCl salt (12 mg (90%). $^1$H NMR (500 MHz, MeOD) δ 1.84-2.01 (m, 4H), 2.86 (s, 3H), 3.19-3.26 (m, 2H), 3.47-3.76 (m, 4H), 3.93 (t, J=11.9 Hz, 1H), 4.03 (d, J=15.9 Hz, 1H), 4.25 (d, J=16.2 Hz, 1H), 4.90 (d, J=10.1 Hz, 1H), 7.05-7.17 (m, 6H), 7.36-7.45 (m, 2H), 7.50 (s, 1H), 7.62-7.75 (m, 4H).

Example 51—Synthesis of Compound ID No. 51 (Compound Reference No. 13376700) N-(2-methoxyethyl)-2-((1S,2S)-3-(methylamino)-2-(naphthalen-2-yl)-1-acetamide Compound No. 8a (0.30 g, 0.77 mmol) in DMF (5 mL) was stirred at 0° C., and sodium hydride (0.092 g, 2.30 mmol) was added. The reaction was stirred at 0° C. for 10 minutes. 2-bromo-N-(2-methoxyethyl)acetamide (0.53 g, 2.7 mmol) in DMF (5 mL) was added over 30 minutes drop-wise. After 24 hours at room temperature, the reaction was diluted with dichloromethane (100 mL) and washed once with water (50 mL). The aqueous phase was back extracted with dichloromethane, and the combined organic layers were dried with magnesium sulfate, filtered, and concentrated in vacuo. The residue was purified by ISCO automated flash chromatography (40 g normal phase), using a 0-100% EtOAc/hexane gradient elution. The relevant fractions were concentrated in vacuo (0.37 g, 97%). This material was dissolved in dichloromethane (15 mL), and trifluoroacetic acid (5 mL, 67.31 mmol) was added in one portion. After 30 minutes at 25° C., the reaction was concentrated in vacuo to give 435 mg of a clear oil, which was purified using ISCO automated flash chromatography (40 gram normal phase), eluting with a ramp of 0-30% 7 N ammonia in MeOH/dichloromethane. The relevant fractions were concentrated, dissolved in a minimum amount of chloroform, diluted in ether, and then diluted with 2.0 N HCl in dioxane. Concentration in vacuo gave Compound ID No. 51 as the HCl salt (solid, 0.24 g, 75%). $^1$H NMR (500 MHz, DMSO-d$_6$) δ 9.25 (br.s., 1H), 9.16 (br.s., 1H), 8.27 (t, J=5.3 Hz, 1H), 7.68-7.83 (m, 3H), 7.61 (s, 1H), 7.39-7.48 (m, 2H), 7.22-7.27 (m, 1H), 7.07-7.18 (m, 5H), 4.87 (d, J=9.8 Hz, 1H), 3.70-3.84 (m, 3H), 3.23-3.44 (m, 8H), 2.66 (t, J=5.3 Hz, 3H).

Example 52—Synthesis of Compound ID No. 52 ((S)-2-(3-(methylamino)-2-(naphthalen-2-yl)propyl) phenol hydrochloride)

The conjugate reduction was performed in the usual way with Compound No. 52b (572 mg, 1.58 mmol) to give 483 mg (1.31 mmol, 83%) of a crude yellow oil. The oil was then dissolved in CH$_2$Cl$_2$ (10 mL), followed by addition of triethylamine (0.44 mL, 3.14 mmol). The solution was chilled to 0° C., and ethyl chloroformate was added (0.15 mL, 1.57 mmol). The solution was allowed to stir at 0° C. for 2 hours and allowed to warm to room temperature overnight. In the morning, the contents were poured into a separatory funnel and extracted with ether (3×15 mL). Organics were dried over MgSO$_4$, filtered, and concentrated to give a residue that was purified via silica gel flash chromatography (35% EtOAc in hexanes) to give 500 mg (1.14 mmol, 87%) of a colorless gum. The ethyl carbamate reduction was performed in the usual way with lithium aluminum hydride (152 mg, 4.0 mmol). The crude free base was dissolved in 5 mL THF and added to an air-free Schlenck flask equipped with a stir bar containing a stirred suspension of 5% Pd/C (150 mg) and CH$_3$OH (5 mL) under a stream of H$_2$. Upon addition, the flask was fitted with a balloon and stirred under H$_2$ for 16 hours. The catalyst was filtered through celite and concentrated. The residue was dissolved in 5 mL of CH$_3$OH followed by addition of 1 mL of 4M HCl in dioxane. The solvents were then evaporated to give a 294 mg (0.9 mmol, 79%) of a white powder. $^1$H NMR (400 MHz, CD$_3$OD) δ 7.88 (d, J=8.5 Hz, 1H), 7.85-7.80 (m, 2H), 7.72 (s, 1H), 7.46 (ddd, J=8.5, 6.0, 1.6 Hz, 3H), 6.99 (td, J=7.7, 1.7 Hz, 1H), 6.79 (td, J=7.9, 1.3 Hz, 2H), 6.60 (td, J=7.4, 1.1 Hz, 1H), 3.60 (dt, J=12.2, 6.1 Hz, 1H), 3.55-3.46 (m, 1H), 3.35 (t, J=2.5 Hz, 1H), 3.15 (dd, J=13.4, 7.2 Hz, 1H), 2.96 (dd, J=13.4, 7.2 Hz, 1H), 2.62 (s, 3H). HRMS (ESI-TOF) calculated for C$_{18}$H$_{19}$N$_2$ (MH$^+$) 292.1696 found 292.1703 (+2.42 ppm, 0.6 mmu).

This racemate was separated into its enantiomers using a chiral stationary phase supercritical fluid chromatography. The first eluting enantiomer was isolated (190 mg of HCl salt). $^1$H NMR (500 MHz, DMSO-d6) δ 2.47 (t, J=4.9 Hz, 2H), 2.88 (dd, J=13.6, 8.1 Hz, 2H), 3.06 (dd, J=13.4, 6.7 Hz, 2H), 3.57 (s, 1H), 6.45-7.96 (m, 11H). Since this enantiomer is more potent at hNET than the second-eluting enantiomer, it was presumed to be (S)-configured.

Example 52a—Synthesis of Compound No. 52a (tert-butyl (3-(2-(benzyloxy)phenyl)-2-(naphthalen-2-yl)propyl)carbamate)

The aldol condensation using sodium ethoxide, ethanol, 2-benzyloxybenzaldehyde (1.07 g, 5.05 mmol) and 2-naphthylacetonitirle (836 mg, 5.0 mmol) was performed in the usual way to give 1.73 g (4.8 mmol, 96%) of a yellow solid. The conjugate reduction was performed in the usual way with a portion (580 mg, 1.6 mmol) of the above compound to give 332 mg (0.9 mmol, 56%) of a crude yellow oil. The oil was then dissolved in 10 mL of THF and cooled to 0° C. Triethylamine (0.55 mL, 3.84 mmol) and DMAP (ca. 5 mg) were added followed by Boc$_2$O (415 mg, 1.9 mmol). The solution was allowed to warm to room temperature overnight. In the morning, 1 mL of water and 10 mL of diethyl ether were added. The contents were poured into a separatory funnel and extracted with ether (2×15 mL). The organics were dried over Na$_2$SO$_4$, filtered, and concentrated. The residue was purified via silica gel flash chromatography (10% EtOAc in hexanes) to give 321 mg (0.69 mmol, 77%) of a colorless gum. $^1$H NMR (400 MHz, CD$_3$OD) δ 7.80-7.63 (m, 3H), 7.51-7.25 (m, 9H), 7.06 (t, J=7.6 Hz, 1H), 6.94 (dd, J=25.5, 7.8 Hz, 2H), 6.72 (t, J=7.4 Hz, 1H), 5.03 (dd, J=27.7, 11.8 Hz, 2H), 3.40 (s, 3H), 3.13-2.99 (m, 2H), 1.29 (s, 9H).

Example 52b—Synthesis of Compound No. 52b
(2-(3-amino-2-(naphthalen-2-yl)propyl)phenol)

To an air-free Schlenk flask under a stream of N$_2$ was added Compound No. 52a (321 mg, 0.69 mmol), 5% Pd/C (120 mg), CH$_3$OH (4 mL), and THF (4 mL). The system was carefully evacuated and backfilled with H$_2$ followed by addition of a stir bar and balloon. The suspension was allowed to stir under a H$_2$ balloon for 16 hours. Catalyst was filtered through celite, and the filtrate was dried over MgSO$_4$ and concentrated. Residue was purified via silica gel flash chromatography to give 178 mg (0.47 mmol, 68%) of a colorless gum. The Boc group was removed by dissolving VII-039 (172 mg, 0.45 mmol) in 4 mL of CH$_3$OH and adding 4 mL of 4N HCl in dioxane at 0° C. After 1 hour at 0° C., the cooling bath was removed, and the solution was allowed to warm to room temperature overnight. In the morning, the solvents were removed in vacuo to give 147 mg (0.44 mmol, 99%) of a white powder. $^1$H NMR (400 MHz, CD$_3$OD) δ 7.89 (d, J=8.5 Hz, 1H), 7.86-7.80 (m, 2H), 7.72 (d, J=1.1 Hz, 1H), 7.51-7.43 (m, 3H), 7.03-6.97 (m, 1H), 6.84 (dd, J=7.5, 1.6 Hz, 1H), 6.78 (dd, J=8.1, 0.9 Hz, 1H), 6.62 (td, J=7.4, 1.1 Hz, 1H), 3.71-3.64 (m, 1H), 3.62-3.49 (m, 1H), 3.42-3.34 (m, 1H), 3.14 (dd, J=13.5, 7.6 Hz, 1H), 2.98 (dd, J=13.4, 7.0 Hz, 1H). HRMS (ESI-TOF) calculated for C$_{19}$H$_{20}$NO (MH$^+$) 278.1539 found 278.1545 (+1.92 ppm, 0.6 mmu).

Example 53—Synthesis of Compound ID No. 53
((2RS,3RS)-2-(3,4-dichlorophenyl)-3-(methylamino)-1-phenylpropan-1-ol)

Compound No. 53b (390 mg, 1.32 mmol) and TEA (0.459 mL, 3.29 mmol) in DCM (20 mL) were added and chilled to 0° C. To the chilled solution was added ethyl chloroformate (0.152 mL, 1.58 mmol) drop-wise over 10 minutes. The ice bath was removed, and the solution was allowed to warm to room temperature over a period of 3 hours. The reaction solution was concentrated and then diluted with ethyl acetate (100 mL) This solution was washed with 0.1N HCl (2×15 mL), saturated sodium bicarbonate (15 mL), and brine (20 mL), then dried over MgSO$_4$, filtered, and concentrated in vacuo. The residue was concentrated to afford 440 mg (91%). The lot of this material (440 mg, 1.19 mmol) was taken up in 25 mL of dry THF and was transferred to a 100 mL 3-neck round bottom flask equipped with a magnetic stirrer, addition funnel, thermometer, and Dean-Stark trap fitted with a condenser and nitrogen inlet. The solution was heated to a gentle reflux (66° C.), and a solution of BH$_3$/SMe$_2$ (1.792 mL, 3.58 mmol) was added drop-wise over 10 minutes. Dimethyl sulfide distillate was collected (bp 38° C.). After 7 hours, the reaction was ~85% complete. Another portion of BH$_3$/SMe$_2$ (1.792 mL, 3.58 mmol) was added, and stirring continued for another 2 hours. The reaction was cooled to room temperature and treated with 4N HCl in dioxane (0.32 mL). The careful addition of methanol (10 mL) was completed with exothermic gas evolution. The reaction was then heated to distill a 1:1 azeotrope of methanol and trimethyl borate. As most of the methanol was distilled, the heat was removed, and the mixture diluted with ether (10 mL) to give a white precipitate. The solid was washed with ether and ethyl acetate to afford 250 mg (60%) the product as an HCl salt. $^1$H NMR (500 MHz, DMSO-d6) δ 2.40-2.61 (m, 3H), 3.29 (s, 2H), 3.48 (br. s., 1H), 4.76 (d, J=5.5 Hz, 1H), 6.04 (br. s., 1H), 7.00-7.34 (m, 5H), 7.46 (d, J=2.1 Hz, 2H), 8.19 (br. s., 1H), 8.49 (br. s., 1H).

Example 53a—Synthesis of Compound No. 53a
(rac-anti-2-(3,4-dichlorophenyl)-3-hydroxy-3-phenylpropanenitrile)

A 250 mL round bottom flask equipped with a magnetic stirring bar, nitrogen inlet, and septum was charged with THF (50 mL) and 1.8 M LDA (9.91 mL, 17.84 mmol). After cooling to −78° C., 2-(3,4-dichlorophenyl)acetonitrile (3.32 g, 17.84 mmol) was added. After 1 hour, benzaldehyde (1.803 mL, 17.84 mmol) was added via syringe. After stirring at −78° C. for 3 hours, the reaction was quenched by the addition of water (20 mL) while stirring at −70° C. The aqueous layer was extracted with Et$_2$O (2×50 mL), and the combined organic extracts were washed with brine (50 mL), dried with MgSO$_4$, and concentrated in vacuo to give the crude aldol. Column chromatography on silica gel eluting with 0-30% of ethyl acetate in hexane afforded the product as 3:1 anti:syn mixture (2.5 g). Recrystallization from DCM (30 mL) and hexane (2:3) gave 700 mg of the anti isomer (13%). $^1$H NMR (500 MHz, CDCl$_3$) δ 2.39 (d, J=3.7 Hz, 1H), 4.03 (d, J=5.5 Hz, 1H), 4.98 (dd, J=5.5, 3.7 Hz, 1H), 6.74-7.55 (m, 8H).

Example 53b—Synthesis of Compound No. 53b
(rac-anti-3-amino-2-(3,4-dichlorophenyl)-1-phenylpropan-1-ol)

Compound No. 53a (650 mg, 2.22 mmol) in THF (25 mL) was heated to a gentle reflux at 76° C. and treated with BH$_3$/SMe$_2$ (6.41 mL, 12.825 mmol) added drop-wise over 5 minutes. Liberated dimethyl sulfide was collected in a Dean-Stark trap. After 3.5 hours. the mixture was allowed to cool to ambient temperature and concentrated in vacuo, and the residue was dissolved in ethyl acetate (100 mL). The combined extracts were washed with saturated aq. NaHCO$_3$ and brine, dried over MgSO$_4$, filtered, and concentrated to give the crude product. The residue was dissolved in DCM and filtered. To the filtrate was added 1 mL of 2N HCl in dioxane which was stirred for 10 minutes before concentration to afford 620 mg (94%) as an HCl salt. $^1$H NMR (500 MHz, DMSO-d6) δ 3.19-3.27 (m, 2H), 3.34-3.47 (m, 2 H), 4.77 (d, J=4.3 Hz, 1H), 5.96 (d, J=3.4 Hz, 1H), 6.99-7.32 (m, 4H), 7.36-7.53 (m, 2H), 7.77 (br. s., 2H).

Example 54—Synthesis of Compound ID No. 54
((2RS,3RS)-2-(4-methoxy-3-methylphenyl)-3-(methylamino)-1-phenylpropan-1-ol)

To LAH (2.218 mL, 2.22 mmol) in dry THF (3 mL) at 55° C. under N$_2$ was added Compound No. 54c (277 mg, 0.81 mmol) in THF (3 mL) drop-wise via syringe over about 5 minutes. The reaction mixture was then heated at reflux for 2 hours. The reaction mixture was quenched carefully with saturated aqueous Na$_2$SO$_4$, and then saturated NaHCO$_3$. The aqueous solution was diluted with ether and stirred briefly. Then, the ether layer was isolated, and the aqueous layer was extracted twice more with ether. The ethereal layers were combined, washed with brine, dried over sodium sulfate, filtered, and concentrated to afford 233 mg (90%) of product. $^1$H NMR (500 MHz, CDCl$_3$) δ 1.85 (t, J=3.4 Hz, 1H) 2.11 (s, 3H) 2.48 (s, 3H) 2.81-2.88 (m, 1H) 3.01 (dd, J=12.1, 3.2 Hz, 1H) 3.19 (dd, J=11.9, 9.5 Hz, 1H) 3.74-3.78 (m, 3H) 4.98 (d, J=7.9 Hz, 1H) 6.62 (d, J=7.9 Hz, 1H) 6.75-6.83 (m, 2H) 7.07-7.22 (m, 5H).

Example 54a—Synthesis of Compound No. 54a (3-hydroxy-2-(4-methoxy-3-methylphenyl)-3-phenylpropanenitrile)

To a 200 mL oven dried round bottom flask charged with THF (95 mL) was added the lithium bis(trimethylsilyl) amide (13.65 mL, 13.65 mmol). The reaction mixture was cooled to −78° C., and the 2-(4-methoxy-3-methylphenyl) acetonitrile (2 g, 12.41 mmol) was added neat via syringe over a period of 5 minutes. The reaction mixture was then stirred at −78° C. for 30 minutes before the benzaldehyde (1.254 mL, 12.41 mmol) was added in 1 mL THF. The reaction mixture was stirred at −78° C. for 1 hour, and then quenched with HOAc. The low temp bath was removed, and the mixture was allowed to warm. After 10 minutes, the solution was diluted with 1N HCl and water. The organic layer was isolated, and the aqueous layer was extracted twice with ether. The combined organic layer was washed with brine, dried over Na$_2$SO$_4$, filtered, and concentrated. Both the syn and anti were isolated via column chromatography using 30% EtOAc in hexanes to afford 2.74 g (83%) of product. $^1$H NMR (500 MHz, CDCl$_3$) δ 2.18 (s, 3H) 3.81 (s, 3H) 3.98 (d, J=5.5 Hz, 1H) 4.93 (d, J=5.4 Hz, 1H) 6.75 (d, J=8.2 Hz, 1H) 7.00 (d, J=2.9 Hz, 2H) 7.27-7.38 (m, 5H).

Example 54b—Synthesis of Compound No. 54b (3-amino-2-(4-methoxy-3-methylphenyl)-1-phenyl-propan-1-ol)

To a solution of Compound No. 54a (2.65 g, 9.91 mmol) in THF (50 mL) heated at 75° C. was added the borane•dimethylsulfide complex (12.39 mL, 24.78 mmol) drop-wise via syringe. The reaction mixture was then heated at 75° C. for 4 hours. LCMS showed no starting material. The reaction mixture was cooled to room temperature and concentrated to remove the THF. The residue was dissolved in EA and carefully washed twice with saturated NaHCO$_3$ followed by brine. The organic layers were dried over sodium sulfate, filtered, and concentrated to give 2.72 g (100%) of the mixed anti and syn product. $^1$H NMR (500 MHz, CDCl$_3$) δ 2.20 (s, 3H) 2.75-2.84 (m, 1H) 2.85-2.88 (m, 1H) 2.87-3.01 (m, 2H) 3.82 (s, 3H) 4.83 (d, J=7.3 Hz, 1H) 6.78 (d, J=8.2 Hz, 1H) 6.98 (s, 2H) 7.23-7.34 (m, 6H).

Example 54c—Synthesis of Compound No. 54c (ethyl 3-hydroxy-2-(4-methoxy-3-methylphenyl)-3-phenylpropylcarbamate)

To a solution/suspension of Compound No. 54b (1 g, 3.69 mmol) in dichloromethane (20 mL) was added TEA (2.06 mL, 14.74 mmol). The reaction mixture was cooled to 0° C., and the ethyl chloroformate (0.423 mL, 4.42 mmol) was added drop-wise via syringe. The reaction mixture was then stirred at 0° C. for several minutes, allowed to warm to room temperature, and stirred for 1 hour. The reaction mixture was diluted with DCM and washed with 1N HCl, saturated NaHCO, and brine, dried (Na SO filtered), and concentrated. The material was purified via 12 g silica gel column using 0% (hold for 4 minutes) to 30% EA/Hex over 15 minutes, resulting in the collection of 297 mg of the anti isomer. $^1$H NMR (500 MHz, DMSO-d6) δ 1.06 (t, J=7.2 Hz, 3H) 2.03 (s, 3H) 2.95-3.05 (m, 1H) 3.29-3.38 (m, 1H) 3.44 (s, 1H) 3.69 (s, 4H), 3.87 (d, J=7.0 Hz, 2H) 4.68 (dd, J=6.7, 4.6 Hz, 1H) 5.34 (d, J=4.6 Hz, 1H) 6.49-6.59 (m, 1H) 6.70 (d, J=7.9 Hz, 1H) 6.78-6.88 (m, 2H) 7.16 (dd, J=19.8, 7.0 Hz, 5H).

Example 55—Synthesis of Compound ID No. 55 ((1S,2S)-2-(4-methoxy-3-methylphenyl)-3-(methylamino)-1-phenylpropan-1-ol)

42 mg of the racemate described in Example 54 was separated into its enantiomers using a chiral stationary phase supercritical fluid chromatography (Multigram III SFC system) on an ADH column (30×250 mm) The 42 mg of sample were diluted in 3 mL of ethanol (0.5% isopropylamine), and stacked injections of 0.5 mL each were run using 18% of isopropanol (0.5% isopropylamine) isocratic at 50 mL/minute, which gave enantiomer retention times of 6.60 and 7.62 minutes, respectively. The combined fractions of the first eluting enantiomer were concentrated in vacuo and converted to an HCl salt, which afforded 13 mg of Compound ID No. 55, which was shown by the above described SCF system to have 99% enantiomeric excess. $^1$H NMR (500 MHz, DMSO-d6) δ 7.08-7.24 (m, 5H) 6.91 (s, 1H) 6.88 (dd, J=8.39, 1.98 Hz, 1H) 6.75 (d, J=8.54 Hz, 1 FT) 5.99 (d, J=2.75 Hz, 1H) 4.72 (d, J=6.71 Hz, 1H) 3.70 (s, 3H) 3.50 (d, J=8.85 Hz, 1H) 3.12-3.26 (m, 2H) 2.50-2.55 (m, 3H) 2.05 (s, 3H). Since this compound was the more potent enantiomer at hNET, it was presumed to be (1S,2S)-configured.

Example 56—Synthesis of Compound ID No. 56 ((1RS,2RS)-3-(methylamino)-2-(naphthalen-2-yl)-1-(o-tolyl)propan-1-ol)

Compound ID No. 56 is the racemate of Compound ID No. 28. It was synthesized as described in Example 28, except that the enantiomers were not separated.

Example 57—Synthesis of Compound ID No. 57 ((S)-3-(2-methoxyphenyl)-N-methyl-2-(naphthalen-2-yl)propan-1-amine)

Carbamate reduction and acidification was done in the usual way using Compound No. 57a (308 mg, 0.79 mmol) to give 226 mg (0.66 mmol, 84%) of a white powder. H NMR (400 MHz, CD$_3$OD) δ 6.31 (d, J=8.6 Hz, 1H), 6.29-6.21 (m, 2H), 6.11 (s, 1H), 5.94-5.88 (m, 2H), 5.85 (dd, J=8.5, 1.8 Hz, 1H), 5.60-5.55 (m, 1H), 5.33 (dd, J=12.2, 4.8 Hz, 2H), 5.15 (t, J=7.4 Hz, 1H), 2.25 (s, 3H), 1.99-1.91 (m, 2H), 1.78 (d, J=10.2 Hz, 1H), 1.61-1.54 (m, 1H), 1.42 (dd, J=13.3, 6.7 Hz, 1H), 1.05 (s, 3H). HRMS (ESI-TOF) calculated for C$_{21}$H$_{24}$NO (MH$^+$) 306.1858 found 306.1863 (+1.6 ppm, 0.5 mmu).

This racemate was separated into its enantiomers using a chiral stationary phase supercritical fluid chromatography (Multigram III SFC system). Enantiomer retention times of 4.82 and 5.47 minutes were achieved. The combined fractions of the second eluting enantiomer were concentrated in vacuo and converted to an HCl salt, affording 33 mg of Compound ID No. 57, which was shown by the previously described SCF system to have >98.2% enantiomeric excess. $^1$H NMR (500 MHz, DMSO-d6) δ 7.78-7.89 (m, 3H), 7.71 (s, 1H), 7.41-7.52 (m, 3H), 7.11 (dd, J=15.56, 1.53 Hz, 1H), 6.88-6.98 (m, 2H), 6.71 (d, J=7.02 Hz, 1H), 3.75 (s, 3H), 3.52-3.62 (m, 1H), 3.29 (s, 1H), 3.14-3.25 (m, 1H), 3.09 (dd, J=13.73, 6.41 Hz, 1H), 2.93 (dd, J=13.73, 8.54 Hz, 1H), 2.48

(s, 3H). Since this enantiomer is more potent at hNET than the first-eluting enantiomer, it was presumed to be (S)-configured.

Example 57a—Synthesis of Compound No. 57a (tert-butyl (3-(2-methoxyphenyl)-2-(naphthalen-2-yl)propyl)carbamate)

The aldol condensation using sodium ethoxide, ethanol, 2-anisaldehyde (0.64 mL, 5.25 mmol), and 2-naphthylacetonitirle (836 mg, 5.0 mmol) was performed in the usual way to give 1.26 g (4.40 mmol, 88%) of a bright yellow solid. The conjugate reduction was performed in the usual way with a portion of the above material (527 mg, 1.93 mmol) to give 489 mg (1.68 mmol, 91%) of a crude yellow oil. The oil was then dissolved in 10 mL of THF and cooled to 0° C. DIEA (0.7 mL, 4 mmol) and DMAP (ca. 5 mg) were added followed by $Boc_2O$ (440 mg, 2.15 mmol). The solution was allowed to warm to room temperature overnight. In the morning, 1 mL of water and 10 mL of diethyl ether were added. The contents were poured into a separatory funnel and extracted with ether (2×15 mL). The organics were dried over $Na_2SO_4$, filtered, and concentrated. The residue was purified via silica gel flash chromatography (10% EtOAc in hexanes) to give 553 mg (1.4 mmol, 84%) of a colorless gum. A portion of this material was used for the preparation of Compound ID No. 57.

Example 58—Synthesis of Compound ID No. 58 (1S,2S or 1R,2R)-1-(5-chlorothiophen-2-yl)-3-(methylamino)-2-(naphthalen-2-yl)propan-1-ol)

anti-3-(5-chlorothiophen-2-yl)-3-hydroxy-2-(naphthalen-2-yl)propanenitrile: A solution of 2-naphthylacetonitrile (1 g, 5.98 mmol) in 50 mL of dry THF was place in an oven-dried round bottom flask containing stirrer under nitrogen. Diisopropylamine (1.006 mL, 7.18 mmol) was added. The mixture was stirred and cooled to −78° C. for 20 minutes. 2.5M butyllithium (2.87 mL, 7.18 mmol) was then added slowly with a syringe. After 30 minutes of stirring at −78° C., 5-chlorothiophene-2-carboxaldehyde (2.87 mL, 7.18 mmol) was added drop-wise via syringe. After 10 minutes, the reaction was quenched quickly with 25 mL 2:1 THF/acetic acid. Cold bath was removed, and the reaction was allowed to reach room temperature. Water was added, and the aqueous layer was extracted with EtOAc (3×25 mL). The combined organic layers were washed with water and brine, dried over $MgSO_4$, and concentrated using a rotary evaporator. The residue was then dissolved in 5 mL of DCM, and hexane was slowly added until the solution turned turbid. This was left overnight at room temperature. Brown crystals were filtered, washed with hexane, and dried (0.666 g, 35.5%). $^1H$ NMR ($CDCl_3$): δ 7.89-7.72 (m, 4H), 7.57-7.49 (m, 2H), 7.32 (dd, 1H, J=8.7, 1.8 Hz), 6.70 (d, 1H, J=3.8 Hz), 6.61 (d, 1H, J=3.8 Hz), 5.22 (d, 1H, J=5.8 Hz), 4.26 (d, 1H, J=5.8 Hz), 2.72 (s, 1H).

anti-3-amino-1-(5-chlorothiophen-2-yl)-2-(naphthalen-2-yl)propan-1-ol and tert-Butyl-3-(5-chlorothiophen-2-yl)-3-hydroxy-2-(naphthalen-2-yl)propyl)carbamate: anti-3-(5-chlorothiophen-2-yl)-3-hydroxy-2-(naphthalen-2-yl) propanenitrile (0.412 g, 1.313 mmol), dissolved in 6 mL of dry THF, was placed in an oven-dried round-bottom flask under nitrogen. To this was added 1M Borane-THF solution (5.25 mL, 5.25 mmol) via syringe. This mixture was stirred at 60° C. overnight while monitoring the reaction progress by TLC. After quenching the reaction with cautious addition of $NaHCO_3$, the reaction mixture was poured into a separatory funnel, and the aqueous layer was extracted with EtOAc (3×25 mL). The combined organic layers were washed with water and brine, dried over $MgSO_4$, and concentrated in vacuo. The residue was dissolved in DCM, 1N HCl was added, and the mixture was stirred. The solvents were evaporated in vacuo, and the resulting salt was leached with DCM and lyophilized yielding the product as an off white solid (0.395 g, 85%). $^1H$ NMR ($CD_3OD$): δ 7.87-7.72 (m, 3H), 7.59 (s, 1H), 7.50-7.41 (m, 2H), 7.27 (d, 1H, J=8.4 Hz), 6.43 (d, 1H, J=3.6 Hz), 6.21 (d, 1H, J=3.6 Hz), 5.12 (d, 1H, J=9.0 Hz), 3.66 (m, 1H), 3.28 (in, 2H). MS m/z (ESI) 318.03 ($MH^+$). This relative configuration of this compound was assigned (1S,2S/1R,2R) based on the high J-value (9.0 Hz) of its benzylic proton.

anti-Ethyl-3-(5-chlorothiophen-2-yl)-3-hydroxy-2-(naphthalen-2-yl)propyl)carbamate: To a solution of anti-3-amino-1-(5-chlorothiophen-2-yl)-2-(naphthalen-2-yl)propan-1-ol hydrochloride (0.4 g, 1.129 mmol) in 10 mL dry DCM at −10° C. was added triethylamine (TEA) (0.472 mL, 3.39 mmol) drop-wise, followed by slow addition of ethyl chloroformate (0.130 mL, 1.355 mmol) via syringe. After stirring for 10 minutes at −10° C., the ice bath was removed, and the mixture was stirred and allowed to reach 0° C. The reaction was quenched with saturated $NaHCO_3$, and the reaction mixture was diluted with DCM and poured into a separatory funnel containing water. The layers were separated, and the aqueous layer was extracted with DCM (3×25 mL). The combined DCM extracts were washed with water, dried over $MgSO_4$, and concentrated under reduced pressure. The resulting residue was purified by flash chromatography over silica gel (eluent: 15-40% EtOAc in hexanes) to afford a gummy, transparent product (0.35 g, 80%). $^1H$ NMR ($CDCl_3$): δ 7.75-7.63 (m, 3H), 7.58 (s, 1H), 7.41-7.33 (m, 2H), 7.22 (bd, 1H, J=8.4 Hz), 6.51 (d, 1H, J=3.6 Hz), 6.40 (d, 1H, J=3.6 Hz), 5.20 (dd, 1H, J=8.7, 4.8 Hz), 4.85 (bt, 1H), 4.23 (bs, 1H), 4.13-4.05 (m, 2H), 3.90 (m, 1H), 3.55 (m, 1H), 3.26 (m, 1H), 1.24 (t, 3H, J=6.7 Hz). MS m/z (ESI) 372.09 $(M+H_2O+H)^+$.

Compound ID No. 58: anti-Ethyl-3-(5-chlorothiophen-2-yl)-3-hydroxy-2-(naphthalen-2-yl)propylcarbamate (2.45 g, 6.39 mmol), dissolved in 50 mL of dry THF, was placed in an oven-dried round-bottom flask under nitrogen. To this, 1M Borane-THF solution (25.6 mL, 25.6 mmol) was added via syringe. The resulting mixture was stirred at 60° C. overnight. After quenching the reaction with cautious addition of $NaHCO_3$, the reaction mixture was poured into a separatory funnel, and the aqueous layer was extracted with EtOAc (3×50 mL) The combined organic layers were sequentially washed with water and brine, dried over $MgSO_4$, and concentrated using a rotary evaporator. The residue was dissolved in DCM, 1N HCl was added, and the mixture was stirred for a few minutes. The solvents were removed in vacuo. The product was leached with DCM and lyophilized yielding an off-white powder with a pungent odor (0.2879 g, 0.782 mmol, 87%). $^1H$ NMR (DMSO-d6) δ 8.59 (br. s., 1H), 8.28 (br. s., 1H), 7.70-8.02 (m, 4H), 7.16-7.65 (m, 3H), 6.31-6.85 (m, 3H), 5.13 (d, 1H, J=5.5 Hz), 2.84-3.79 (m, 5H). MS m/z (ESI) 332.22 ($MH^+$). This racemic anti-compound was resolved by Multigram II SFC Chiral chromatography system. $^1H$ NMR (500 MHz, DMSO-d6) δ 7.80-7.94 (m, 3H), 7.75 (s, 1H) 7.38-7.57 (m, 3H), 6.72 (d, 1 h, J=4.0 Hz), 6.62-6.69 (m, 1H), 6.40 (d, 1H, J=3.7 Hz) 5.13 (d, 1H, J=6.4 Hz) 3.53-3.65 (m, 1H) 3.34-3.46 (m, 2H) 2.53 (t, 3H, J=5.3 Hz). Compound ID No. 58 could be either 1S,2S or 1R,2R configured as the two enantiomers could not be assigned absolute configuration because of their similar inhibitory activity on the hNET.

Example 59—Synthesis of Compound ID No. 59 ((S)-2-(3,4-dichlorophenyl)-N-methyl-3-(pyridin-3-yl)propan-1-amine)

Compound No. 59b (858 mg, 2.42 mmol) was dissolved in $CH_2Cl_2$ (15 mL), followed by addition of triethylamine (1.7 mL, 12.1 mmol). The solution was chilled to 0° C., and ethyl chloroformate was added (0.32 mL, 3.4 mmol). The solution was allowed to stir at 0° C. for 2 hours and warmed to room temperature overnight. In the morning, the contents were poured into a separatory funnel and extracted with EtOAc (3×15 mL). Organics were dried over $MgSO_4$, filtered, and concentrated to give a residue that was purified via silica gel flash chromatography (75% EtOAc in hexanes) to give 179 mg (0.51 mmol, 21%) of a colorless gum. To an oven dried 2 neck 100 mL round bottom flask equipped with a stir bar and a nitrogen inlet was added a portion of the above material (177 mg, 0.5 mmol) and 10 mL of dry THF. With stirring was added a 1M solution of $BH_3$/THF (3.0 mL, 3.0 mmol) in THF. Upon addition of borane, the system was fitted with a reflux condenser and heated to 80° C. for 24 hours. After cooling to room temperature, 5 mL of methanol was carefully added. Upon cessation of bubbles, the system was heated to reflux for 1 hour. The volatiles were then removed in vacuo, and to the residue was added 10 mL of methanol and 2 mL of a 4M HCl solution in dioxane. The homogenous solution was concentrated to give a white amorphous solid that after trituration with diethyl ether was free based and purified via silica gel flash chromatography (8% $CH_3OH$ in $CH_2Cl_2$ with 1 mL $NH_4OH$ per 100 mL eluent) to give 59 mg (0.2 mmol, 40%) of the free base. $^1H$ NMR (400 MHz, $CD_3OD$) δ 8.30 (dd, J=4.8, 1.3 Hz, 1H), 8.17 (d, J=1.9 Hz, 1H), 7.55 (d, J=7.8 Hz, 1H), 7.41 (d, J=8.3 Hz, 1H), 7.34 (d, J=2.0 Hz, 1H), 7.28 (dd, J=7.9, 4.8 Hz, 1H), 7.10 (dd, J=8.3, 2.0 Hz, 1H), 3.16-3.07 (m, 2H), 2.93-2.81 (m, 3H), 2.35 (s, 3H). HRMS (ESI-TOF) calculated for $C_{15}H_{17}Cl_2N_2$ ($MH^+$) 295.0763 found 295.0770 (+4.58 ppm, 0.7 mmu).

This racemate was separated into its enantiomers using a chiral stationary phase supercritical fluid chromatography (Multigram III SFC system) on an ADH column (21.1×250 mm). Isocratic elution using 17% i-PrOH (containing 0.5% dimethylamine) at an appropriate flow rate gave enantiomer retention times of 8.76 and 10.88 minutes, respectively. The combined fractions of the second eluting enantiomer were concentrated in vacuo, and converted to an HCl salt that afforded 31 mg of Compound ID No. 59, which was shown by the previously described SCF system to have 96.6% enantiomeric excess. $^1H$ NMR (300 MHz, $CDCl_3$) δ 8.41 (d, J=3.4 Hz, 1H) 8.29 (d, J=1.5 Hz, 1H), 7.33 (d, J=7.9 Hz, 1H), 7.27-7.32 (m, 1H), 7.23 (d, J=2.3 Hz, 1H), 7.13 (dd, J=7.9, 4.9 Hz, 1H), 6.94 (dd, J=8.3, 1.9 Hz, 1H), 2.95-3.12 (m, 2H), 2.72-2.92 (m, 3H), 2.38 (s, 3H). Since this enantiomer was more potent at hNET than the first eluting enantiomer, it was presumed to be (5)-configured.

Example 59a—Synthesis of Compound No. 59a (2-(3,4-dichlorophenyl)-3-(pyridin-3-yl)propanenitrile)

An oven dried 2 neck 250 mL round bottom flask was charged with 3,4-dichlorophenyl acetonitrile (763 mg, 4.1 mmol). The system was degassed and backfilled with $N_2$. Dry DMF (25 mL) was added followed by addition of NaH (60% dispersion in oil, 384 mg, 9.6 mmol). The dark red solution was allowed to stir for 30 minutes at room temperature. 3-(bromomethyl)pyridine hydrobromide (1.01 g, 4.0 mmol) was added in one portion. Upon addition, the solution was stirred for an additional 0.5 hours. The red solution was quenched by the addition water (10 mL) and brine (5 mL). 20 mL of EtOAc was added, and the contents of the flask were poured into a separatory funnel, extracted with EtOAc (3×40 mL), and dried over $Na_2SO_4$. The residue was concentrated and purified via silica gel flash chromatography (50% EtOAc in hexane) to give 322 mg (1.16 mmol, 29%) of a yellow oil. $^1H$ NMR (400 MHz, $CDCl_3$) δ 8.55 (d, J=3.5 Hz, 1H), 8.35 (d, J=1.7 Hz, 1H), 7.49 (dt, J=7.8, 1.8 Hz, 1H), 7.45 (d, J=8.3 Hz, 1H), 7.37 (d, J=2.2 Hz, 1H), 7.31-7.23 (m, 1H), 7.07 (dd, J=8.3, 2.2 Hz, 1H), 4.03 (t, J=7.1 Hz, 1H), 3.18 (dd, J=7.1, 1.7 Hz, 2H).

Example 59b—Synthesis of Compound No. 59b (2-(3,4-dichlorophenyl)-3-(pyridin-3-yl)propan-1-amine dihydrochloride)

To an oven dried 2 neck 100 mL round bottom flask equipped with a stir bar and a nitrogen inlet was added Compound No. 59a (640 mg, 2.3 mmol) and 15 mL of dry THF. With stirring was added $BH_3/SMe_2$ (5.8 mL, 11.5 mmol). Upon addition of borane, the system was fitted with a reflux condenser and heated to reflux for 6 hours. After cooling to room temperature, 5 mL of methanol was carefully added. Upon cessation of bubbles, the system was heated to reflux for 1 hour. The volatiles were then removed in vacuo, and to the residue was added 10 mL of methanol and 2 mL of a 4M HCl solution in dioxane. The homogenous solution was concentrated to give a white amorphous solid that after trituration with diethyl ether yielded 813 mg of the dihydrochloride (2.3 mmol, >99%). $^1H$ NMR (400 MHz, $CD_3OD$) δ 8.70 (d, J=5.6 Hz, 1H), 8.66 (d, J=0.9 Hz, 1H), 8.44-8.36 (m, 1H), 7.98 (dd, J=8.1, 5.8 Hz, 1H), 7.53 (t, J=5.2 Hz, 2H), 7.26 (dd, J=8.3, 2.1 Hz, 1H), 3.49-3.38 (m, 4H), 3.18 (dd, J=15.2, 11.6 Hz, 2H). HRMS (ESI-TOF) calculated for $C_{14}H_{15}Cl_2N_2$ ($MH^+$) 281.0607, found 281.0581 (−9.08 ppm, 2.6 mmu).

Example 60—Synthesis of Compound ID No. 60 ((1R,2S)-1-(2-fluorophenyl)-3-(methylamino)-2-(naphthalen-2-yl)propan-1-ol)

The syn-nitrile aldol (Compound No. 60a, described in Example 15a above; 285 mg, 0.98 mmol) was reduced and acidified in the usual way with $BH_3$/THF (1M in THF, 4.9 mL, 4.9 mmol) and 4 N HCl in dioxane (2 mL) to afford 308 mg of a white solid (0.93 mmol, 95%) that was used directly in the next step. A portion of this HCl salt (298 mg, 0.9 mmol) was carbamylated with ethyl chloroformate (0.12 mL, 1.3 mmol) and triethylamine (0.5 mL, 3.6 mmol) in $CH_2Cl_2$ at 0° C. in the usual way to give 276 mg (0.75 mmol, 84%) of a white foamy solid. The entire lot of this material was reduced with $LiAlH_4$ (86 mg, 2.25 mmol) in dry THF (10 mL) in the usual way to give 184 mg (0.59 mmol, 79%) of a solid white powder. $^1H$ NMR (400 MHz, $CD_3OD$) δ 7.81-7.72 (m, 3H), 7.62 (s, 1H), 7.45-7.36 (m, 3H), 7.22 (t, J=7.1 Hz, 2H), 7.06-6.95 (m, 2H), 5.35 (d, J=6.3 Hz, 1H), 3.36 (s, 1H), 3.14-3.02 (m, 1H), 2.85 (dd, J=11.9, 5.3 Hz, 1H), 2.27 (s, 3H). HRMS (ESI-TOF) calculated for $C_{20}H_{21}FNO$ ($MH^+$) 310.1602 found 310.1616 (4.67 ppm, 1.4 mmu).

This racemate was separated into its enantiomers using a chiral stationary phase supercritical fluid chromatography (Multigram III SFC system) on an Amylose column (21.1×250 mm). Isocratic elution using 7.5% MeOH (containing 0.5% isopropylamine) at an appropriate flow rate gave enantiomer retention times of 9.81 and 10.01 minutes, respectively. The combined fractions of the second eluting enantiomer were concentrated in vacuo and converted to an HCl salt that afforded 67.5 mg of Compound ID No. 60, which was shown by the previously described SCF system to have 85% enantiomeric excess. $^1$H NMR (300 MHz, CDCl$_3$) δ 7.67-7.83 (m, 3H), 7.61 (s, 1H), 7.28-7.48 (m, 4H), 7.15 (d, J=7.6 Hz, 1H), 7.02 (t, J=7.6 Hz, 1H), 6.92 (d, J=9.7 Hz, 1H), 5.46 (d, J=5.9 Hz, 1H), 3.48 (q, J=6.3 Hz, 1 H), 2.95-3.10 (m, 2H), 2.37 (s, 3H). Since this syn-enantiomer is more potent at hNET than the first-eluting enantiomer, it was presumed to be (1R,2S)-configured.

Example 61—Synthesis of Compound ID No. 61 (2S,3R)-3-chloro-N-methyl-2-(naphthalen-2-yl)-3-phenylpropan-1-amine)

To a solution of (1S,2S)-3-(methylamino)-2-(naphthalen-2-yl)-1-phenylpropan-1-ol hydrochloride, (0.100 g, 0.343 mmol) in 5 mL of dry DCM in an oven-dried round bottom flask was added thionyl chloride (2 mL, 0.343 mmol). The reaction flask was covered with aluminum foil, and the solution was stirred at room temperature for 30 minutes. The solvents were evaporated in vacuo, and the resulting salt was washed with ether, dried, and lyophilized to furnish the product as a white solid (0.102 g, 96%). $^1$H NMR (CD$_3$OD) δ 7.76-7.56 (m, 4H), 7.39-7.29 (m, 2H), 7.24 (d, 1H, J=9.6 Hz), 7.19-7.11 (m, 2H), 7.07-6.92 (m, 2H), 5.31 (d, 1H, J=9.8 Hz), 3.98-3.78 (m, 2H), 3.76-3.61 (m, 1H), 2.60 (s, 3H). MS m/z (ESI) 310.19 (MH$^+$) [α]$_D^{20}$+14.4 (c, 0.235, 9:1 EtOH: H$_2$O). The stereochemistry, according to the J value (9.8 Hz) of the benzylic proton, suggested an S,S configuration with total retention of configuration.

Example 62—Synthesis of Compound ID No. 62 ((1R,2R and 1S,2S)-3-(methylamino)-2-(naphthalen-2-yl)-1-(pyridin-3-yl)propan-1-ol)

anti-3-hydroxy-2-(naphthalen-2-yl)-3-(pyridin-3-yl)propanenitrile: 2-Naphthylacetonitrile (5.0 g, 29.9 mmol) was dissolved in 200 mL of dry THF under nitrogen. Diisopropylamine (5.03 mL, 35.9 mmol) was added, and the mixture cooled to −78° C. and stirred for 20 minutes. 2.5 M n-butyllithium (14.35 mL, 35.9 mmol) was then added slowly with a syringe. After 30 minutes of stirring at −78° C., pyridine 3-carboxaldehyde (3.56 mL, 35.9 mmol) was added into the reaction mixture. TLC showed completion of reaction after 100 minutes. The reaction was rapidly quenched with 25 mL 2:1 THF/acetic acid. The cold bath was removed, and the reaction was allowed to reach room temperature. Water was added, and the aqueous layer was extracted with EtOAc (3×25 mL) The combined organic layers were washed with water and brine, and dried over MgSO$_4$. Evaporation of the volatiles under reduced pressure gave a residue that was then crystallized twice with a 50:120 isopropyl alcohol:ether mixture to afford the diastereomeric products as a white fluffy solid (1.2 g, 14.6%). $^1$H NMR (DMSO-d$_6$) as a mixture of diastereomers (1:5) δ 8.94 (bs, 1H), 8.77 (d, 1H, J=5.4 Hz), 8.12-7.90 (m, 5H), 7.63-7.40 (m, 3H), 5.48 (d, minor isomer 1H, J=5.7 Hz), 5.38 (d, major isomer 1H, J=4.5 Hz), 4.97 (d, 1H, J=4.5 Hz), 2.50 (s, 1H). MS m/z (ESI) 275.23 (MH$^+$). The majority of the mass balance was a mixture of diastereomers that was separated at a later stage.

anti-3-amino-2-(naphthalen-2-yl)-1-(pyridin-3-yl)propan-1-ol: To a solution of anti-3-hydroxy-2-(naphthalen-2-yl)-3-(pyridin-3-yl) propanenitrile (0.650 g, 2.370 mmol) in 10 mL of dry THF was slowly added 1M borane-THF solution (9.48 mL, 9.48 mmol) via syringe under nitrogen. The resulting mixture was stirred at 60° C. overnight. The reaction progress was monitored by TLC. After cooling to ambient temperature, the reaction was quenched by cautious addition of NaHCO$_3$, and the reaction mixture was poured into a separatory funnel for phase separation. The aqueous layer was extracted with EtOAc (3×50 mL) The combined organic layers were washed with water and brine, dried over MgSO$_4$, and concentrated using a rotary evaporator. 4N HCl in Dioxane was added to the residue, and the mixture was vigorously stirred for a few minutes. The volatiles were evaporated in vacuo leaving a solid that was leached with ether several times and then dried high vacuum (0.74 g, 89%). $^1$H NMR (CD$_3$OD) as a mixture of diastereomers (1:2)$^1$H NMR δ (minor isomer-(1R,2S and 1S,2R)) 5.57 (d, 1H, J=3.0 Hz), and (major isomer-(1S,2S and 1R,2R)) 5.35 (d, 1H, J=9.3 Hz). MS m/z (ESI) 279.03 (MH$^+$).

anti-tert-Butyl-3-hydroxy-2-(naphthalen-2-yl)-3-(pyridin-3-yl)propylcarbamate: (anti-3-amino-2-(naphthalen-2-yl)-1-(pyridin-3-yl)propan-1-ol dihydrochloride (0.6 g, 1.708 mmol) was suspended in 10 mL of anhydrous DCM in an oven dried round bottom flask. Triethylamine (0.714 mL, 5.12 mmol) was then added, followed by slow addition of Boc anhydride (0.410 g, 1.879 mmol). The reaction mixture was stirred at room temperature and judged completed after 2 hours. After quenching the reaction with saturated NaHCO$_3$, the reaction mixture was poured into a separatory funnel, and the aqueous layer was extracted with DCM (3×25 mL). The combined organic layers were washed with water and brine, dried over MgSO$_4$, and concentrated using a rotary evaporator. The resulting residue was purified by flash chromatography over silica gel (elution with 50% EtOAc in hexanes) to afford a small amount of anti-product as a sticky yellowish solid (0.05 g, 8%) while the majority (68%) of the mixture could not be separated and was carried to the next step. $^1$H NMR (CDCl$_3$) δ 8.37 (bs, 1H), 8.27 (d, 1H, J=3.9 Hz), 7.74-7.66 (m, 3H), 7.55-7.32 (m, 4H), 7.16 (dd, 1H, J=7.8, 1.4 Hz), 7.04 (dd, 1H, J=7.8, 5.1 Hz), 4.98 (d, 1H, J=9.0 Hz), 4.84 (bm, 1H), 4.65 (bs, 1H), 3.90 (m, 1H), 3.58 (s, 1H), 3.22 (m, 1H), 1.44 (s, 9H). MS m/z (ESI) 379.03 (MH$^+$).

anti-3-(methylamino)-2-(naphthalen-2-yl)-1-(pyridin-3-yl)propan-1-ol: anti-tert-Butyl-3-hydroxy-2-(naphthalen-2-yl)-3-(pyridin-3-yl)propylcarbamate (0.050 g, 0.132 mmol) dissolved in 1 mL of dry THF was placed in an oven-dried round-bottom flask under nitrogen. Next, 1M borane-THF solution (0.528 mL, 0.528 mmol) was added via syringe. This mixture was stirred at 60° C. overnight while monitoring the reaction progress by TLC. After quenching the reaction with cautious addition of NaHCO$_3$, the reaction mixture was poured into a separatory funnel, and the aqueous layer was extracted with EtOAc (3×25 mL) The combined organic layers were washed with water and brine, dried over MgSO$_4$, and concentrated using a rotary evaporator. The residue was dissolved in DCM, 1N HCl was added, and the mixture was stirred for a few minutes. The solvents were evaporated in vacuo, and the resulting salt was leached with ether and dried under high vacuum furnishing the product as a white solid (0.041 g, 85%). $^1$H NMR (CD$_3$OD) δ 8.61 (d, 1H, J=5.65 Hz), 8.50 (s, 1H), 8.40 (d, 1H, J=8.1 Hz), 7.92-7.74 (m, 4H), 7.68 (s, 1H), 7.52-7.45 (m, 2H), 7.32 (dd, 1H, J=8.5, 1.7 Hz), 5.34 (d, 1H, J=9.2 Hz), 4.01-3.89 (m, 1H), 3.49-3.93 (m, 2H), 2.77 (s, 3H). MS m/z (ESI) 293.36 (MH$^+$).

3-Methylamino-2-(naphthalen-2-yl)-1-(pyridin-3-yl)propan-1-ol: To a solution of tert-butyl 3-hydroxy-2-(naphthalen-2-yl)-3-(pyridin-3-yl)propylcarbamate (0.350 g, 0.925 mmol) in 4 mL of dry THF was added under nitrogen via syringe a 1 M borane-THF solution (3.7 mL, 3.70 mmol). This mixture was stirred at 60° C. overnight while monitoring the reaction progress by TLC. After quenching the reaction with cautious addition of NaHCO$_3$, the reaction mixture was poured into a separatory funnel, and the aqueous layer was extracted with EtOAc (3×25 mL). The combined organic layers were washed with water and brine, dried over MgSO$_4$, and concentrated using a rotary evaporator. The residue was dissolved in DCM, 1N HCl was added, and the mixture was stirred for a few minutes. The solvents were evaporated in vacuo, and the resulting salt was leached with ether and dried under high vacuum furnishing the product as a white solid (0.320 g, 94.67%). MS m/z (ESI) 293.39 (MH$^+$).

anti- and syn-tert-Butyl-3-hydroxy-2-(naphthalen-2-yl)-3-(pyridin-3-yl)propyl(methyl)carbamate: To a suspension of 3-(methylamino)-2-(naphthalen-2-yl)-1-(pyridin-3-yl)propan-1-ol hydrochloride (0.320 g, 0.878 mmol) in 10 mL dry DCM at −10° C. was added triethylamine (TEA) (0.595 mL, 4.27 mmol) drop-wise. This was followed by slow addition of Boc anhydride (0.342 g, 1.566 mmol). After stirring for 1 hour at −10° C., the ice bath was removed, and the mixture was allowed to warm to 0° C. The reaction was quenched with saturated NaHCO$_3$, and the aqueous layer was extracted with DCM (3×25 mL). The combined DCM extracts were washed with water, dried over MgSO$_4$, and concentrated using a rotary evaporator. The resulting residue was purified by flash chromatography over silica gel (elution with 70% EtOAc in hexanes). The Boc-protected secondary amines were easier to separate by chromatography. The anti-diastereomer (identified by a high J value of 8.4 Hz) was isolated as a sticky yellowish solid (yield 0.150 g, 43.5%). $^1$H NMR (CDCl$_3$) δ 8.45 (d, 1H, J=1.8 Hz), 8.34 (d, 1H, J=6.6 Hz), 7.78-7.10 (m, 3H), 7.58 (m, 2H), 7.44-7.37 (m, 2H), 7.30 (bd, 1H, J=9.6 Hz), 7.10 (dd, 1H, J=7.8, 4.8 Hz), 5.07 (d, 1H, J=8.4 Hz), 3.84 (m, 2H), 3.40 (m, 1H), 2.50 (s, 3H), 1.44 (s, 9H). MS m/z (ESI) 393.09 (MH$^+$). syn-diastereomer was isolated as a white solid (0.100 g, 29.0%). $^1$H NMR (CDCl$_3$) δ 8.42-8.21 (m, 37.76-7.50 (m, 3H), 7.42 (bm, 2H), 7.26 (m, 1H), 6.93 (bm, 1H), 5.04 (m, 2H), 4.52 (m, 1H), 3.30-3.01 (m, 2H), 3.00 (s, 3H), 1.52 (s, 9H). MS m/z (ESI) 393.09 (MH$^+$).

Compound ID No. 62: anti-3-(methylamino)-2-(naphthalen-2-yl)-1-(pyridin-3-yl)propan-1-ol: tert-Butyl 3-hydroxy-2-(naphthalen-2-yl)-3-(pyridin-3-yl)propyl(methyl)carbamate (0.150 g, 0.382 mmol) suspended in 6 mL of 2N HCl in dioxane was stirred at room temperature for an hour. The solvents were evaporated using a rotary evaporator. The product was then washed and leached with ether, dried, and lyophilized to afford the product as a white solid (0.037 g, 29.4%). $^1$H NMR (CD$_3$OD) δ 8.61 (d, 1H, J=5.7 Hz), 8.50 (s, 1H), 8.40 (d, 1H, J=8.1 Hz), 7.92-7.74 (m, 4H), 7.68 (s, 1H), 7.52-7.45 (m, 2H), 7.32 (dd, 1H, J=8.48, 1.7 Hz), 5.34 (d, 1H, J=9.2 Hz), 4.01-3.89 (m, 1H), 3.49-3.93 (m, 2H), 2.77 (s, 3H). MS m/z (ESI) 293.39 (MH$^+$). $^1$H NMR (500 MHz, DMSO-d6) δ 8.93 (br. s., 1H), 8.61 (br. s., 2H), 8.46 (br. s., 1H), 8.19 (d, 1H, J=7.9 Hz), 7.67-7.93 (m, 4H), 7.49 (dq, 2H, J=4.9, 4.7 Hz), 7.39 (d, 1H, J=8.5 Hz), 5.18 (d, 1H, J=7.9 Hz), 3.36-3.75 (m, 4H), 2.46-2.67 (m, 3H).

Example 63—Synthesis of Compound ID No. 63 ((1R,2S)-1-(3-aminophenyl)-2-(3,4-dichlorophenyl)-3-(methylamino)propan-1-ol)

Compound No. 63c (4.5 g, 10.89 mmol) in THF (50 mL) was preheated at 76° C. for gentle-refluxing. Borane•dimethylsulfide complex (27.2 mL, 54.45 mmol) was added drop-wise over 30 minutes, and a Dean-Stark trap was set up to collect liberated SMe$_2$. The material was refluxed overnight and cooled to room temperature. The reaction mixture cooled in a cold water bath, and treated with 4M HCl in dioxane (1.5 mL) to generate a HCl salt. Then 10 mL of MeOH was added slowly to quench extra BH$_3$, maintaining the temperature under 25° C. Gas bubbles were formed as MeOH was added. The reaction mixture was heated to 64° C. (to make sure all of BH$_3$ was quenched) for 3 hours when the B(OMe)$_3$-MeOH complex was collected in a Dean-Stark trap. The reaction mixture was concentrated to give a white solid as an HCl salt of the desired product. The HCl salt was stirred in CHCl$_3$ (100 mL)/NaHCO$_3$ (saturated) for 10 minutes, the organic layer was separated from the aqueous, and the aqueous layer was extracted with CHCl$_3$ (20 mL×2). The combined CHCl$_3$ layer was dried over MgSO$_4$ and evaporated to give a yellow stinky oil. The yellow oil was added to a silica gel column and was eluted with 0-10% MeOH in CH$_2$Cl$_2$. The collected fractions gave the nitrophenyl aminoalcohol as a colorless gel 2.36 g (61% yield), and the desired anilino product was collected to give 150 mg (4.2%) of a colorless gel. Spectral data for desired aniline compound: $^1$H NMR (300 MHz, CDCl$_3$) δ 7.30 (d, J=8.2 Hz, 1H) 7.23 (d, J=2.1 Hz, 1H) 7.02 (t, J=7.7 Hz, 1H) 6.94 (dd, J=8.3, 2.0 Hz, 1H) 6.52 (dd, J=8.0, 2.3 Hz, 1H) 6.46 (d, J=7.8 Hz, 1H) 6.43 (d, J=1.9 Hz, 1H) 4.77 (d, J=5.9 Hz, 1H) 3.13 (q, J=6.6 Hz, 1H) 2.68-2.87 (m, 2H) 2.29 (s, 3H). The racemic anilino compound was separated using SFC (ADH column, 27% iPrOH with 0.5% dimethylethylamine) gave enantiomer retention times of 5.8 and 7.6 minutes, respectively. The combined fractions of the first eluting enantiomer were concentrated in vacuo and acidified in the usual way yielding 45 mg of Compound ID No. 63 as an HCl salt, which was shown by the above described SCF system to have >99% enantiomeric excess. $^1$H NMR (300 MHz, CDCl$_3$) δ 7.31 (d, J=8.0 Hz, 1H) 7.24 (d, J=2.1 Hz, 1H) 7.04 (t, J=7.6 Hz, 1H) 6.95 (dd, J=8.2, 1.9 Hz, 1H) 6.55 (dd, J=8.4, 1.7 Hz, 1H) 6.42-6.51 (m, 2H) 4.84 (d, J=5.5 Hz, 1H) 3.59 (br. s., 2H) 3.18 (q, J=6.5 Hz, 1H) 2.74-2.93 (m, J=11.9, 11.9, 11.8, 7.0 Hz, 2H) 2.36 (s, 3H). Since this compound was the more potent syn-enantiomer at hNET, it was presumed to be (1R,2S)-configured.

Example 63a—Synthesis of Compound No. 63a (2-(3,4-dichlorophenyl)-3-hydroxy-3-(3-nitrophenyl) propanenitrile)

2-(3,4-dichlorophenyl)acetonitrile (6 g, 32.25 mmol) was dissolved in THF (70 mL) and cooled to −75° C. n-Butyl lithium (22.17 mL, 35.48 mmol) was added slowly, and the reaction was stirred at −75° C. for 20 minutes. 3-nitrobenzaldehyde (5.36 g, 35.48 mmol) in THF (20 mL) was added drop-wise, maintaining the temperature under −70° C. After the addition, the reaction was stirred at −75° C. for another hour. Then, acetic acid (2.77 mL, 48.38 mmol) was added at −75° C. to quench the reaction. The reaction mixture was warmed to room temperature and diluted with saturated NaHCO$_3$ (50 mL), and the organic layer was separated from the aqueous layer. The aqueous layer was extracted with ether (100 mL×2), and the combined organic layer was dried through MgSO$_4$ and evaporated to give an orange colored oil. This residue was added to a silica gel column and was eluted with 0-100% EtOAc in hexane. Most of the fractions were a mixture of anti and syn isomers. The combined collection of the mixtures was evaporated to give a sticky yellow oil (11.1 g, 87% yield) containing both syn and anti isomers. ¹H NMR (300 MHz, CDCl₃) δ 8.19-8.26 (m, 1H) 8.13-8.19 (m, 1H) 7.52-7.71 (m, 2H) 7.41-7.49 (m, 1H) 7.33-7.41 (m, 1H) 7.02-7.14 (m, 1H) 5.15 (dd, J=6.6, 3.3 Hz, 1H) 4.09 (d, J=6.5 Hz, 1H) 2.60-2.78 (m, 1H).

Example 63b—Synthesis of Compound No. 63b
(3-amino-2-(3,4-dichlorophenyl)-1-(3-nitrophenyl)
propan-1-ol)

Compound No. 63a (11 g, 27.83 mmol) in THF (100 mL) was preheated at 76° C. for gentle refluxing. The solution of borane dimethyl sulfide complex (34.8 mL, 69.57 mmol) in THF was added drop-wise over 15 minutes, and a Dean-Stark trap was set up to collect liberated dimethylsulfide. The reaction was allowed to stir while heating for 4 hours. Upon cooling, the reaction mixture was cooled in a cold water bath and quenched with extra BH₃ with 20 mL of MeOH slowly, maintaining the temperature under 25° C. Gas bubbles were formed as MeOH was added. The reaction mixture was heated to 64° C. (to make sure all of BH₃ was quenched) for 10-15 minutes when the B(OMe)₃-MeOH complex was collected in a Dean-Stark trap. The reaction mixture was concentrated to give a pale-yellow foam as the desired product (11.6 g, 122% yield). To further purify this material, the pale-yellow foam was fully dissolved in 100 mL of CH₂Cl₂, and then 4M HCl in dioxane (10 mL) was added. As soon as HCl was added, lots of white solid was precipitated. The white solid was filtered and washed with CH₂Cl₂, (30 mL×2) to give a white solid as the HCl salt of the desired product. The collected white solid was suspended in 500 mL of CH₂Cl₂, and basified with NaHCO₃ (saturated). Most of white solid was back into CH₂Cl₂, but a small amount of white solid could not be dissolved. The product solution in CH₂Cl₂ was separated from the white solid and saturated. NaHCO₃ solution and the later were continuously extracted with CH₂Cl₂ (100 mL×10). The combined CH₂Cl₂ extraction was dried over MgSO₄ and evaporated to give an off-white foam as the desired product (7.45 g, 78% yield, 95% purity). ¹H NMR data matched the proposed structures.

Example 63c—Synthesis of Compound No. 63c
(ethyl syn-2-(3,4-dichlorophenyl)-3-hydroxy-3-(3-
nitrophenyl)propylcarbamate)

Compound No. 63b (7.3 g, 20.33 mmol) was diluted in CH₂Cl₂ (100 mL) at room temperature, and TEA (4.25 mL, 30.49 mmol) was added. The reaction mixture was cooled to 0° C. Ethyl chloroformate (2.342 mL, 24.39 mmol) was added slowly at 0° C. After the addition, the reaction was stirred at room temperature for several hours. The reaction was washed with 0.5 N HCl (100 mL), saturated NaHCO₃ (50 mL) and water (100 mL), dried over MgSO₄, and then evaporated to give a yellow oil. The yellow oil was added to a silica gel column and was eluted with 0-100% EtOAc in hexane to give three fractions: anti isomer, syn isomer, and an unknown. The anti isomer fraction was evaporated to give a pale-yellow oil (1.58 g, 18.81% yield), the desired syn-isomer fraction was evaporated to give a pale-yellow oil (4.57 g, 54.5% yield), and the unknown fraction as a yellow oil (400 mg). ¹H NMR (300 MHz, CDCl₃) δ 7.97-8.05 (m, 2H) 7.41 (t, J=7.5 Hz, 1H) 7.35 (t, J=8.0 Hz, 0H) 7.20-7.25 (m, 2H) 6.93 (dd, J=8.2, 2.1 Hz, 1H) 5.16 (t, J=3.9 Hz, 1H) 4.99 (br. s., 1H) 4.18 (q, J=7.2 Hz, 2H) 3.83-4.02 (m, 1H) 3.26 (dt, J=14.5, 5.5 Hz, 1H) 2.98 (ddd, J=9.9, 5.8, 3.7 Hz, 1H) 1.27 (t, J=7.1 Hz, 3H).

Example 64—Synthesis of Compound ID No. 64
((6R,7R)-6-(naphthalen-2-yl)-7-phenyl-1,4-ox-
azepane (6R,7R)-1-chloroethyl 6-(naphthalen-2-yl)-7-phenyl-1,4-oxazepane-4-carboxylate: A solution of (6R,7R)-4-methyl-6-(naphthalen-2-yl)-7-phenyl-1,4-oxazepane (Compound ID No. 124) (0.880 g, 2.77 mmol) in 1,2-dichloroethane (20 mL) was cooled at 0° C. and 1-chloroethyl carbonochloridate (1.795 mL, 16.63 mmol) was added dropwise over 5 minutes. The reaction was kept at 0° C. for another 10 minutes. The ice bath was removed and the reaction mixture was refluxed overnight. The reaction mixture was cooled to r.t, diluted with CHCl₃ (100 mL), and basified with 1N NaOH. The organic layer was separated, washed with water, and dried through MgSO₄ and evaporated to give a yellow stinky oil. The yellow oil was added to a silica gel column and was eluted with 0-5% ammoniated MeOH in CH₂CL₂. Product containing fractions were evaporated to give a crude product (0.370 g, (32.6%).

Compound ID No. 64: (6R,7R)-1-chloroethyl 6-(naphthalen-2-yl)-7-phenyl-1,4-oxazepane-4-carboxylate (0.350 g, 0.89 mmol) in MeOH (5 mL) was gently refluxed at 70° C. for several hours. The reaction mixture was concentrated to give a yellow gum that was eluted with 0-5% ammoniated MeOH in CH₂Cl₂ on a silica gel column to give Compound ID No. 64 as a colorless gum (77% yield, 98% purity). A portion of the desired product was converted to a HCl salt of the desired product (0.095 g) as a light-yellow solid. ¹HNMR (CDCl₃) δ 7.79-7.61 (m, 3H), 7.55 (s, 1H), 7.34-7.45 (m, 2H), 7.30 (dd, 1H, J=8.4, 1.5 Hz), 7.01-7.17 (m, 5H), 4.85 (d, 1H, J=9.9 Hz), 4.19 (dt, 1H, J=12.5, 3.7 Hz), 3.83-3.97 (m, 1H), 3.24-3.48 (m, 3H), 3.17 (dd, 2H, J=6.9, 3.7 Hz). MS m/z (ESI) 303.58 (M1⁺). [α]$_D^{20}$–129 (ethanol).

Example 65—Synthesis of Compound ID No. 65
((1R,2S)-2-(3,4-dichlorophenyl)-3-(methylamino)-1-
(2-nitrophenyl)propan-1-ol)

Compound No. 65b (2.33 g, 5.64 mmol) and 50 mL THF were transferred to a 500 mL r.b. flask equipped with a magnetic stirrer, addition funnel, thermometer, and Dean-Stark trap fitted with a condenser and nitrogen inlet. A solution of borane•dimethylsulfide complex (14.10 mL, 28.19 mmol) was added slowly, and then the solution was heated to reflux (75° C.). Dimethyl sulfide was removed from the Dean-Stark trap over 30 minutes, and then the reaction was allowed to heat at that temperature for an additional hour. Another 10 mL of borane•dimethylsulfide complex was added, dimethyl sulfide was removed from the dean-stark trap over 30 minutes, and the reaction was allowed to heat at 75° C. on a timer for 6 hours and then sat at room temperature overnight. At room temperature, the reaction was stirred vigorously, and 15 mL of MeOH was added drop-wise with gas evolution. 5 mL of 4M HCl in dioxane was added drop-wise. The solution was stirred for 20 minutes, then evaporated, and taken back up in CH₂Cl₂ and 50 mL of saturated sodium carbonate and 50 mL of water. It was extracted three times with CH₂Cl₂. All organics were combined, dried with MgSO₄, filtered, evaporated, and ran through a column of silica with a ramp of 0-20% MeOH (10% 7N NH₃ in MeOH)/CH₂Cl₂. The product was collected 0.72 g (35.7%).

This racemic compound was separated using SFC (ADH column, 20% iPrOH with 0.5% isopropylamine), which gave enantiomer retention times of 12.7 and 19.0 minutes, respectively. The combined fractions of the first eluting enantiomer were concentrated in vacuo and acidified in the usual way, yielding 15 mg of Compound ID No. 65 as an HCl salt, which was shown by the above described SCF system to have >99% enantiomeric excess. $^1$H NMR data matched the proposed structure. Since this compound was the more potent syn-enantiomer at hNET, it was presumed to be (1R,2S)-configured.

Example 65a—Synthesis of Compound No. 65a
(2-(3,4-dichlorophenyl)-3-hydroxy-3-(2-nitrophenyl)
propanenitrile)

2-(3,4-dichlorophenyl)acetonitrile (3.20 g, 17.20 mmol) was taken up in THF (50 mL) and cooled to −75° C. in an acetone dry ice bath. The internal temperature was monitored. BuLi (7.43 mL, 18.58 mmol) (1.6 M in hexane) was added drop-wise, and the temperature was maintained below −60° C. Once the last drop was added, the reaction was allowed to stir for 15 minutes. 2-nitrobenzaldehyde (2.60 g, 17.20 mmol) dissolved in THF (15 mL) was added slowly drop-wise while maintaining the temperature below −55° C. The solution was very dark brown/black at this point and allowed to stir for 1 hour at −75° C. The reaction was worked up with acetic acid (1.477 mL, 25.81 mmol) dissolved in 5 mL of diethyl ether and added drop-wise while the reaction was maintained below −55° C. LCMS showed mostly one peak with the desired mass. The reaction was worked up by adding 100 mL of water, and layers were separated in a separatory funnel. The material was extracted with ethyl acetate from a water wash, extracted three times with EtOAc, and dried over MgSO$_4$. The residue was purified via column chromatography using a gradient of 0-60% EtOAc/hexane. NMR revealed a high ratio of one enantiomer over the other. LCMS revealed one smaller peak with the same M+ as the desired larger peak. $^1$H NMR data matched the proposed structure.

Example 65b—Synthesis of Compound No. 65b
(ethyl 2-(3,4-dichlorophenyl)-3-hydroxy-3-(2-nitrophenyl)propylcarbamate)

Compound No. 65a (4.65 g, 13.79 mmol) was dissolved in THF (125 mL), stirred in a 500 mL flask fitted with a dean stark trap and condenser, and heated to 85° C. To this colorless solution was added, via gas tight syringe in several portions, 2.0 M borane dimethysulfide complex in THF (13.79 ml, 27.58 mmol). Bubbling occurred with each addition. The material was heated to 95° C., which produced a vigorous reflux. It was allowed to stir for 1.5 hours. Removing solvent from the Dean-Stark stark trap increased the concentration of the reaction as well as removed most of the dimethyl sulfide. It was stirred until the reaction had reached room temperature. 10 mL MeOH was added drop-wise at first. A vigorous reaction occurred early in the addition and dissipated towards the end of the 10 mL addition. It was reheated to reflux and distilled into a Dean-Stark trap for 30 minutes. It was cooled to room temperature, and 150 mL of 10% sodium bicarbonate in water was added. The material was extracted with CH$_2$Cl$_2$ three times. The organics were combined, washed with brine, dried with MgSO$_4$, filtered, and evaporated to crude semi-solid. This semi-solid was pumped down overnight and analyzed the next day.

3-amino-2-(3,4-dichlorophenyl)-1-(2-nitrophenyl)propan-1-ol (5.18 g, 110%) was analyzed to contain an undesired by-product. This material was carried onto the next step without any further purification. A portion of this material (5.15 g, 15.09 mmol) was dissolved in CH$_2$Cl$_2$ (79 mL) at room temperature, and TEA (3.16 mL, 22.64 mmol) was added. The reaction mixture was cooled to 0° C. Ethyl chloroformate (1.740 mL, 18.11 mmol) was added slowly at 0° C. After the addition, the reaction was stirred at room temperature for 1.5 hours and worked up by diluting with 150 mL of CH$_2$Cl$_2$. 75 mL of saturated NaHCO$_3$ was diluted with 125 mL of water and added. This mixture was shaken several times, and then the layers were separated. The aqueous layer was extracted with two more equal portions of CH$_2$Cl$_2$. All organics were combined, dried with MgSO$_4$, filtered, and evaporated to give a crude oil. This material was run through a column and was dissolved in CHCl$_3$ and MeOH to be absorbed onto silica gel. The material was passed through a column with a ramp from 0-100% EtOAc/hexane. The desired syn-isomer 65b (2.98 g, 47.8%) isomer as well as the anti isomer (0.370 g, 5.93%) were collected. $^1$H NMR data matched the proposed structure.

Example 66—Synthesis of Compound ID No. 66
((1S,2R)-2-((methylamino)methyl)-1,4-diphenylbutan-1-ol)

To lithium aluminum hydride (1.848 mL, 1.85 mmol) solution in THF (3 mL) at 55° C. under nitrogen was added Compound No. 66b (220 mg, 0.67 mmol) in THF (3 mL) drop-wise via syringe over about 5 minutes. The reaction mixture was then heated at reflux for 1.5 hours. The reaction mixture was quenched carefully with saturated Na$_2$SO$_4$ and then saturated NaHCO$_3$. The aqueous solution was diluted with ether and stirred briefly, then the ether layer was isolated, and the aqueous layer was extracted twice more with ether. The ethereal layers were combined, washed with saturated NaHCO$_3$ and brine, dried (Na$_2$SO$_4$), filtered, and concentrated to give 170 mg (83%) of an oil. $^1$H NMR data matched the proposed structure. Since this compound was the less potent enantiomer at hNET, it was presumed to be (1S,2R)-configured.

Example 66a—Synthesis of Compound No. 66a
(2-(hydroxy(phenyl)methyl)-4-phenylbutanenitrile)

To a 500 mL oven dried flask was charged with THF (95 mL) was added diisopropylamine (2.454 mL, 17.22 mmol), and the reaction flask cooled to 0° C. n-BuLi (9.47 mL, 15.15 mmol) was then added drop-wise via syringe, and the resulting LDA solution was stirred for 30 minutes at 0° C. The reaction mixture was then further cooled to −78° C., and 4-phenylbutanenitrile (2.055 mL, 13.77 mmol) was added neat via syringe. The reaction was stirred for 20 minutes before benzaldehyde (1.392 mL, 13.77 mmol) was added in THF (10 mL) via syringe over 5 minutes. The reaction mixture was then stirred at −78° C. for 60 minutes, quenched with saturated NaHCO$_3$, and warmed to room temperature. The organic layer was isolated, and the aqueous layer was extracted twice with DCM. The organics were combined, washed with brine, dried over Na$_2$SO$_4$, filtered, concentrated, and purified via column chromatography using a gradient of 0-40% EA/Hex. 1.75 g (51%) of product was collected. $^1$H NMR (500 MHz, DMSO-d6) δ 1.65 (dd, 1H) 1.85 (dq, J=9.9, 6.9 Hz, 2H) 2.56-2.83 (m, 2H) 2.94 (d, J=4.6 Hz, 0H) 3.05 (t, J=5.8 Hz, 1H) 4.76 (d, J=4.3 Hz, 1H) 5.96 (d, J=4.3 Hz, 1H) 6.00 (d, J=4.6 Hz, 0H) 7.10-7.23 (m, 3H) 7.23-7.32 (m, 3H) 7.32-7.44 (m, 5H).

Example 66b—Synthesis of Compound No. 66b
(ethyl syn-2-(hydroxy(phenyl)methyl)-4-phenylbutylcarbamate)

To a solution of Compound No. 66a (1.78 g, 7.08 mmol) in THF (25 mL) heated at 75° C. was added the borane•dimethylsulfide complex (8.85 mL, 17.71 mmol) drop-wise via syringe. The reaction mixture was then heated at 75° C. for 3.5 hours, at which time the TLC showed no remaining starting material. The reaction mixture was cooled to room temperature and concentrated to remove the THF. The residue was dissolved in ethyl acetate and carefully washed twice with saturated NaHCO$_3$ and brine, dried over Na$_2$SO$_4$, filtered, and concentrated to give 1.73 g of material that was used directly in the next step. The lot of the previous material (1.73 g, 6.77 mmol) in dichloromethane (30 mL) was added to triethylamine (3.78 mL, 27.10 mmol). The reaction mixture was cooled to 0° C., and ethyl chloroformate (0.777 mL, 8.13 mmol) was added drop-wise via syringe. The reaction mixture was then stirred at 0° C. for several minutes, then allowed to warm to room temperature, and stirred for 1.5 hours. The reaction mixture was diluted with DCM, washed with 1N HCl, saturated NaHCO$_3$, and brine, dried over Na$_2$SO$_4$, filtered, concentrated to give 900 mg of crude product, and purified via silica column using a gradient of 0 to 30% EA/Hex. This mixture of stereoisomers was subjected to SFC. The third fraction, which contained 220 mg (10%) of the first eluting syn-enantiomer, was carried on to the next step. $^1$H NMR (500 MHz, DMSO-d6) δ 1.16 (t, J=7.0 Hz, 3H) 1.33-1.48 (m, 1H) 1.48-1.61 (m, 1H) 1.73-1.84 (m, 1H) 2.23-2.37 (m, 1H) 2.51 (br. s., 1H) 3.00 (s, 1H) 3.04-3.20 (m, 1H) 3.99 (q, J=7.0 Hz, 2H) 4.69 (t, J=4.6 Hz, 1H) 5.15 (d, J=4.6 Hz, 1H) 7.02-7.08 (m, 1H) 7.12 (d, J=7.3 Hz, 1H) 7.20 (t, J=7.3 Hz, 2H) 7.30 (d, J=4.3 Hz, 4H).

Example 67—Synthesis of Compound ID No. 67 ((2S,3S)—N-methyl-3-((3-methyl-1,2,4-oxadiazol-5-yl)methoxy)-2-(naphthalen-2-yl)-3-phenylpropan-1-amine)

A solution of Compound No. 67a (90 mg, 0.18 mmol) in 4M HCl in dioxane was incubated at room temperature for 1 hour, concentrated to dryness, and triturated with ether (3×), and the resulting white solid dried in vacuo at 60° C. overnight to give 69.4 mg (91%) of the desired product as an HCl salt. $^1$H NMR data matched the proposed structure.

Example 67a—Synthesis of Compound No. 67a (tert-butylmethyl((2S,3S)-3-((3-methyl-1,2,4-oxadiazol-5-yl)methoxy)-2-(naphthalen-2-yl)-3-phenylpropyl)carbamate)

To an ice-cooled stirred suspension of Compound No. 8a (200 mg, 0.51 mmol) in 5 mL DMF was added in one portion sodium hydride (75 mg, 1.88 mmol). The mixture was stirred for 30 minutes in ice bath. Upon cooling, a solution of 5-(chloromethyl)-3-methyl-1,2,4-oxadiazole (110 mg, 0.83 mmol) in 1 mL DMF was added drop-wise. The resulting mixture was stirred at the ice bath temperature for 0.5 hours (dark red-orange color), diluted with ether (30 mL), and washed with water and brine. The aqueous layer was back-extracted with ether, and the organics were combined, dried, and concentrated to give crude product. This residue was purified via column chromatography using a gradient of 0-50% EtOAc/hexane to give 90 mg (36%) of the desired product. $^1$H NMR data matched the proposed structure.

Example 68—Synthesis of Compound ID No. 68 (2-((1S,2S)-3-(methylamino)-2-(naphthalen-2-yl)-1-phenylpropoxy)-N-(2,2,2-trifluoroethyl)acetamide)

Compound No. 68a (0.190 g, 0.36 mmol) was taken up in 15 mL of CH$_2$Cl$_2$ and stirred at room temperature. TFA (5 mL, 67.31 mmol) was added in one portion, and the mixture stirred for 30 minutes at room temperature and evaporated to give a residue, which was purified via column chromatography using 5% (MeOH with NH$_4$OH) in CH$_2$Cl$_2$. The purified free base was acidified with 4 N HCl in dioxane in the usual way to afford 140 mg (78%) of the desired material. $^1$H NMR (500 MHz, CDCl$_3$) δ 8.53 (br. s., 1H) 7.70 (dd, J=6.1, 3.4 Hz, 1H) 7.52-7.66 (m, 2H) 7.36-7.47 (m, 3H) 7.26 (s, 1H) 7.06-7.15 (m, 3H) 6.96-7.06 (m, 1H) 5.43 (br. s., 1H) 4.75 (d, J=10.1 Hz, 1H) 3.93-4.14 (m, 3H) 3.80-3.93 (m, 1H) 3.70 (t, J=11.1 Hz, 1H) 3.32 (dd, J=12.5, 3.4 Hz, 1H) 2.72 (s, 3H).

Example 68a—Synthesis of Compound No. 68a

Compound No. 8a (0.313 g, 0.80 mmol) in DMF (5 mL) was stirred at 0° C., and sodium hydride (0.096 g, 2.40 mmol) was added. The reaction was stirred at 0° C. for 10 minutes. 2-bromo-N-(2,2,2-trifluoroethyl)acetamide (0.616 g, 2.80 mmol) in 5 mL of DMF was added dropwise over a period of 30 minutes. The solution turned from an opaque white slurry to a slightly yellow slurry over the course of this addition and by the time the whole amount was added, the reaction had become quite clear and lost its yellow color. This was allowed to stir at room temperature overnight, and worked up the next day by diluting with CH$_2$Cl$_2$ and washing with water. It was extracted two times with CH$_2$Cl$_2$. The organic extracts were combined, dried with MgSO$_4$, filtered, and evaporated. Crude material was run through an ISCO column, 40 gram blue column with 0-100% EtOAc/hexane to give 0.190 g (44.8%) of the desired product. $^1$H NMR data matched the proposed structure.

Example 69—Synthesis of Compound ID No. 69 ((2RS,3RS)-2-(3-(methylamino)-2-(naphthalen-2-yl)propyl)phenol)

Compound ID No. 69, is the racemic form of Compound ID No. 52. It was prepared as in Example 52, except that enantiomers were not separated.

Example 70—Synthesis of Compound ID No. 70 ((1R,2S)-2-(3,4-dichlorophenyl)-3-(methylamino)-1-phenylpropan-1-ol)

A 250 mL round bottom flask equipped with a magnetic stirring bar, nitrogen inlet, and septum was charged with THF (200 mL) and 1.8 M LDA (59.7 mL, 107.50 mmol). After cooling to −78° C., 2-(3,4-dichlorophenyl)acetonitrile (20 g, 107.50 mmol) was added, and after 60 minutes, benzaldehyde (10.86 mL, 107.5 mmol) was added via syringe. After stirring at −78° C. for 3 hours, the reaction was quenched at −70° C. by the addition of acetic acid (6.15 mL) Aqueous workup, extraction, and concentration in vacuo afforded the crude aldol (35 g). ISCO purification on silica gel eluting with 0-50% of ethyl acetate in hexane afforded a 1:1 anti:syn mixture of the aldols (19 g). A portion of this material (2-(3,4-dichlorophenyl)-3-hydroxy-3-phenylpropanenitrile, 9 g, 30.81 mmol) was dissolved in THF (100 mL) and heated to reflux, and borane•dimethylsulfide complex (45.0 mL, 90 mmol) was added drop-wise over 5 minutes. Liberated dimethyl sulfide was collected in a Dean-Stark trap, and after 3.5 hours, the mixture was allowed to cool to ambient temperature, quenched with ethanol, and concentrated in vacuo. The residue was dissolved in dioxane (100 mL), and 4N HCl in dioxane (9 mL) was added. After stirring for 30 minutes, the sample was concentrated in vacuo, triturated with ether, washed with ether, ethyl acetate, and hexane, and dried to afford the primary amine hydrochloride (10 g, 98%). These synthetic steps were then repeated to afford another 10 g of the hydrochloride salt of amino-2-(3,4-dichlorophenyl)-1-phenylpropan-1-ol. The combined samples (20 g, 67.52 mmol) were combined with triethylamine (23.53 mL, 168.81 mmol) in dichloromethane (100 mL) and chilled to 0° C. To the chilled solution was added ethyl chloroformate (7.78 mL, 81.03 mmol) over 10 minutes, and the reaction was allowed to stir at ambient temperature for 12 hours. The material was concentrated in vacuo, diluted with ethyl acetate (300 mL), washed with 0.1 N HCl (2×150 mL), saturated sodium bicarbonate (150 mL), and brine (200 mL), dried over magnesium sulfate, filtered, and concentrated in vacuo to give the product as a foam (20 g) that was then subjected to stereoisomer separation by SFC in order to separate the four stereoisomers (2 anti stereoisomers and 2 syn stereoisomers). The portion of the second-eluting syn enantiomer (2 g, 5.43 mmol) and 25 mL THF were transferred to a 100 mL 3-neck r.b. flask equipped with a magnetic stirrer, addition funnel, thermometer, and Dean-Stark trap fitted with a condenser and nitrogen inlet. The solution was heated to reflux, and a solution of borane•dimethylsulfide complex (13.6 mL, 26.2 mmol) was added drop-wise over 10 minutes. Dimethyl sulfide distillate was collected (bp 38° C.). After 7 hours, the reaction was cooled to ambient temperature, and methanol (10 mL) was added, causing an exotherm and gas evolution. Concentration in vacuo was performed followed by taking up the free base in dioxane and treating it with 4 N HCl in dioxane (1.5 mL). The dioxane was removed, and the crude solid was triturated with ethyl acetate and hexane to afford 1.2 g of the HCl salt (64%) as a white solid. $^1$H NMR analysis using the TBPTA shift reagent gave coupling constants $J_{12}$ of 4.8 Hz for each, confirming their relative stereochemistry as syn-. $^1$H NMR (500 MHz, DMSO-$d_6$) δ 2.50 (s, 3H), 3.31 (s, 3H), 4.96 (br. s., 1H), 6.47 (s, 1H), 7.07 (dd, J=8.4, 2.0 Hz, 0H), 7.17-7.30 (m, 5H), 7.48 (d, J=8.2 Hz, 2H). Since this compound was the more potent syn-enantiomer at hNET, it was presumed to be (1R,2S)-configured.

Example 71—Synthesis of Compound ID No. 71 (N-methoxy-N-methyl-2-((1S,2S)-3-(methylamino)-2-(naphthalen-2-yl)-1-phenylpropoxy)acetamide)

Compound No. 71a (350 mg, 0.71 mmol) was dissolved in DCM (2 mL), and TFA (0.274 mL, 3.55 mmol) was added. The mixture was stirred at room temperature for 2 hours, and LCMS indicated the reaction was completed. DCM and TFA were evaporated, and to the resulting mixture was added ethyl acetate. The resulting mixture was washed with sodium bicarbonate (aqueous) and brine. The organic phase was separated and dried with sodium sulfate. The solvent was removed in vacuo. The resulting crude amine was purified by ISCO (alumina column) eluting with 0-10% of methanol in DCM to afford 200 mg (72%) of the clean product. $^1$H NMR data matched the proposed structure.

Example 71a—Synthesis of Compound No. 71a (tert-butyl (2S,3S)-3-(2-(methoxy(methyl)amino)-2-oxoethoxy)-2-(naphthalen-2-yl)-3-phenylpropyl (methyl)carbamate)

Compound No. 8a (300 mg, 0.77 mmol) in DMF was treated with NaH (92 mg, 2.30 mmol) at 0° C. for 20 minutes. 2-chloro-N-methoxy-N-methylacetamide (158 mg, 1.15 mmol) in DMF was added at 0° C. slowly into the stirring solution. The resulting mixture was warmed to room temperature and stirred for 15 hours at room temperature before LCMS indicated the reaction was complete. The reaction was diluted with 100 mL of ethyl acetate, washed with plenty of water and brine, dried with sodium sulfate, filtered, and concentrated under reduced pressure. ISCO purification eluting with 0-80% ethyl acetate in hexane afforded 350 mg (95%) of a clean product. Both LCMS and NMR data matched the proposed structure.

Example 72—Synthesis of Compound ID No. 72 ((1R,2S and 1S,2R)-3-(methylamino)-2-(naphthalen-2-yl)-1-(pyridin-2-yl)propan-1-ol)

syn-3-Hydroxy-2-(naphthalen-2-yl)-3-(pyridin-2-yl)propanenitrile: A solution of 2-naphthylacetonitrile (5 g, 29.9 mmol) in 200 mL of dry THF was placed in an oven-dried round bottom flask with under nitrogen. Diisopropylamine (5.03 mL, 35.9 mmol) was added, and the reaction mixture was stirred and cooled to −78° C. for 20 minutes. 2.5M butyllithium (14.35 mL, 35.9 mmol) was then added slowly with a syringe. After 30 minutes of stirring at −78° C., pyridine 2-carboxaldehyde (3.56 mL, 35.9 mmol) was added drop-wise via syringe. After 10 minutes, the reaction was quenched quickly with 25 mL 2:1 THF/acetic acid. The cold bath was removed, and the reaction was allowed to reach room temperature. Water was added, and the aqueous layer was extracted with EtOAc (3×25 mL) The combined organic layers were sequentially washed with water and brine, then dried over $MgSO_4$, and concentrated using a rotary evaporator. The residue was dissolved in DCM, and hexane was slowly added until a turbid solution resulted. The turbid solution was allowed to stand for 15 minutes. The major syn-isomer that separated as off-white crystals was isolated by filtration (1.033 g, 7.53 mmol, 25.2%). $^1$H NMR (DMSO.d6) δ 8.51 (d, 1H, J=4.3 Hz), 7.91-7.77 (m, 3H), 7.74-7.65 (m, 2H), 7.55-7.46 (m, 2H), 7.34-7.22 (m, 3H), 6.37 (d, 1H, J=5.5 Hz), 5.19 (t, 1H, J=5.5 Hz), 4.86 (d, 1H, J=5.5 Hz). MS m/z (ESI) 275.30 (MH$^+$).

syn-3-amino-2-(naphthalen-2-yl)-1-(pyridin-2-yl)propan-1-ol: To a solution of syn-3-hydroxy-2-(naphthalen-2-yl)-3-(pyridin-2-yl)propanenitrile (0.650 g, 2.370 mmol) in 10 mL of dry THF was added 1M borane-THF solution (9.48 mL, 9.48 mmol) under nitrogen slowly via syringe. This mixture was stirred at 60° C. overnight while monitoring the reaction progress by TLC. After quenching the reaction with cautious addition of $NaHCO_3$, the reaction mixture was poured into a separatory funnel, and the aqueous layer was extracted with EtOAc (3×50 mL) The combined organic layers were washed with water and brine, and dried over $MgSO_4$. Concentration of the volatiles using a rotary evaporator afforded a residue that was dissolved in DCM. 1N HCl was added, and the mixture was stirred for a few minutes. The solvents were evaporated on a rotary evaporator. The product was washed, leached with ether, and lyophilized to afford a white solid (0.700 g, 84%). $^1$H NMR (CD$_3$OD) δ 8.55 (t, 1H, J=7.5 Hz), 8.35 (d, 1H, J=5.8 Hz), 8.22 (d, 1H, J=8.1 Hz), 7.86-7.73 (m, 4H), 7.71 (s, 1H), 7.51-7.43 (m, 2H), 7.36-7.28 (m, 1H), 5.81 (d, 1H, J=2.6 Hz), 3.89-3.74 (in, 3H). A low J-value of the benzylic proton signal (2.6 Hz) indicated that the compound had syn-configuration. MS m/z (ESI) 279.06 (MH$^+$).

syn-Ethyl 3-hydroxy-2-(naphthalen-2-yl)-3-(pyridin-2-yl)propylcarbamate: To syn-3-amino-2-(naphthalen-2-yl)-1-(pyridin-2-yl)propan-1-ol dihydrochloride (0.5 g, 1.432 mmol) in 5 mL dry DCM at −10° C. was added triethylamine (TEA) (0.595 mL, 4.27 mmol) drop-wise, followed by slow addition of ethyl chloroformate (0.218 mL, 2.277 mmol). After stirring for 1 hour at −10° C., the ice bath was removed, and the mixture was allowed to warm to 0° C. TLC showed completion of reaction after 1 hour. The reaction was quenched with saturated NaHCO$_3$, and the mixture poured into a separatory funnel. The organic layer was separated, and the aqueous layer was extracted with DCM (3×25 mL). The combined DCM extracts were washed with water, dried over MgSO$_4$, filtered, and concentrated. The resulting residue was purified by flash chromatography over silica gel (eluent: 50-60% EtOAc in hexanes). The combined organic layers were concentrated using a rotary evaporator, which yielded the product as a gummy off white solid (0.182 g, 36.5%). $^1$H NMR (CDCl$_3$) δ 8.27 (d, 1H, J=4.7 Hz), 7.70-7.56 (m, 2H), 7.54 (d, 1H, J=8.7 Hz), 7.49-7.40 (m, 2H), 7.37-7.28 (m, 2H), 7.12 (d, 2H, J=7.5 Hz), 6.96 (t, 1H, J=5.8 Hz), 5.13 (d, 1H, J=3.2 Hz), 4.87 (br s, 1H), 4.11-3.98 (m, 2H), 3.97-3.83 (m, 1H), 3.60-3.37 (m, 2H), 1.24-1.08 (overlapping t, 3H) MS m/z (ESI) 351.34 (MH$^+$).

Compound ID No. 72: syn-Ethyl 3-hydroxy-2-(naphthalen-2-yl)-3-(pyridin-2-yl)propylcarbamate (0.5 g, 1.427 mmol) was dissolved in 6 mL of dry THF and placed in a dry flask. To this, 1M borane-THF solution (5.71 mL, 5.71 mmol) was added via syringe. This mixture was stirred at 60° C. overnight while monitoring the reaction progress by TLC. The reaction was quenched by cautious addition of NaHCO$_3$ and poured into a separatory funnel. The two layers were separated, and the aqueous layer was extracted with EtOAc (3×25 mL). The combined organic layers were washed with water and brine, dried over MgSO$_4$, and concentrated under reduced pressure. The resulting residue was purified by flash chromatography over silica gel (eluent: 0.5% TEA in 5% MeOH/DCM). The desired fractions were combined, concentrated, and dried under high vacuum. The residue was mixed with 1N HCl and concentrated under rotary evaporation. High vacuum drying afforded the product as a sticky yellowish solid (0.49 g, 94%). $^1$H NMR (500 MHz, DMSO-d6) δ 8.99 (br. s. 1H), 8.52 (d, 2H, J=4.6 Hz), 7.66-8.15 (m, 4H), 7.37-7.55 (m, 4H), 7.60 (s, 1H), 7.12-7.25 (m, 1H), 5.44 (br. s. 1H), 3.75-3.98 (m, 1H), 3.45-3.68 (m, 2H), 2.53-2.65 (m, 3H). MS m/z (ESI) 293.42 (MH$^+$).

Example 73—Synthesis of Compound ID No. 73 ((1RS,2RS)-anti-2-(3-chloro-4-fluorophenyl)-3-(methylamino)-1-phenylpropan-1-ol)

Compound No. 73a (1.8 g, 6.53 mmol) was dissolved in THF (50 mL) and heated to reflux, and borane•dimethylsulfide complex (13.1 mmol, 26.2 mL) was added drop-wise over 5 minutes. Liberated dimethyl sulfide was collected in a Dean-Stark trap, and after 3.5 hours, the mixture was allowed to cool to ambient temperature, quenched with ethanol, and concentrated in vacuo. The residue was dissolved in ethyl acetate (100 mL) The organic layer was washed with water, sodium bicarbonate, and brine, dried over MgSO$_4$, filtered, and concentrated to afford 2 g (>100%). A portion of this material (900 mg, 3.22 mmol) and TEA (0.673 mL, 4.83 mmol) in DCM (30 mL) was added and chilled to 0° C. To the chilled solution was added ethyl carbonochloridate (0.371 mL, 3.86 mmol) over 10 minutes. The ice bath was removed, and the solution was allowed to warm to room temperature for 3 hours. The reaction solution was reduced to 5 mL (in DCM), diluted with ethyl acetate (100 mL), washed with 0.1N HCl (2×15 mL), saturated sodium bicarbonate (15 mL), and brine (20 mL), then dried over MgSO$_4$, filtered, and concentrated in vacuo. Residual solvents were evaporated to give 3 g product as a foam. Purification by ISCO (40 g of silica gel) eluting with 0-50% of ethyl acetate in hexane over 15 minutes gave two peaks (3:1 ratio). The entire fractions for peak 1 and peak 2 were collected, and all the solvents were removed to afford two diastereomers. $^1$H NMR confirmed the relative stereochemistry of the two diastereomers: 160 mg (14%) of the anti, and 100 mg (9%) of the syn diastereomers were collected. A portion of the anti diastereomer (100 mg, 0.28 mmol) and 25 mL of THF were transferred to a 100 mL 3-neck r.b. flask equipped with a magnetic stirrer, addition funnel, thermometer, and Dean-Stark trap fitted with a condenser and nitrogen inlet. The solution was heated to reflux (66° C.), and a solution of borane•dimethylsulfide complex (0.711 mL, 1.42 mmol) was added drop-wise over 10 minutes. Dimethyl sulfide distillate was collected (bp 38° C.). After 7 hours, the reaction was cooled to room temperature and treated with 4N HCl in dioxane (0.1 mL, 1.07 eq) and the careful addition of ethanol (10 mL) resulting in an exothermic and gas evolution. The reaction mixture was then put on rotary evaporator to remove ethanol and trimethyl borate. After most of the ethanol was removed, the mixture was diluted with ether (10 mL) to give a crude white precipitate. The material was neutralized with Et$_3$N in DCM and prepared for LC purification. The amine (50 mg) was converted to HCl salt by dissolving in dioxane and adding 0.1 mL of 4N HCl in dioxane. It was stirred for 10 minutes before removing the solvent, and dried in vacuo to afford the product as an HCl salt (30 mg, 36%). $^1$H NMR analysis using the TBPTA shift reagent gave coupling constants J$_{12}$ of 9.3 Hz for each, confirming their relative stereochemistry as anti-. $^1$H NMR (500 MHz, DMSO-d6) δ 2.49 (s, 3H), 3.31 (s, 1H), 3.46 (ddd, J=17.6, 12.7, 5.3 Hz, 2H), 4.75 (d, J=7.9 Hz, 1H), 6.95-8.11 (m, 8H).

Example 73a—Synthesis of Compound No. 73a (2-(3-chloro-4-fluorophenyl)-3-hydroxy-3-phenylpropanenitrile)

A 250 mL round bottom flask equipped with a magnetic stirring bar, nitrogen inlet, and septum was charged with THF (50 mL) and 1.8 M LDA (6.55 mL, 11.79 mmol). After cooling to −78° C., 2-(3-chloro-4-fluorophenyl)acetonitrile (2 g, 11.79 mmol) was added, and after 60 minutes, benzaldehyde (1.192 mL, 11.79 mmol) was added via syringe. After stirring at (−78° C.) for 3 hours, the reaction was quenched by the addition of water (20 mL) while stirring at −70° C. The aqueous layer was extracted with Et$_2$O (2×50 mL), and the combined organic extracts were washed with brine (50 mL), dried (MgSO$_4$), and concentrated in vacuo to give the crude aldol. ISCO purification on silica gel eluting with 0-40% of ethyl acetate in hexane afforded 1.8 g (55.4%) of the product as anti/syn mixture.

Example 74—Synthesis of Compound ID No. 74 ((RS)—N-methyl-2-(naphthalen-2-yl)-3-(pyridin-3-yl)propan-1-amine)

Compound ID No. 74 was the racemate that was resolved to afford Compound ID No. 48. $^1$H NMR (400 MHz, CD$_3$OD) δ 8.60 (d, J=5.6 Hz, 1H), 8.51 (s, 1H), 8.35 (d, J=8.1 Hz, 1H), 7.94 (d, J=8.5 Hz, 1H), 7.92-7.78 (m, 3H), 7.72 (s, 1H), 7.54-7.45 (m, 3H), 3.68-3.48 (m, 5H), 2.70 (s, 3H). HRMS (ESI-TOF) calculated for C$_{18}$H$_{21}$N$_2$ (MH$^+$) 277.1699 found 277.1705 (+2.14 ppm, 0.6 mmu).

Example 75—Synthesis of Compound ID No. 75 ((RS)—N-methyl-3-phenyl-2-(quinolin-6-yl)propan-1-amine dihydrochloride)

A 500 mL round bottom flask was charged with AIBN (820 mg, 5.0 mmol) and NBS (9.85 g, 55 mmol). The system was degassed and backfilled with $N_2$ three times followed by addition of $CCl_4$ (200 mL). This suspension was heated to reflux, and upon initiation (evidenced by $N_2$ gas formation), 6-methylquinoline (6.71 mL, 50 mmol) was added. The reflux was allowed to continue under $N_2$ for 16 hours. In the morning, the mixture was allowed to cool, and the succinimide was filtered through celite. The filtrate was concentrated, and the resulting residue was dissolved in 40 mL of EtOH and warmed to 40° C. An aqueous solution of KCN (9.8 g of KCN, 150 mmol in 35 mL $H_2O$) was then added. The solution was allowed to stir at 40° C. for 1 hour. The excess EtOH was then removed. The residue was extracted with $Et_2O$ (3×20 mL), dried over $MgSO_4$, filtered, and concentrated. The residue was purified via column chromatography (75% EtOAc in hexanes) to give 2.66 g (15.8 mmol, 32%) of a yellow solid. The aldol condensation using sodium ethoxide, ethanol, benzaldehyde, and a portion of the above material (718 mg, 4.27 mmol) was performed in the usual way to give 1.03 g (4.03 mmol, 94%) of a pale yellow solid. The conjugate reduction and acidification were performed in the usual way with a portion of the above material (505 mg, 1.97 mmol) to give 462 mg (1.38 mmol, 70%) of white powder. $^1$H NMR (500 MHz, $CD_3OD$) δ 9.03 (dd, J=4.9, 1.6 Hz, 1H), 8.77 (d, J=8.3 Hz, 1H), 8.14 (d, J=8.8 Hz, 1H), 8.01 (d, J=1.7 Hz, 1H), 7.96 (dd, J=8.8, 2.0 Hz, 1H), 7.85 (dd, J=8.3, 5.0 Hz, 1H), 7.16 (ddd, J=7.5, 4.4, 1.3 Hz, 2H), 7.12-7.06 (m, 3H), 3.58-3.50 (m, 1H), 3.50-3.38 (m, 2H), 3.21 (dd, J=13.7, 6.2 Hz, 1H), 3.04 (dd, J=13.6, 9.0 Hz, 1H). HRMS (ESI-TOF) calculated for $C_{18}H_{19}N_2$ (MH$^+$) 263.1543 found 263.1550 (+2.63 ppm, 0.7 mmu) This material was assayed as a racemic mixture.

Example 76—Synthesis of Compound ID No. 76 ((1S,2S)-1-(3-bromophenyl)-2-(3,4-dichlorophenyl)-3-(methylamino)propan-1-ol)

Compound No. 76a (4.6 g, 10.29 mmol) in THF (50 mL) was heated to reflux. Borane-THF complex (25.7 mL, 25.7 mmol) was added drop-wise over 15 minutes. After six hours at reflux, the mixture was cooled to room temperature and placed in to an ice bath. This chilled mixture was treated with 5 mL HCl and then 10 mL of MeOH slowly to quench extra $BH_3$, maintaining the temperature under 25° C. The reaction mixture was heated to 64° C. (to make sure all of $BH_3$ was quenched) for 10-15 minutes, and then concentrated to a pale-yellow oil. The reaction mixture was concentrated to give a yellow gum as an HCl salt of the desired product. The HCl salt was stirred in $CHCl_3$ (100 mL)/$NaHCO_3$ (saturated) for 10 minutes, the organic layer separated from the aqueous layer, and the aqueous layer was extracted with $CHCl_3$ (20 mL×2). The combined $CHCl_3$ layer was dried through $MgSO_4$ and evaporated to give a yellow stinky oil. The yellow oil was added to a silica gel column and was eluted with 0-10% MeOH in $CH_2Cl_2$ to afford 2.69 g (67%) of material. The enantiomers were separated by SFC (ADH column, 17% MeOH with 0.5% isopropylamine), and the enantiomer retention times were 5.02 and 5.81 minutes, respectively. The combined fractions of the second eluting enantiomer were concentrated in vacuo and acidified in the usual way yielding 39 mg of Compound ID No. 76 as an HCl salt, which was shown by the above described SCF system to have 90% enantiomeric excess. $^1$H NMR (300 MHz, $CDCl_3$) δ 7.38 (t, J=1.6 Hz, 1H) 7.29 (dd, J=7.9, 2.0 Hz, 1H) 7.25 (d, J=5.9 Hz, 1H) 7.12 (d, J=2.1 Hz, 1H) 7.02 (t, J=7.8 Hz, 1H) 6.89 (d, J=7.6 Hz, 1H) 6.82 (dd, J=8.3, 2.0 Hz, 1H) 4.90 (d, J=8.0 Hz, 1H) 3.19 (dd, J=12.3, 9.7 Hz, 1H) 3.01 (dd, J=12.1, 3.1 Hz, 1H) 2.85 (ddd, J=17.8, 8.2, 3.1 Hz, 1H) 2.49 (s, 3H). Since this compound was the more potent enantiomer at hNET, it was presumed to be (1S,2S)-configured.

Example 76a—Synthesis of Compound No. 76a (anti-ethyl 3-(3-bromophenyl)-2-(3,4-dichlorophenyl)-3-hydroxypropylcarbamate)

2-(3,4-dichlorophenyl)acetonitrile (5.78 g, 30.45 mmol) was dissolved in ether (35 mL)/THF (15 mL) and cooled to −75° C. BuLi (20.93 mL, 33.49 mmol) was added slowly, and the reaction was stirred at −75° C. for 20 minutes. 3-bromobenzaldehyde (6.20 g, 33.49 mmol) in THF (15 mL) was added drop-wise, maintaining the temperature under −60° C. After the addition, the reaction was stirred at −75° C. for another hour. Then, acetic acid (2.61 mL, 45.67 mmol) was added at −75° C. to quench the reaction. The reaction mixture was warmed to room temperature, and the organic layer was separated from the aqueous layer. The aqueous layer was extracted with Ether (100 mL×3), and the combined organic layer was dried over $MgSO_4$ and evaporated to give 13.8 g (>100%) of an orange oil, which was used for the next step directly without further purification. A portion of this material (12.88 g, 30 mmol) was dissolved in THF (55 mL) and was heated to reflux. The solution of borane-methyl sulfide complex (52.5 mL, 105.00 mmol) in THF was added drop-wise over 30 minutes, and a Dean-Stark trap was set up to collect liberated $SMe_2$. After 12 hours, the reaction mixture was cooled in a cold water bath, acidified with 4M HCl in dioxane (10 mL), and quenched the excess $BH_3$ with 20 mL of MeOH slowly, maintaining the temperature under 25° C. The reaction mixture was heated to 64° C. (to ensure complete $BH_3$ quenching) for 10-15 minutes. The $B(OMe)_3$-MeOH complex was collected in a Dean-Stark trap. The reaction mixture was concentrated to give a pale-yellow oil. The pale-yellow oil was fully diluted in 200 mL of $CH_2Cl_2$, basified with $NaHCO_3$ (saturated), washed with brine, dried over $MgSO_4$, and evaporated to give a crude oil that was used in the next step without any further purification. A portion of this material (11.25 g, 30 mmol) was diluted in $CH_2Cl_2$ (100 mL) at room temperature and TEA (6.27 mL, 45.00 mmol) was added. The reaction mixture was cooled to 0° C., and ethyl carbonochloridate (3.46 mL, 36.00 mmol) was added slowly at 0° C. and allowed to stir at 0° C. for 3 hours. The reaction was washed with 0.5 N HCl (150 mL), saturated $NaHCO_3$ (100 mL), and water (100 mL), dried over $MgSO_4$, and then evaporated to give a pale-yellow oil. The pale-yellow oil was added to a silica gel column and was eluted with 0-100% EtOAc in hexane to give two fractions: the anti-isomer 76a and syn-isomer 76b. The anti-isomer fraction (relative stereochemistry determined by $^1$H NMR) was evaporated to give a pale-yellow oil (4.70 g, 3-step yield: 35%, 95% purity) and the syn-isomer collection was evaporated to give a pale-yellow oil (5.16 g, 3-step yield: 38.5%, 95% purity). $^1$H NMR data matched the proposed structures.

Example 77—Synthesis of Compound ID No. 77 ((6S,7S)-4-methyl-6-(naphthalen-2-yl)-7-phenyl-1,4-oxazepane)

(6S,7S)-4-methyl-6-(naphthalen-2-yl)-7-phenyl-1,4-oxazepan-3-one (Example 129) was reduced with lithium aluminum hydride as described for the 1R,2R-enantiomer (Example 124). (6S,7S)-4-methyl-6-(naphthalen-2-yl)-7-phenyl-1,4-oxazepane (145 mg, 0.46 mmol) in $CH_2Cl_2$ (2 mL) was mixed with HCl (0.457 mL, 0.91 mmol). The mixture was evaporated to dryness under high vacuum overnight at 40° C. $^1$H NMR (500 MHz, DMSO-d6) δ ppm 11.10 (br. s., 1H) 7.71-7.85 (m, 3H) 7.58-7.71 (m, 1H) 7.39-7.51 (m, 2H) 7.13-7.34 (m, 6H) 5.04 (d, J=10.7 Hz, 1H) 4.10-4.33 (m, 3H) 3.97-4.09 (m, 1H) 3.60 (br. s., 1H) 3.46 (d, J=12.8 Hz, 1H) 2.82-2.98 (m, 3H). MS m/z (ESI) 318.3 $(MH)^+$.

Example 78—Synthesis of Compound ID No. 78 ((1R,2R)-1-(2-fluorophenyl)-3-(methylamino)-2-(naphthalen-2-yl)propan-1-ol)

Compound ID No. 78 is the enantiomer of the compound in Example 15. The combined fractions of the second eluting enantiomer were concentrated in vacuo and converted to an HCl salt, which afforded 83 mg of Compound ID No. 78, which was shown by the previously described SCF system to have 80% enantiomeric excess. $^1$H NMR (300 MHz, $CD_3OD$) δ 7.68-7.82 (m, 3H), 7.62 (s, 1H), 7.38-7.54 (m, 3H), 7.26 (dd, J=8.7, 1.5 Hz, 1H), 7.03-7.20 (m, 2H), 6.66-6.90 (m, 1H), 5.36 (d, J=9.0 Hz, 1H), 3.77-3.91 (m, 1H), 3.46-3.61 (m, 2H), 2.75 (s, 3H). Since this enantiomer was less potent at hNET than the first-eluting enantiomer, it was presumed to be (R,R)-configured.

Example 79—Synthesis of Compound No. 79 (1-methyl-6-(((1S,2S)-3-(methylamino)-2-(naphthalen-2-yl)-1-phenylpropoxy)methyl)pyridin-2(1H)-one)

A solution of Compound No. 79a (180 mg, 0.35 mmol) in 4 M HCl in dioxane was let stand at room temperature for 0.5 hours, then concentrated to dryness, and triturated with ether (3×). The resulting white solid was dried in vacuo at 60° C. overnight to give 1-methyl-6-(((1S,2S)-3-methylamino)-2-(naphthalen-2-yl)-1-phenylpropoxy)methyl)pyridin-2(1H)-one (124 mg, 79%). $^1$H NMR data matched the proposed structure.

Example 79a—Synthesis of Compound No. 79a (tert-butyl methyl((2S,3S)-3-((1-methyl-6-oxo-1,6-dihydropyridin-2-yl)methoxy)-2-(naphthalen-2-yl)-3-phenylpropyl)carbamate)

To an ice-cooled stirred solution of Compound No. 8a (205 mg, 0.52 mmol) in 4.5 mL DMF was added in one portion sodium hydride (75 mg, 1.88 mmol). The mixture was stirred for 10 minutes in an ice bath and treated with drop-wise addition of a solution of the 6-(bromomethyl)-1-methylpyridin-2(1H)-one (110 mg, 0.54 mmol) in DMF. The resulting mixture was stirred for 1 hour (pinkish color), diluted with ether (30 mL), washed with water and brine, and aqueous back-extracted with ether. The organics were combined, dried, and concentrated to give a crude product. This was subjected to ISCO chromatography eluting with a 0-100% EtOAc/hexanes gradient to give the desired product (180 mg, 67.1%). $^1$H NMR data matched the proposed structure.

Example 80—Synthesis of Compound ID No. 80 ((RS)-2-(3,4-dichlorophenyl)-N-methyl-3-(pyridin-3-yl)propan-1-amine)

Compound No. 80b (858 mg, 2.42 mmol) was dissolved in $CH_2Cl_2$ (15 mL), followed by addition of triethylamine (1.7 mL, 12.1 mmol). The solution was chilled to 0° C., and ethyl chloroformate was added (0.32 mL, 3.4 mmol). The solution was allowed to stir at 0° C. for 2 hours and was warmed to room temperature overnight. In the morning, the contents were poured into a separatory funnel and extracted with EtOAc (3×15 mL) The organics were dried over $MgSO_4$, filtered, and concentrated to give a residue that was purified via silica gel flash chromatography (75% EtOAc in hexanes) to give 179 mg (0.51 mmol, 21%) of a colorless gum. To an oven dried 2 neck 100 mL round bottom flask equipped with a stir bar and a nitrogen inlet was added a portion of the above material (177 mg, 0.5 mmol) and dry THF (10 mL) A 1 M solution of $BH_3$*THF (3.0 mL, 3.0 mmol) in THF was added with stirring. Upon addition of borane, the system was fitted with a reflux condenser and heated to 80° C. for 24 hours. After cooling to room temperature, 5 mL of methanol was carefully added. Upon cessation of bubbles, the system was heated to reflux for 1 hour. The volatiles were then removed in vacuo, and to the residue was added 10 mL of methanol and 2 mL of a 4M HCl solution in dioxane. The homogenous solution was concentrated to give a white amorphous solid that after trituration with diethyl ether was free based and purified via silica gel flash chromatography (8% $CH_3OH$ in $CH_2Cl_2$ with 1 mL $NH_4OH$ per 100 mL eluent) to give 59 mg (0.2 mmol, 40%) of the free base. $^1$H NMR (400 MHz, $CD_3OD$) δ 8.30 (dd, J=4.8, 1.3 Hz, 1H), 8.17 (d, J=1.9 Hz, 1H), 7.55 (d, J=7.8 Hz, 1H), 7.41 (d, J=8.3 Hz, 1H), 7.34 (d, J=2.0 Hz, 1H), 7.28 (dd, J=7.9, 4.8 Hz, 1H), 7.10 (dd, J=8.3, 2.0 Hz, 1H), 3.16-3.07 (m, 2H), 2.93-2.81 (m, 3H), 2.35 (s, 3H). HRMS (ESI-TOF) calculated for $C_{15}H_{17}Cl_2N_2$ $(MH^+)$ 295.0763, found 295.0770 (+4.58 ppm, 0.7 mmu).

Example 80a—Synthesis of Compound No. 80a (2-(3,4-dichlorophenyl)-3-(pyridin-3-yl)propanenitrile)

To an oven dried 2 neck 250 mL round bottom flask equipped with a stir bar and nitrogen inlet was added 3,4-dichlorophenyl acetonitrile (763 mg, 4.1 mmol). The system was degassed and backfilled with $N_2$. Dry DMF (25 mL) was added followed by addition of NaH (60% dispersion in oil, 384 mg, 9.6 mmol). The dark red solution was allowed to stir for 30 minutes at room temperature. 3-(bromomethyl)pyridine hydrobromide (1.01 g, 4.0 mmol) was added in one portion. Upon addition, the solution was stirred for additional 0.5 hours. The red solution was quenched by the addition of water (10 mL) and brine (5 mL). 20 mL of EtOAc was added, and the contents of the flask were poured into a separatory funnel, extracted with EtOAc (3×40 mL), and dried over $Na_2SO_4$. The residue was concentrated and purified via silica gel flash chromatography (50% EtOAc in hexane) to give 322 mg (1.16 mmol, 29%) of a yellow oil. $^1$H NMR (400 MHz, $CDCl_3$) δ 8.55 (d, J=3.5 Hz, 1H), 8.35 (d, J=1.7 Hz, 1H), 7.49 (dt, J=7.8, 1.8 Hz, 1H), 7.45 (d, J=8.3 Hz, 1H), 7.37 (d, J=2.2 Hz, 1H), 7.31-7.23 (m, 1H), 7.07 (dd, J=8.3, 2.2 Hz, 1H), 4.03 (t, J=7.1 Hz, 1H), 3.18 (dd, J=7.1, 1.7 Hz, 2H).

Example 80b—Synthesis of Compound No. 80b (2-(3,4-dichlorophenyl)-3-(pyridin-3-yl)propan-1-amine dihydrochloride)

To an oven dried 2 neck 100 mL round bottom flask equipped with a stir bar and a nitrogen inlet was added Compound No. 80a (640 mg, 2.3 mmol) and 15 mL of dry THF. $BH_3/SMe_2$ (5.8 mL, 11.5 mmol) was added with stirring. Upon addition of borane, the system was fitted with a reflux condenser and heated to reflux for 6 hours. After cooling to room temperature, 5 mL of methanol was carefully added. Upon cessation of bubbles, the system was heated to reflux for 1 hour. The volatiles were then removed in vacuo, and to the residue was added 10 mL of methanol and 2 mL of a 4M HCl solution in dioxane. The homogenous solution was concentrated to give a white amorphous solid that after trituration with diethyl ether yielded 813 mg of the dihydrochloride (2.3 mmol, >99%). $^1$H NMR (400 MHz, CD$_3$OD) δ 8.70 (d, J=5.6 Hz, 1H), 8.66 (d, J=0.9 Hz, 1H), 8.44-8.36 (m, 1H), 7.98 (dd, J=8.1, 5.8 Hz, 1H), 7.53 (t, J=5.2 Hz, 2H), 7.26 (dd, J=8.3, 2.1 Hz, 1H), 3.49-3.38 (m, 4H), 3.18 (dd, J=15.2, 11.6 Hz, 2H). HRMS (ESI-TOF) calculated for C$_{14}$H$_{15}$Cl$_2$N$_2$ (MH$^+$) 281.0607, found 281.0581 (−9.08 ppm, 2.6 mmu).

Example 81—Synthesis of Compound ID No. 81 ((R)-2-((1S,2S)-3-(methylamino)-2-(naphthalen-2-yl)-1-phenylpropoxy)-1-(pyrrolidin-1-yl)propan-1-one)

Compound No. 81a (120 mg, 0.23 mmol) and 4 N HCl in dioxane (2 mL, 8.00 mmol) were allowed to stand at room temperature for 0.5 hours and were concentrated to near dryness. The solid was washed with ether (3×) and dried in vacuo at 60° C. overnight to give purified (R)-2-((1S,2S)-3-(methylamino)-2-(naphthalen-2-yl)-1-phenylpropoxy)-1-(pyrrolidin-1-yl)propan-1-one (95 mg, 91%) as an HCl salt. $^1$H NMR data matched the proposed structure.

Example 81a—Synthesis of Compound No. 81a (tert-butyl methyl((2S,3S)-2-(naphthalen-2-yl)-3-((R)-1-oxo-1-(pyrrolidin-1-yl)propan-2-yloxy)-3-phenylpropyl)carbamate)

To an ice-cooled stirred solution of Compound No. 8a (205 mg, 0.52 mmol) in 4.5 mL DMF was added in one portion the sodium hydride (75 mg, 1.88 mmol). The mixture was stirred for 10 minutes in ice bath and treated with drop-wise addition of a solution of 2-chloro-1-(pyrrolidin-1-yl)propan-1-one (105 mg, 0.65 mmol) in DMF. The resulting mixture was stirred for 3 hours (yellowish color), diluted with ether (30 mL), washed with water and brine, and aqueous back-extracted with ether. The organics were combined, dried, and concentrated to give crude product. This was subjected to ISCO chromatography eluting with a 0-100% EtOAc/hexanes gradient to give separated, purified tert-butyl methyl((2S,3S)-2-(naphthalen-2-yl)-3-((S)-1-oxo-1-(pyrrolidin-1-yl)propan-2-yloxy)-3-phenylpropyl)carbamate (90 mg, 33%) followed by tert-butyl methyl((2S,3S)-2-(naphthalen-2-yl)-3-((R)-1-oxo-1-(pyrrolidin-1-yl)propan-2yloxy)-3-phenylpropyl)carbamate (120 mg, 44%). $^1$H NMR data matched the proposed structures.

Example 82—Synthesis of Compound ID No. 82 ((2S,3S)—N$^1$,N$^1$-dimethyl-2-(naphthalen-2-yl)-3-phenylpropane-1,3-diamine)

Lithium aluminum hydride (0.182 g, 4.8 mmol) was placed along with THF (5 mL) in a round bottom flask equipped with a stir bar and water condenser. A solution of tert-butyl (2S,3S)-3-azido-2-(naphthalen-2-yl)-3-phenylpropyl(methyl)carbamate (Example 87) (0.250 g, 0.6 mmol) in 15 mL of THF was introduced into the flask, and the reaction mixture was heated at 60° C. under nitrogen overnight. The reaction was quenched by cautious drop-wise addition of 10% NaOH at 0° C. via syringe. The layers were separated, and the aqueous layer was extracted with ethyl acetate (3×25 mL) The combined organic layers were washed with water and brine, dried over MgSO$_4$, and concentrated using a rotary evaporator. The product was purified by HPLC (eluent: 10% B-100% B in 30 minutes, B=80% aq. CH$_3$CN with 0.1% TFA, A=H$_2$O with 0.1% TFA; FR=8 mL/min; 254 nm, room temperature, retention time 18.45 minutes). The fractions were collected and evaporated in vacuo. To the resulting residue, 1 mL 1N HCl was added, and the material was lyophilized to give the product as an off white solid (0.1517 g, 83%). $^1$H NMR (CDCl$_3$) δ 7.72-7.58 (m, 3H), 7.43-7.38 (m, 3H), 7.15-7.06 (m, 6H), 3.90 (d, 1H, J=9.6 Hz), 3.67-3.59 (m, 1H), 3.31-3.16 (m, 2H), 2.54 (s, 3H), 2.28 (s, 3H) MS m/z (ESI) 305.22 (MH)$^+$. $^1$H NMR (CD$_3$OD) δ 7.86-7.74 (m, 3H), 7.64 (s, 1H), 7.52-7.44 (m, 2H), 7.35-7.25 (m, 3H), 7.19-7.12 (m, 3H), 4.76 (d, 1H, J=7.83 Hz), 4.13-4.00 (m, 1H), 3.76 (dd, 1H, J=12.6, 3.6 Hz), 3.66-3.53 (m, 1H), 2.66 (s, 3H), 2.52 (s, 3H).

Example 83—Synthesis of Compound ID No. 83 ((1S,2S)-3-(dimethylamino)-2-(naphthalen-2-yl)-1-phenylpropan-1-ol)

tert-Butyl (2S,3S)-3-hydroxy-2-(naphthalen-2-yl)-3-phenylpropyl(methyl)-carbamate (Compound No. 8a) (0.350 g, 0.894 mmol) was dissolved in 10 mL of THF in a round bottom flask equipped with a stir bar and water condenser. LiAlH$_4$ (0.217 g, 7.15 mmol) was cautiously added in small portions. The mixture was then heated at 60° C. under nitrogen overnight. The reaction was quenched by drop-wise addition of 10% NaOH. The organic and aqueous layers were then separated in a separatory funnel, and the aqueous layer was extracted in ethyl acetate (3×50 mL). The combined organic layers were washed with water and brine, dried with Na$_2$SO$_4$, and concentrated under reduced pressure. The resulting residue was purified by flash chromatography using silica gel with 0.1% TEA in 5% MeOH/DCM as eluent. The product containing fractions were pooled and concentrated to leave an oil that was converted to a hydrochloride by adding 1N HCl. The product was lyophilized to yield an off-white solid (256 mg, 94%). $^1$H NMR (CD$_3$OD) δ 7.81-7.69 (m, 3H), 7.62 (s, 1H), 7.48-7.39 (m, 2H), 7.28-7.22 (m, 1H), 7.21-7.06 (m, 5H), 5.05 (d, 1H, J=9.0 Hz), 4.15-4.04 (m, 1H), 3.66-3.53 (m, 2H), 3.01 (s, 6H). MS m/z (ESI) 306 (MH$^+$).

Example 84—Synthesis of Compound ID No. 84 (methyl 2-(((1S,2S)-3-(methylamino)-2-(naphthalen-2-yl)-1-phenylpropoxy)methyl)oxazole-4-carboxylate)

Compound No. 84a (0.15 g, 0.28 mmol) was taken up in 15 mL of CH$_2$Cl$_2$ and stirred at room temperature. 2,2,2-trifluoroacetic acid (5 mL, 67.31 mmol) (protein sequencing grade) was added in one portion, and the mixture was stirred for 30 minutes at room temperature, and concentrated in vacuo 102 mg of a clear oil remained on Monday morning. This material was absorbed onto silica gel directly and ran through an ISCO blue 40 gram normal phase silica column with a ramp of 0-30% MeOH (20% 7N NH$_3$ MeOH)/CH$_2$Cl$_2$. This ammonia MeOH presumably freed the TFA salt. The majority of this peak was evaporated down from CHCl$_3$ several times, then taken up in a minimal amount of CHCl$_3$, and diluted with diethyl ether. 2.0 N HCl was added. This material was taken down from ether once, then scraped from the flask, and dried to afford 0.070 g (45.8%) of the desired product as an HCl salt. ¹H NMR (500 MHz, DMSO-d6) 8.85 (s, 1H) 8.60 (br. s., 1H) 8.53 (br. s., 1H) 7.78-7.84 (m, 1H) 7.75 (d, J=8.5 Hz, 2H) 7.62 (s, 1H) 7.40-7.50 (m, 2H) 7.09-7.30 (m, 6H) 4.93 (d, J=8.9 Hz, 1H) 4.45-4.57 (m, 2H) 3.83 (s, 2H) 3.63-3.75 (m, 2H) 3.33-3.50 (m, 2H) 2.59 (t, J=5.3 Hz, 2H).

Example 84a—Synthesis of Compound No. 84a (2-(((1S,2S)-3-(tert-butoxycarbonyl(methyl)amino)-2-(naphthalen-2-yl)-1-phenylpropoxy)methyl)oxazole-4-carboxylate)

Compound No. 8a (0.25 g, 0.64 mmol) in DMF was treated with NaH (0.038 g, 0.96 mmol) at 0° C. for 10 minutes when methyl 2-(chloromethyl)oxazole-4-carboxylate in DMF was added at 0° C. slowly into the stirring solution drop-wise over 10-15 minutes. The resulting mixture was warmed to room temperature and allowed to stir for 12 hours at room temperature. The material was worked up by diluting with 75 mL of CH₂Cl₂ and adding to 75 mL of water. Another 25 mL of each solvent was added. The organic suspension was separated, and MeOH was added to it until it was a clear solution (about 10 mL) with a slightly yellow orange tint. Another 100 mL of CHCl₃ was used to extract the aqueous one more time. Organics were combined, dried with MgSO₄, filtered, evaporated, and then pumped down under high vacuum to remove DMF. The crude material was purified via ISCO column with a 40 gram blue column eluting with 0-100% EtOAc/hexane. 0.155 g (45.7%) of this material was taken on to the next step, considering purity by weight to be approximately 80%.

Example 85—Synthesis of Compound ID No. 85 ((1S,3S)-4-(methylamino)-3-(naphthalen-2-yl)-1-phenylbutan-1-ol)

To LiAlH₄ (0.809 mL, 0.81 mmol) solution in THF (3 mL) at 55° C. under N₂ was added Compound No. 85c (147 mg, 0.40 mmol) in THF (1 mL) drop-wise via syringe over about 5 minutes. The reaction mixture was then heated at reflux for 2.5 hours. The reaction mixture was quenched carefully with saturated Na₂SO₄ and then diluted with saturated NaHCO₃. The aqueous solution was diluted with ether and stirred briefly, and then the ether layer was isolated. The aqueous layer was extracted twice more with ether. The ethereal layers were combined, washed with saturated NaHCO₃ and brine, dried, filtered, and concentrated to a white solid (116 mg, 84%). 1H NMR (500 MHz, DMSO-d6) δ 2.09 (td, J=13.6, 6.6 Hz, 2H) 2.44 (t, J=5.3 Hz, 3H) 3.15 (d, J=3.2 Hz, 1H) 3.20-3.45 (m, 3H) 4.41 (t, J=6.8 Hz, 1H) 5.18-5.46 (m, 1H) 7.22-7.29 (m, 3H) 7.33 (t, J=7.4 Hz, 2H) 7.45 (dd, J=8.5, 1.6 Hz, 1H) 7.52 (tt, J=7.3, 5.2 Hz, 2H) 7.76 (s, 1H) 7.90 (dd, J=9.7, 7.9 Hz, 1H) 8.04-8.17 (m, 1H) 8.61-8.76 (m, 1H). This compound is a pure stereoisomer of known (S)-configuration at C1. Its C3-epimer is Compound ID No. 93. Since Compound ID No. 85 was more potent at hNET than Compound ID No. 93, it was presumed that it is (1S,3S)-configured.

Example 85a—Synthesis of Compound No. 85a ((2S,4S)-4-hydroxy-2-(naphthalen-2-yl)-4-phenylbutanenitrile)

To a solution of n-BuLi (8.66 mL, 21.64 mmol) in THF (40 mL) at 0° C. was added diisopropylamine (3.08 mL, 21.64 mmol), and the mixture was stirred for 15 minutes. A solution of 2-(naphthalen-2-yl)acetonitrile (3.62 g, 21.64 mmol) and TMEDA (3.27 mL, 21.64 mmol) in THF (20 mL) was added. This solution was stirred at 0° C. for 30 minutes before (R)-2-phenyloxirane (1.903 mL, 16.65 mmol) was added neat. The reaction was stirred at 0° C. and allowed to warm to room temperature overnight. LCMS indicated product formation plus unreacted nitrile (in excess). The reaction mixture was diluted with 1N HCl, and the organic layer was isolated. The organic layer was washed twice more with 1N HCl, once with saturated NaHCO₃, washed with brine, dried, filtered, concentrated, and purified on ISCO using an 80 g SiO₂ column using 0-80% EA/Hex over 20 minutes. This mixture of diastereomers was separated using SCF, affording a single diastereomer Compound No. 85a (530 mg, 11%), comprising (2S,4S)-4-hydroxy-2-(naphthalen-2-yl)-4-phenylbutanenitrile was isolated. ¹H NMR 1H NMR (500 MHz, CDCl₃) δ 2.09-2.19 (m, 1H) 2.29 (dd, J=10.1, 4.4 Hz, 2H) 4.37-4.47 (m, 1H) 5.03-5.12 (m, 1H) 7.33-7.54 (m, 10H) 7.84 (dd, J=13.6, 2.1 Hz, 4H). A mixed fraction of diastereomers was also obtained, and is described further in Example 93 below.

Example 85b—Synthesis of Compound No. 85b ((1S 3S)-4-amino-3-(naphthalen-2-yl)-1-phenylbutan-1-ol)

To a solution of Compound No. 85a (530 mg, 1.84 mmol) in THF (15 mL) heated at 75° C. was added the BH₃.SMe₂ (2.306 mL, 4.61 mmol) drop-wise via syringe. The reaction mixture was then heated at 75° C. for 3 hours. The reaction mixture was cooled to room temperature and diluted. The combined acidic layer was made basic with 1 N NaOH and extracted 5 times with DCM. The combined DCM layer was washed with brine, dried (Na₂SO₄), filtered, and concentrated to a white solid (203 mg, 38%). ¹H NMR (500 MHz, CDCl₃) δ 2.25 (d, J14.0 Hz, 1H) 2.38 (d, J=6.6 Hz, 1H) 2.70 (t, J=6.9 Hz, 1H) 3.00 (br. s., 2H) 4.74 (t, J=6.2 Hz, 1H) 7.26-7.30 (m, 2H) 7.30-7.38 (m, 4H) 7.45 (td, J=7.4, 1.4 Hz, 2H) 7.53 (s, 1H) 7.76-7.83 (m, 3H).

Example 85c—Synthesis of Compound No. 85c (ethyl (2S,4S)-4-hydroxy-2-(naphthalen-2-yl)-4-phenylbutylcarbamate)

To a solution/suspension of Compound No. 85b (200 mg, 0.69 mmol) in DCM (6 mL) was added the TEA (0.383 mL, 2.75 mmol). The reaction mixture was cooled to 0° C., and the ethyl carbonochloridate (0.079 mL, 0.82 mmol) was added drop-wise via syringe. The reaction mixture was then stirred at 0° C. for several minutes and allowed to warm to room temperature with continued stirring for 1 hour. The reaction mixture was diluted with DCM and washed with 1N HCl, saturated NaHCO₃, and brine, dried, filtered, and concentrated (273 mg—oil). The material was purified via ISCO using a 12 g SiO₂ column using 0% (hold for 2 minutes) to 60% ethyl acetate/hexane over 15 minutes. The compound did not elute even at 100% ethyl acetate. The column was flushed with 0-7% MeOH/DCM over 15 minutes. The material was eluted with baseline impurities and further purified via preparative TLC using 50% ethyl acetate/hexane. ¹H NMR (500 MHz, CDCl₃) δ ppm 1.15 (t, J=7.2 Hz, 3H) 2.17 (d, J=6.9 Hz, 1H) 2.23-2.36 (m, 1H) 2.89-3.01 (m, 1H) 3.32-3.47 (m, 1H) 3.59-3.74 (m, 1H) 4.04 (q, J=7.0 Hz, 2H) 4.41-4.53 (m, 1H) 4.60-4.74 (m, 1H) 7.26-7.38 (m, 6H) 7.48 (ddd, J=7.6, 5.7, 1.6 Hz, 2H) 7.59 (s, 1H) 7.81 (td, J=8.9, 7.1 Hz, 3H).

Example 86—Synthesis of Compound ID No. 86 (3-(dimethylamino)-2-methyl-2-(naphthalen-2-yl)-1-phenylpropan-1-ol)

A 50 mL round bottom flask was charged with Compound No. 86c (115.4 mg, 0.35 mmol), methanol (5 mL), formalin (0.9 mL), NaBH$_3$CN (44 mg, 0.7 mmol), and ZnCl$_2$ (53 mg, 0.39 mmol). This mixture was allowed to stir overnight at room temperature. In the morning, ether was added (15 mL), and the contents were poured into a separatory funnel. The organic layer was separated, and the aqueous layer was treated with saturated NaHCO$_3$ and extracted with Et$_2$O (3×10 mL). The combined organic layers were dried over MgSO$_4$, filtered, and concentrated to give a residue that was purified via column chromatography (8% MeOH in CH$_2$Cl$_2$) to give 121 mg (0.34 mmol, 97%) after acidification with 4 N HCl in dioxane. This compound was assayed as a racemic mixture.

Example 86a—Synthesis of Compound No. 86a ((RS)-2-(naphthalen-2-yl)propanenitrile)

An oven dried 2 neck 250 mL round bottom flask was charged with 2-naphthylacetonitrile (8.36 g, 50 mmol). The system was degassed and backfilled with N$_2$. Dry THF (100 mL) was added followed by addition of NaH (60% dispersion in oil, 2.1 mg, 52.5 mmol). The orange suspension was allowed to stir for 30 minutes at room temperature. The flask was fitted with an addition funnel containing a solution of iodomethane (3.1 mL, 50 mmol) in 40 mL of dry THF. The iodomethane solution was added drop-wise over a period of 0.5 hours from an addition funnel. Upon addition, the solution was stirred for additional 0.5 hours. The red solution was quenched by the addition of a saturated ammonium chloride solution (15 mL). The contents of the flask were poured into a separatory funnel, extracted with EtOAc (3×20 mL), dried over MgSO$_4$, and evaporated onto celite. The celite was placed onto a silica gel column and was eluted with a 10% EtOAc in hexane solution. 5.31 g (29.3 mmol, 59%) of a white powder was collected. $^1$H NMR (400 MHz, CDCl$_3$) δ 7.91-7.81 (m, 4H), 7.56-7.48 (m, 2H), 7.43 (dd, J=8.5, 2.0 Hz, 1H), 4.07 (q, J=7.3 Hz, 1H), 1.73 (d, J=7.3 Hz, 3H).

Example 86b—Synthesis of Compound No. 86b (3-hydroxy-2-methyl-2-(naphthalen-2-yl)-3-phenyl-propanenitrile)

An oven dried 2 neck 100 mL round bottom flask was charged with Compound No. 86a (1.81 g, 10 mmol) and dry THF (25 mL). The solution was cooled to −78° C. under a N$_2$ atmosphere. LDA (2.0 M in hexane, 5.25 mL, 10.5 mmol) was added drop-wise via a syringe. The solution was stirred at −78° C. for 45 minutes. A saturated aqueous solution of NH$_4$Cl was added at −78° C., and the cooling bath was removed. After 10 minutes, 1 M HCl (10 mL) and Et$_2$O (10 mL) were added, and the contents of the flask were poured into a separatory funnel. The organic layer was collected. The aqueous layer was extracted with ether (2×15 mL), and the combined organic layers were dried over MgSO$_4$, filtered, and concentrated. The residue was purified via column chromatography (25% EtOAc in hexanes) to give 640 mg (2.2 mmol, 22%) of a less polar diastereomer (Compound No. 86b) and 773 mg (2.7 mmol, 27%) of a more polar diastereomer.

Example 86c—Synthesis of Compound No. 86c (3-amino-2-methyl-2-(naphthalen-2-yl)-1-phenylpropan-1-ol hydrochloride)

Compound No. 86b (450 mg, 1.56 mmol) was reduced and acidified in the usual way with BH$_3$/THF (1M in THF, 6.25 mL, 6.25 mmol) and 4 N HCl in dioxane (2 mL) to afford 213 mg of a white solid (0.65 mmol, 42%).

Example 87—Synthesis of Compound ID No. 87 ((2S,3S)—N$^1$-methyl-2-(naphthalen-2-yl)-3-phenyl-propane-1,3-diamine)

tert-Butyl (2S,3S)-3-azido-2-(naphthalen-2-yl)-3-phenyl-propylmethylcarbamate: To a solution of tert-butyl (2S,3R)-3-hydroxy-2-(naphthalen-2-yl)-3-phenylpropylmethylcarbamate (Example 9, 0.343 g, 0.343 mmol) in 5 mL of THF at 0° C. was added triphenylphosphine (0.230 g, 0.876 mmol) under nitrogen. This was followed by sequential drop-wise addition of diisopropyl azodicarboxylate (DIAD) (0.172 mL, 0.177 mmol) and diphenylphosphoryl azide (DPPA) (0.187 mL, 0.876 mmol). The resulting mixture was slowly warmed to room temperature and stirred overnight. The progress of the reaction was monitored by TLC. After quenching the reaction with aqueous NaHCO$_3$, the aqueous phase was extracted with EtOAc (3×25 mL). The organic layers were combined, washed with water and brine, dried over MgSO$_4$, filtered, and evaporated under reduced pressure, leaving an oily residue that was purified by flash chromatography (eluent: 10% EtOAc/hexane) to furnish the desired N-Boc-protected azide as colorless gum (0.327 g, 90%). $^1$H NMR (CDCl$_3$) δ 7.84-6.94 (m, 12H), 4.78 (s, 1H), 3.94-3.89 (br m, 1H), 3.76-3.61 (m, 1H), 3.59-3.31 (m, 1H), 2.55 and 2.49 (two s, 3H), 1.28 (s, 9H). MS m/z (ESI) 439.35 (MNa$^+$).

tert-Butyl (2S,3S)-3-amino-2-(naphthalen-2-yl)-3-phenylpropylmethyl carbamate: A suspension of tert-butyl (2S,3S)-3-azido-2-(naphthalen-2-yl)-3-phenylpropylmethylcarbamate (0.300 g, 0.720 mmol) in 20 mL of methanol and 100 mg of 10% Pd in charcoal was hydrogenated at room temperature for 4 hour and then filtered through Celite. The MeOH was evaporated off under reduced pressure to leave a residue that was purified by flash chromatography over silica gel (eluent: 5% MeOH/DCM to 0.05% TEA in 5% MeOH/DCM) to afford a white solid (0.154 g, 54.8%). $^1$H NMR (CDCl$_3$) δ 7.83-6.49 (m, 12H), 4.25 (s, 1H), 3.81 (s, 2H), 3.58-3.14 (m, 1H), 2.54 and 2.42 (two s, 3H), 1.73 (s, 2H), 1.32 (s, 9H). MS m/z (ESI) 391.20 (MNa$^+$).

Compound ID No. 87: 2 N HCl (6.0 mL in dioxane) was added to a solution of tert-butyl (2S,3S)-3-amino-2-(naphthalen-2-yl)-3-phenylpropylmethylcarbamate (0.154 g, 0.394 mmol), and the acidic mixture was stirred at room temperature for 1 hour under nitrogen. Dioxane was evaporated off using a rotary evaporator. The crude product was purified by reverse phase HPLC (Vydac column, C-18, 2.2×25 cm; eluting with 10% B-100% B in 30 minutes; A=H$_2$O with 0.1% TFA, B=80% aq. CH$_3$CN with 0.1% TFA; FR 8 mL/min; 254 nm. RT=17.863 minutes). The product containing fractions (MS monitoring) were evaporated in vacuo, and the residue was converted to HCl salt. Further purification was achieved by dissolving the salt in 2 mL of MeOH and adding 4 mL of ether that resulted in immediate precipitation of the product. The supernatant was decanted off. This crystallization was repeated two more times. The isolated product was a white powder (0.065 g, 45.4%). $^1$H NMR (DMSO-d$_6$) δ 8.98 (br s, 1H), 8.44 (br s, 1H), 7.88-7.80 (m, 1H), 7.80-7.72 (m, 2H), 7.65 (s, 1H), 7.52-7.44 (m, 2H), 7.32-7.16 (m, 6H), 4.86 (d, 1H, J=9.0 Hz), 4.08-3.92 (m, 1H), 3.72 (d, 1H, J=>8 Hz), 3.57 (s, 3H), 3.54-3.43 (m, 1H). $^1$H NMR (DMSO-d$_6$) δ 8.98 (br s, 1H), 8.44 (br s, 1H), 7.88-7.80 (m, 1H), 7.80-7.72 (m, 2H), 7.65 (s, 1H), 7.52-7.44 (m, 2H), 7.32-7.16 (m, 6H), 4.86 (d, 1H, J=9.0 Hz), 4.08-3.92 (m, 1H), 3.72 (d, 1H, J=10.7 Hz), 3.57 (s, 3H), 3.54-3.43 (in, 1H). MS m/z (ESI) 291.45 (MH$^+$).

Example 88—Synthesis of Compound ID No. 88 ((1R,2R)-3-amino-2-(naphthalen-2-yl)-1-phenylpropan-1-ol)

anti-Racemic mixture of 3-amino-2-(naphthalen-2-yl)-1-phenylpropan-1-ol (1 g, 3.61 mmol) was purified by chiral SFC separation into two enantiomers (S,S and R,R). The purified material LCMS indicated no other impurities presented. $^1$H NMR (500 MHz, DMSO-d6) δ 6.64-7.98 (m, 12H), 4.93 (d, J=7.9 Hz, 1H), 3.24 (d, J=5.8 Hz, 1H), 2.96-3.14 (m, 2H) MS m/z (ESI) 278.2 (MH)$^+$. This enantiomer was assigned R,R configuration based its conversion to (1R,2R)-3-(methylamino)-2-(naphthalen-2-yl)-1-phenylpropan-1-ol whose X-ray was reported earlier. This compound was assigned 1R,2R configuration because of the high J-value (9.0 Hz) of the benzylic proton and lower potency at hNET compared to its 1S,2S antipode.

Example 89—Synthesis of Compound ID No. 89 (2-((1S,2S)-3-(dimethylamino)-2-(naphthalen-2-yl)-1-phenylpropoxy)ethanol)

Ethyl 2-((1S,2S)-3-(tert-butoxycarbonyl(methyl)amino)-2-(naphthalen-2-yl)-1-phenylpropoxy)acetate (Compound No. 8b) (0.090 g, 0.177 mmol) dissolved in 5 mL of dry THF and LiAlH$_4$ (0.027 g, 0.709 mmol) were added to a round bottom flask equipped with a stir bar and water condenser. The mixture was refluxed (at 60° C.) under nitrogen overnight. The reaction was quenched by cautious addition of 10% NaOH drop-wise. The reaction mixture was poured into a separatory funnel, and the layers were separated. The aqueous layer was extracted with ethyl acetate (3×25 mL), and the combined organic layers were washed with water and brine, and dried over MgSO$_4$. The organic layer was concentrated using a rotary evaporator. To the resulting residue about 1 mL 1N HCl was added, and the mixture was stirred and then lyophilized yielding a white solid. $^1$H NMR (CD$_3$OD)) δ 7.81-7.67 (m, 3H), 7.62 (s, 1H), 7.49-7.40 (m, 2H), 7.28-7.20 (m, 1H), 7.19-7.09 (m, 5H), 4.90 (d, 1H, J=10.4 Hz), 4.26-4.12 (s, 1H), 3.88-3.67 (m, 3H), 3.59-3.43 (m, 3H), 3.13 (m, 3H), 3.01 (s, 3H) MS m/z (ESI) 350.04 (MH$^+$).

Example 90—Synthesis of Compound ID No. 90 ((R)-2-(3-(methylamino)-2-(naphthalen-2-yl)propyl) phenyl)methanol)

This compound is the enantiomer (second eluting) of Compound ID No. 2. Separation details were performed as described in Example 2. The combined fractions of the second eluting enantiomer were concentrated in vacuo and converted to an HCl salt that afforded 39 mg of Compound ID No. 90, which was shown by the above described SCF system to have 84% enantiomeric excess. $^1$H NMR (500 MHz, CD$_3$OD) δ 1.78-1.88 (m, 1H), 1.95 (dd, J=13.9, 6.3 Hz, 1H), 2.02 (s, 3H), 2.10 (dd, J=11.3, 3.1 Hz, 1H), 2.18-2.34 (m, 2H), 2.18-2.34 (m, 1H), 3.20-3.41 (m, 1H), 3.20-3.27 (m, 1H), 3.33-3.40 (m, 1H), 5.71 (d, J=7.3 Hz, 1H), 5.80 (t, J=7.0 Hz, 1H), 5.87 (t, J=7.3 Hz, 1H), 6.03 (d, J=7.6 Hz, 1H), 6.12-6.24 (m, 3H), 6.44 (s, 1H), 6.49-6.54 (m, 1H), 6.54-6.59 (m, 1H), 6.62 (d, J=8.5 Hz, 1H). Since this compound was less potent at the hNET than the first eluting enantiomer, it was presumed to be (R)-configured.

Example 91—Synthesis of Compound ID No. 91 ((1R,2S)-3-amino-2-(naphthalen-2-yl)-1-phenylpropan-1-ol)

anti- and syn-3-amino-2-(naphthalen-2-yl)-1-phenylpropan-1-ol: A 2-L three neck round bottom flask equipped with a mechanical stirrer, nitrogen inlet, thermometer, and septum was charged with THF (625 mL) and diisopropylethylamine (18.71 mL, 131.24 mmol) and chilled to −78° C. Butyllithium (50.0 mL, 125.00 mmol) was added and the resulting mixture stirred for 5 min. A solution of 2-(naphthalen-2-yl) acetonitrile (20.9 g, 125.00 mmol) in THF (625 mL) was added and stirred for 30 min. Benzaldehyde (12.67 mL, 125.00 mmol) was added via syringe and after an additional 5 min the reaction was quenched with saturated aqueous NH$_4$Cl (125 ml) while still at −70.0° C. The reaction mixture was diluted with 1N HCl (250 ml) and Et$_2$O (300 ml) layers separated and the aqueous layer was extracted with Et$_2$O (2×150 ml)), and the combined organic extracts were washed with brine (150 ml) and dried (MgSO$_4$). Concentrated in vacuo to give the crude aldol. Recrystallization from DCM (300 ml) and hexanes (600 ml) gave 24.8 g of anti-product with a small amount of syn-isomers by NMR. A second recrystallization with DCM (300 ml) and hexanes (400 ml) gave pure anti. The filtrate was evaporated to give a 2:1 mixture of syn and anti-isomers.

Compound ID No. 91: The 1:2 anti- and syn-mixture of 3-Hydroxy-2-(naphthalen-2-yl)-3-phenylpropanenitrile (2.73 g, 10 mmol) in THF (10 mL) was chilled to 0° C. and borane-DMS (3.51 mL, 37.00 mmol) was added dropwise over 10 minutes and the reaction stirred overnight while warming to ambient temperature. Reaction was heated to 80° C. and 5.5 ml distillate collected. Reaction was then cooled to ambient temperature and borane-DMS (2 mL) was added and the reaction heated to reflux for 30 minutes. Reaction was cooled to room temperature, treated with 6 N HCl (20 mL) and heated to 80° C. for 1 hour. After cooling to 0° C., the reaction mixture was basified with NaOH (6 g) and extracted with ether (2×50 mL). The combine organic fractions were dried (K$_2$CO$_3$), filtered and concentrated to give 3.9 g of the crude product. Flash chromatography on silica gel (400 mL) with 5-50% methanol/DCM gradient elution gave 1.45 g (52%) of the syn isomers and 0.4 g (14%) of the anti isomers. The racemic syn-3-amino-2-(naphthalen-2-yl)-1-phenylpropan-1-ol (1.1 g, 3.97 mmol) was resolved by SFC, and the first-eluting enantiomer (Compound ID No. 91) was assumed to be 1R,2S-configured based on its higher potency on hNET.

Example 92—Synthesis of Compound ID No. 92 ((1S,2S)-1-(5-methoxypyridin-3-yl)-3-(methylamino)-2-(naphthalen-2-yl)propan-1-ol)

A solution of Compound No. 92c (320 mg, 0.84 mmol) in THF (20.00 mL) was added over 5 minutes to a stirred suspension of borane-tetrahydrofuran complex (4.21 mL, 4.21 mmol) heated to 45° C. The reaction was heated 4 hours at reflux (internal temp at 66° C., oil bath at 72° C.) to give a bright purple suspension. The suspension was cooled to ambient temperature and carefully quenched with 4N HCl in dioxane diluted with methanol stirred for 15 minutes at 60° C. before removal of the solvent. The crude material was dissolved in 10 mL of ethanol and stirred for 10 minutes at 60° C. All the solvents were removed to afford a crude HCl salt that was washed with ether, ethyl acetate/hexane (1:1), and hexane to afford the HCl salt of the product. This was converted to basic amine, and ISCO purification eluting 0-10% of methanol in DCM (alumina column) afforded 150 mg of the desired product. $^1$H NMR data matched the proposed structures. Because Compound ID No. 92 was more potent at hNET than its enantiomer Compound ID No. 122, it was considered to be (1S,2S)-configured.

Example 92a—Synthesis of Compound No. 92a (3-hydroxy-3-(5-methoxypyridin-3-yl)-2-(naphthalen-2-yl)propanenitrile)

A 250 mL round bottom flask equipped with a magnetic stirring bar, nitrogen inlet, and septum was charged with THF (100 mL) and butyllithium (7.29 mL, 18.23 mmol). After cooling to −78° C., 2-(naphthalen-2-yl)acetonitrile (3.05 g, 18.23 mmol) was added, and after 60 minutes, 5-methoxynicotinaldehyde (2.5 g, 18.23 mmol) was added via syringe. After stirring at (−78° C.) for 3 hours, the reaction was quenched by the addition of acetic acid (2.1 mL) while stirring at −70° C. The aqueous layer was extracted with Et$_2$O (2×250 mL), and the combined organic extracts were washed with brine (250 mL) and dried (MgSO$_4$). The material was concentrated in vacuo to give a crude aldol (6 g). ISCO purification on silica gel eluting with 0-100% of ethyl acetate in hexane afforded the product as an anti:syn mixture (4 g, 72%). $^1$H NMR (500 MHz, CDCl$_3$) δ 2.80 (d, J3.7 Hz, 1H), 3.78 (s, 3H), 4.24 (d, J=5.2 Hz, 1H), 5.12 (d, J=3.4 Hz, 1H), 7.18-7.38 (m, 4H), 7.47-7.61 (m, 2H), 7.73-7.93 (m, 5H), 8.04 (d, J=1.5 Hz, 1H), 8.23 (d, J=2.7 Hz, 1H).

Example 92b—Synthesis of Compound No. 92b (3-amino-1-(5-methoxypyridin-3-yl)-2-(naphthalen-2-yl)propan-1-ol)

A solution of Compound No. 92a (2.5 g, 8.21 mmol) in THF (100 mL) was added over 5 minutes to a stirred suspension of 1.0 M in THF borane-tetrahydrofuran complex (24.64 mL, 24.64 mmol) heated to 45° C. The reaction was heated for 3 hours at reflux (internal temp at 66° C., oil bath at 72° C.). The solution was cooled to ambient temperature and carefully quenched with 8 mL of 4N of HCl in dioxane diluted with 10 mL of methanol. The mixture was stirred for 15 minutes at 60° C., and then all the solvent was removed. 10 mL of ethanol was added, and the mixture was stirred at 60° C. for 10 minutes. All the solvents were removed to afford the crude product, which was washed with ethyl acetate twice and dried in vacuo. 3.4 g of the HCl solid was obtained, which was quenched with 8 mL of 4 N of HCl in dioxane diluted with 10 mL of methanol. The mixture was stirred for 15 minutes at 60° C., and all the solvent was removed. 10 mL of ethanol was added, and the mixture was stirred at 60° C. for 10 minutes before removal of all the solvents to afford the crude product, which was washed with ethyl acetate twice and dried in vacuo to yield 3.4 g (>100%) of white HCl solid. $^1$H NMR data matched the proposed structures.

Example 92c—Synthesis of Compound No. 92c (ethyl 3-hydroxy-3-(5-methoxypyridin-3-yl)-2-(naphthalen-2-yl)propylcarbamate)

Compound No. 92b (2.53 g, 8.21 mmol) and TEA (3.43 mL, 24.63 mmol) in DCM (100 mL) were added and chilled to 0° C. To the chilled solution was added ethyl carbonochloridate (0.946 mL, 9.85 mmol) over 10 minutes. The ice bath was removed, and the solution was allowed to warm to room temperature and stirred for 2 hours. The reaction solution was reduced to 5 mL (in DCM), diluted with ethyl acetate (200 mL), washed with minimum 0.1 N HCl (2×10 mL), saturated sodium bicarbonate (150 mL), and brine (200 mL), then dried over MgSO$_4$, filtered, and concentrated in vacuo. The residual solvents were evaporated to give product as a form (2.2 g). The mixture was purified on ISCO eluting with 0-100% of ethyl acetate in hexane over 35 minutes. The major peak was collected, and all the solvent evaporated. 1.5 g of a mixture of diastereomers were collected. This mixture was separated into four isomers using SCF chromatography. The 1.5 g of sample were diluted in about 25 mL of EtOH (0.5% isopropylamine), and stacked injections of 0.35-0.5 mL each were run using 23% of EtOH (0.5% isopropylamine) isocratic at 110 mL/minute. The compounds of the first two peaks were well separated and gave 320 mg each. The compounds of the third and fourth peaks were combined and reprocessed with a 30 mm×250 mm Phenomenex Cellulose-2 column using 27.5% i-PrOH (0.5% isopropylamine) at 110 mL/minute and gave 300 mg from peak 3 fractions and 320 mg from peak 4 fractions. The second-eluting compound from this pair (Peak 4) was determined to possess anti-relative stereochemistry carried on to the next step (see Example 92). The first-eluting compound from this pair (Peak 3) was used in the preparation of Compound ID No. 122. $^1$H NMR data matched the proposed structures.

Example 93—Synthesis of Compound ID No. 93 ((1S,3R)-4-(methylamino)-3-(naphthalen-2-yl)-1-phenylbutan-1-ol)

To LiAlH$_4$ (0.413 mL, 0.41 mmol) solution in THF (2 mL) at 55° C. under N$_2$ was added Compound No. 93b (75 mg, 0.21 mmol) in THF (1 mL) drop-wise via syringe over about 5 minutes. The reaction mixture was then heated at reflux for 2.5 hours. The reaction mixture was quenched carefully with saturated Na$_2$SO$_4$, and then diluted with saturated NaHCO$_3$. The mixture was diluted with ether and stirred briefly, and then the ether layer was isolated. The aqueous layer was extracted twice more with ether. The ethereal layers were combined, washed with saturated NaHCO$_3$ and brine, dried, filtered, and concentrated to a white solid (46 mg). The foamy solid was converted to an HCl salt using 4 M HCl in dioxane and triturated with ether to give a white solid (44 mg, 65%). This compound is a pure stereoisomer of known (S)-configuration at C1. Since this compound is less potent at hNET than its C3-epimer (Compound ID No. 85), it is presumed to be (1S,3R)-configured. $^1$H NMR (500 MHz, DMSO-d6) δ ppm 1.94 (d, J=11.4 Hz, 1H) 1.99-2.13 (m, 1H) 2.50 (br. s., 7H) 3.57 (br. s., 1H) 4.12 (d, J=10.2 Hz, 1H) 5.35 (br. s., 1H) 7.14-7.32 (m, 5H) 7.45-7.62 (m, 3H) 7.94 (ddd, J=18.0, 9.0, 8.8 Hz, 4H) 8.17-8.34 (m, 1H) 8.69-8.85 (m, 1H).

Example 93a—Synthesis of Compound No. 93a (ethyl (2R,4S)-4-hydroxy-2-(naphthalen-2-yl)-4-phenylbutylcarbamate)

Compound No. 93a (see Example 85 above, 284 mg, 0.99 mmol) which consists of a mixture of diastereomers ((2S, 4S)-4-hydroxy-2-(naphthalen-2-yl)-4-phenylbutanenitrile and (2R,4S)-4-hydroxy-2-(naphthalen-2-yl)-4-phenylbutanenitrile)) were treated with BH$_3$/SMe$_2$ (1.24 mL, 2.48 mmol) dropwise via syringe. The reaction mixture was then heated at 75° C. for 3 hours. The reaction mixture was then cooled to r.t. and diluted. The combined acidic layer was made basic with 1 N NaOH and extracted 5 times with DCM. The combined DCM layer was washed with brine, dried, filtered and concentrated to afforded a white solid (278 mg, 97%). This crude material was dissolved in DCM (6 mL) followed by addition of triethylamine (0.532 mL, 3.82 mmol). The reaction mixture was cooled to 0° C. and the ethyl carbonochloridate (0.109 mL, 1.14 mmol) was added dropwise via syringe. The reaction mixture was then stirred at 0° C. for several minutes, then allowed to warm to r.t. and continued stirring for 1 hour, then diluted with DCM and washed with 1N HCl, saturated $NaHCO_3$, brine, dried, filtered, and concentrated to afford 309 mg of as a mixture of diastereomers. SCF chromatography was able to afford 78 mg (22%) of Compound No. 93b, which is the C2-epimer of Compound No. 85c.

Example 94—Synthesis of Compound ID No. 94 ((1R,2S)—N-(3-((1R,2S)-2-(3,4-dichlorophenyl)-1-hydroxy-3-(methylamino)propyl)phenyl)acetamide)

The enantiomers from Compound No. 94a were separated by SFC (ADH column, 25% iPrOH with 0.5% dimethylethylamine). The second-eluting enantiomer was isolated and converted to an HCl salt in the usual way to afford 8 mg (20%), which was shown to have a >99% enantiomeric excess. $^1$H NMR data matched the proposed structure. Since this compound was the more potent enantiomer at hNET, it was presumed to be (1R,2S)-configured.

Example 94a—Synthesis of Compound No. 94a (N-(3-((syn-2-(3,4-dichlorophenyl)-1-hydroxy-3-(methylamino)propyl)phenyl)acetamide)

The nitro compound described in Example 63 (550 mg, 1.55 mmol) and iron (346 mg, 6.19 mmol) in acetic acid (1.5 mL)/EtOH (1.5 mL) were refluxed at 100° C. for 1 hour. Upon cooling, the reaction mixture was neutralized with saturated $Na_2CO_3$ solution and then extracted with $CHCl_3$. The combined organic layer was dried, filtered, and concentrated to a dark brown oil. The crude product was added to a silica gel column and was eluted with 0-10% ammoniated MeOH in $CH_2Cl_2$ to give 42 mg (7.4%) as a pale-yellow gum.

Example 95—Synthesis of Compound ID No. 95 ((1R,2S)-3-amino-1-(3-chloropyridin-4-yl)-2-(naphthalen-2-yl)propan-1-ol)

anti- and syn-3-(3-chloropyridin-4-yl)-3-hydroxy-2-(naphthalen-2-yl)propanenitrile: These compounds were made in a standard LDA-mediated reaction of 2-naphthylacetonitrile and 3-chloro-4-pyridine carboxaldehyde at −78° C. in THF. These diastereomers were separated by either recrystallization or chromatography. anti-isomer: $^1$H NMR ($CDCl_3$) δ 8.57 (1, 1H), 8.30 (d, 1H, J=5.1 Hz), 7.83-7.76 (m, 1H), 7.75-7.68 (m, 2H), 7.61 (bs, 1H), 7.53-7.49 (m, 2H), 7.12 (dd, 1H, J=8.4, 1.6 Hz), 7.08 (d, 1H, J=4.8 Hz), 5.86 (t, 1H, J=4.5 Hz), 4.46 (d, 1H, J=4.5 Hz), 2.86 (d, 1H, J=4.5 Hz).

((1R,2S)-3-amino-1-(3-chloropyridin-4-yl)-2-(naphthalen-2-yl)propan-1-ol): A solution of syn-3-(3-chloropyridin-4-yl)-3-hydroxy-2-(naphthalen-2-yl)propanenitrile (1.4 g, 4.53 mmol), in 20 mL of dry THF, was placed in an oven-dried round-bottom flask with a reflux condenser under nitrogen. Next, 1M borane-THF solution (18.14 mL, 18.14 mmol) was added via syringe. This mixture was stirred at 60° C. overnight while monitoring the reaction progress by TLC. After quenching the reaction with cautious addition of saturated $NaHCO_3$, the reaction mixture was poured into a separatory funnel. The layers were separated; the aqueous layer was extracted with EtOAc (3×50 mL). The combined organic layers were washed with water and brine, and dried over $MgSO_4$, and were concentrated using a rotary evaporator. The residue was dissolved in DCM. 4N HCl in dioxane was added, and the mixture was stirred. The solvents were evaporated in vacuo and the resulting salt was washed with ether, dried and lyophilized yielding a white solid (1.367 g, 78%). $^1$H NMR ($CDCl_3$) δ 8.45 (s, 1H), 8.21 (d, 1H, J=5.1 Hz), 7.59-7.88 (m, 4H), 7.39-7.57 (m, 2H), 7.21-7.36 (m, 1H), 7.19 (d, 1H, J=5.1 Hz), 5.64 (d, 1H, J=3.4 Hz), 3.37 (d, 3H, J=4.2 Hz). Small J-value (3.4 Hz) of the benzylic proton indicated syn-relative configuration. MS m/z (ESI) 313.11 ($MH^+$). The Multigram II SFC chiral chromatography system of the racemate furnished two fractions containing the opposite enantiomers. Compound ID No. 95 recovered from the second-eluting enantiomer was assigned (1R,2S)-configuration based on its higher inhibitory activity on the hNET compared to the first-eluting enantiomer.

Example 96—Synthesis of Compound ID No. 96 ((1S,2R)-1-(2-fluorophenyl)-3-(methylamino)-2-(naphthalen-2-yl)propan-1-ol)

This compound is the enantiomer (first eluting) of Compound ID No. 60. Separation details are described in Example 60. The combined fractions of the first eluting enantiomer were concentrated in vacuo and converted to an HCl salt that afforded 69.7 mg of Compound ID No. 96, which was shown by the previously described SCF system to have 85% enantiomeric excess. $^1$H NMR (300 MHz, $CD_3OD$) δ 7.70-7.85 (m, 3H), 7.61 (s, 1H), 7.45 (dddd, J=6.4, 3.6, 3.4, 3.2 Hz, 2H), 7.33 (dd, J=8.7, 1.5 Hz, 1H), 7.18 (d, J=7.9 Hz, 1H), 7.14-7.23 (m, 1H), 7.09 (t, J=7.5 Hz, 1H), 7.01 (dd, J=9.6, 0.9 Hz, 1H), 6.90 (t, J=7.5 Hz, 1H), 5.45 (d, J=4.1 Hz, 1H), 3.69-3.81 (m, 1H), 3.56 (ddd, J=9.6, 4.1, 4.0 Hz, 2H), 2.68 (s, 3 H). Since this enantiomer is less potent at hNET than the second eluting enantiomer, it was presumed to be (1S,2R)-configured.

Example 97—Synthesis of Compound ID No. 97 ((1R,2S)-2-(3,4-dichlorophenyl)-3-(methylamino)-1-(2-(methylthio)phenyl)propan-1-ol)

To a stirred solution of the 2-(3,4dichlorophenyl)acetonitrile (5.6 g, 30.10 mmol) in dry THF (60 mL) at −75° C. was added drop-wise n-BuLi. After 20 minutes stirring at −75° C., a solution of the 2-(methylthio)benzaldehyde (3.88 mL, 30.10 mmol) in THF (20 mL) was added drop-wise (color faded). After 30 minutes stirring at −75° C., a solution of acetic acid (2.1 mL, 36.68 mmol) in THF (5 mL) was added drop-wise. After stirring the resulting clear solution for 15 minutes, a borane-tetrahydrofuran complex (100.0 mL, 100.00 mmol) was added drop-wise, and the dry ice bath was removed. The mixture was allowed to warm to room temperature (gas evolution observed) and then heated at mild reflux for 2 hours. The mixture was chilled to 0° C. with an ice bath, 2N HCl (60 mL) was cautiously added drop-wise, the ice bath was removed, and the mixture was heated at mild reflux for 2 hours. The mixture was cooled, and the volatiles were removed on rotary evaporator. The white suspension was diluted with chloroform (150 mL) and cooled to 0° C. With vigorous stirring, the mixture was made basic by drop-wise addition of 1N NaOH. The layers were separated, and the aqueous layer was extracted with chloroform (2x). The organics were combined, washed with half-saturated brine, dried. The concentration to dryness afforded a white solid (10.3 g, 100%), which was used directly in the next step. The lot of this compound (10.3 g, 30.09 mmol) and Et$_3$N (6.27 mL, 45.0 mmol) in DCM (140 mL) were treated with a solution of ethyl chloroformate (3.8 mL, 39.57 mmol) in DCM (40 mL). This mixture was stirred for 2 hours and concentrated. The residue was partitioned between ether and aqueous sodium bicarbonate, and extracted with ether (2x). The organic extracts were combined, washed with brine, dried, and concentrated to give crude product (10 g) as a white solid. Approximately half of this material was subjected to chromatography (ISCO 220 g column) eluting with a 0-50% EtOAc/hexanes gradient to give in order 1.0 g (syn isomer) followed by 1.6 g (anti isomer). The lot of the syn isomer (1.0 g, 2.4 mmol) was dissolved in dry THF (10 mL) and added drop-wise to borane-tetrahydrofuran complex (10 mL, 10.0 mmol) at 0° C. The mixture was warmed to room temperature and heated to reflux for 3 hours. The clear solution was chilled with an ice bath and cautiously treated with drop-wise addition of 3 N HCl (10 mL). The resulting solution was warmed to room temperature and heated at reflux for 2 hours. The volatiles were removed on rotary evaporator. The white suspension was diluted with chloroform (150 mL) and cooled to 0° C. With vigorous stirring, the mixture was made basic by drop-wise addition of 1 N NaOH. The layers were separated, and the aqueous layer was extracted with chloroform (2x). The organics were combined, washed with half-saturated brine, and dried. Concentration to dryness afforded a white solid (1.1 g). This solid was resolved into its two component enantiomers using SCF. The first eluting enantiomer was acidified with 4 N HCl in dioxane in the usual way to afford 370 mg (0.94 mmol, 3% overall yield) of the HCl salt. $^1$H NMR data matched the proposed structure. Since this compound was the more potent enantiomer at hNET, it was presumed to be (1R,2S)-configured.

Example 98—Synthesis of Compound ID No. 98 (N-(3-((1S,2R)-2-(3,4-dichlorophenyl)-1-hydroxy-3-(methylamino)propyl)phenyl)acetamide)

The enantiomers from Compound No. 94a were separated by SFC (ADH column, 25% iPrOH with 0.5% dimethylethylamine). The first eluting enantiomer was isolated and converted to an HCl salt in the usual way to afford 10 mg (23%), which was shown to have a >99% enantiomeric excess. $^1$H NMR data matched the proposed structure. Since this compound was the less potent enantiomer at hNET, it was presumed to be (1S,2R)-configured.

Example 99—Synthesis of Compound ID No. 99 ((1S,2R)-3-(methylamino)-2-(naphthalen-2-yl)-1-(pyridin-2-yl)propan-1-ol)

(1R,2S and 1S,2R)-3-(methylamino)-2-(naphthalen-2-yl)-1-(pyridin-2-yl)propan-1-ol (Example 72) was a pair of R,S and S,R enantiomers. The enantiomers were separated using chiral Multigram II SFC system. The enantiomer corresponding to the first-eluting peak was assigned the (1S,2R) configuration based on its lower inhibitory activity compared to the second-eluting peak. $^1$H NMR (500 MHz, DMSO-d6) δ ppm 8.99 (br. s., 1H) 8.39-8.59 (m, 2H), 7.89 (br. s., 0H), 7.73-7.85 (m, 3H), 7.71 (d, 1H, J=8.55 Hz), 7.59 (s, 1H), 7.38-7.49 (m, 4H), 7.20 (d, 2H, J=8.55 Hz), 5.39 (br. s., 1H,) 3.79-3.88 (m, 1H), 3.47-3.63 (m, 2H), 2.59 (t, 3H, J=5.49 Hz).

Example 100—Synthesis of Compound ID No. 100 ((1R,2S)-2-(3,4-dichlorophenyl)-3-(methylamino)-1-(2-(thiophen-2-yl)phenyl)propan-1-ol)

2-(3,4-dichlorophenyl)-3-hydroxy-3-(2-(thiophen-2-yl) phenyl)propanenitrile: A solution of 2-(3,4-dichlorophenyl) acetonitrile (4.5 g, 24.19 mmol) in 30 mL ether and 30 mL THF was placed under nitrogen in an oven dried round bottom flask with a stir bar and cooled to −75° C. in an acetone dry ice bath. Butyllithium (16.33 mL, 26.12 mmol) (1.6 M in hexane) was added slowly while maintaining the internal temperature of the reaction mixture below −55° C. After stirring for 15 minutes, 2-(thiophen-2-yl)benzaldehyde (4.55 g, 24.19 mmol) dissolved in 20 mL THF was added drop-wise via syringe. The reaction mixture was allowed to stir for 2.5 hours at −75° C. and then quenched with a solution of acetic acid (2.077 mL, 36.28 mmol) in 5 mL of diethyl ether. The quenched mixture was slowly warmed to room temperature. Water (100 mL) was added, and the organic layer was separated in a separatory funnel. The aqueous layer was extracted with EtOAc (x3). The combined organic extracts were washed with saturated aqueous sodium bicarbonate, dried with MgSO$_4$, filtered, and evaporated to a thick clear, pale yellow oil (9.42 g). The crude was purified by chromatography (eluent: 0-60% EtOAc in hexane) yielding 2-(3,4-dichlorophenyl)-3-hydroxy-3-(2-(thiophen-2-yl)phenyl)propanenitrile (6.90 g, 76%) and taken to the next step. $^1$H NMR in CDCl$_3$ showed the presence of the expected mixture of diastereomers. $^1$H NMR data were consistent with the desired structure. MS m/z (ESI) 396.1 (MNa$^+$).

3-amino-2-(3,4-dichlorophenyl)-1-(2-(thiophen-2-yl) phenyl)propan-1-ol: A solution of 2-(3,4-dichlorophenyl)-3-hydroxy-3-(2-(thiophen-2-yl)phenyl) propanenitrile (6.9 g, 18.44 mmol) in 160 mL THF was placed and stirred under nitrogen in a 500 mL flask fitted with a Dean-Stark trap. Next, borane-methyl sulfide complex (23.04 mL, 46.09 mmol) was added in several portions. The resulting reaction mixture was heated to 75° C. under mild reflux for 3 hours. After cooling in an ice bath, the reaction was quenched with 9 mL of 4M HCl in dioxane. MeOH (20 mL) was cautiously added. Addition of MeOH caused vigorous gas evolution. After the gas evolution ceased, the reaction was heated to 80° C. for 30 minutes generating B(OMe)$_3$.etherate, which was collected into the Dean-Stark trap. The reaction was then cooled to room temperature, and the solvents were evaporated. The resulting sticky white/yellow solid was dissolved in 150 mL of CHCl$_3$ and washed with saturated, aqueous NaHCO$_3$ to free the HCl salt. The layers were separated, and the aqueous layer was extracted twice with CHCl$_3$. Organic extracts were combined, dried with MgSO$_4$, filtered, and concentrated to a tacky orange gum. The crude product (3-amino-2-(3,4-dichlorophenyl)-1-(2-(thiophen-2-yl)phenyl)propan-1-ol; 7.05 g, 101%) was carried to the next step without further purification. $^1$H NMR in CDCl$_3$ showed the presence of the expected mixture of diastereomers. MS m/z (ESI) 378.2 (MH$^+$).

syn-tert-butyl (2-(3,4-dichlorophenyl)-3-hydroxy-3-(2-(thiophen-2-yl)phenyl)propyl)carbamate: A mixture of 3-amino-2-(3,4-dichlorophenyl)-1-(2-(thiophen-2-yl)phenyl)propan-1-ol (7.02 g, 18.56 mmol) and TEA (3.88 mL, 27.83 mmol) in 97 mL of CH$_2$Cl$_2$ was placed under nitrogen in an oven dried round bottom flask equipped with a stirrer and cooled to 0° C. Ethyl chloroformate (2.139 mL, 22.27 mmol) was added slowly, and the resulting mixture was stirred at room temperature for 1.5 hours. The reaction mixture was then diluted with 100 mL of $CH_2Cl_2$. Saturated, aqueous $NaHCO_3$ (75 mL) and 50 mL of water were added, and the reaction mixture was poured into a separatory funnel. The organic phase was separated, and the aqueous phase was extracted with two equal portions of $CH_2Cl_2$. All organic extracts were combined and dried with $MgSO_4$, then filtered, and evaporated to a yellow foamy oil. The crude material was subjected to Flash chromatography (eluent: 20-80% EtOAc/hexane). The first eluting product was the syn-pair of isomers (2.47 g). The second eluting product was the anti-pair of enantiomers, (2.44 g). MS m/z (ESI) 472.2 ($MNa^+$). $^1$HNMR in $CDCl_3$ showed the presence of the expected structure.

Compound ID No. 100: A solution of (2R,3S and 2S,3R)-ethyl(2-(3,4-dichlorophenyl)-3-hydroxy-3-(2-(thiophen-2-yl)phenyl)propyl)carbamate (2.45 g, 5.44 mmol) in 50 mL THF was transferred to a 500 mL round bottom flask equipped with a magnetic stirrer, addition funnel, thermometer, and Dean-Stark trap fitted with a condenser and nitrogen inlet. A solution of borane-methyl sulfide complex (13.60 mL, 27.20 mmol) was added slowly, and the solution was heated to reflux (75° C.). Dimethyl sulfide that collected in the Dean-Stark trap over 30 minutes was removed, and then the reaction was allowed to heat at that temperature for an additional hour. Another 10 mL of borane-methyl sulfide complex was added, dimethyl sulfide was removed from the Dean-Stark trap over 30 minutes, and the reaction was allowed to heat at 75° C. overnight. The reaction mixture was cooled to room temperature, and 4.0 M HCl (9 mL) in dioxane was added drop-wise. 20 mL of MeOH was added drop-wise, the reaction was heated to 80° C., and the distillate was collected in a Dean-Stark condenser for 30 minutes. The reaction mixture was cooled to room temperature, and the solvents were evaporated to an oil. The oil was dissolved in $CHCl_3$ and adsorbed directly onto an ISCO column and run with a ramp of 0-20% $MeOH/CH_2Cl_2$. The product with a mass of 1.6 grams was isolated, of which 0.550 g was subjected to separation into the two syn-enantiomers. The material resulted in two portions, about 800 mL of volume each. These volumes were respectively concentrated, and the crude residues were separately dissolved in $CH_2Cl_2$, washed with 10% $NaHCO_3$ in water, and extracted two times with $CH_2Cl_2$. Organic extracts were combined, dried with $MgSO_4$, and evaporated. The two crude enantiomers were separately dissolved in ether and mixed with 2.0 M HCl to form the HCl salts. The salts were finally dissolved in EtOH (1-2 mL) and precipitated with excess hexane. The crystals were filtered, washed with hexane, and dried to afford two distinct enantiomeric compounds as hydrochlorides with 96% enantiomeric excess or greater. Compound ID No. 100 corresponded to the first eluting peak from the SFC chiral chromatography and was assigned an (1R,2S)-configuration based on its higher inhibitory activity on the hNET compared to the second-eluting enantiomer. $^1$H NMR (500 MHz, DMSO-d6) δ 8.89 (br. s., 1H), 8.06 (br. s, 1H), 7.67 (d, 1H, J=4.3 Hz), 7.48 (d, 1H, J=8.6 Hz), 7.15-7.33 (m, 6H), 6.95-7.09 (m, 2H), 5.77 (d, 1H, J=4.3 Hz), 5.20 (t, 1H, J=4.3 Hz), 3.25-3.47 (m, 2H), 3.02 (d, 1H, J=11.0 Hz), 2.38 (s, 3H). MS m/z (ESI) 392.2.

Example 101—Synthesis of Compound ID No. 101 ((1S,2S)-2-(3,4-dichlorophenyl)-3-(methylamino)-1-(3-(methylsulfonyl)phenyl)propan-1-ol)

2-(3,4-dichlorophenyl)-3-hydroxy-3-(3-(methylthio)phenyl)propanenitrile: 2-(3,4-dichlorophenyl)acetonitrile (5.8 g, 30.55 mmol) was dissolved in ether (35 mL)/THF (15 mL) and cooled to -75° C. under nitrogen. Butyllithium (13.44 mL, 33.61 mmol) was added slowly and the reaction was stirred at -75° C. for 20 min Next, 3-(methylthio)benzaldehyde (5.12 g, 33.61 mmol) in THF (15 mL) was added dropwise while maintaining the temperature under -60° C. After the addition, the reaction was stirred at -75° C. for another hour. Then, acetic acid (2.62 mL, 45.83 mmol) was added at -75° C. to quench the reaction. The reaction mixture was warmed to room temperature, and the organic layer was separated from the aqueous layer. The aqueous layer was extracted with ether (100 mL×3) and the combined organic layer was dried over $MgSO_4$ and evaporated to give an orange oil, which was used for next step directly without further purification. Isomer A—$^1$H NMR ($CDCl_3$) δ 4.99 (d, 1H, J=6.1 Hz), 4.06 (d, 1H, J=6.1 Hz). Isomer B—$^1$H NMR ($CDCl_3$) δ 4.93 (d, 1H, J=5.5 Hz), 4.01 (d, 1H, J=5.2 Hz).

3-amino-2-(3,4-dichlorophenyl)-1-(3-(methylthio)phenyl)propan-1-ol: 2-(3,4-dichlorophenyl)-3-hydroxy-3-(3-(methylthio)phenyl)propanenitrile (10.15 g, 30 mmol) in THF (55 mL) was preheated at 76° C. for gentle-refluxing. To this, a solution of borane-methyl sulfide complex (45.0 mL, 90.00 mmol) in THF was added dropwise over 30 min (Dean-Stark trap was set up to collect liberated $SMe_2$) and the reaction mixture was stirred for 12 h before cooling in a cold water bath. The mixture was cautiously acidified with 4M HCl in dioxane (10 mL) MeOH (20 mL) was then added to quench the extra $BH_3$ while maintaining the temperature under 25° C. After the evolution of gas bubbles subsided, the reaction mixture was heated to 64° C. for 10-15 min to convert all $BH_3$ to $B(OMe)_3$-MeOH complex that was collected in a Dean-Stark trap during heating. The reaction mixture was concentrated to give a pale-yellow oil. Since the $^1$H NMR spectrum of the crude in $CDCl_3$ showed the presence of the expected mixture of anti- and syn-structures, it was taken to the next step without further purification.

anti-Ethyl-2-(3,4-dichlorophenyl)-3-hydroxy-3-(3-(methylthio)phenyl)propyl-(methyl)carbamate and syn-ethyl-2-(3,4-dichlorophenyl)-3-hydroxy-3-(3-(methylthio)phenyl)propyl(methyl)carbamate: The HCl salt of 3-amino-2-(3,4-dichlorophenyl)-1-(3-(methylthio)phenyl)propan-1-ol (11.36 g, 30 mmol), obtained above, was suspended in 100 mL of $CH_2Cl_2$ at r.t. TEA (12.54 mL, 90.00 mmol) was added to effect complete solution. This clear solution was cooled to 0° C. before adding ethyl carbonochloridate (3.46 mL, 36.00 mmol) in a dropwise fashion. The reaction mixture was stirred at r.t. for 3 h. The reaction mixture was then sequentially washed with 0.5N HCl (150 mL), saturated $NaHCO_3$ (100 mL), water, and brine, then dried over $MgSO_4$ and evaporated to give a pale-yellow oil. The crude oil was subjected to Flash silica gel column chromatography (eluent: 0-100% EtOAc in hexane) to give two collections: anti-isomer and syn-isomer. The anti-isomer collection was evaporated to give a pale-yellow oil (4.85 g, 39.0%). $^1$H NMR ($CDCl_3$) δ 7.28 (d, 1H, J=8.4 Hz), 7.19 (d, 1H, J=2.1 Hz), 7.07-7.18 (m, 2H), 7.05 (s, 1H), 6.86-6.95 (m, 2H), 4.85 (br. s., 1H), 4.81 (dd, 1H, J=7.9, 3.7 Hz), 4.10 (q, 2H, J=7.0 Hz), 3.66-3.81 (m, 1H), 3.52-3.66 (m, 1H), 3.17 (br. s., 1H), 3.02-3.12 (m, 1H), 2.39 (s, 3H), 1.22 (t, 3H, J=7.2 Hz). The large J-value of the benzylic proton (7.9 Hz) indicated anti-relative configuration. MS m/z (ESI) 314.01 ($MNa^+$). The syn-isomer collection was evaporated to give a pale yellow oil (5.14 g, 41.4%)$^1$H NMR ($CDCl_3$) δ 7.23-7.30 (m, 2H), 7.05-7.20 (m, 2H), 6.98 (s, 1H), 6.93 (dd, 1H, J=8.3, 2.0 Hz) 6.87 (d, 1H, J=7.2 Hz), 4.96 (t, 1H, J=4.0 Hz), 4.78 (br. s., 1H), 4.11 (q, 2H, J=7.2 Hz), 3.63-3.86 (m, 1H), 3.24-3.39 (m, 1H), 3.11 (br. s., 1H), 2.98 (td, 1H, J=7.7, 4.6 Hz), 2.36 (s, 3H), 1.23 (t, 3H J=7.3 Hz). Small J-value (4.0 Hz) of the benzylic proton indicated syn-relative configuration. MS m/z (ESI) 436.15 (MNa+).

anti-2-(3,4-dichlorophenyl)-3-(methylamino)-1-(3-(methylthio)-phenyl)propan-1-ol: A solution of anti-ethyl-2-(3,4-dichlorophenyl)-3-hydroxy-3-(3-(methylthio)phenyl) propyl carbamate (4.7 g, 11.34 mmol) in THF (50 mL) was set to reflux at 76° C. BH$_3$.THF (34.0 mL, 34.03 mmol) was added dropwise over 15 minutes, and the refluxing was allowed to continue overnight. The reaction mixture was cooled in a cold water bath, treated first with 5 mL HCl and then with dropwise addition of 10 mL of MeOH to quench extra BH$_3$ while maintaining the temperature under 25° C. After the evolution of gas bubbles subsided, the reaction mixture was heated to 64° C. (to make sure all of BH$_3$ quenched) for 10-15 minutes, and then concentrated to a pale-yellow oil. The HCl salt was stirred in 100 mL CHCl$_3$/saturated NaHCO$_3$ for 10 minutes. The organic layer was separated, and the aqueous layer was extracted with CHCl$_3$ (20 mL×5). A significant amount of white solid was not basified and extracted into CHCl$_3$. The combined CHCl$_3$ layer was dried over MgSO$_4$ and evaporated to give a yellow oil. The product from this oil was isolated by Flash silica gel chromatography (eluent: 0-10% MeOH in CH$_2$Cl$_2$). The relevant collections were collected and evaporated under reduced pressure to give the desired anti-product (1.725 g, 42.6%). $^1$H NMR (CDCl$_3$) δ 7.24 (d, 1H, overlapping with CHCl$_3$) 7.13 (d, 1H, J=2.1 Hz), 7.09 (s, 1H), 7.10 (d, 1H, J=9.5 Hz), 7.03 (br. s., 1H), 6.87 (dt, 1H, J=7.0, 1.7 Hz), 6.83 (dd, 1H, J=8.3, 2.0 Hz), 4.92 (d, 1H, J=8.0 Hz), 3.20 (dd, 1H, J=12.1, 9.7 Hz), 3.03 (dd, 1H, J=12.1, 3.1 Hz), 2.87 (ddd, 1H, J=9.7, 8.0, 3.2 Hz), 2.50 (s, 3H), 2.37 (s, 3H). MS m/z (ESI) 356.11 (MH+).

anti-tert-butyl-2-(3,4-dichlorophenyl)-3-hydroxy-3-(3-(methylthio)phenyl)propyl(methyl)carbamate: A suspension of anti-2-(3,4-dichlorophenyl)-3-(methylamino)-1-(3-(methylthio)phenyl)propan-1-ol (1 g, 2.81 mmol) and triethylamine (0.312 g, 3.09 mmol) in dichloromethane (5 mL) was cooled to 0° C. Boc anhydride (0.674 g, 3.09 mmol) was added portionwise and the mixture was allowed to warm room temperature over 1 hour. The reaction mixture was then diluted with CH$_2$Cl$_2$ (100 mL), washed with water (10 mL×2), dried through MgSO$_4$ and evaporated in vacuo. The crude product was purified by Flash silica gel chromatography (eluent: 0-100% EtOAc in hexane) to give the desired product as a colorless foam (0.850 g, 66.4%).

(2S,3S)-tert-Butyl 2-(3,4-dichlorophenyl)-3-hydroxy-3-(3-(methylsulfonyl)phenyl)propyl(methyl)carbamate: A solution of oxone (1.429 g, 2.33 mmol) in water (4 mL) was cooled to 5° C., and its pH was adjusted to ca. 6 by adding aqueous K$_2$CO$_3$. To this solution, tert-butyl anti-2-(3,4-dichlorophenyl)-3-hydroxy-3-(3-(methylthio)phenyl)propyl (methyl)carbamate (0.379 g, 0.83 mmol) in methanol (4 mL) was added slowly and the reaction mixture was allowed to warm to r.t and stirred for several hours. During the reaction, the pH was periodically checked and adjusted to ~6 by K$_2$CO$_3$. After stirring for 8 hours at room temperature, the reaction mixture was kept in refrigerator overnight before the work-up. MeOH was removed by rotary evaporation from the reaction mixture. The reaction residual was washed with CHCl$_3$ (100 mL×3), dried over MgSO$_4$ and evaporated to dryness. The crude product was added to a silica gel column and eluted with 0-100% EtOAc in hexane to give the desired product as a colorless gum (0.235 g, 57.9%). $^1$H NMR (CDCl$_3$) δ 7.72 (dd, 1H, J=7.6, 1.3 Hz), 7.67 (br. s., 1H), 7.48-7.58 (m, 1H), 7.42 (t, 1H, J=7.6 Hz), 7.24-7.33 (m, 1H), 7.20 (br. s., 1H), 6.97 (d, 1H, J=8.0 Hz), 4.89 (br. s, 1H), 3.59-3.86 (m, 2H), 3.12-3.27 (m, 1H), 2.91 (br. s, 3H), 2.58 (s, 3H), 1.36 (br. s, 9H). MS m/z (ESI) 510.15 (MNa+).

tert-Butyl (2S,3S)-2-(3,4-dichlorophenyl)-3-hydroxy-3-(3-(methylsulfonyl)phenyl)propyl(methyl)carbamate and tert-butyl (2R,3R)-2-(3,4-dichlorophenyl)-3-hydroxy-3-(3-(methylsulfonyl)phenyl)propyl(methyl)carbamate: The two enantiomers were purified twice by chiral SFC (Phenomenex Cellulose-2 column, 20% iPrOH with 0.5% isopropylamine) as Peak 1 and Peak 2. Each fraction obtained was concentrated separately. $^1$H NMR (CDCl$_3$) δ 7.72 (d, 1H, J=8.0 Hz), 7.67 (s, 1H), 7.48-7.56 (m, 1H), 7.42 (t, 1H, J=7.8 Hz), 7.28 (d, 1H, J=8.4 Hz), 7.20 (s, 1H), 6.97 (d, 1H, J=8.0 Hz), 4.88 (d, 1H, J=7.2 Hz), 3.62-3.80 (m, 2H), 3.19 (q, 1H, J=6.7 Hz), 2.91 (s, 3H), 2.57 (s, 3H), 1.37 (br. s., 9H). MS m/z (ESI) 510.15 (MNa+). The first-eluting enantiomer was retrospectively presumed to be 1S,2S-configured based on the higher potency of its completely deprotected form on hNET, relative to that from the second-eluting enantiomer (see below).

(1S,2S)-2-(3,4-dichlorophenyl)-3-(methylamino)-1-(3-(methylsulfonyl)-phenyl)propan-1-ol: tert-Butyl (1S,2S)-2-(3,4-dichlorophenyl)-3-hydroxy-3-(3-(methylsulfonyl)phenyl) propyl(methyl) carbamate (0.125 g, 0.26 mmol) was stirred in the presence of 4N HCl in dioxane/THF=3:1 (1 mL) at r.t for 3 h. The volatiles were removed in vacuo to give a white solid as the desired product (0.110 g, 100% yield, 95% purity). $^1$H NMR (CD$_3$OD) δ 7.79 (dt, J=4.2, 2.2 Hz, 1H), 7.67 (s, 1H), 7.51 (d, 2H, J=4.9 Hz), 7.41 (d, 1H, J=8.3 Hz), 7.30 (d, 1H, J=1.9 Hz), 7.05 (dd, 1H, J=8.1, 2.1 Hz), 5.00 (d, 1H, J=9.0 Hz), 3.79 (dd, 1H, J=12.4, 7.9 Hz), 3.41 (dd, 1H, J=12.6, 5.8 Hz), 3.19-3.28 (m, 1H partially covered under MeOH), 2.98 (s, 3H), 2.75 (s, 3H). MS m/z (ESI) 388.1.

Example 102—Synthesis of Compound ID No. 102 ((1S,2S)-2-(3,4-dichlorophenyl)-3-(methylamino)-1-(3-nitrophenyl)propan-1-ol)

2-(3,4-dichlorophenyl)-3-hydroxy-3-(3-nitrophenyl)propanenitrile: A solution of 2-(3,4-dichlorophenyl)acetonitrile (6 g, 32.25 mmol) in 70 mL of THF was placed under nitrogen in an oven dried round bottom flask with a stirrer. This solution was cooled to −75° C., butyllithium (22.17 mL, 35.48 mmol) was added slowly, and the reaction was stirred at −75° C. for 20 min 3-Nitrobenzaldehyde (5.36 g, 35.48 mmol) dissolved in 20 mL of THF was added dropwise, maintaining the temperature under −70° C. After the addition, the reaction was stirred at −75° C. for another hour. Then, acetic acid (2.77 mL, 48.38 mmol) was added at −75° C. to quench the reaction. The reaction mixture was warmed to room temperature, diluted with 50 mL saturated NaHCO$_3$, and the organic layer was separated from the aqueous layer. The aqueous layer was extracted with ether (100 mL×2), and the combined organic extracts were dried over MgSO$_4$ and evaporated to give an orange oil. The orange oil was added to a silica gel column and was eluted with 0-100% EtOAc in hexane. Most of the fractions were a mixture of anti- and syn-isomers. The combined collection of the mixture was evaporated to give sticky yellow oil (11.1 g, 87%). A small amount of the end collection that was obtained as a pale-yellow sticky solid (0.612 g, 5.63% yield, 98% purity) after evaporation was determined to be pure anti-isomer. $^1$H NMR (CDCl$_3$) δ 8.23 (dt, 1H, J=7.8, 1.9 Hz), 8.14-8.20 (m, 1H), 7.59-7.64 (m, 1H), 7.57 (t, 1H, J=7.8 Hz), 7.44 (d, 1H, J=8.2 Hz), 7.37 (d, 1H, J=2.3 Hz), 7.07 (dd, 1H, J=8.3, 2.2

Hz), 5.15 (dd, 1H, J=6.5, 3.4 Hz), 4.08 (d, 1H, J=6.3 Hz), 2.50 (br. s., 1H). MS m/z (ESI) 359.07 (MNa+).

3-amino-2-(3,4-dichlorophenyl)-1-(3-nitrophenyl)propan-1-ol: dichlorophenyl)-3-hydroxy-3-(3-nitrophenyl)propanenitrile (11 g, 27.83 mmol) in 100 mL of THF was preheated at 76° C. for gentle-refluxing. A solution of borane-methyl sulfide complex (34.8 mL, 69.57 mmol) in THF was added dropwise over 15 min. The liberated SMe$_2$ collected in a Dean-Stark trap. Four hours after the addition, the reaction mixture was cooled in a cold water bath, and the extra BH$_3$ was quenched by cautious addition of MeOH (20 mL), maintaining the temperature under 25° C. resulting in vigorous evolution of gas bubbles. After the addition, the reaction mixture was heated to 64° C. (to make sure all of BH$_3$ quenched) for 10-15 min while the B(OMe)$_3$-MeOH complex was collected in a Dean-Stark trap. The reaction mixture was concentrated to give a pale-yellow foam as the desired product (11.6 g, 122%). The pale-yellow foam was dissolved in 100 mL of CH$_2$Cl$_2$, and then 4M HCl in dioxane (10 mL) was added. The addition of HCl generated a solid that precipitated out as a white foam. The white solid was filtered and washed with CH$_2$Cl$_2$ (30 mL×2). The HCl salt of the desired product, thus obtained, was suspended in 500 mL of CH$_2$Cl$_2$, and basified with saturated NaHCO$_3$; most of white solid diffused into CH$_2$Cl$_2$ phase but a small amount of white solid remained undissolved. The product solution was separated from the white solid and saturated NaHCO$_3$ layer was continuously extracted with CH$_2$Cl$_2$ (100 mL×10). The combined CH$_2$Cl$_2$ extracts were dried over MgSO$_4$, and evaporated to give the desired product as an off-white foam (7.45 g, 78%). Based on the integration of the relevant proton, the anti- and syn-isomers were determined to be in a 2:1 ratio. MS m/z (ESI) 341.1 (MH+). A very small amount of white solid, which couldn't be extracted back to CH$_2$Cl$_2$, was collected as the desired product also (0.260 g, 2.74%). $^1$H NMR in CDCl$_3$ showed the presence of the expected structure. MS m/z (ESI) 341.1 (MNa+).

anti- and syn-ethyl (2-(3,4-dichlorophenyl)-3-hydroxy-3-(3-nitrophenyl)propyl(methyl)carbamate: A mixture of 3-amino-2-(3,4-dichlorophenyl)-1-(3-nitrophenyl)propan-1-ol (7.3 g, 20.33 mmol) and TEA (4.25 mL, 30.49 mmol) in 100 mL of CH$_2$Cl$_2$ cooled to 0° C. Ethyl carbonochloridate (2.342 mL, 24.39 mmol) was slowly added and the resulting mixture was stirred at r.t. for 2 h. The reaction was quenched by adding 100 mL 0.5N HCl. The acid was neutralized with 50 mL saturated NaHCO$_3$. The organic phase was separated and dried over MgSO$_4$ and evaporated to give a yellow oil. Flash silica gel chromatography with 0-100% EtOAc in hexane gave three collections: anti-isomer, syn-isomer and an unknown. The anti-isomer collection was evaporated to give a pale-yellow oil (1.58 g, 18.81% yield, 98% purity)$^1$H NMR (CDCl$_3$) δ 8.09-8.15 (m, 1H), 7.99-8.09 (m, 1H), 7.43-7.50 (m, 1H), 7.38 (t, 1H, J=7.8 Hz), 7.31 (d, 1H, J=8.2 Hz), 7.20 (d, 1H, J=1.9 Hz), 6.94 (dd, 1H, J=8.2, 2.1 Hz), 4.96 (dd, 1H, J=8.3, 4.3 Hz), 4.82 (br. s., 1H), 4.14 (q, 2H, J=6.9 Hz), 3.79-3.99 (m, 1H), 3.37-3.55 (m, 1H), 3.08 (dt, 1H, J=8.4, 5.1 Hz), 1.25 (t, 3H, J=7.1 Hz). A large J-value (8.3 Hz) indicated anti-configuration. The syn-isomer collection was evaporated to give a pale-yellow oil (4.57 g, 54.5%)$^1$H NMR (CDCl$_3$) δ 7.97-8.05 (m, 2H), 7.41 (t, 1H, J=7.5 Hz), 7.35 (t, 0H, J=8.0 Hz), 7.20-7.25 (m, 2H), 6.93 (dd, 1H, J=8.2, 2.1 Hz), 5.16 (t, 1H, J=3.9 Hz), 4.99 (br. s., 1H), 4.18 (q, 2H, J=7.2 Hz), 3.83-4.02 (m, 1H), 3.26 (dt, 1H, J=14.5, 5.5 Hz), 2.98 (dd, 1H, J=9.9, 5.8, 3.7 Hz), 1.27 (t, 3H, J=7.1 Hz). MS m/z (ESI) 413.35 (MH+). A small J-value (3.9 Hz) indicated syn-configuration.

(1S,2S)-2-(3,4-dichlorophenyl)-3-(methylamino)-1-(3-nitrophenyl)propan-1-ol: anti-2-(3,4-dichlorophenyl)-3-hydroxy-3-(3-nitrophenyl)propylcarbamate (1.57 g, 3.72 mmol) in THF (50 mL) was preheated at 76° C. for gentle-refluxing. To this, borane-methyl sulfide complex (6.52 mL, 13.03 mmol) was added dropwise over 109 minutes. A Dean-Stark trap was set up to collect liberated SMe$_2$. Seven hours after the addition, the mixture was allowed to cool in a cold water bath and was treated with 4M HCl in dioxane (1.5 ml) to generate a HCl salt. Then 10 mL of MeOH was added slowly to quench the extra BH$_3$, maintaining the temperature under 25° C. After the gas bubbles ceased, as formed as MeOH was added, the reaction mixture was heated to 64° C. (to make sure all of BH$_3$ quenched) for 10-15 min. The B(OMe)3-MeOH complex was collected in a Dean-Stark trap. The reaction mixture was cooled and concentrated to give a yellow gum as a HCl salt of the desired product. The HCl salt was stirred in CHCl$_3$ (100 mL)/NaHCO$_3$(sat'd) for 10 min, separated the organic layer from the aqueous and extracted the aqueous layer with CHCl$_3$ (20 mL×2). The combined CHCl$_3$ layer was dried over MgSO$_4$ and evaporated to give a yellow stinky oil. The yellow oil was added to a silica gel column and was eluted with 0-10% MeOH in CH$_2$Cl$_2$. Collected fractions were evaporated in vacuo to give a colorless gel as the desired product (900 mg, 68.1% yield, 98% purity). $^1$H NMR (300 MHz, CDCl$_3$) δ 8.12 (t, 1H, J=1.8 Hz) 8.03 (ddd, 1H, J=7.8, 2.2, 1.6 Hz), 7.23-7.36 (m, 3H), 7.10 (d, 1H, J=2.1 Hz), 6.80 (dd, 1H, J=8.2, 2.1 Hz), 5.07 (d, 1H, J=8.4 Hz) 3.26 (dd, 1H, J=12.2, 10.2 Hz), 3.06 (dd, 1H, J=12.1, 2.8 Hz), 2.86 (ddd, 1H, J=10.5, 8.2, 2.7 Hz), 2.54 (s, 3H). This anti-mixture was subjected to chiral Multigram II SFC system for enantiomeric separation (ADH column, 22% EtOH with 0.5% isopropylamine). The Compound ID No. 102 recovered from the second-eluting fraction was assigned (1S,2S)-configuration because it was more potent at hNET than the first-eluting enantiomer. $^1$H NMR (CDCl$_3$) δ 8.11 (t, 1H, J=1.7 Hz), 8.01 (ddd, 1H, J=7.7, 2.0, 1.9 Hz), 7.22-7.36 (m, 3H), 7.10 (d, 1H, J=1.9 Hz), 6.81 (dd, 1H, J=8.2, 2.1 Hz), 5.05 (d, 1H, J=8.4 Hz), 3.25 (dd, 1H, J=12.1, 10.4 Hz), 3.04 (dd, 1H, J=12.3, 2.9 Hz), 2.82-2.92 (m, 1H), 2.52 (s, 3H).

Example 103—Synthesis of Compound ID No. 103 ((1R,2R)-3-(methylamino)-2-(naphthalen-2-yl)-1-(pyridin-3-yl)propan-1-ol)

This compound was prepared by SCF separation of the racemate (1S,2S and 1R,2R)-3-(methylamino)-2-(naphthalen-2-yl)-1-(pyridin-3-yl)propan-1-ol) (Compound ID No. 62). Compound ID No. 103 is the second-eluting enantiomer.

Since Compound ID No. 103 was less potent at hNET than its enantiomer (Compound ID No. 49), it was assigned the (1R,2R)-configuration. $^1$H NMR (500 MHz, CDCl$_3$) δ 8.32 (dd, 2H, J=5.8, 2.7 Hz), 7.74 (d, 1H, J=9.2 Hz), 7.63-7.71 (m, 2H), 7.38-7.49 (m, 4H), 7.06 (td, 2H, J=8.5, 2.3 Hz), 5.19 (d, 1H, J=8.9 Hz), 3.41 (dd, 1H, J=12.1, 10.5 Hz), 3.16 (dd, 1H, J=12.2, 3.1 Hz), 2.56 (s, 3H) 3.07 (br. s., 1H).

Example 104—Synthesis of Compound ID No. 104 ((1R,2S)-2-(3,4-dichlorophenyl)-1-(2-methoxypyridin-3-yl)-3-(methylamino)propan-1-ol)

2-(3,4-Dichlorophenyl)-3-hydroxy-3-(2-methoxypyridin-3-yl)propanenitrile: A solution of 2-(3,4-dichlorophenyl)acetonitrile (2.92 g, 15.68 mmol) in 20 mL THF and 20 mL diethyl ether was placed under nitrogen in an oven dried round bottom flask with stirrer. After cooling to −75° C. in an acetone dry ice bath, butyllithium (6.77 mL, 16.93 mmol) (2.5 M in hexane) was added dropwise. Internal temperature was monitored and maintained below −60° C. After the addition, the reaction was allowed to stir for 15 min. To this, 2-methoxynicotinaldehyde (2.15 g, 15.68 mmol) dissolved in 20 mL of THF was added dropwise, maintaining the temperature below −60° C. The reaction mixture was allowed to stir for 1.5 hours at −75° C. and then quenched at the same temperature with a solution of acetic acid (1.346 mL, 23.52 mmol in 10 mL of THF) and the cold bath removed. After adding 100 mL of water, the two layers were separated in a separatory funnel. The aqueous layer was extracted with ethyl acetate (3×). The combined organic layers were washed with brine, dried over $MgSO_4$, filtered and evaporated in vacuo. The crude product was purified by chromatography (elution with ethyl acetate/$CH_2Cl_2$ 0-100%) to yield 2-(3,4-dichlorophenyl)-3-hydroxy-3-(2-methoxypyridin-3-yl)propanenitrile (4.64 g, 92%). $^1$H NMR in $CDCl_3$ showed the presence of the expected mixture of anti- and syn-structures. MS m/z (ESI) 323.13 ($MH^+$).

3-Amino-2-(3,4-dichlorophenyl)-1-(2-methoxypyridin-3-yl)propan-1-ol: 2-(3,4-dichlorophenyl)-3-hydroxy-3-(2-methoxypyridin-3-yl)propanenitrile (4.64 g, 14.36 mmol) was dissolved in 115 mL THF and heated to 80° C. in a 100 mL flask equipped with a stirrer and water condenser. To this colorless solution was added, via gas tight syringe in several portions, the borane reagent (28.7 mL, 28.72 mmol) as a 1.0 M solution in THF. The heating was allowed to continue which produced a gentle reflux for 5 h. The reaction mixture was cooled and quenched with slow addition of MeOH (10 mL) Vigorous reaction occurred early in the addition and dissipated towards the end of the addition. The reaction mixture was then reheated to reflux. for 30 min. After cooling to r.t., 150 mL of 10% sodium bicarbonate in water was added and the aqueous phase extracted with $CH_2Cl_2$ 3 times. The organic layers were combined, washed with brine, dried with $MgSO_4$, filtered, evaporated and dried to a clear, oily semi-solid (4.58 g). Since the $^1$H NMR in $CDCl_3$ of the crude showed the presence of the expected mixture of anti- and syn-structures, it was taken to the next step without further purification.

Ethyl-2-(3,4-dichlorophenyl)-3-hydroxy-3-(2-methoxypyridin-3-yl)propylcarbamate: To a vigorously stirring mixture of 3-amino-2-(3,4-dichlorophenyl)-1-(2-methoxypyridin-3-yl)propan-1-ol (4.58 g, 14.00 mmol) and TEA (2.93 mL, 21.00 mmol) in 100 mL $CH_2Cl_2$ was added ethyl chloroformate (1.606 mL, 16.80 mmol) in one portion at r.t. After stirring overnight, the reaction mixture was diluted with water (125 mL) and $CH_2Cl_2$ (150 mL). The organic layer was separated and the aqueous phase was extracted with two more equal portions of $CH_2Cl_2$. All the organic layers were combined and dried with $MgSO_4$, then filtered and evaporated to a crude oil (5.56 g).

(1R,2S)-2-(3,4-dichlorophenyl)-1-(2-methoxypyridin-3-yl)-3-(methylamino)propan-1-ol: A diastereomeric racemate ethyl 2-(3,4-dichlorophenyl)-3-hydroxy-3-(2-methoxypyridin-3-yl)propylcarbamate (0.800 g, 2.00 mmol) was dissolved in 10 mL THF, stirred and heated to 80° C. To this colorless solution was added, via gas tight syringe in several portions, the borane reagent (1.0M THF solution) (10.02 mL, 10.02 mmol). Bubbling occurred with each addition. The reaction was kept at a constant 80° C. which produced a mild reflux for 10 h. The reaction was allowed to reach r.t under $N_2$ overnight and then quenched with careful addition of 5 mL of MeOH. After the bubbling subsided, 1 mL of 1.0M HCl in dioxane was added and the mixture heated to reflux for 15 min then cooled to r.t. The volatiles were evaporated on a rotary evaporator. 10% $NaHCO_3$ was added and the aqueous layer was extracted 3 times with an equal volume of $CH_2Cl_2$. The organic extracts were combined, washed with water, dried with $MgSO_4$, filtered and evaporated in vacuo. The crude was then immediately purified by chromatography (elution with 0-20% MeOH/$CH_2Cl_2$) giving a fraction (0.600 g) of the syn-pair of enantiomers as determined by the $^1$H-NMR analysis (small J-value of 4.3 Hz) of a complexed sample of the product with the chiral shift reagent (butylphenyl-phosphinothioic acid, TBPTA, S-(−) isomer). $^1$H NMR ($CDCl_3$) δ 8.00 (dd, 1H, J=4.9, 1.83 Hz), 7.51 (dd, 1H, J=7.3, 1.8 Hz), 7.22-7.34 (m, 2H), 6.96 (dd, 1H, J=8.55, 1.8 Hz), 6.80 (dd, 1H, J=7.33, 4.9 Hz), 5.32 (d, 1H, J=4.3 Hz), 3.84 (s, 3H), 3.31-3.43 (m, 1H), 3.03-3.12 (m, 1H), 2.95-3.03 (m, 1H), 2.47 (s, 3H). The racemic syn-sample was submitted for SFC chiral separation and the fractions received after purification were individually evaporated on a rotary evaporator. The corresponding residues were mixed with diethyl ether/$CHCl_3$ and HCl etherate (about 1 mL), then evaporated and dried for 1 h at 70° C. under high vacuum giving the two enantiomers (as hydrochloride salts) of the desired product (1R,2S)-2-(3,4-dichlorophenyl)-1-(2-methoxypyridin-3-yl)-3-methylamino)propan-1-ol and (1S,2R)-2-(3,4-dichlorophenyl)-1-(2-methoxypyridin-3-yl)-3-(methylamino) propan-1-ol as slightly yellow/orange solids (total yield of the two enantiomers 0.542 g, 65.3%). The Compound ID No. 104 recovered from the first-eluting peak was assigned (1R,2S)-configuration based on its higher inhibitory activity on the hNET compared to the second-eluting enantiomer.

Example 105—Synthesis of Compound ID No. 105 ((1RS,2RS)-2-(3,4-dichlorophenyl)-3-(dimethylamino)-1-phenylpropan-1-ol)

anti-(3,4-dichlorophenyl)-3-hydroxy-3-phenylpropanenitrile: To a 250 mL round bottom flask equipped with a magnetic stirring bar, nitrogen inlet, and septum and charged with THF (50 mL) was added LDA (1.8 M, 9.91 mL, 17.84 mmol). After cooling to −78° C., 2-(3,4-dichlorophenyl) acetonitrile (3.32 g, 17.84 mmol) was added. After 60 minutes, benzaldehyde (1.803 mL, 17.84 mmol) was added via syringe, and the resulting reaction mixture was stirred for 3 hours. The reaction was quenched by the addition of water (20 mL) at −78° C., and the mixture was allowed to warm to room temperature. The aqueous layer was extracted with $Et_2O$ (2×50 mL) and the combined organic extracts were washed with brine (50 mL), dried over $MgSO_4$, and concentrated in vacuo to give the crude aldol. ISCO purification on silica gel eluting with 0-30% of ethyl acetate in hexane afforded the product as 3:1 anti:syn-mixture (2.5 g). Recrystallization from DCM (30 mL) and hexane (40 mL) at 0° C. overnight afforded almost pure anti-isomer. NMR indicated the presence of 3% syn-isomer. The product was recrystalized again to afford the pure anti-isomer (0.700 g). $^1$H NMR ($CDCl_3$) δ 7.55-6.74 (m, 8H), 4.98 (dd, 1H, J=5.5, 3.7 Hz), 4.03 (d, 1H, J=5.5 Hz), 2.39 (d, 1H, J=3.7 Hz). MS m/z (ESI) 314.01 ($MNa^+$).

anti-3-amino-2-(3,4-dichlorophenyl)-1-phenylpropan-1-ol: A solution of anti-2-(3,4-dichlorophenyl)-3-hydroxy-3-phenylpropanenitrile (0.650 g, 2.22 mmol) in THF (25 mL) was heated to gentle reflux at 76° C. and treated with dropwise addition of borane-methyl sulfide complex (6.41 mL, 12.825 mmol) over 5 minutes. Liberated dimethyl sulfide was collected in a Dean-Stark trap. After 3.5 hours, the mixture was allowed to cool to ambient temperature, concentrated in vacuo, and the residue was dissolved in EtOAc (100 mL). The EtOAc solution of the product was washed with saturated aq. NaHCO$_3$, brine, then dried over MgSO$_4$, filtered, and concentrated. The residue was taken up in DCM and filtered to remove undissolved inorganic materials (derived from Borane-complexes). One mL of 2N HCl in dioxane was added and the suspension was stirred for 10 min. Rotary evaporation of the volatiles furnished a hydrochloride salt of the product as anti-mixture (0.620 g). $^1$H NMR (DMSO-d$_6$) δ 7.77 (br. s., 2H), 7.53-7.36 (m, 2H), 7.32-6.99 (m, 4H), 5.96 (d, 1H, J=3.4 Hz), 4.77 (d, 1H, J=4.3 Hz), 3.47-3.34 (m, 2H), 3.27-3.19 (m, 2H). MS m/z (ESI) 296.1 (MH$^+$).

anti-2-(3,4-dichlorophenyl)-3-(dimethylamino)-1-phenylpropan-1-ol: To a stirred solution of anti-3-amino-2-(3,4-dichlorophenyl)-1-phenylpropan-1-ol in 10 mL of methanol was added 37% formaldehyde aqueous solution at r.t. This was followed by the addition of a suspension of sodium cyanoborohydride and zinc chloride (0.600 mL, 0.3 mmol) (0.5M in THF) in 5 mL methanol. After the reaction mixture was stirred at r.t for 4 h, the solution was taken up in 0.1 N NaOH (4 mL) and most of methanol was evaporated under reduced pressure. The remaining aqueous solution was extracted with ethyl acetate (50 mL×2). The combined extracts were washed with water and brine, dried over anhydrous sodium sulfate, and evaporated to dryness. The residue was re-dissolved in dioxane and treated with 0.2 mL of 4N HCl in dioxane. After stirring for 10 min, the solvents were evaporated in vacuo to leave a solid that was washed with ether and dried under vacuum to afford the product as HCl salt. $^1$H NMR (CD$_3$OD) δ 7.50-6.89 (m, 8H), 4.88 (d, 1H, J=8.9 Hz), 4.05-3.86 (m, 1H), 4.05-3.86 (m, 1H), 3.47 (dt, 2H, J=9.5, 4.7 Hz), 3.09-2.85 (m, 6H). MS m/z (ESI) 324.09 (MH$^+$). The anti-configuration was confirmed by a large J-value (8.9 Hz) of the benzylic proton in CD$_3$OD.

Example 106—Synthesis of Compound ID No. 106 (1R,2R)-2-(3,4-dichlorophenyl)-3-(methylamino)-1-(thiophen-3-yl)propan-1-ol anti-2-(3,4-dichlorophenyl)-3-hydroxy-3-(thiophen-3-yl)propanenitrile: This compound was prepared in a standard fashion from the aldol reaction of 3,4-dichlorophenylacetonitrile and 3-thiophene carboxaldehyde. anti-i-Isomer: $^1$H NMR (CDCl$_3$) δ 7.41 (d, 1H, J=8.3 Hz), 7.36-7.33 (m, 2H), 7.19 (d, 1H, J=1.87 Hz), 7.06 (dd, 1H, J=8.3, 2.09 Hz), 7.02-6.98 (m, 1H), 5.10 (t, 1H, J=4.6, 4.6 Hz), 4.05 (d, 1H, J=5.32 Hz), 2.46 (d, 1H, J=3.9 Hz).

anti-3-amino-2-(3,4-dichlorophenyl)-1-(thiophen-3-yl) propan-1-ol: An oven-dried round-bottom flask with a stir bar was charged with a solution of anti-2-(3,4-dichlorophenyl)-3-hydroxy-3-(thiophen-3-yl)propanenitrile (0.6 g, 2.012 mmol) in 8 mL of dry THF and placed under nitrogen. Next, 1M borane-THF solution (8.05 mL, 8.05 mmol) was added via syringe. The resulting mixture was stirred at 60° C. overnight. The reaction was checked for completion by TLC and was quenched with cautious addition of NaHCO$_3$. The reaction was poured from the reaction vessel into a separatory funnel. The layers were separated; the aqueous layer was extracted with EtOAc (3×50 mL). The combined organic layers were sequentially washed with water and brine, then dried over MgSO$_4$, filtered, and concentrated using a rotary evaporator. Dioxane/HCl was added and mixed with the residue by magnetic stirring. The solvents were then evaporated off and DCM was added to dissolve the crude product. Hexane was slowly added, a white solid precipitated out which was filtered off, dried and lyophilized yielding the desired anti-product (identified by its large J-value (8.3 Hz) of the benzylic proton) as a white solid (0.620 g, 91%). $^1$H NMR (CD$_3$OD) δ 7.42 (d, 1H, J=8.3 Hz), 7.36-7.30 (m, 2H), 7.13-7.08 (m, 2H), 6.99-6.96 (m, 1H), 5.01 (d, 1H, J=8.3 Hz), 3.68-3.59 (m, 1H), 3.63-3.22 (m, 2H, hidden in MeOD peak). MS: m/z (ESI) 302.02 (MH$^+$).

anti-tert-Butyl-2-(3,4-dichlorophenyl)-3-hydroxy-3-(thiophen-3-yl)propylcarbamate: anti-3-amino-2-(3,4-dichlorophenyl)-1-(thiophen-3-yl)propan-1-ol (0.6 g, 1.772 mmol) was suspended in 10 mL of anhydrous DCM. Triethylamine (0.741 mL, 5.31 mmol) was then added, followed by the addition of Boc anhydride (0.425 g, 1.949 mmol). The reaction mixture was stirred at r.t. for about 1 h and checked for completion of reaction by TLC. On completion, the reaction was quenched with saturated NaHCO$_3$. The layers were separated and the aqueous layer was extracted with DCM (3×25 mL) The combined organic layers were washed with water and brine, and dried over MgSO$_4$, and concentrated using a rotary evaporator. The resulting residue was purified by flash chromatography over silica gel (elution with 70% EtOAc in hexanes) to afford the product as a sticky white solid (0.61 g, 86%)$^1$H NMR (CDCl$_3$) δ 7.22 (t, 1H, J=8.3, 8.3 Hz), 7.14-7.11 (m, 2H), 6.92 (d, 1H, J=2.4 Hz), 6.86 (dd, 1H, J=8.3, 2.0 Hz), 6.80 (dd, 1H, J=4.98, 1.0 Hz), 4.87 (dd, 1H, J=8.10, 4.1 Hz), 4.64 (br s, 1H), 3.65-3.39 (m, 3H), 3.04-2.98 (m, 1H), 1.36 (s, 9H). MS: m/z (ESI) 423.78 (MNa$^+$).

(1R,2R)-2-(3,4-dichlorophenyl)-3-(methylamino)-1-(thiophen-3-yl)propan-1-ol: An oven-dried round-bottom flask with a stir bar was charged with a solution of anti-tert-butyl-2-(3,4-dichlorophenyl)-3-hydroxy-3-(thiophen-3-yl) propylcarbamate (0.3 g, 0.746 mmol) in 5 mL of dry THF and placed under nitrogen. To this, 1M borane-THF solution (2.98 mL, 2.98 mmol) was added via syringe. This mixture was stirred at 60° C. overnight. The reaction was monitored by TLC. After completion, the reaction was quenched with cautious addition of NaHCO$_3$. The reaction was poured from the reaction vessel into a separatory funnel. The layers were separated and the aqueous layer was extracted with EtOAc (3×50 mL) The combined organic layers were washed with water and brine, dried over MgSO$_4$ and concentrated using a rotary evaporator. Dioxane/HCl was added to the residue under stirring. The solvents were removed by rotary evaporation and the product was dried under high vacuum. The crude was dissolved in MeOH and ether was slowly added which resulted in turbidity. The suspension was left to crystallize for one half hour at r.t. Off white crystals were filtered and washed with ether, dried, and lyophilized to yield an off-white solid (0.198 g, 75%). $^1$H NMR (CD$_3$OD) δ 7.30 (d, 1H, J=8.3 Hz), 7.25-7.17 (m, 2H), 7.01-6.94 (m, 2H), 6.86 (dd, 1H, J=5.1, 1.0 Hz), 4.89 (d, 1H, J=8.7 Hz), 3.66-3.54 (m, 1H), 3.31-3.23 (m, 2H), 2.63 (s, 3H). MS: m/z (ESI) 316.02 (MH$^+$). The Multigram II SFC chiral chromatography system of this compound furnished two fractions containing the opposite enantiomers. The first-eluting Compound ID No. 106 was assigned (1R,2R)-configuration based on its lower potency at hNET compared to the second-eluting enantiomer. $^1$H NMR (CDCl$_3$) δ 7.27 (s, 1H), 7.11-7.18 (m, 2H), 6.93 (d, 1H, J=2.7 Hz), 6.87 (dd, 1H, J=8.2, 2.1 Hz), 6.79 (d, 1H, J=4.9 Hz), 5.07 (d, 1H, J=7.9 Hz), 3.18 (dd, 1H, J=11.9, 9.8 Hz), 3.03 (dd, 1H, J=12.1, 3.2 Hz), 2.91 (br. s., 1H), 2.49 (s, 3H). MS (ESI) m/z 316.1/ 318.1 (MH$^+$).

Example 107—Synthesis of Compound ID No. 107 ((1R,2S)-3-amino-1-(2,4-difluorophenyl)-2-(naphthalen-2-yl)propan-1-ol)

syn-3-(2,4-difluorophenyl)-3-hydroxy-2-(naphthalen-2-yl)propanenitrile: 2-Naphthylacetonitrile (2.5 g, 14.95 mmol) was taken in an oven-dried round bottom flask containing a stir bar and 170 mL of dry THF was added under nitrogen. Diisopropylamine (2.5 mL, 17.94 mmol) was added and the mixture was stirred and cooled to −78° C. for 20 minutes. Butyllithium (2.5 M in hexane, 7.18 mL, 17.94 mmol) was then added slowly via syringe. After 30 minutes, 2,4-difluorobenzaldehyde (1.964 mL, 17.94 mmol) was added dropwise via syringe slowly. After 10 min, the reaction was quenched with quick addition of a mixture of 10 mL 2:1 THF/acetic acid (add all at once). Cold bath was removed, and the reaction was warmed to room temperature. Water was added, and the layers were separated. The aqueous layer was extracted with EtOAc (3×100 mL), and the combined organic layers were washed with water and brine, and dried over $MgSO_4$. The combined organic layers were concentrated using a rotary evaporator. The residue was dissolved in 25 mL of DCM and 80 mL of hexane. A turbid solution resulted that was kept at 4° C. for 2 hours. After filtration, the product from first crystallization was redissolved in 30 mL of DCM, and 150 ml of hexane was slowly added. The resulting white crystals were filtered and dried under vacuum (yield 0.5 g, 4.85 mmol, 32.4%). $^1$H NMR (CDCl$_3$) δ 7.88-7.76 (m, 3H), 7.70 (s, 1H), 7.57-7.48 (m, 2H), 7.40-7.26 (m, 2H), 6.89-6.72 (m, 2H), 5.47 (t, 1H, J=4.9 Hz), 4.35 (d, 1H, J=6.0 Hz), 2.42 (d, 1H, J=6.0 Hz). MS m/z (ESI) 309.45 (MH$^+$).

Syn-3-amino-1-(2,4-difluorophenyl)-2-(naphthalen-2-yl)propan-1-ol: syn-3-(2,4-difluorophenyl)-3-hydroxy-2-(naphthalen-2-yl)propanenitrile (0.82 g, 2.65 mmol), dissolved in 15 mL of dry THF, was placed in an oven-dried round-bottom flask under nitrogen. Next, 1M Borane-THF solution (10.60 mL, 10.60 mmol) of was added via syringe. This mixture was stirred at 60° C. overnight while monitoring the reaction progress by TLC. After quenching the reaction with cautious addition of NaHCO3, the reaction mixture was poured into a separatory funnel. The layers were separated; the aqueous layer was extracted with EtOAc (3×25 mL) Combined organic layers were washed with water and brine, and dried over MgSO4. The combined organic layers were concentrated using a rotary evaporator. 1N HCl was added and the resulting salt was lyophilized. The product was leached with DCM and dried under high vacuum (0.59 g, 1.69 mmol, 63.6% yield). Relative syn-stereochemistry to the product was assigned due to low benzylic proton J-value (4.1 Hz) in the $^1$H NMR. $^1$H NMR (CD$_3$OD) δ 7.85-7.71 (m, 3H), 7.61 (s, 1H), 7.49-7.41 (m, 2H), 7.36-7.29 (m, 1H), 7.12-7.02 (m, 1H), 6.91-6.80 (m, 1H), 6.72-6.62 (m, 1H), 5.42 (d, 1H, J=4.1 Hz), 3.65-3.43 (m, 3H); $^1$H NMR for Compound ID No. 107 (500 MHz, CDCl$_3$) δ 7.71-7.84 (m, 3H), 7.68 (s, 1H), 7.46 (dd, J=9.6, 2.3 Hz, 2H), 7.28-7.40 (m, 2H), 3.18-3.31 (m, 2H), 6.63-6.81 (m, 2H), 5.44 (d, J=5.5 Hz, 1H), 3.09 (d, 1H). MS m/z (ESI) 314.33=(M1$^+$). The racemic amine was subjected to SFC chiral chromatography and the first-eluting enantiomer (Compound ID No. 107) was assigned 1R,2S based on its higher potency on hNET.

Example 108—Synthesis of Compound ID No. 108 ((1S,2S or 1R,2R)-2-(3,4-dichlorophenyl)-1-(3-(dimethylamino)phenyl)-3-(methylamino)propan-1-ol)

2-(3,4-dichlorophenyl)-3-(3-(dimethylamino)phenyl)-3-hydroxypropanenitrile: 2-(3,4-dichlorophenyl)acetonitrile (5.75 g, 30.29 mmol) was dissolved in 35 mL of ether (and 15 mL of THF and cooled to −75° C. under nitrogen. Butyllithium (20.82 mL, 33.32 mmol) was added slowly, and the reaction was stirred at −75° C. for 20 minutes. 3-(dimethylamino)benzaldehyde (4.97 g, 33.32 mmol) was dissolved in 15 mL of THF and was added dropwise, maintaining the temperature under −60° C. After the addition, the reaction was stirred at −75° C. for another hour. Then, acetic acid (2.60 mL, 45.43 mmol) was added at −75° C. to quench the reaction. The reaction mixture was slowly warmed to room temperature, water was added and the organic layer was separated from the aqueous layer. The aqueous layer was extracted with ether (3×100 mL). The combined organic layer was dried over $MgSO_4$ and concentrated under reduced pressure to give orange oil. Small amounts of pure anti- and syn-compound could be isolated but most of the fractions came out mixed. anti Isomer—$^1$H NMR (CDCl$_3$) δ 7.37 (s, 1H), 7.33 (d, 1H, J=2.1 Hz), 7.18 (m, 1H), 7.05 (td, 1H, J=8.6, 2.2 Hz), 6.68 (m, 1H), 6.50-6.60 (m, 2H), 4.88 (d, 1H, J=5.5 Hz), 4.02 (d, J=5.5 Hz, 1H), 2.90 (s, 6H); syn Isomer-$^1$H NMR (CDCl$_3$) δ 7.39 (s, 1H), 7.30 (d, 1H, J=2.1 Hz), 7.18 (m, 1H), 7.05 (td, 1H, J=8.6, 2.2 Hz), 6.68 (m, 1H), 6.50-6.60 (m, 2H), 4.95 (d, 1H, J=6.1 Hz), 4.08 (d, 1H, J=6.1 Hz), 2.90 (s, 6H).

3-Amino-2-(3,4-dichlorophenyl)-1-(3-(dimethylamino)phenyl)propan-1-ol: A solution of borane-methyl sulfide complex (45.0 mL, 90.00 mmol) in THF was added dropwise over 30 min to 2-(3,4-dichlorophenyl)-3-(3-(dimethylamino)phenyl)-3-hydroxypropanenitrile (10.06 g, 30 mmol) in 55 mL THF preheated at 76° C. under nitrogen. A Dean-Stark trap was set up to collect the liberated SMe$_2$. After 12 h, the reaction mixture was cooled in a cold water bath and acidified with 10 mL 4M HCl in dioxane. The extra BH$_3$ was quenched by slow addition of 20 mL of MeOH while maintaining the temperature under 25° C. After the evolution of gas bubbles ceased, the reaction mixture was heated to 64° C. (to make sure all of BH$_3$ quenched) for 10-15 min while the B(OMe)$_3$-MeOH complex was collected in the Dean-Stark trap. The volatiles were then removed under reduced pressure to give a pale-yellow oil which was diluted in 200 L of $CH_2Cl_2$, and basified with saturated NaHCO$_3$. The organic layer was separated and washed with brine, dried over $MgSO_4$, and concentrated to give a pale-yellow oil. The residue was then purified by chromatography (eluting solvent: 0-5% ammoniated MeOH in $CH_2Cl_2$). Both anti- and syn isomers co-eluted together but the impurities were removed. Collected fractions were concentrated in vacuo to give the product mixture as a colorless oil (6.9 g, 67.8%). $^1$H NMR in CDCl$_3$ showed the presence of the expected mixture of anti- and syn-structures.

syn/anti-Ethyl-2-(3,4-dichlorophenyl)-3-(3-(dimethylamino)phenyl)-3-hydroxypropylcarbamate: To a cold (0° C.) mixture of 3-amino-2-(3,4-dichlorophenyl)-1-(3-(dimethylamino)phenyl)propan-1-ol (10.18 g, 30 mmol) and TEA (6.27 mL, 45.00 mmol) in 100 mL of $CH_2Cl_2$ was added ethyl carbonochloridate (3.46 mL, 36.00 mmol). After the addition, the reaction mixture was stirred at r.t for 3 h. The organic phase was sequentially washed with 0.5N HCl (150 mL), saturated NaHCO$_3$ (100 mL), and water (100 mL), then dried over $MgSO_4$ and concentrated under reduced pressure to give a pale-yellow oil. The purification of the pale-yellow oil was achieved by adding it to a silica gel column and eluting with 0-100% EtOAc in hexane to give two desired collections: anti-isomer and syn-isomer. The anti-isomer collection was evaporated to give a colorless gel (3.01 g, 24.39%). $^1$H NMR (CDCl$_3$) δ 7.28 (d, 1H, overlapping with CDCl$_3$) 7.19 (d, 1H, J=2.1 Hz), 7.10 (t, 1H, J=7.9 Hz), 6.92 (dd, 1H, J=8.3, 2.0 Hz), 6.57 (dd, 1H, J=8.2, 2.3 Hz), 6.51 (d, 1H, J=7.8 Hz), 6.46 (s, 1H), 4.88 (br. s., 1H), 4.80 (dd, 1H, J=7.7, 3.3 Hz), 4.09 (q, 2H, J=7.0 Hz), 3.54-3.75 (m, 2H), 3.05-3.18 (m, 1H), 2.86 (s, 6H), 1.21 (t, 3H, J=7.1 Hz). Large J-value (7.7 Hz) of the benzylic proton indicated anti-relative configuration. MS: m/z (ESI) 411.24 (MH$^+$). The syn-isomer collection was evaporated to give a colorless gel (3.57 g, 28.9%). $^1$H NMR (CDCl$_3$) δ 7.27-7.33 (m, 2H), 7.13 (t, 1H, J=7.8 Hz), 6.99 (dd, 1H, J=8.3, 2.0 Hz), 6.60 (dd, 1H, J 8.2, 2.1 Hz), 6.50 (d, 1H, J=7.4 Hz), 6.44 (d, 1H, J=1.9 Hz), 4.88 (dd, 1H, J=4.8, 3.4 Hz), 4.65 (br. s., 1H), 4.08 (q, 2H, J=7.0 Hz), 3.51-3.77 (m, 1H), 3.33 (ddd, 1H, J=13.9, 7.9, 5.7 Hz), 3.04 (td, 1H, J=7.6, 5.6 Hz), 2.85 (s, 6H), 2.59 (br. s., 1H), 1.20 (t, 3H, J=7.1 Hz). Small J-value 4.8 Hz) of the benzylic proton indicated syn-relative configuration. MS m/z (ESI) 412.9 (MH$^+$).

(1S,2S) or (1R,2R)-2-(3,4-dichlorophenyl)-1-(3-(dimethylamino)phenyl)-3-(methylamino)propan-1-ol: anti-Ethyl-2-(3,4-dichlorophenyl)-3-(3-(dimethylamino)phenyl)-3-hydroxy propyl carbamate (2.9 g, 7.05 mmol) in 30 mL THF was preheated at 76° C. for gentle-refluxing. BH$_3$.THF (21.15 mL, 21.15 mmol) was added dropwise over 15 min. After the addition, the reaction mixture was stirred for 3 h and then cooled to r.t and kept overnight. The reaction mixture was cooled in a cold water bath, and treated with 5 mL HCl followed by slow addition of 10 mL of MeOH taking care not to allow the temperature to rise above 25° C. After the gas evolution ceased, the reaction mixture was heated to 64° C. for 10-15 min, and then concentrated under reduced pressure to give the hydrochloride salt of the desired product as a yellow gum. The HCl salt was stirred in 100 mL of CHCl$_3$/saturated NaHCO$_3$ for 10 min. The organic layer was separated from the aqueous layer and the aqueous layer was extracted with CHCl$_3$ (2×220 mL) The combined CHCl$_3$ layer was dried over MgSO$_4$ and evaporated to give a yellow stinky oil. The yellow oil was loaded on to a silica gel column and eluted with 0-10% MeOH in CH$_2$Cl$_2$. Collected fractions were concentrated in vacuo to give the desired product (1.821 g, 72.2%). $^1$H NMR (CDCl$_3$) δ 7.24 (d, 1H, overlapping with CHCl$_3$) 7.18 (d, 1H, J=2.1 Hz), 7.07 (t, 1H, J=7.9 Hz), 6.89 (dd, 1H, J=8.2, 2.1 Hz), 6.56 (dd, 1H, J=8.2, 2.5 Hz), 6.51 (d, 1H, J=7.6 Hz), 6.47 (br. s., 1H), 4.91 (d, 1H, J=7.6 Hz), 3.17 (dd, 1H, J=12.0, 8.9 Hz), 3.03 (dd, 1H, J=12.0, 3.5 Hz), 2.92 (td, 1H, J=8.3, 3.6 Hz), 2.84 (s, 6H), 2.48 (s, 3H). MS m/z (ESI) 354.92 (MH$^+$).

The two enantiomers of the anti-isomers were separated by SCF (ODH column, 20% MeOH with 0.5% isopropylamine) The free base of the desired product was converted to a hydrochloride salt by diluting it with 2 mL of CH$_2$Cl$_2$ and adding 0.5 mL of 2M HCl and then evaporating to give as a white solid (0.101 g, 18.4% recovery). $^1$H NMR (CDCl$_3$) δ 7.22 (d, 1H, J=8.2 Hz), 7.16 (d, 1H, J=1.9 Hz), 7.06 (t, 1H, J=7.8 Hz), 6.87 (dd, 1H, J=8.3, 2.0 Hz), 6.55 (dd, 1H, J=8.3, 2.6 Hz), 6.50 (d, 1H, J=7.6 Hz), 6.45 (br. s., 1H), 4.86 (d, 1H, J=7.6 Hz), 3.14 (dd, 1H, J=11.9, 8.9 Hz), 2.99 (dd, 1H, J=11.7, 3.8 Hz), 2.91 (td, 1H, J=8.3, 3.8 Hz), 2.83 (s, 6H), 2.45 (s, 3H). MS m/z (ESI) 353.12 (MH$^+$). Both enantiomers exhibited similar but weak potency for inhibition of hNET. Example 108 is derived from the second-eluting enantiomer.

Example 109—Synthesis of Compound ID No. 109 ((1R,2R)-2-(3,4-dichlorophenyl)-1-(5-methoxypyridin-3-yl)-3-(methylamino)propan-1-ol)

2-(3,4-dichlorophenyl)-3-hydroxy-3-(5-methoxypyridin-3-yl)propanenitrile: A 250 mL round bottom flask equipped with a magnetic stirring bar, nitrogen inlet, and septum was charged with 100 mL of THF and LDA (9.12 mL, 18.23 mmol). After cooling to −78° C., 2-(3,4-dichlorophenyl) acetonitrile (3.39 g, 18.23 mmol) was added. After 60 min, 5-methoxynicotinaldehyde (2.5 g, 18.23 mmol) was added via syringe. The reaction mixture was allowed to stir at −78° C. for 3 h at which point the reaction was quenched by adding acetic acid (2.1 mL). The cold bath was removed and the temperature of the contents of the flask was allowed to reach r.t. Water was added and the aqueous layer was extracted with Et$_2$O (2×250 mL) The combined organic extracts were washed with 250 mL brine, dried over MgSO$_4$, and concentrated in vacuo to give the crude aldol (8 g). ISCO purification on silica gel eluting with 0-100% of ethyl acetate in hexane afforded the product as a mixture of (1S,2S and 1R,2R) and (1R,2S and 1S,2R) (5 g). MS: m/z (ESI) 323.06 (MH$^+$). Recrystallization from THF (10 mL) and hexane (25 mL) at 0° C. overnight did not separate the (1S,2S and 1R,2R)- and (1R,2S and 1S,2R)-isomers, hence the mixture was used for the borane reduction without further purification. $^1$H NMR spectrum in CDCl$_3$ showed the presence of the expected mixture of (1S,2S and 1R,2R)- and (1R,2S and 1S,2R)-isomers. MS: m/z (ESI) 323.06 (MH$^+$).

3-Amino-2-(3,4-dichlorophenyl)-1-(5-methoxypyridin-3-yl)propan-1-ol: A solution of 2-(3,4-dichlorophenyl)-3-hydroxy-3-(5-methoxypyridin-3-yl)propanenitrile (4.2 g, 13.00 mmol) in 100 mL THF was added over 5 min to a stirred suspension of 1.0 M in THF borane complex (39.0 mL, 38.99 mmol) heated to 45° C. The reaction was heated at reflux (internal temp at 66° C., oil bath at 72° C.) for 3 h. The solution was cooled to ambient temperature and carefully quenched with 4 mL of 4N HCl in dioxane diluted with 10 mL of methanol. The mixture was stirred for 15 min at 60° C. The solvents were the evaporated off and 10 mL of ethanol was added. The reaction mixture was stirred at 60° C. for 10 min before removing all the solvents to afford the product. The crude product was washed with ethyl acetate twice and dried under vacuum to obtain 6 g of white HCl salt of the mixture of the two diastereomers. $^1$H NMR spectrum showed the presence of the expected mixture of (1S,2S and 1R,2R)- and (1R,2S and 1S,2R)-isomers. MS: m/z (ESI) 327.08 (MH$^+$).

Ethyl 2-(3,4-dichlorophenyl)-3-hydroxy-3-(5-methoxypyridin-3-yl)propylcarbamate: A suspension of the HCl salt of 3-Amino-2-(3,4-dichlorophenyl)-1-(5-methoxypyridin-3-yl)propan-1-ol in DCM was treated with TEA and the solution was chilled to 0° C. Ethyl carbonochloridate was dropped into this chilled solution over 10 min. Ice bath was removed and the solution was allowed to warm to r.t. and stirred for 2 h. Reaction solution (in DCM) was reduced to 5 mL under reduced pressure, diluted with ethyl acetate and washed sequentially with 0.1N HCl, saturated sodium bicarbonate, and brine, then dried over MgSO$_4$, filtered, and concentrated in vacuo. Residual solvents were evaporated the mixture was purified by chromatography to afford a mixture of diastereomers.

2-(3,4-dichlorophenyl)-1-(5-methoxypyridin-3-yl)-3-(methylamino)propan-1-ol and the separation of (1S,2S and 1R,2R)- and (1R,2S and 1S,2R)-enantiomers: A solution of ethyl 2-(3,4-dichlorophenyl)-3-hydroxy-3-(5-methoxypyridin-3-yl)propylcarbamate (0.100 g, 0.25 mmol) in THF (20.00 mL) was added over 5 minutes to a stirred suspension of borane. THF complex (1.252 mL, 1.25 mmol) heated to 45° C. The reaction was heated for 4 h at reflux (internal temp at 66° C., oil bath at 72° C.) to give a bright purple suspension. The suspension was cooled to ambient temperature and carefully quenched with 4N HCl in dioxane. MeOH was added carefully and the mixture was heated to 60° C.

and stirred for 15 min before removing all the solvent. The crude was re-dissolved in 10 mL of ethanol and stirred for 10 min at 60° C. The volatiles were evaporated in vacuo to afford the crude HCl salt, which was sequentially washed with ether, ethyl acetate/hexane (1:1), and hexane, and then dried in high vacuum. MS m/z (ESI) 341.2 (MH$^+$). A 0.600 g lot of (1S,2S and 1R,2R) and (1R,2S and 1S,2R) amine mixture was subjected to chiral SFC system separation of the four isomers. The Multigram III SFC system was used with a 30 mm×250 mm ChiralPak ADH column. The diastereomeric mixture sample was diluted in ~8 mL of EtOH [0.5% isopropylamine], and stacked injections of 0.5 mL each were isocratically run using 35% iPrOH/1% isopropylamine at 120 mL/min. The peaks were well separated; timing was adjusted to minimize the contaminants. The first eluting enantiomer was presumed to be 1R,2R-configured because of its relatively lower potency on the hNET.

Example 110—Synthesis of Compound ID No. 110 ((1R,2R)-2-(4-bromo-3-chlorophenyl)-3-(methylamino)-1-phenylpropan-1-ol)

2-(4-bromo-3-chlorophenyl)-3-hydroxy-3-phenylpropanenitrile: A 250 mL round bottom flask equipped with a magnetic stirring bar, nitrogen inlet, and septum was charged with THF (200 mL) and 2.0 M LDA (27.6 mL, 55.10 mmol). After cooling to −78° C., 2-(4-bromo-3-chlorophenyl)acetonitrile (12.7 g, 55.10 mmol) was added. After 60 min of stirring, benzaldehyde (5.57 mL, 55.10 mmol) was added via syringe and the reaction mixture was stirred at −78° C. for 3 h. The reaction was quenched by adding acetic acid (20 mL) at the same temperature and the cold bath was removed to allow the reaction to warm to r.t. The aqueous layer was extracted with Et$_2$O (2×50 mL)), and the combined organic extracts were washed with brine (50 mL) and dried over MgSO$_4$, and concentrated in vacuo to give the crude aldol (21 g, 85%). ISCO purification on silica gel eluting with 0-30% of ethyl acetate in hexane afforded the product as 3:1 anti:syn mixture (16 g). Since the $^1$H NMR spectrum of the crude in CDCl$_3$ showed the presence of the expected mixture of anti- and syn-structures, it was taken to the next step without further purification. MS m/z (ESI) 359 (MNa$^+$).

3-Amino-2-(4-bromo-3-chlorophenyl)-1-phenylpropan-1-ol: A diastereomeric mixture of syn-anti-2-(4-bromo-3-chlorophenyl)-3-hydroxy-3-phenylpropanenitrile (16 g, 47.53 mmol) in THF (150 mL) was heated to a gentle reflux at 76° C. and then treated with dropwise addition of borane methyl sulfide complex (93 mL, 186 mmol) over 15 min. The liberated dimethyl sulfide was collected in a Dean-Stark trap. After 3.5 h the mixture was allowed to cool to ambient temperature, HCl (4N in dioxane, 12 mL) and MeOH (20 mL) were sequentially added slowly to quench extra BH$_3$, maintaining the temperature under 25° C. Addition of MeOH caused evolution of gas bubbles. After the gas bubbles subsided, the reaction mixture was heated to 64° C. (to make sure all of BH$_3$ quenched) for 10-15 min, and then concentrated to remove all the trimethyl borates to afford a yellow oil. EtOH (15 mL) was added and evaporated off under reduced pressure to afford a yellow gum as a HCl salt of the desired product. This was diluted with ether to give a white precipitate that was collected, washed with ether and dried to give 17 g final product as a diastereomeric mixture of amines MS m/z (ESI) 340.02 (MH$^+$).

Ethyl 2-(4-bromo-3-chlorophenyl)-3-hydroxy-3-phenylpropylcarbamate: A suspension of the HCl salt of 3-amino-2-(4-bromo-3-chlorophenyl)-1-phenylpropan-1-ol (15 g, 44.03 mmol) in DCM (100 mL) was treated with TEA (15.34 mL, 110.09 mmol) and the clear solution was chilled to 0° C. Ethyl carbonochloridate (5.07 mL, 52.84 mmol) was dropped into this chilled solution over 10 min. Ice bath was removed and the solution was allowed to warm to r.t. and stirred for 2 h. Reaction solution (in DCM) was reduced to 5 mL under reduced pressure, diluted with ethyl acetate (200 mL), and washed sequentially with 0.1N HCl (2×150 mL), saturated sodium bicarbonate (150 mL), and brine (200 mL), then dried over MgSO$_4$, filtered, and concentrated in vacuo. Residual solvents were evaporated to give the product as a foam (14 g). The mixture was purified by ISCO chromatography, eluting with 0-40% of ethyl acetate in hexane over 15 min Collected fractions were sent for SFC separation of 4 isomers from this diastereomeric mixture to give at total of 11 g of the products. The Multigram III SFC system was used with a 30 mm×250 mm Phenomenex Lux CE-2 column. A 11 g of sample were diluted in 40-50 mL of EtOH [0.5% isopropylamine], and stacked injections of 0.5 mL each were run using 25% of EtOH [0.5% isopylamine] isocratically at 110 mL/min. All the peaks were well separated with little tailing. For peak 3 (isomer 3), NMR with shift reagent "TBPTA" complex showed $J_{12}$=8.3 Hz, which indicated "anti" isomer (2.4 g). MS m/z (ESI) 396.44 (MNa$^+$). For peak 4 (isomer 4), NMR with shift reagent "TBPTA" complex showed $J_{12}$=8.1 Hz, which also indicated "anti" isomer (2.4 g). MS m/z (ESI) 396.44 (MNa$^+$). The first eluting isomer was assigned (1R,2R) configuration retrospectively because of the lower potency of its borane-reduced product compared to the (1S,2S) enantiomer (see below).

Compound ID No. 110: BH$_3$.THF (29.1 mL, 29.08 mmol) was added dropwise over 15 min to a refluxing (76° C.) solution of ethyl (2R,3R)-2-(4-bromo-3-chlorophenyl)-3-hydroxy-3-phenylpropylcarbamate (1.2 g, 2.91 mmol) in THF (50 mL). After overnight of refluxing, the reaction mixture was cooled to r.t, chilled in a 0° C. water bath, and treated first with 5 mL HCl (4N in dioxane) and then 10 mL of MeOH while maintaining the temperature under 25° C. After the evolution of gas bubbles subsided, the reaction mixture was heated to 64° C. for 10-15 min, then concentrated to remove all the trimethyl borates to afford a yellow oil. EtOH (5 mL) was then added and evaporated off in vacuo to afford a yellow gum as a hydrochloride salt of the desired product. This was diluted with ether to give a white precipitate that was collected, washed with ether and dried to give 1 g final product. $^1$H NMR (DMSO-d6) δ 7.60 (d, 1H, J=8.2 Hz), 7.45 (d, 1H, J=2.1 Hz), 7.30-7.11 (m, 5H), 7.06 (dd, 1H, J=8.2, 2.1 Hz) 4.76 (d, 1H, J=7.3 Hz), 3.47 (d, 1H, J=7.3 Hz), 3.40-3.31 (m, 2H), 2.50 (dt, 3H, J=3.7, 1.8 Hz). MS m/z (ESI) 354.02 (MH$^+$). The large J-value (7.3 Hz) of the benzylic proton indicated anti-relative configuration.

Example 111—Synthesis of Paroxetine or Paxil (Assigned Compound ID No. 111)

Paroxetine was synthesized using techniques similar to those described herein.

Example 112—Synthesis of Compound ID No. 112 ((S)-2-(3,4-dichlorophenyl)-3-(pyridin-3-yl)propan-1-amine)

An oven dried 2 neck 100 mL round bottom flask was charged with nitrogen, Compound No. 42a (640 mg, 2.3 mmol), and 15 mL of dry THF. BH$_3$/SMe$_2$ (2 M in THF, 5.8 mL, 11.5 mmol) was added with stirring. Upon addition of borane, the system was fitted with a reflux condenser and heated to reflux for 4 hours. After cooling to room temperature, 5 mL of methanol was carefully added. Upon cessation of bubbles, the system was heated to reflux for 1 hour. The volatiles were then removed in vacuo, and to the residue was added 10 mL of methanol and 1 mL of a 4 M HCl solution in dioxane. The homogenous solution was concentrated to give a white solid that was triturated with diethyl ether to give 813 mg (2.3 mmol, >99%) of the dihydrochloride salt. $^1$H NMR (400 MHz, CD$_3$OD) δ 8.70 (d, J=5.6 Hz, 1H), 8.66 (d, J=0.9 Hz, 1H), 8.44-8.36 (m, 1H), 7.98 (dd, J=8.1, 5.8 Hz, 1H), 7.53 (t, J=5.2 Hz, 2H), 7.26 (dd, J=8.3, 2.1 Hz, 1H), 3.49-3.38 (m, 4H), 3.18 (dd, J=15.2, 11.6 Hz, 2H). HRMS (ESI-TOF) calculated for C$_{14}$H$_{15}$Cl$_2$N$_2$ (MH$^+$) 281.0607 found 281.0581 (−9.08 ppm, 2.6 mmu). This racemate was converted to its free base and separated into its enantiomers using a chiral stationary phase supercritical fluid chromatography (Multigram III SFC system) on an ADH column (21.1×250 mm). Isocratic elution using 15% i-PrOH (containing 0.5% dimethylethanamine) at a flow rate of 50 mL/minute gave enantiomer retention times of 15.22 and 15.88 minutes, respectively. The combined fractions of the first eluting enantiomer were concentrated in vacuo to yield 27 mg of Compound ID No. 112, which was shown by the previously described SCF system to have 99% enantiomeric excess. $^1$H NMR (300 MHz, CDCl$_3$) δ 2.69-3.10 (m, 4H), 6.95 (dd, J=8.2, 1.9 Hz, 1H), 7.13 (dd, J=7.6, 4.8 Hz, 1H), 7.19-7.42 (m, 3H), 8.31 (s, 1H), 8.41 (d, J=4.6 Hz, 1H). Since this enantiomer is more potent at hNET than the second eluting enantiomer, it was presumed to be (S)-configured.

Example 113—Synthesis of Compound ID No. 113 ((1RS,2RS)-2-(1,1'-biphenyl)-4-yl)-3-(methylamino)-1-phenylpropan-1-ol)

(1S,2S and 1R,2R)-2-(biphenyl-4-yl)-3-hydroxy-3-phenylpropanenitrile: A solution of 2-(biphenyl-4-yl)acetonitrile (1 g, 5.17 mmol) in 50 mL of dry THF was placed in an oven-dried round bottom flask with under nitrogen. Diisopropylamine (0.880 mL, 6.21 mmol) was added, and the reaction mixture was stirred and cooled to −78° C. for 20 minutes. 2.5M butyllithium (2.48 mL, 6.21 mmol) was then added slowly with a syringe. After 30 minutes of stirring at −78° C., benzaldehyde (0.633 mL, 6.21 mmol) was added drop-wise via syringe. After 1 h, the reaction was quenched quickly with 25 mL 2:1 THF/acetic acid. The cold bath was removed, and the reaction was allowed to reach room temperature. Water was added, and the aqueous layer was extracted with EtOAc (3×25 mL). The combined organic layers were sequentially washed with water and brine, then dried over MgSO$_4$, and concentrated using a rotary evaporator. The residue was dissolved in 150 mL DCM, and 150 mL hexane was slowly added until a turbid solution resulted. The turbid solution was allowed to stand for 5-6 h at 4° C. minutes. The major (1S,2S and 1R,2R)-isomer that separated as off-white crystals was isolated by filtration (0.654 g, 42.2%). $^1$H NMR (CDCl$_3$) δ 7.59-7.54 (m, 4H), 7.47-7.42 (m, 2H), 7.38-7.33 (m, 7H), 7.25 (s, 1H), 5.02 (dd, 1H, J=5.4, 3.6 Hz), 4.11 (d, 1H, J=5.54 Hz).

(1S,2S and 1R,2R)-3-amino-2-(biphenyl-4-yl)-1-phenylpropan-1-ol: To a solution of (1S,2S and 1R,2R)-2-(biphenyl-4-yl)-3-hydroxy-3-phenylpropanenitrile (0.300 g, 1.002 mmol) in 8 mL of dry THF was added 1M borane-THF solution (3.01 mL, 3.01 mmol) under nitrogen slowly via syringe. This mixture was stirred at 60° C. overnight while monitoring the reaction progress by TLC. After quenching the reaction with cautious addition of NaHCO$_3$, the reaction mixture was poured into a separatory funnel, and the aqueous layer was extracted with EtOAc (3×25 mL). The combined organic layers were washed with water and brine, and dried over MgSO$_4$. Concentration of the volatiles using a rotary evaporator afforded a residue that was dissolved in DCM. 1N HCl was added, and the mixture was stirred for a few minutes. The solvents were evaporated on a rotary evaporator. The product was washed, leached with DCM, and lyophilized to afford a white solid (0.268 g, 88%). $^1$H NMR (CD$_3$OD) δ 7.58-7.47 (m, 4H), 7.42-7.37 (m, 2H), 7.33-7.28 (m, 1H), 7.19-7.15 (m, 7H), 4.94 (d, 1H, J=8.8 Hz), 4.11 (d, 1 J=5.54 Hz), NH$_2$ peak hidden in the water peak. A large J-value of the benzylic proton signal (8.8 Hz) indicated that the compound had (1S,2S and 1R,2R)-configuration. MS m/z (ESI) 304.4 (MH$^+$).

Ethyl (2S,3S and 2R,3R)-2-(biphenyl-4-yl)-3-hydroxy-3-phenylpropylcarbamate: To (1S,2S and 1R,2R)-3-amino-2-(biphenyl-4-yl)-1-phenylpropan-1-ol (0.268 g, 0.788 mmol) in 5 mL dry DCM at −10° C. was added triethylamine (TEA) (0.329 mL, 2.363 mmol) drop-wise, followed by slow addition of ethyl chloroformate (0.083 mL, 0.868 mmol). After stirring for 1 hour at −10° C., the ice bath was removed, and the mixture was allowed to warm to 0° C. TLC showed completion of reaction after 1 hour. The reaction was quenched with saturated NaHCO$_3$, and the mixture poured into a separatory funnel. The organic layer was separated, and the aqueous layer was extracted with DCM (3×25 mL) The combined DCM extracts were washed with water, dried over MgSO$_4$, filtered, and concentrated. The resulting residue was purified by flash chromatography over silica gel (eluent: 30% EtOAc in hexanes). The combined organic layers were concentrated using a rotary evaporator, which yielded the product as a sticky solid (0.116 g, 39.2%). $^1$H NMR (CDCl$_3$) δ 7.61-7.12 (m, 14H), 4.92 (d, 1H, J=8.2 Hz), 4.11 (q, 2H, J=7.09 Hz), 3.82-3.35 (m, 2H), 3.22-3.13 (m, 1H), 1.28-1.15 (overlapping t, 3H) MS m/z (ESI) 357.9 (M−H$_2$O+1$^+$).

Compound ID No. 113: Ethyl (2S,3S and 2R,3R)-2-(biphenyl-4-yl)-3-hydroxy-3-phenylpropylcarbamate (0.1099 g, 0.293 mmol) was dissolved in 4 mL of dry THF and placed in a dry flask. To this, 1M borane-THF solution (0.732 mL, 0.732 mmol) was added via syringe. This mixture was stirred at 60° C. overnight while monitoring the reaction progress by TLC. The reaction was quenched by cautious addition of NaHCO$_3$ and poured into a separatory funnel. The two layers were separated, and the aqueous layer was extracted with EtOAc (3×25 mL). The combined organic layers were washed with water and brine, dried over MgSO$_4$, and concentrated under reduced pressure. The residue was mixed with 2N HCl and concentrated under rotary evaporation. High vacuum drying afforded the product as a white solid. $^1$H NMR (300 MHz, DMSO-d$_6$) δ 8.65-8.04 (m, 2H), 7.61 (d, 2H, J=7.4 Hz), 7.54 (d, 2H, J=8.2 Hz), 7.43 (t, 2H, J=7.5 Hz), 7.35 (d, 1H, J=7.2 Hz), 7.11-7.27 (m, 5H), 6.07 (br. s., 1H), 4.82 (d, 1H, J=6.5 Hz), 3.15-3.49 (m, 3H), 2.31-2.72 (m, 3H). MS m/z (ESI) 318.2 (MH$^+$).

Example 114—Synthesis of Compound ID No. 114 ((1R,2R)-2-(3,4-dichlorophenyl)-3-(methylamino)-1-phenylpropan-1-ol)

2-(3,4-dichlorophenyl)-3-hydroxy-3-phenylpropanenitrile: A 250 mL round bottom flask equipped with a magnetic stirring bar, nitrogen inlet, and septum was charged with 50 mL of THF and 1.8 M lithium diisopropylamide (LDA) (9.91 mL, 17.84 mmol). After cooling to −78° C., 2-(3,4-dichlorophenyl)acetonitrile (3.32 g, 17.84 mmol) was added. The reaction mixture was stirred for 60 minutes at −78° C. Next, benzaldehyde (1.803 mL, 17.84 mmol) was added via syringe. After stirring at −78° C. for 3 hours, the reaction was quenched by adding 20 mL water, and the cold bath was removed. The aqueous layer was extracted with $Et_2O$ (2×50 mL). The combined organic extracts were washed with 50 mL brine and dried over $MgSO_4$. Concentration of the dried extracts in vacuo gave the crude aldol. ISCO purification on silica gel eluting with 0-30% of ethyl acetate in hexane afforded the product as 3:1 anti: syn mixture (2.5 g). Recrystallization from DCM (30 mL) and hexane (40 mL) at 0° C. overnight afforded only the anti isomer. $^1$H NMR ($CDCl_3$) δ 7.55-6.74 (m, 8H), 4.98 (dd, 1H, J=5.5, 3.7 Hz), 4.03 (d, 1H, J=5.5 Hz), 2.39 (d, 1H, J=3.7 Hz). MS m/z (ESI) 314.01 ($MNa^+$).

anti-3-amino-2-(3,4-dichlorophenyl)-1-phenylpropan-1-ol: A solution of anti-2-(3,4-dichlorophenyl)-3-hydroxy-3-phenylpropanenitrile (0.650 g, 2.22 mmol) in 25 mL of THF was heated to a gentle reflux at 76° C. Borane-methyl sulfide complex (6.41 mL, 12.825 mmol) was added drop-wise via syringe over 5 minutes. Liberated dimethyl sulfide was collected in a Dean-Stark trap. After 3.5 hours, the mixture was allowed to cool to ambient temperature and concentrated in vacuo. The resulting crude product was dissolved in 100 mL of ethyl acetate and washed with saturated aqueous $NaHCO_3$ and brine, dried over $MgSO_4$, filtered, and concentrated. The residue was dissolved in DCM and filtered. To the filtrate was added 1 mL of 2 N HCl in dioxane, and the resulting mixture was stirred for 10 minutes before evaporating all the solvents to afford the HCl salt of the product as an anti mixture (0.620 g). $^1$H NMR (DMSO-d6) δ 7.77 (hr. s., 2H), 7.53-7.36 (m, 2H), 6.99-7.32 (m, 4H), 5.96 (d, 1H, J=3.4 Hz), 4.77 (d, 1H, J=4.3 Hz), 3.47-3.34 (m, 2H), 3.27-3.19 (m, 2H). MS m/z (ESI) 296.1 ($MH^+$).

anti-ethyl (2S,3S)-2-(3,4-dichlorophenyl)-3-hydroxy-3-phenylpropylcarbamate: A mixture of the HCl salt of (1S,2S and 1R,2R)-3-amino-2-(3,4-dichlorophenyl)-1-phenyletha-nol-1-ol (0.390 g, 1.32 mmol) and TEA (0.459 mL, 3.29 mmol) in 20 mL of DCM was chilled to 0° C. To this, ethyl carbonochloridate (0.152 mL, 1.58 mmol) was added over 10 minutes. The ice bath was removed, and the solution was allowed to warm to room temperature for 3 hours. The volume of the reaction solution (in DCM) was reduced to 5 mL Ethyl acetate (100 mL) was added, and the clear solution was sequentially washed with 0.1 N HCl (2×15 mL), saturated sodium bicarbonate (15 mL), and brine (20 mL), then dried over $MgSO_4$, filtered, and concentrated in vacuo. Residual solvents were evaporated to give 0.440 g product as a foamy solid. $^1$H NMR in $CDCl_3$ showed the presence of the expected structure. MS m/z (ESI) 390.06 ($MNa^+$).

(1R,2R)-2-(3,4-dichlorophenyl)-3-(methylamino)-1-phenylpropan-1-ol: A solution of ethyl-(2S,3S and 2R,3R)-2-(3,4-dichlorophenyl)-3-hydroxy-3-phenylpropylcarbamate (440 mg, 1.19 mmol) in 25 mL THF were transferred to a 100 mL 3-neck round bottom flask equipped with a magnetic stirrer, addition funnel, thermometer, and Dean-Stark trap fitted with a condenser and nitrogen inlet. The solution was heated to a gentle reflux (66° C.), and a solution of borane-methyl sulfide complex (1.792 mL, 3.58 mmol) was added drop-wise over 10 minutes. Dimethyl sulfide distillate was collected (bp 38° C.). After 7 hours, the reaction was about 85% complete. Another portion of borane-methyl sulfide complex (1.792 mL, 3.58 mmol) was added, and stirring was allowed to continue for 2 hours. The reaction was cooled to room temperature and treated with 4 N HCl in dioxane (0.32 mL, 1.07 eq). MeOH (10 mL) was carefully added (exothermic with gas evolution), and the reaction mixture was then heated to distill a 1:1 azeotrope of methanol and trimethyl borate. As most of the methanol was distilled, the heat was removed, and the mixture was diluted with 10 mL of ether. This immediately produced a white precipitate, which was filtered and washed with additional lots of ether and ethyl acetate to afford product as HCl salt (0.250 g). $^1$H NMR (DMSO-$d_6$) δ 8.49 (br. s., 1H), 8.19 (br. s., 1H), 7.46 (d, 2H, J=2.1 Hz), 7.00-7.34 (m, 5H), 6.04 (br. s., 1H), 4.76 (d, 1H, J=5.5 Hz), 3.48 (br. s., 1H), 3.29 (s, 2H), 2.61-2.40 (m, 3H). The large J-value of the benzylic proton (5.5 Hz) indicated anti-configuration. MS m/z (ESI) 310.07 ($MH^+$).

A solution of (1S,2S and 1R,2R)-2-(3,4-dichlorophenyl)-3-(methylamino)-1-phenylpropan-1-ol (0.150 g, 0.48 mmol) in DCM was treated with 1 N NaOH (0.484 mL, 0.48 mmol). The organic phase was separated and dried over sodium sulfate. The solvents were evaporated to afford the free amine for SFC separation. The Multigram II SFC system was used to separate the enantiomers. A 0.060 g lot of the free amine was converted to the HCl salt by dissolving in 0.15 mL of 4 N HCl in dioxane, stirring for 10 minutes, and evaporating under reduced pressure. The resulting solid was washed with ether and ethyl acetate/hexane to afford the title compound as a hydrochloride salt. $^1$H NMR (DMSO-d6) δ 8.84 (br. s, 1H), 8.40 (br. s., 1H), 7.80-6.72 (m, 8H), 6.04 (br. s., 1H), 4.76 (d, 1H, J=6.4 Hz), 3.57 (br. s., 1H), 3.44 (d, 2H, J=7.6 Hz), 3.57 (br. s., 1H), 2.50 (br. s., 3H). The first-eluting enantiomer was presumed to be 1R,2R-configured because of its weak hNET potency. MS m/z (ESI) 310.08 ($MH^+$).

Example 115—Synthesis of Compound ID No. 115 ((R)-2-(3,4-dichlorophenyl)-N-methyl-3-(pyridin-3-yl)propan-1-amine)

Compound ID No. 115 is the enantiomer (first eluting) of Compound ID No. 59. The combined fractions of the first eluting enantiomer were concentrated in vacuo and converted to an HCl salt that afforded 28.6 mg of Compound ID No. 115, which was shown by the previously described SCF system to have 99% enantiomeric excess. $^1$H NMR (300 MHz, $CDCl_3$) δ 8.41 (d, J=4.1 Hz, 1H) 8.30 (s, 1H) 7.33 (d, J=8.3 Hz, 1H) 7.27-7.31 (m, 1H) 7.23 (d, J=2.3 Hz, 1H) 7.13 (dd, J=7.9, 4.9 Hz, 1H) 6.94 (dd, J=8.3, 1.9 Hz, 1H), 2.94-3.10 (m, 2H) 2.70-2.93 (m, 3H) 2.38 (s, 3 H). Since this enantiomer is less potent at hNET than the second eluting enantiomer, it was presumed to be (R)-configured.

Example 116—Synthesis of Compound ID No. 116 ((1R,2R or 1S,2S)-2-(3,4-dichlorophenyl)-3-(methylamino)-1-(3-(methylsulfinyl)phenyl)propan-1-ol)

anti-2-(3,4-dichlorophenyl)-3-(methylamino)-1-(3-(methylthio)phenyl)propan-1-ol: This material was prepared as set forth in Example 120.

anti-tert-butyl (2R,3R)-2-(3,4-dichlorophenyl)-3-hydroxy-3-(3-(methylthio)phenyl)propyl(methyl)carbamate: A solution of anti-2-(3,4-dichlorophenyl)-3-(methylamino)-1-(3-(methylthio)phenyl)propan-1-ol (1 g, 2.81 mmol) and triethylamine (0.312 g, 3.09 mmol) in dichloromethane (5 mL) was cooled to 0° C. Boc-anhydride was added into the above reaction mixture in small portions, and the reaction mixture was allowed to warm to room temperature. One hour later, LCMS showed mainly the desired product. The mixture was diluted with $CH_2Cl_2$ (100 mL), washed with water (100 mL×2), dried over MgSO$_4$, and then evaporated to dryness. The crude product was added to a silica gel column and was eluted with 0-100% EtOAc in hexane to give a colorless foam as the desired product (850 mg, 66.4% yield, 98% purity). $^1$H NMR in CDCl$_3$ was consistent with desired product.

(1S,2S and 1R,2R)-Butyl-2-(3,4-dichlorophenyl)-3-hydroxy-3-(3-(methylsulfinyl)phenyl)propyl(methyl)carbamate: Sodium periodate (0.271 g, 1.27 mmol) in water (2 mL) was slowly added into a stirred solution of anti-tert-butyl-2-(3,4-dichlorophenyl)-3-hydroxy-3-(3-(methylthio)phenyl)propyl(methyl)carbamate (0.165 g, 0.36 mmol) in THF (2 mL) at room temperature. After stirring for 3 hours, the reaction mixture was diluted with CHCl$_3$ (100 mL), washed with water (50 mL×2), dried through MgSO$_4$, and then evaporated under reduced pressure to dryness. The crude product was added to a silica gel column and eluted with 0-10% MeOH in CH$_2$Cl$_2$ to give a colorless foam as the desired product (0.173 g, 101%). $^1$H NMR (CDCl$_3$) δ 7.12-7.45 (m, 6H), 6.95 (d, 1H, J=8.0 Hz), 4.83 (br. s., 1H), 3.72-3.94 (m, 1H), 3.56-3.72 (m, 1H), 3.19 (br. s., 1H), 2.59 (br. s., 3H), 2.52 (d, 3H, J=5.5 Hz), 1.35 (br. s., 9H). The two singlets of diastereomeric CH$_3$ groups of the sulfoxide moiety were found at 2.51 and 2.52 ppm. MS m/z (ESI) 472.2 (MH$^+$).

(1S,2S or 1R,2R)-2-(3,4-dichlorophenyl)-3-(methylamino)-1-(3-(methylsulfinyl)phenyl)propan-1-ol: A solution of tert-butyl 1S,2S or 1R,2R dichlorophenyl)-3-hydroxy-3-(3-(methylsulfinyl)phenyl)propyl(methyl)carbamate (0.165 g, 0.35 mmol) in 2 mL of 10% TFA in CH$_2$Cl$_2$ was stirred at room temperature for 30 minutes. Another 0.5 mL of TFA was added, and stirring was continued for another hour. Then the reaction mixture was basified with saturated NaHCO$_3$ (10 mL) and extracted with CH$_2$Cl$_2$ (5 mL×5). The organic layer was dried over MgSO$_4$ and evaporated in vacuo to give a light-yellow gum. The light-yellow gum was added to a silica gel column and eluted with 0-10% MeOH in CH$_2$Cl$_2$. Collected fractions were evaporated under reduced pressure to give the desired product as an off-white foamy solid (0.115 g, 88% yield). $^1$H NMR (CDCl$_3$) δ 7.27-7.59 (m, 3H), 7.14-7.25 (m, 2H), 7.04 (dd, 1H, J=8.4, 2.1 Hz), 6.79 (dd, 1H, J=8.4, 2.1 Hz), 5.01 (dd, 1H, J=8.6, 4.0 Hz), 3.23-3.44 (m, 1H), 2.90-3.18 (m, 2H), 2.52-2.61 (m, 6H). MS m/z (ESI) 372.1 (MH$^+$). The enantiomers were separated by chiral SFC system. Compound ID No. 116 was obtained by evaporating the first-eluting peak. However, both the anti-enantiomers were equipotent at hNET.

Example 117—Synthesis of Compound ID No. 117 ((2-(1R,2R)-3-(methylamino)-2-(naphthalen-2-yl)-1-phenylpropoxy)acetamide)

tert-Butyl ((2R,3R)-3-hydroxy-2-(naphthalen-2-yl)-3-phenylpropyl)(methyl) carbamate: To a solution of (1R,2R)-3-(methylamino)-2-(naphthalen-2-yl)-1-phenylpropan-1-ol (1.0 g, 3.05 mmol) in 25 mL of DCM was added triethylamine (1.28 mL, 9.15 mmol) at room temperature. To this was added Boc$_2$O (0.766 g, 3.51 mmol) portionwise and the reaction mixture was left stirred for 10 min while monitoring the reaction progress by TLC. Upon completion of the reaction, 1N HCl (15 mL) was added to an acidic pH 6 and the crude product was isolated by extraction with DCM (3×). The combined extracts were washed with water and dried with MgSO$_4$ to furnish crude that was deemed pure for the next step. $^1$H NMR (DMSO-d6) δ 7.73-7.70 (m, 3H), 7.61 (m, 1H), 7.41-7.39 (m, 3H), 7.22-7.04 (m, 5H), 5.55 (bd, 1H), 4.86 (dd, 1H, J=7.2, 4.8 Hz), 3.90 (bt, 1H), 3.66 (dd, 1H, J=13.8, 3.9 Hz), 2.08 (s, 3H), 1.14, 1.08 (two s, 9H). MS m/z (ESI) 414.22 (MNa+).

Ethyl 2-((1R,2R)-4-((tert-butylcarbamoyl)oxy)-2-(naphthalen-2-yl)-1-phenylbutoxy)acetate: Sodium hydride (60% in oil) (0.037 g, 0.766 mmol) was washed with pentane (3 mL) in an oven dried round bottom flask. t-Butyl (2R,3R)-3-hydroxy-2-(naphthalen-2-yl)-3-phenylpropyl(methyl)carbamate (0.200 g, 0.511 mmol) was dissolved in 5 mL of anhydrous DMF at 0° C. and added to the flask containing NaH, and the reaction mixture was stirred for 10 minutes under nitrogen. Ethyl bromoacetate (0.085 mL, 0.766 mmol) was added drop-wise to the reaction mixture, and the reaction mixture was stirred at room temperature overnight. After quenching the reaction cautiously with 2 mL of saturated NH$_4$Cl cautiously, the reaction mixture was poured into a separatory funnel containing water, and the aqueous layer was extracted with EtOAc (3×25 mL). The combined organic layers were washed with water and brine, dried over MgSO$_4$, and concentrated using a rotary evaporator. The resulting residue was purified by flash chromatography over silica gel (elution with 10% EtOAc in hexanes) to afford the product as a colorless oil (0.103 g, 42.2%). $^1$H NMR (CDCl$_3$): δ 7.76-7.60 (m, 3H), 7.47-7.38 (m, 3H), 7.22 (m, 1H), 7.18-7.01 (m, 5H), 4.7 (d, 1H, J=8.3 Hz), 4.21-3.80 (m, 7H), 2.17 (s, 3H), 1.31-1.18 (m, 12H). MS m/z (ESI) 478.09 (MH$^+$), and 500.16 (MNa$^+$).

Ethyl 2-((1R,2R)-3-(methylamino)-2-(naphthalen-2-yl)-1-phenylpropoxy) acetate: Ethyl 2-((1R,2R)-3-(tert-butoxycarbonyl(methyl)amino)-2-(naphthalen-2-yl)-1-phenylpropoxy)acetate (0.5 g, 1.047 mmol) was mixed with 10 mL of 1:1 TFA:DCM, and the reaction mixture was stirred at room temperature for 1 hour. The reaction mixture was poured into a separatory funnel containing water, and the aqueous layer was extracted with EtOAc (3×25 mL) The combined organic layers were washed with water and brine, dried over MgSO$_4$, and concentrated under reduced pressure. The resulting residue was purified by flash chromatography over silica gel (elution with 10% EtOAc in hexanes) to afford a colorless sticky solid (0.254 g, 64.3%). $^1$H NMR (CDCl$_3$) δ 11.43 (br s, NH), 8.62 (br s, NH), 7.77-7.55 (m, 3H), 7.49-7.35 (m, 3H), 7.19-6.97 (m, 6H), 4.71 (d, 1H, J=10.17 Hz), 4.36-4.22 (M, 2H), 4.20-4.07 (m, 2H), 3.87 (d, 1H, J=16.8 Hz), 3.74-3.60 (m, 1H), 3.51-3.39 (m, 1H) 2.87 (s, 3H), 1.32 (t, 3H, J=7.2 Hz) MS m/z (ESI) 378.03 (MH$^+$).

2-(1R,2R)-3-(methylamino)-2-(naphthalen-2-yl)-1-phenylpropoxy)acetamide: Dry ammonia gas was continuously passed through a solution of ethyl 2-((1R,2R)-3-(methylamino)-2-(naphthalen-2-yl)-1-phenylpropoxy)acetate (0.154 g, 0.408 mmol) in 15 mL of MeOH for 15 minutes. The reaction flask was sealed, and the reaction mixture left stirred for 40 hours at room temperature. The solvents were evaporated using a rotary evaporator. The product was dissolved in MeOH and was purified by RP-HPLC (Vydac column, C-18, 2.2×25 cm; elution with 10% B-100% B in 30 minutes, B=80% aq. CH$_3$CN with 0.1% TFA, A=H$_2$O with 0.1% TFA); FR 8 mL/min; l$_{max}$=254 nm. RT=22.457 minutes). The product containing fractions were evaporated using a rotary evaporator, and the residue was mixed with 1 N HCl and was evaporated. The residue was then washed with ether to remove impurities. The product was lyophilized, yielding the product as a colorless sticky solid. $^1$H NMR (CD$_3$OD) δ 7.79-7.64 (m, 3H), 7.54 (s, 1H), 7.47-7.39 (m, 2H), 7.19-7.08 (m, 6H), 1H hidden in the H$_2$O peak, 4.11 (d, 1H, J=16.0 Hz), 4.01-3.89 (m, 2H), 3.67-3.54 (m, 1H), 3.43-3.36 (m, 1H), 2.86 (s, 3H). MS m/z (ESI) 348.91 (MH$^+$).

Example 118—Synthesis of Compound ID No. 118 (1R,2R)-3-amino-1-(3-chloropyridin-4-yl)-2-(naphthalen-2-yl)propan-1-ol)

anti-3-(3-chloropyridin-4-yl)-3-hydroxy-2-(naphthalen-2-yl)propanenitrile: These compounds were made in a standard LDA-mediated reaction of 2-naphthylacetonitrile and 3-chloro-4-pyridine carboxaldehyde at −78° C. in THF. The syn- and anti-diastereomers were separated by either recrystallization or chromatography. anti-isomer: $^1$H NMR (CDCl$_3$) δ 8.57 (1, 1H), 8.30 (d, 1H, J=5.1 Hz), 7.83-7.76 (m, 1H), 7.75-7.68 (m, 2H), 7.61 (bs, 1H), 7.53-7.49 (m, 2H), 7.12 (dd, 1H, J=8.4, 1.6 Hz), 7.08 (d, 1H, J=4.8 Hz), 5.86 (t, 1H, J=4.5 Hz), 4.46 (d, 1H, J=4.5 Hz), 2.86 (d, 1H, J=4.5 Hz).

(1R,2R)-3-amino-1-(3-chloropyridin-4-yl)-2-(naphthalen-2-yl)propan-1-ol: A solution of anti-3-(3-chloropyridin-4-yl)-3-hydroxy-2-(naphthalen-2-yl)propanenitrile (1.4 g, 4.53 mmol) in 20 mL of dry THF was placed in an oven-dried round-bottom flask fitted with a reflux condenser under nitrogen. Next, 1M borane-THF solution (18.14 mL, 18.14 mmol) was added via syringe. The resulting clear solution was stirred at 60° C. overnight while monitoring the progress by TLC. After quenching the reaction with cautious addition of saturated NaHCO$_3$, the reaction mixture was poured into a separatory funnel. The layers were separated, and the aqueous layer was extracted with EtOAc (3×50 mL). The combined organic layers were washed with water and brine, dried over MgSO$_4$, and were concentrated using a rotary evaporator. The residue was dissolved in DCM, and 4N HCl in dioxane was added. The mixture was stirred for 15 minutes. The solvents were evaporated in vacuo, and the residue was washed with ether, dried, and lyophilized, yielding a white solid (1.367 g, 78%). $^1$H NMR (Free amine). $^1$H NMR (300 MHz, CDCl$_3$) δ 8.49 (d, 1H, J=5.1 Hz), 8.37 (s, 1H), 7.70-7.92, (in, 4H), 7.65 (d, 1H, J=5.1 Hz), 7.39-7.54 (m, 2H), 7.35 (dd, 1H, J=8.5, 1.4 Hz), 5.66 (d, 1H, J=5.3 Hz), 3.05-3.53 (in, 3H). $^1$H NMR (500 MHz, CD$_3$OD) δ 8.71 (d, J=5.49 Hz, 1H), 8.65 (s, 1H), 8.15-8.23 (m, 1H), 7.75-7.87 (m, 4H), 7.44-7.54 (m, 2H), 7.41 (dd, J=8.39, 1.68 Hz, 1H), 5.57 (d, J=6.71 Hz, 1H), 3.68-3.79 (m, 1H), 3.52-3.62 (m, 2H). MS m/z (ESI) 313.05 (MH$^+$). This compound was assigned anti-relative configuration based on its higher J-value of the benzylic proton (6.7 Hz) in CD$_3$OD. The racemate was resolved into 1S,2S and 1R,2R enantiomers by chiral SFC chromatography. The first-eluting enantiomer was presumed to be 1R,2R-configured based on its lower potency on hNET.

Example 119—Synthesis of Compound ID No. 119 ((1R,2R)-1-(3-aminophenyl)-2-(3,4-dichlorophenyl)-3-(methylamino)propan-1-ol)

(1R,2R)-(3-aminophenyl)-2-(3,4-dichlorophenyl)-3-(methylamino)propan-1-ol: The nitro precursor (1R,2R and 1S,2S)-2-(3,4-dichlorophenyl)-3-(methylamino)-1-(3-nitrophenyl)propan-1-ol (Example 102) (630 mg, 1.77 mmol) and iron (396 mg, 7.09 mmol) in acetic acid (1.5 mL)/EtOH (1.5 mL) were refluxed at 100° C. for 1 hour. The reaction mixture was neutralized with saturated Na$_2$CO$_3$ solution, and then extracted with CHCl$_3$ (50 mL, 25 mL, 25 mL). The combined organic layer was dried with MgSO$_4$, filtered, and concentrated to a dark brown oil. The crude product was added to a silica gel column and was eluted with 0-10% ammoniated MeOH in CH$_2$Cl$_2$ to give a brown-yellow gum (76% yield, 95% purity).

Separation of the enantiomers of anti-3-amino-1-(3-aminophenyl)-2-(3,4-dichlorophenyl)propan-1-ol was performed as follows. The two chiral compounds were separated by SFC (ADH column, 30% iPrOH with 0.5% isopropylamine) as Peak 1 and Peak 2. Each fraction was concentrated separately. The first-eluting fraction was acidified with TFA (2 mL) for 5 minutes, basified with 1N NaOH (15 mL×2), dried through MgSO$_4$, and concentrated to a yellow oil. The yellow oil added to a silica gel column and was eluted with 0-5% ammoniated MeOH in CH$_2$Cl$_2$ to give the desired product as a colorless gel. The free base of the desired product was diluted with 2 mL of CH$_2$Cl$_2$; 0.5 mL of 2M HCl in ether was added and then evaporated to give its HCl salt as a white solid (0.0339 g, 21.75% recovery, 95% purity). $^1$H NMR (CDCl$_3$) δ 7.24 (d, J=8.9 Hz, 1H partially covered under the solvent-CHCl$_3$) 7.18 (d, J=2.1 Hz, 1H), 6.96 (t, J=7.8 Hz, 1H), 6.88 (dd, 1H, J 8.2, 1.9 Hz), 6.55 (s, 1H), 6.49 (dd, 1H, J=8.0, 2.1 Hz), 6.43 (d, 1H, J=7.6 Hz), 4.86 (d, 1H, J=7.6 Hz), 3.56 (br. s., 2H), 3.11-3.22 (m, 1 IA), 2.97-3.05 (m, 1H), 2.90 (td, 1H, J=8.4, 3.4 Hz), 2.47 (s, 3H). MS m/z (ESI) 325.09 (MH$^+$). Large J-value (7.6 Hz) of the benzylic proton indicated anti-relative configuration. Based on its lower inhibitory activity on the hNET, Compound ID No. 119 recovered from the first-eluting fraction was assigned an (1R,2R) configuration.

Example 120—Synthesis of Compound ID No. 120 ((1R,2R)-2-(3,4-dichlorophenyl)-3-(methylamino)-1-(3-(methylthio)phenyl)propan-1-ol)

2-(3,4-dichlorophenyl)-3-hydroxy-3-(3-(methylthio)phenyl)propanenitrile: A solution of 2-(3,4-dichlorophenyl)acetonitrile (5.8 g, 30.55 mmol) in ether (35 mL) and THF (15 mL) was cooled to −75° C. BuLi (13.44 mL, 33.61 mmol) was added slowly, and the reaction was stirred at −75° C. for 20 minutes. Next, 3-(methylthio)benzaldehyde (5.12 g, 33.61 mmol) in THF (15 mL) was added drop-wise, maintaining the temperature under −60° C. After the addition, the reaction was stirred at −75° C. for another hour. To quench the reaction, acetic acid (2.62 mL, 45.83 mmol) was added at −75° C. The reaction mixture was warmed to room temperature, and the organic layer was separated from the aqueous layer. The aqueous layer was extracted with ether (100 mL×3), and the combined organic layer was dried through MgSO$_4$ and evaporated to give an orange oil, which was used directly for the next step without further purification. Isomer A—$^1$H NMR (CDCl$_3$) δ 4.99 (d, 1H, J=6.1 Hz), 4.06 (d, 1H, J=6.1 Hz), Isomer B—$^1$H NMR (CDCl$_3$) δ 4.93 (d, 1H, J=5.5 Hz), 4.01 (d, 1H, J=5.2 Hz).

3-Amino-2-(3,4-dichlorophenyl)-1-(3-(methylthio)phenyl)propan-1-ol: 2-(3,4-dichlorophenyl)-3-hydroxy-3-(3-(methylthio)phenyl)propanenitrile (10.15 g, 30 mmol) in THF (55 mL) was preheated at 76° C. for gentle-refluxing. To this, a solution of borane-methyl sulfide complex (45.0 mL, 90.00 mmol) in THF was added drop-wise over 30 minutes, and a Dean-Stark trap was set up to collect liberated SMe$_2$. Twelve hours later, the reaction mixture was cooled in a cold water bath, acidified with 4M HCl in dioxane (10 mL), and the extra BH$_3$ was quenched with 20 mL of MeOH slowly, maintaining the temperature under 25° C. The reaction mixture was heated to 64° C. (to make sure all of BH$_3$ quenched) for 10-15 minutes during which time the B(OMe)$_3$-MeOH complex was collected in a Dean-Stark trap. The reaction mixture was concentrated to give a pale-yellow oil. Since the ¹H NMR spectrum of the crude in CDCl₃ showed the presence of the expected mixture of anti- and syn-structures, it was taken to the next step without further purification.

Ethyl-2-(3,4-dichlorophenyl)-3-hydroxy-3-(3-(methylthio)phenyl) propylcarbamate: A mixture of HCl salt of 3-amino-2-(3,4-dichlorophenyl)-1-(3-(methylthio)phenyl) propan-1-ol (11.36 g, 30 mmol) and TEA (12.54 mL, 90.00 mmol) in CH₂Cl₂ (100 mL) was stirred for 20 minutes and then cooled to 0° C. Ethyl carbonochloridate (3.46 mL, 36.00 mmol) was added drop-wise at 0° C. After the addition, the reaction mixture was stirred at room temperature for 3 hours, then washed with 0.5N HCl (150 mL), saturated NaHCO₃ (100 mL), and water (100 mL), dried through MgSO₄, and evaporated to give a pale-yellow oil. The pale-yellow oil was added to a silica gel column and was eluted with 0-100% EtOAc in hexane to give two desired collections: anti-isomer and syn-isomer. The anti-isomer collection was evaporated to give a pale-yellow oil (4.85 g, 39.0%). ¹H NMR (CDCl₃) δ 7.28 (d, 1H, J=8.4 Hz), 7.19 (d, 1H, J=2.1 Hz), 7.07-7.18 (m, 2H), 7.05 (s, 1H), 6.86-6.95 (m, 2H), 4.85 (br. s., 1H), 4.81 (dd, 1H, J=7.9, 3.7 Hz), 4.10 (q, 2H, J=7.0 Hz), 3.66-3.81 (m, 1H), 3.52-3.66 (m, 1H), 3.17 (br. s., 1H), 3.02-3.12 (m, 1H), 2.39 (s, 3H), 1.22 (t, 3H, J=7.2 Hz). MS m/z (ESI) 314.01 (MNa⁺). The relative configuration of this compound was determined to be anti-based on the large J-value (7.9 Hz) of the benzylic proton. The syn-isomer collection was evaporated to give a pale yellow oil (5.14 g, 41.4%). ¹H NMR (CDCl₃) δ 7.23-7.30 (m, 2H), 7.05-7.20 (m, 2H), 6.98 (s, 1H), 6.93 (dd, 1H, J=8.3, 2.0 Hz), 6.87 (d, 1H, J=7.2 Hz), 4.96 (t, 1H, J=4.0 Hz), 4.78 (br. s., 1H), 4.11 (q, 2H, J=7.2 Hz), 3.63-3.86 (m, 1H), 3.24-3.39 (m, 1H), 3.11 (br. s., 1H), 2.98 (td, 1H, J=7.7, 4.6 Hz), 2.36 (s, 3H), 1.23 (t, 3H, J=7.3 Hz). The relative configuration of this compound was determined to be syn-based on the small J-value (4.0 Hz) of the benzylic proton. MS m/z (ESI) 436.15 (MNa⁺).

anti-2-(3,4-dichlorophenyl)-3-(methylamino)-1-(3-(methylthio)phenyl)propan-1-ol: anti-Ethyl-2-(3,4-dichlorophenyl)-3-hydroxy-3-(3-(methylthio)phenyl)propyl carbamate (4.7 g, 11.34 mmol) in THF (50 mL) was preheated at 76° C. for gentle-refluxing. BH₃.THF (34.0 mL, 34.03 mmol) was added drop-wise over 15 minutes, and the refluxing was allowed to continue at 76° C. overnight. The reaction mixture was cooled in a cold water bath and treated with 5 mL HCl. MeOH (10 mL) was slowly added to quench extra BH₃, maintaining the temperature under 25° C. Evolution of gas bubbles was observed during the addition of MeOH. The reaction mixture was heated to 64° C. (to make sure all of BH₃ quenched) for 10-15 minutes, and then concentrated to a pale-yellow oil. After concentration of the volatiles in vacuo, the desired product (HCl salt) was obtained as a yellow gum. The HCl salt was stirred into a mixture of 100 mL CHCl₃ and saturated NaHCO₃ and stirred for 10 minutes. The organic layer was separated, and the aqueous layer was extracted with CHCl₃ (20 mL×5). A significant amount of white solid was not basified and extracted into CHCl₃. The combined CHCl₃ layer was dried through MgSO₄ and evaporated to give a yellow foul-smelling oil. The yellow oil was added to a silica gel column and was eluted with 0-10% MeOH in CH₂Cl₂. Collected fractions were evaporated under reduced pressure to give the desired anti-product (1.725 g, 42.6%). ¹H NMR (CDCl₃) δ 7.24 (d, 1H, overlapping with CHCl₃) 7.13 (d, 1H, J=2.1 Hz), 7.09 (s, 1H), 7.10 (d, 1H, J=9.5 Hz), 7.03 (br. s., 1H), 6.87 (dt, 1H, J=7.0, 1.7 Hz), 6.83 (dd, 1H, J=8.3, 2.0 Hz), 4.92 (d, 1H, J=8.0 Hz), 3.20 (dd, 1H, J=12.1, 9.7 Hz), 3.03 (dd, 1H, J=12.1, 3.1 Hz), 2.87 (ddd, 1H, J=9.7, 8.0, 3.2 Hz), 2.50 (s, 3H), 2.37 (s, 3H). MS m/z (ESI) 356.11 (MH⁺).

(1R,2R)-2-(3,4-dichlorophenyl)-3-(methylamino)-1-(3-(methylthio)phenyl)-propan-1-ol: The two chiral compounds were separated by SFC (ADH column, 17% MeOH with 0.5% isopropylamine) as Peak 1 and Peak 2. Each fraction was concentrated separately.

The "peak 1" collection contained a trace amount of product-related complex, and its baseline was not clean as determined by NMR. The "peak 1" sample was acidified with TFA (2 mL), stirred for 5 minutes, then basified with 1N NaOH (15 mL×2), dried through MgSO₄, and concentrated to yellow oil. The yellow oil was added to a silica gel column and eluted with 0-5% ammoniated MeOH in CH₂Cl₂ to give the desired product, P1, as a colorless gel (0.039 g, 95% purity, 90% ee), containing some solvents. ¹H NMR (CDCl₃) δ 7.24 (d, 1H, J=8.2 Hz), 7.13 (d, 1H, J=2.1 Hz), 7.05-7.11 (m, 2H), 7.02 (s, 1H), 6.86 (d, 1H, J=7.3 Hz), 6.82 (dd, 1H, J=8.2, 2.1 Hz), 4.91 (d, 1H, J=7.9 Hz), 3.19 (dd, 1H, J=12.2, 9.8 Hz), 3.02 (dd, 1H, J=−12.1, 3.2 Hz), 2.86 (ddd, 1H, J=9.7, 8.2, 3.2 Hz), 2.49 (s, 3H), 2.37 (s, 3H). MS m/z (ESI) 356.06 (MH⁺). The free base of the desired product was diluted with 2 mL of CH₂Cl₂, and 0.5 mL of 2M HCl in ether was added and then evaporated to dryness to give its HCl salt as a white solid (0.031 g, 14.96% recovery). ¹H NMR (DMSO-d₆) δ 8.51 (hr. s., 1H), 8.18 (br. s., 1H), 7.45-7.54 (m, 2H), 7.11-7.22 (m, 2H), 7.04-7.10 (m, 1H), 7.01 (s, 1H), 6.94 (d, 1H, J=7.5 Hz), 6.06 (br. s., 1H), 4.75 (d, 1H, J=6.0 Hz), 3.20-3.55 (m, 6H), 2.37 (s, 3H).

Compound ID No. 120 recovered from the first eluting peak was assigned (1R,2R) configuration based on its ¹H NMR as well as its lower inhibitory activity on the hNET compared to the (1S,2S) enantiomer.

Example 121—Synthesis of Compound ID No. 121 (N-(3-((1R,2R)-2-(3,4-dichlorophenyl)-1-hydroxy-3-(methylamino)propyl)phenyl)-1,1,1-trifluoromethanesulfonamide)

tert-butyl ((2R,3R and 2S,3S)-3-(3-aminophenyl)-2-(3,4-dichlorophenyl)-3-hydroxypropyl)carbamate: A solution of (1R,2R and 1S,2S)-)-1-(3-aminophenyl)-2-(3,4-dichlorophenyl)-3-(methylamino)propan-1-ol (Example 119) (0.311 g, 0.96 mmol) and TEA (0.147 mL, 1.05 mmol) in dichloromethane (4 mL)/MeOH (1 mL) was cooled to 0° C. Boc-anhydride (0.244 mL, 1.05 mmol) in dichloromethane (1 mL) was added into the above reaction mixture slowly. After the addition, the reaction was stirred at room temperature for several hours. The reaction mixture was diluted with CH₂Cl₂ (50 mL), washed with 1N NaOH (20 mL), and water (50 mL), dried through MgSO₄, and then evaporated to remove the solvents. The crude product was added to a silica gel column and eluted with 0-100% EtOAc in hexane to give a light-yellow gum as the desired product (0.2618 g, 64.4%). ¹H NMR (CDCl₃) δ 7.30 (br. s., 1H), 7.26 (d, 1H, J=8.4 Hz), 7.00 (t, 2H, J=7.4 Hz), 6.50 (d, 1H, J=8.0 Hz), 6.54 (br. s., 2H), 4.72 (d, 1H, J=6.3 Hz), 3.43-3.97 (m, 4H), 3.22 (br. s., 1H), 2.54 (br. s., 3H), 1.36 (br. s., 9H). MS m/z (ESI) 425.22 (MH⁺). The bis-Boc by-product was isolated as a colorless gum (0.1272 g, 25.3%). ¹H NMR (CDCl₃) δ 7.31 (br. s., 1H), 7.25 (d, 2H, J=8.4 Hz), 7.07-7.22 (m, 2H), 6.99 (d, 1H, J=7.2 Hz), 6.84 (d, 1H, J=7.2 Hz), 6.58 (br. s., 1H), 4.77 (d, 1H, J=6.3 Hz), 3.51-3.85 (m, 2H), 3.23 (br. s., 1H), 2.53 (br. s., 3H), 1.50 (s, 9H), 1.35 (br. s., 9H). MS m/z (ESI) 525.27 (MH⁺).

(2R,3R and 2S,3S)-tert-butyl (2-(3,4-dichlorophenyl)-3-hydroxy-3-(3-(trifluoromethylsulfonamido)phenyl)propyl)

carbamate: A mixture of (2R,3R and 2S,3S)-tert-butyl (3-(3-aminophenyl)-2-(3,4-dichlorophenyl)-3-hydroxy-propyl)carbamate (0.261 g, 0.61 mmol) and triethylamine (0.155 g, 1.53 mmol) in dichloromethane (3 mL) were cooled to 0° C. Trifluoromethanesulfonic anhydride (0.277 g, 0.98 mmol) was added into the above reaction mixture slowly and cooled to room temperature. 1 hour later, the mixture was diluted with $CH_2Cl_2$ (100 mL), washed with water (100 mL×2), dried through $MgSO_4$, and evaporated to dryness. The crude product was added to a silica gel column and eluted with 0-100% EtOAc in hexane to give a colorless gum as the desired product (0.152 g, 45%). The sample was subjected to SFC chiral purification.

Separation of (1S,2S) and (1R,2R) enantiomers of tert-butyl(2-(3,4-dichlorophenyl)-3-hydroxy-3-(3-(trifluoromethylsulfonamido)phenyl)propyl)-carbamate: The two chiral compounds were purified twice by chiral SFC (ADH column, 20% iPrOH with 1% isopropylamine) as Peak 1 and Peak 2. Each fraction was concentrated separately.

The first-eluting enantiomer collection was evaporated to give a light yellow gel (0.020 g, 95% purity, 12.83% recovery). $^1$H NMR ($CDCl_3$) δ 7.20 (d, 2H, J=8.4 Hz), 7.00-7.11 (m, 2H), 6.92-7.00 (m, 1H), 6.89 (d, 1H, J=8.0 Hz), 6.75 (d, 1H, J=5.5 Hz), 5.34 (br. s., 4H), 4.73 (d, 1H, J=7.6 Hz), 3.55-3.77 (m, 2H), 3.13-3.27 (m, 1H), 2.49 (br. s., 3H), 1.38 (br. s., 9H). MS m/z (ESI) 557 ($MH^+$).

This enantiomer, after removal of Boc group (see below), was assigned 1R,2R-configuration because of its lower potency on the hNET compared to the second-eluting enantiomer.

N-(3-((1R,2R)-2-(3,4-dichlorophenyl)-1-hydroxy-3-(methylamino)propyl)phenyl)-1,1,1-trifluoromethanesulfonamide: First-eluting Boc-derivative, tert-Butyl (2R,3R)-2-(3,4-dichlorophenyl)-3-hydroxy-3-(3-(trifluoromethylsulfonamido)phenyl)-propyl(methyl)carbamate (0.063 g, 0.11 mmol) was stirred in 3N HCl (MeOH:water=3:1; 1 mL) at room temperature for 1 hour. The reaction mixture was evaporated to give a white foam-like solid as the desired product (0.0554 g, 95% purity). $^1$H NMR ($CD_3OD$) δ 7.35 (d, 1H, J=8.3 Hz), 7.20-7.29 (m, 2H), 7.15 (s, 1H), 7.02-7.11 (m, 2H), 6.99 (dd, 1H, J=8.3, 1.9 Hz), 4.86 (d, 1H, J=9.4 Hz), 3.76 (dd, 1H, J=12.4, 8.3 Hz), 3.36-3.44 (m, 1H), 3.19 (td, 1H, J=8.7, 6.0 Hz), 2.74 (s, 3H). MS m/z (ESI) 457.04 ($MH^+$).

Example 122—Synthesis of Compound ID No. 122 (1R,2R)-1-(5-methoxypyridin-3-yl)-3-(methylamino)-2-(napthalen-2-yl)propan-1-ol 3-Hydroxy-3-(5-methoxypyridin-3-yl)-2-(naphthalen-2-yl)propanenitrile: A 250 mL round bottom flask equipped with a magnetic stirring bar, nitrogen inlet, and septum was charged with THF (100 mL) and butyllithium (7.29 mL, 18.23 mmol). After cooling to −78° C., 2-(naphthalen-2-yl)acetonitrile (3.05 g, 18.23 mmol) was added. After 60 minutes, 5-methoxynicotinaldehyde (2.5 g, 18.23 mmol) was added via syringe, and the reaction mixture was stirred at −78° C. for 3 hours. The reaction was quenched by the addition of acetic acid (2.1 mL) while stirring at −70° C. The aqueous layer was extracted with ether (2×250 mL), and the combined organic extracts were washed with brine (250 mL), dried over $MgSO_4$, and concentrated in vacuo to give the crude aldol (6.0 g). ISCO purification on silica gel eluting with 0-100% ethyl acetate in hexane afforded the product as anti:syn mixture (4.0 g). Recrystallization from THF (10 mL) and hexane (25 mL) at 0° C. overnight afforded anti mixture as a solid (1.4 g) and anti/syn mixture (1:1.5) as an oil (2.5 g). Second recrystallization of the anti mixture from THF/hexane afforded the pure anti diastereomer (1.2 g). $^1$H NMR ($CDCl_3$) δ 8.23 (d, 1H, J=2.7 Hz), 8.04 (d, 1H, J=1.5 Hz), 7.93-7.73 (m, 5H), 7.61-7.47 (m, 2H), 7.38-7.18 (m, 4H), 5.12 (d, 1H, J=3.4 Hz), 4.24 (d, 1H, J=5.2 Hz), 3.78 (s, 3H), 2.80 (d, 1H, J=3.7 Hz). MS m/z (ESI) 305.13 ($MH^+$).

3-Amino-1-(5-methoxypyridin-3-yl)-2-(naphthalen-2-yl)propan-1-ol: A solution of 3-hydroxy-3-(5-methoxypyridin-3-yl)-2-(naphthalen-2-yl)propanenitrile (2.5 g, 8.21 mmol) in 100 mL of THF was added over 5 minutes to a stirred suspension of 1.0 M in THF borane tetrahydrofuran complex (24.64 mL, 24.64 mmol) heated to 45° C. The reaction was heated for 3 hours at reflux (internal temp at 66° C., oil bath at 72° C.). The solution was cooled to ambient temperature and carefully quenched with 8 mL of 4N of HCl in dioxane diluted with 10 mL of methanol. The mixture was stirred for 15 minutes at 60° C., and then all solvents were evaporated off. 10 mL of ethanol was added, and the reaction mixture was stirred at 60° C. for 10 minutes. The volatiles were evaporated in vacuo, and the crude product was washed with EtOAc twice and dried under vacuum to afford 3.4 g of the HCl salt of the desired product as a white solid. Since the $^1$H NMR spectrum of the crude in $CDCl_3$ showed the presence of the expected mixture of anti- and syn-structures, the crude mixture was taken to the next step without further purification.

anti-syn-Ethyl-3-hydroxy-3-(5-methoxypyridin-3-yl)-2-(naphthalen-2-yl)propylcarbamate: The HCl salt of 3-amino-1-(5-methoxypyridin-3-yl)-2-(naphthalen-2-yl)propan-1-ol (2.53 g, 8.21 mmol) was dissolved in 100 mL of DCM in an oven dried round bottom flask equipped with a stirrer under nitrogen. TEA (3.43 mL, 24.63 mmol) was added, and then the solution was chilled to 0° C. To this, ethyl carbonochloridate (0.946 mL, 9.85 mmol) was slowly added over 10 minutes. The ice bath was removed, and the solution was allowed to warm to room temperature and stirred for 2 hours. The reaction solution volume (in DCM) was reduced to 5 mL. The residue was diluted with 200 mL ethyl acetate and washed with minimum amount of 0.1N HCl (2×10 mL), 150 mL saturated sodium bicarbonate, and 200 mL brine, then dried over $MgSO_4$, filtered, and concentrated in vacuo. Residual solvents were evaporated to give the product as a foam (2.2 g). MS m/z (ESI) 381.2 ($MH^+$). The mixture was purified on ISCO eluting with 0-100% of ethyl acetate in hexane over 35 minutes. The major peak was collected, and the solvents were evaporated in vacuo. $^1$H NMR analysis indicated anti-stereochemistry.

(1R,1R)-2-(3,4-dichlorophenyl)-1-(5-methoxypyridin-3-yl)-3-(methylamino)propan-1-ol: A solution of ethyl (1S,2S and 1R,1R)-3-hydroxy-3-(5-methoxypyridin-3-yl)-2-(naphthalen-2-yl)propylcarbamate (0.275 g, 0.72 mmol) in THF (20.00 mL) was added over 5 minutes to a stirred suspension of borane tetrahydrofuran complex (2.169 mL, 2.17 mmol) heated to 45° C. The reaction was heated for 4 hours at reflux (internal temp at 66° C., oil bath at 72° C.) to give a bright purple suspension. The suspension was cooled to ambient temperature and carefully quenched with 4N HCl in dioxane diluted with methanol. The quenched mixture was stirred for 15 minutes at 60° C. The volatiles were removed in vacuo, and the crude was redissolved in 10 mL of ethanol and stirred for 10 minutes at 60° C. The solvents were then evaporated to afford the crude HCl salt, which was washed with ether, ethyl acetate/hexane (1:1), and hexane to afford the HCl salt of the product. NMR and LCMS showed 80% purity. The HCl salt was converted to basic amine, and ISCO alumina column chromatography eluting with 0-10% MeOH in DCM afforded the pure amine as product (0.135 g). $^1$H NMR (CDCl$_3$) δ 8.02 (d, 1H, J=2.7 Hz), 7.86 (d, 1H, J=1.5 Hz), 7.80-7.60 (m, 3H), 7.42 (quin, 1H, J=6.0 Hz), 7.26 (s, 0H), 7.09 (dd, 1H J=8.4, 1.7 Hz), 6.99 (d, 1H, J=2.1 Hz), 5.18 (d, 1H, J=8.5 Hz), 4.15 (dd, 1H, J=12.1, 2.9 Hz), 3.64 (s, 3H), 3.39 (dd, 1H, J=11.9, 10.4 Hz), 3.05 (dd, 1H, J=18.8, 2.9 Hz), 2.54 (s, 3H). MS m/z (ESI) 323.17 (MH$^+$). NMR with shift reagent "TBPTA" complex showed J12=10.2 Hz, which indicated the presence of "anti" stereochemistry. Large J-value (8.5 Hz) of the benzylic proton indicated anti-relative configuration. The anti-racemate was subjected to chiral SFC separation into the two anti-enantiomers. Compound ID No. 122 recovered from the first eluting enantiomer was assigned (1R,2R) configuration based on its lower inhibitory activity on the hNET compared to the second eluting (1S,2S) enantiomer.

Example 123—Synthesis of Compound ID No. 123 (6S,7R)-4-methyl-6-(naphthalen-2-yl)-7-phenyl-1,4-oxazepane)

2-Bromo-N-((2S,3R)-3-hydroxy-2-(naphthalen-2-yl)-3-phenylpropyl)-N-methylacetamide: This compound was made by reacting (1R,2S)-3-(methylamino)-2-(naphthalen-2-yl)-1-phenylpropan-1-ol (Example 9) with bromoacetyl bromide in the presence of TEA in dichloromethane in a manner similar to the one described in Example 129. The $^1$H NMR spectrum of the crude material in CDCl$_3$ showed the presence of the expected structure.

(6S,7R)-4-methyl-6-(naphthalen-2-yl)-7-phenyl-1,4-oxazepan-3-one: This compound was prepared by cyclizing 2-bromo-N-((2S,3R)-3-hydroxy-2-(naphthalen-2-yl)-3-phenylpropyl)-N-methylacetamide in the presence of sodium hydride in a polar aprotic solvent in a manner similar to the one described in Example 129. $^1$H NMR spectrum of the crude material in CDCl$_3$ showed the presence of the expected structure.

Compound ID No. 123: (6S,7R)-4-methyl-6-(naphthalen-2-yl)-7-phenyl-1,4-oxazepan-3-one was reduced with lithium hydride in THF as set forth in Example 129. $^1$H NMR (CD$_3$OD) δ 7.66-7.59 (m, 1H), 7.58-7.51 (m, 1H), 7.46 (d, 1H, J 8.7 Hz), 7.37-7.26 (m, 2H), 7.22 (s, 1H), 7.06-6.82 (m, 5H), 6.77-6.68 (m, 1H), 5.13 (d, 1H, J=6.8 Hz), 4.37-4.03 (m, 4H), 3.73-3.47 (m, 3H), 2.99 (s, 3H).

Example 124—Synthesis of Compound ID No. 124 ((6R,7R)-4-methyl-6-(naphthalen-2-yl)-7-phenyl-1,4-oxazepane)

Optical resolution of anti-3-(methylamino)-2-(naphthalen-2-yl)-1-phenylpropan-1-ol into 1S,2S and 1R,2R-enantiomers: L-(+)-tartaric acid (2.217 g, 14.77 mmol) was added to a solution of racemic 3-(methylamino)-2-(naphthalen-2-yl)-1-phenylpropan-1-ol (4.3 g, 14.77 mmol) in 4:1 H$_2$O:EtOH (100 mL). The resulting suspension was stirred at 60° C. until all of the material was taken into solution. The mixture was then removed from heat and allowed to cool. Scratching the inner sides of the flask resulted in crystallization of the desired 2S,3S isomer. The crystals were filtered and rinsed with cold 4:1 (H$_2$O:EtOH) and dried. This solid was redissolved in 4:1 H$_2$O:EtOH (45 mL) at 60° C. and recrystallized.

Conversion of purified product to HCl salt: The (1S,2S)-3-(methylamino)-2-(naphthalen-2-yl)-1-phenylpropan-1-ol ((+)-tartaric acid salt, 1.87 g, 4.25 mmol) was added to a reparatory funnel along with 2N NaOH to a basic pH. The resulting suspension was extracted with DCM (3×). The combined extracts were treated with 2N HCl, and the DCM was removed by rotary evaporation. The remaining aqueous solution was lyophilized to furnish the product as a white solid. [α]$_D^{20}$=+128 (EtOH/H$_2$O 10:1).

By using the D-(−)-tartaric acid, (1R,2R)-3-(methylamino)-2-(naphthalen-2-yl)-1-phenylpropan-1-ol was obtained in similar yield and opposite optical rotation value.

tert-Butyl (2R,3R)-3-hydroxy-2-(naphthalen-2-yl)-3-phenylpropyl(methyl)carbamate: To a solution of (1R,2R)-3-(methylamino)-2-(naphthalen-2-yl)-1-phenylpropan-1-ol (1.0 g, 3.05 mmol) in 25 mL of DCM was added triethylamine (1.28 mL, 9.15 mmol) at room temperature. To this was added Boc$_2$O (0.766 g, 3.51 mmol) portion-wise, and the reaction mixture was left stirring for 10 minutes while monitoring the reaction progress by TLC. Upon completion of the reaction, 1N HCl (15 mL) was added to an acidic pH 6, and the crude product was isolated by extraction with DCM (3×). The combined extracts were washed with water and dried with MgSO$_4$ to furnish a crude that was deemed pure for the next step. $^1$H NMR (DMSO-d$_6$): δ 7.73-7.70 (m, 3H), 7.61 (m, 1H), 7.41-7.39 (m, 3H), 7.22-7.04 (m, 5H), 5.55 (bd, 1H), 4.86 (dd, 1H, J=7.2, 4.8 Hz), 3.90 (bt, 1H), 3.66 (dd, 1H, J=13.8, 3.9 Hz), 2.08 (s, 3H), 1.14, 1.08 (two s, 9H). MS m/z (ESI) 414.22 (MNa$^+$).

tert-Butyl 2-((1R,2R)-3-((tert-butoxycarbonyl)(methyl)amino)-2-(naphthalen-2-yl)-1-phenylpropoxy)acetate: Sodium hydride (60% in oil; 0.255 g, 5.31 mmol) was repeatedly washed with pentane and covered with 20 mL of DMF. The resulting suspension was cooled to 0° C., and a solution of tert-Butyl (2R,3R)-3-hydroxy-2-(naphthalen-2-yl)-3-phenylpropyl(methyl)carbamate (1.6 g, 4.09 mmol) in 15 mL of DMF was added slowly via cannula under nitrogen. After 5 minute of stirring at 0° C., t-butylbromoacetate (1.196 g, 6.13 mmol)) was added, and the reaction mixture was stirred for one half hour. Cautious quenching with 3 mL of saturated NH$_4$Cl at 0° C. was followed by extraction with EtOAc (3×25 mL). The combined organic layers were washed with water and brine, dried over MgSO$_4$, and concentrated using a rotary evaporator. The resulting residue was purified by flash chromatography over silica gel (elution with 10% EtOAc in hexanes) to afford the product as a colorless oil (1.66 g, 80%). $^1$H NMR (CDCl$_3$) δ 7.70-7.64 (m, 3H), 7.60-7.36 (m, 3H), 7.26 (s, 1H), 7.10-6.91 (m, 5H), 4.92 (d, 1H, J=8.5 Hz), 4.10 (m, 1H), 3.96 (d, 1H, J=8.5 Hz), 3.92 (d, 1H, J=16.2 Hz), 3.68 (t, 1H, J=16.2 Hz), 3.41 (m, 1H), 2.62-2.51 (m, 3 H), 1.48 and 1.44 (two s, 9H), 1.5 and 1.21 (two s, 9H). MS m/z (ESI) (MH$^+$) 506.16; 528.16 (MNa$^+$).

2-((1R,2R)-3-(methylamino)-2-(naphthalen-2-yl)-1-phenylpropoxy)acetic acid: A solution of t-butyl 2-((1R,2R)-3-((tert-butoxycarbonyl)(methyl)amino)-2-(naphthalen-2-yl)-1-phenylpropoxy)acetate (1.24 g, 2.46 mmol) in 1:1 mixture of TFA/DCM was placed in a clean dry round bottom flask and left stirred at room temperature under nitrogen for 1 hour. After completion of the reaction (monitored by mass spectrometry), volatiles were removed by rotary evaporation. The crude material was co-evaporated with DCM to ensure complete removal of traces of the TFA. The product (a gooey solid; 1.08 g, 98%) was used in the following reaction without further purification. $^1$H NMR (TFA salt) (CD$_3$OD): δ 7.66-7.57 (m, 3H), 3.09 (m, 2H), 7.42 (s, 1H), 7.35-7.31 (m, 2H), 7.10-7.04 (m, 6H), 4.82 (d, 1H, J=10.2), 4.07-3.82 (m, 3H), 3.47 (td, 1H, J=10.24, 3.01), 3.28 (td, 1H, J=12.7, 2.8), 2.7 (s, 3H). MS m/z (ESI) 350.08 (MH$^+$).

(6R,7R)-4-methyl-6-(naphthalen-2-yl)-7-phenyl-1,4-oxazepan-3-one: 2-((1R,2R)-3-(methylamino)-2-(naphthalen-2-yl)-1-phenylpropoxy)acetic acid (1.08 g, 2.42 mmol) was placed in an oven dried round bottom flask along with a stir bar. This was followed by sequential addition of 3,4,5-trifluoroboronic acid catalyst (0.431 g, 2.42 mmol), sodium acetate (0.595 g, 7.26 mmol), and anhydrous toluene (4.5 mL) The contents of the flask were sealed under Argon. The reaction was allowed to stir at room temperature overnight. Completion of the reaction was monitored by MS and TLC (50% EtOAc/hex). The crude mixture was shaken with saturated sodium bicarbonate solution, and the aqueous phase was extracted with ethyl acetate (3×). The organic layers were combined, rinsed with water and brine, and dried over $MgSO_4$. The solvent was removed under vacuum. The crude product was chromatographed with 50% EtOAc/hex to furnish the product as a white solid (0.753 g, 94%). $^1H$ NMR ($CDCl_3$): δ 7.72-7.64 (m, 3H), 7.45-7.36 (m, 3H), 7.16-7.01 (m, 6H), 4.80 (d, 1H, J=10.0 Hz), 4.54 (AB Quart, 2H, J=15.4 Hz), 3.96 (dd, 1H, J=14.5, 3.01), 3.78 (dd, 1H, J=14.7, 6.5 Hz), 3.99-3.33 (m, 1H), 2.93 (s, 3H). MS m/z (ESI) 332.08 (M1$^+$).

(6R,7R)-4-methyl-6-(naphthalen-2-yl)-7-phenyl-1,4-oxazepane: A mixture of lithium aluminum hydride (0.0345 g, 9.09 mmol) and dry tetrahydrofuran (40 mL) were placed in an oven dried round bottom flask under nitrogen and cooled to 0° C. The N-methyloxepanone (0.753 g, 2.27 mmol) was dissolved in a minimal amount of dry THF and added to the stirring LAH suspension. The mixture was allowed to return to room temperature before being heated to 60° C. for 2 hours. The reaction was monitored by MS and TLC (50% EtOAc/hex). The mixture was cooled in an ice bath and carefully quenched with a mixture of methanol and water. The solvent was removed by rotary evaporation. The crude material was taken up in EtOAc, added to a separatory funnel, and washed with water (3×). The organic phase was collected and dried over $MgSO_4$. The crude material was purified by silica gel chromatography using 75% EtOAc/hex as eluent. After evaporation of relevant fractions, a white solid was obtained (0.451 g, 62.5%). The free amine was converted to HCl salt by precipitation with ether. MS (ESI) m/z (ESI) M$^{+1}$=318.14. $[α]_D^{20}$=−120 (4 mg/mL, HCl salt in ethanol). $^1H$ NMR ($CD_3OD$): d 7.72-7.57 (m, 3H), 7.50 (s, 1H), 7.39-7.29 (m, 2H), 7.15-6.99 (m, 6H), 4.85 (d, 1H, J=10.9 Hz), 4.35-4.06 (m, 3H), 3.82-3.64 (m, 2H), 3.59-3.36 (m, 2H), 2.98 (s, 3H).

Example 125—Synthesis of Compound ID No. 125 ((1R,2R)-2-(3,4-dichlorophenyl)-3-(methylamino)-1-(3-morpholinophenyl)propan-1-ol)

2-(3,4-dichlorophenyl)-3-hydroxy-3-(3-morpholinophenyl)propanenitrile: A solution of 2-(3,4-dichlorophenyl)acetonitrile (4.5 g, 24.19 mmol) in 40 mL ether was cooled to −75° C. As the temperature reached to −30° C., 2-(3,4-dichlorophenyl) acetonitrile began to precipitate out as a white solid. Therefore, 20 mL THF was added to maintain a clear solution at −75° C. Butyllithium (16.33 mL, 26.12 mmol) was added slowly, and the reaction was stirred at −75° C. for 20 minutes. To this, 3-morpholinobenzaldehyde (5.00 g, 26.12 mmol) in 15 mL THF was added drop-wise, maintaining temperature under −60° C. After the addition, the reaction was stirred at −75° C. for another hour. Then, acetic acid (2.077 mL, 36.28 mmol) was added at −75° C. to quench the reaction. The reaction mixture was warmed to room temperature, and the organic layer was separated from the aqueous layer. The aqueous layer was extracted with EtOAc (100 mL×3), and the combined organic layer was dried through $MgSO_4$ and evaporated to give an orange oil. The orange oil was added to a silica gel column and was eluted with 0-60% EtOAc in hexane to give a yellow oil (9.0 g), which contained 50% of the benzaldehyde reagent based on TLC, NMR, and LCMS. The yellow oil was diluted with EtOAc (200 mL), washed with saturated $NaHSO_3$, dried through $MgSO_4$, and evaporated to give a yellow oil. The yellow oil was added to a silica gel column and was eluted with 0-100% EtOAc in hexane to give a pale-yellow oil as the desired product, which was judged to be a mixture of diastereomers (5.3 g, 58.1%, syn: anti ratio 2:3). anti-Isomer (about 60%): $^1H$ NMR ($CDCl_3$). δ 7.38 (s, 1H), 7.31 (d, 1H, J=2.1 Hz), 7.19-7.24 (m, 1H), 7.07 (dd, 1H, J=8.3, 2.2 Hz), 6.82-6.94 (m, 1H), 6.66-6.79 (m, 2H), 4.92 (dd, 1H, J=5.2, 3.5 Hz), 4.01 (d, 1H, J=5.3 Hz), 3.83 (m, 4H), 3.09 (m, 4H), 2.44 (d, 1H, J=3.4 Hz). Syn-isomer (about 40%): $^1H$ NMR ($CDCl_3$) δ 7.41 (s, 1H), 7.19-7.24 (m, 2H), 7.03 (dd, 1H, J=8.3, 2.2 Hz), 6.82-6.94 (m, 1H), 6.66-6.79 (m, 2H), 4.98 (dd, 1H, J=6.0, 3.3 Hz), 4.07 (d, 1H, J=5.8 Hz), 3.83 (m, 4H), 3.09 (m, 4H), 2.37 (d, 1H, J=3.4 Hz). MS m/z (ESI) 377.4 (MH$^+$).

3-Amino-2-(3,4-dichlorophenyl)-1-(3-morpholinophenyl)propan-1-ol: A solution of 2-(3,4-dichlorophenyl)-3-hydroxy-3-(3-morpholinophenyl)propanenitrile (5.3 g, 14.05 mmol) in 100 mL of THF was placed in dry flask fitted with a reflux condenser and a Dean-Stark trap and preheated at 76° C. for gentle-refluxing. While refluxing, a solution of borane-methyl sulfide complex (17.56 mL, 35.12 mmol) in 13 mL THF was added drop-wise over 15 minutes. During this time, the Dean-Stark trap collected liberated $SMe_2$. After 11 hours refluxing, the reaction mixture was cooled in a cold water bath and was treated with 4M HCl in Dioxane (5 mL) to generate a HCl salt. Then 10 mL of MeOH was added cautiously to quench extra $BH_3$, maintaining the temperature under 25° C. and allowing the generated gas bubbles to escape. The reaction mixture was heated to 64° C. for 10-15 minutes when the $B(OMe)_3$-MeOH complex was collected in a Dean-Stark trap. The reaction mixture was concentrated to give a yellow gum as a HCl salt of the desired product. The HCl salt was stirred in 100 mL $CHCl_3$/saturated $NaHCO_3$ for 10 minutes. The organic layer was separated from the aqueous layer, and the aqueous layer was extracted with $CHCl_3$ (20 mL×2). The combined $CHCl_3$ layer was dried through $MgSO_4$ and evaporated to give a yellow sticky liquid as the desired product (5.65 g, 105%). Since the $^1H$ NMR spectrum of the crude in $CDCl_3$ showed the presence of the expected mixture of anti- and syn-structures, the crude mixture was taken to the next step without further purification. MS m/z (ESI) 381.22 (MH$^+$).

Ethyl (2-(3,4-dichlorophenyl)-3-hydroxy-3-(3-morpholinophenyl)propyl)-carbamate: 3-Amino-2-(3,4-dichlorophenyl)-1-(3-morpholinophenyl)propan-1-ol (5.65 g, 13.34 mmol) was diluted in 65 mL of $CH_2Cl_2$ at room temperature, and TEA (2.79 mL, 20.00 mmol) was added. The reaction mixture was cooled to 0° C. Ethyl carbonochloridate (1.54 mL, 16.00 mmol) was added slowly at 0° C. After the addition, the reaction was stirred at room temperature. Three hours later, the reaction mixture was diluted with 100 mL of $CH_2Cl_2$, washed with 100 mL of 0.5N HCl, 50 mL saturated $NaHCO_3$, and 100 mL water, dried through $MgSO_4$, and then evaporated to give a yellow oil. The yellow oil was added to a silica gel column and was eluted with 0-100% EtOAc in hexane to give two collections: anti-isomer and syn-isomer. The anti-isomer collection was evaporated to give a pale-yellow oil (2.80 g, 46.3%). The anti-relative configuration was confirmed by large J-value (7.8 Hz) of the benzylic proton. $^1H$ NMR ($CDCl_3$) δ 7.26 (d, 1H, J=9.4 Hz), 7.08-7.18 (m, 2H), 6.90 (dd, 1H, J=8.3, 2.0 Hz), 6.74 (dd, 1H, J=8.0, 2.1 Hz), 6.60-6.70 (m, 2H), 4.85

(br. s., 1H), 4.80 (dd, 1H, J=7.8, 3.4 Hz), 4.10 (q, 2H, J=7.2 Hz), 3.81 (t, 4H, J=4.7 Hz), 3.54-3.77 (m, 2H), 3.06-3.12 (m, 1H), 3.00-3.06 (m, 4H), 2.89 (br. s., 1H), 1.22 (t, 3H, J=7.1 Hz). MS m/z (ESI) 453.23 (MH$^+$). The anti-relative configuration was confirmed by small J-value (4.0 Hz) of the benzylic proton. The syn-isomer collection was evaporated to give a pale-yellow oil (1.53 g, 25.3%). $^1$H NMR (CDCl$_3$) δ 7.22-7.33 (m, 2H), 7.15 (t, 1H, J=7.9 Hz), 6.95 (dd, 1H, J=8.2, 2.1 Hz), 6.74 (dd, 1H, J=8.3, 1.8 Hz), 6.64 (d, 1H, J=7.6 Hz), 6.57 (s, 1H), 4.93 (t, 1H, J=4.0 Hz), 4.71 (br. s., 1H), 4.10 (q, 2H, J=7.2 Hz), 3.81 (t, 4H, J=4.8 Hz), 3.73 (br. s., 1H), 3.33 (ddd, 1H, J=13.6, 6.7, 6.4 Hz), 3.01 (q, 4H, J=4.9 Hz), 2.92-3.10 (m, 1H), 2.84 (br. s., 1H), 1.22 (t, 3H, J=7.1 Hz). MS m/z (ESI) 453.23 (MH$^+$).

anti-2-(3,4-dichlorophenyl)-3-(methylamino)-1-(3-morpholinophenyl)propan-1-ol: Ethyl (2S,3S/2R,3R)-2-(3,4-dichlorophenyl)-3-hydroxy-3-(3-morpholino-phenyl)propyl carbamate (2.79 g, 6.03 mmol) in 50 mL THF was preheated at 76° C. for gentle-refluxing. Borane-methyl sulfide complex (7.54 mL, 15.08 mmol) was added drop-wise over 109 minutes, and a Dean-Stark trap was set up to collect liberated SMe$_2$. Four hours, 30 minutes after the addition, the reaction mixture was cooled to room temperature and kept overnight at room temperature. The reaction mixture was cooled in a cold water bath and was treated with 4M HCl in Dioxane (1.5 mL) to generate HCl salt. Then, MeOH (10 mL) was cautiously added to quench extra BH$_3$, maintaining the temperature under 25° C. The reaction mixture was heated to 64° C. for 10-15 minutes, and the liberated B(OMe)$_3$-MeOH complex was collected in a Dean-Stark trap. The reaction mixture was concentrated to give a yellow gum as a hydrochloride salt of the desired product. The HCl salt was stirred in 100 mL CHCl$_3$/saturated NaHCO$_3$ for 10 minutes. The organic layer was separated from the aqueous layer, and the aqueous layer was extracted with CHCl$_3$ (20 mL×2). The combined CHCl$_3$ layer was dried through MgSO$_4$ and evaporated to give a yellow oil, which was purified by Flash chromatography over silica gel eluting with 0-10% ammoniated MeOH in CH$_2$Cl$_2$. Collected fractions were evaporated in vacuo to give a colorless gel as the desired product (1.25 g, 52.4%). $^1$H NMR (CDCl$_3$) δ 7.23 (d, 1H, J=8.2 Hz), 7.12 (d, 1H, J=2.1 Hz), 7.11 (t, 1H, J=7.9 Hz), 6.84 (dd, 1H, J=8.2, 2.1 Hz), 6.71 (dd, 1H, J=8.2, 2.3 Hz), 6.66 (d, 1H, J=7.6 Hz), 6.59 (d, 1H, J=1.9 Hz), 4.90 (d, 1H, J=8.0 Hz), 3.81 (t, 4H, J=4.7 Hz), 3.20 (dd, 1H, J=12.1, 9.6 Hz), 3.04-3.09 (m, 1H), 2.94-3.04 (m, 4H), 2.81-2.92 (m, 1H), 2.50 (s, 3H). MS m/z (ESI) 429.36 (MNa$^+$).

(1R,2R)-2-(3,4-dichlorophenyl)-3-(methylamino)-1-(3-morpholinophenyl)-propan-1-ol: The two chiral compounds were separated by SFC (Lux Amylose 2 column, 23% iPrOH with 0.5% isopropylamine) as Peak 1 and Peak 2. These fractions were separately evaporated in vacuo and dried to furnish enantiomers. $^1$H NMR (CDCl$_3$) δ 7.22 (d, 1H, J=8.2 Hz), 7.06-7.14 (m, 2H), 6.82 (dd, 1H, J 8.3, 2.0 Hz), 6.70 (dd, 1H, J=8.2, 2.5 Hz), 6.65 (d, 1H, J=7.6 Hz), 6.57 (br. s., 1H), 4.86 (d, 1H, J=8.0 Hz), 3.80 (t, 4H, J=4.8 Hz), 3.18 (dd, 1H, J=12.1, 9.6 Hz), 2.93-3.09 (m, 5H), 2.86 (td, 1H, J=8.7, 3.5 Hz), 2.47 (s, 3H). The free base of the desired product was diluted with 2 mL of CH$_2$Cl$_2$, and 0.5 mL of 2M HCl in ether was added and then evaporated to dry the product solution to give its HCl salt as a white solid (0.223 g, 35.3% recovery). $^1$H NMR (DMSO-d6) δ 8.51 (br. s., 1H), 8.20 (br. s., 1H), 7.49 (d, 1H, J=8.3 Hz), 7.46 (d, 1H, J=1.9 Hz), 7.15 (dd, 1H, J=8.3, 1.7 Hz), 7.10 (d, 1H, J=7.7 Hz), 6.78 (d, 1H, J=7.3 Hz), 6.60-6.73 (m, 2H), 4.70 (d, 1H, J=7.2 Hz), 3.72 (t, 4H, J=4.6 Hz), 3.23-3.53 (m, 3H), 2.87-3.06 (m, 4H). MS m/z (ESI) 395.13 (MH$^+$). Compound ID No. 125 recovered from the second eluting fractions was assigned (1R,2R) configuration based on its $^1$H NMR as well as its lower inhibitory activity on the hNET compared to the (1S,2S) enantiomer.

Example 126—Synthesis of Compound ID No. 126 ((1R,2R)-1-(6-chloropyridin-3-yl)-3-(amino)-2-(naphthalen-2-yl)propan-1-ol)

anti-3-(6-chloropyridin-3-yl)-3-hydroxy-2-(naphthalen-2-yl)propanenitrile: A solution of 2-naphthylacetonitrile (5 g, 29.9 mmol) in 200 mL of dry THF was placed in an oven-dried round bottom flask with stirrer under nitrogen. After cooling to −78° C., diisopropylamine (5.03 mL, 35.9 mmol) was added followed by drop-wise addition of 2.5M butyllithium (14.35 mL, 35.9 mmol). After 30 minutes of stirring at −78° C., 2-chloropyridine 5-carboxaldehyde (5.08 g, 35.9 mmol) was added drop-wise via syringe. After 10 minutes, the reaction was quenched quickly with rapid addition of 25 mL 2:1 THF/acetic acid. The cold bath was removed, and the reaction was allowed to reach ambient temperature. Water was added, and the aqueous layer was extracted with EtOAc (3×25 mL) The combined organic layers were washed with water and brine, dried over MgSO$_4$, and were concentrated using a rotary evaporator. The residue was dissolved in DCM, and hexane was slowly added. A turbid solution resulted, which was kept at room temperature for 15 minutes. Off-white crystals were filtered and dried. The anti-diastereomer crystallized out as the major isomer as an off white solid (yield 1.679 g, 18.19%). $^1$H NMR (DMSO.d$_6$) δ 8.40 (d, 1H, J=1.8 Hz), 7.99-7.92 (m, 5H), 7.58-7.49 (m, 4H), 6.42 (d, 1H, J=5.0 Hz), 5.18 (t, 1H, J=5.1 Hz), 4.79 (d, 1H, J=5.3 Hz). The syn-diastereomer was also isolated from the supernatant as a white solid (yield 0.712 g, 7.71%). $^1$H NMR (CDCl$_3$) δ 8.09 (d, 1H, J=1.8 Hz), 7.94-7.85 (m, 3H), 7.71-7.62 (m, 2H), 7.55-7.50 (m, 2H), 7.44 (d, 1H, J=7.4 Hz), 7.32 (bd, 1H, J=7.4 Hz), 6.47 (d, 1H, J=4.3 Hz), 5.25 (dd, 1H, J=5.1, 5.1 Hz), 4.83 (d, 1H, J=6.0).

Compound ID No. 126: anti-3-(6-chloropyridin-3-yl)-3-hydroxy-2-(naphthalen-2-yl)propanenitrile (1.4 g, 4.53 mmol), dissolved in 18 mL of dry THF, was placed in an oven-dried round-bottom flask under nitrogen. A solution of 1M borane-THF solution (18.14 mL, 18.14 mmol) was added via syringe, and the reaction mixture was stirred at 60° C. overnight. The reaction progress was monitored by TLC. After quenching the reaction with cautious addition of NaHCO$_3$, the reaction mixture was poured into a separatory funnel. The layers were separated, and the aqueous layer was extracted with EtOAc (3×50 mL) The combined organic layers were washed with water and brine, dried over MgSO$_4$, and were concentrated using a rotary evaporator. The residue was dissolved in DCM, 4N HCl in dioxane was added, and the mixture was left stirring for a few minutes. The solvents were evaporated in vacuo, and the resulting salt was leached with ether and lyophilized yielding a white solid (1.367 g, 78%). $^1$H NMR (free amine) (CDCl$_3$) δ 8.09 (s, 1H), 7.81-7.60 (m, 3H), 7.51-7.33 (m, 4H), 7.11-6.97 (m, 2H), 5.22 (d, 1H, J=8.5 Hz), 3.60-3.30 (m, 2H), 3.10-2.91 (m, 1H). MS m/z (ESI) 313.11 (MH$^+$). $^1$NMR (500 MHz, CD$_3$OD) d 7.96 (d, 1H, J=2.14 Hz), 7.69-7.81 (m, 3H), 7.61 (dd, 1H, J=8.54, 2.44 Hz), 7.53 (s, 1H), 7.37-7.46 (m, 2H), 7.22 (d, 2H, J=8.24 Hz), 5.02 (d, 1H, J=9.46 Hz), 3.56 (dd, 1H, J=12.66, 5.95 Hz), 3.21-3.27 (m, 1H), 3.12-3.20 (m, 1H). A large J-value (9.5 Hz) indicated anti-configuration. The above compound, which was a racemate, was resolved into chiral S,S and R,R enantiomers by Multigram II SFC chiral chromatography system, which returned two fractions containing the opposite enantiomers. Compound ID No. 126 recovered from the first-eluting fraction was assigned (1R, 2R)-configuration based on lower potency on the hNET. $^1$H NMR (500 MHz, CD$_3$OD) δ 7.99 (d, 1H, J=2.14 Hz), 7.73-7.85 (m, 3H), 7.56-7.66 (m, 2H), 7.41-7.51 (m, 2H), 7.20-7.28 (m, 2H), 5.11 (d, 1H, J=9.61 Hz), 3.86 (dd, 1H, J=12.89, 7.40 Hz), 3.42 (dd, 1H, J=12.82, 6.71 Hz), 3.32-3.36 (m, 1H).

Example 127—Synthesis of Compound ID No. 127 (N-(3-((1R,2S)-2-(3,4-dichlorophenyl)-1-hydroxy-3-(methylamino)propyl)phenyl)-1,1,1-trifluoromethanesulfonamide)

syn-2-(3,4-dichlorophenyl)-3-(methylamino)-1-(3-nitrophenyl)propan-1-ol: syn-Ethyl-2-(3,4-dichlorophenyl)-3-hydroxy-3-(3-nitrophenyl)propyl carbamate (Example 102) (4.5 g, 10.89 mmol) in THF (50 mL) was preheated at 76° C. for gentle-refluxing. Borane-methyl sulfide complex (27.2 mL, 54.45 mmol) was added drop-wise over 30 minutes, and a Dean-Stark trap was set up to collect liberated SMe$_2$. The reaction mixture was refluxed overnight and then cooled to room temperature. After cooling in a cold water bath and treating with 4M HCl in dioxane (1.5 mL) to generate a HCl salt, 10 mL of MeOH was added slowly to quench the extra BH$_3$ while maintaining the temperature under 25° C. Addition of MeOH caused an evolution of gas. The reaction mixture was heated to 64° C. (to make sure all of BH$_3$ quenched) for 3 hours. During this time, the B(OMe)$_3$-MeOH complex was collected in a Dean-Stark trap. The reaction mixture was concentrated to give a white solid as HCl salt of the desired product. The HCl salt was stirred in 100 mL CHCl$_3$/saturated NaHCO$_3$ for 10 minutes, and the organic layer was separated from the aqueous layer and extracted with CHCl$_3$ (20 mL×2). The combined CHCl$_3$ layer was dried over MgSO$_4$ and evaporated to give a yellow stinky oil. The yellow oil was added to a silica gel column and was eluted with 0-10% MeOH in CH$_2$Cl$_2$. Collected fractions were evaporated to give a colorless gel as the desired product (2.36 g, 61%). $^1$H NMR (CDCl$_3$) δ 8.02-8.12 (m, 2H), 7.36 (t, 1H, J=8.1 Hz), 7.26-7.33 (m, 2H), 7.15 (d, 1H, J=2.1 Hz), 6.91 (dd, 1H, J=8.3, 2.0 Hz), 5.24 (d, 1H, J=4.4 Hz), 3.28-3.42 (m, 1H), 2.86-3.16 (m, 2H), 2.49 (s, 3H). MS m/z (ESI) 355.13 (MH$^+$).

syn-1-(3-aminophenyl)-2-(3,4-dichlorophenyl)-3-(methylamino)propan-1-ol: syn-2-(3,4-dichlorophenyl)-3-(methylamino)-1-(3-nitrophenyl)propan-1-ol (0.550 g, 1.55 mmol) and iron (0.346 g, 6.19 mmol) in acetic acid (1.5 mL)/EtOH (1.5 mL) were refluxed at 100° C. for 1 hour. After cooling to room temperature, the reaction mixture was neutralized with saturated Na$_2$CO$_3$ solution and then extracted with CHCl$_3$ (50 mL, 25 mL, and 25 mL) The combined organic layer was dried over MgSO$_4$, filtered, and concentrated to a dark brown oil. The crude product was added to a silica gel column and was eluted with 0-10% ammoniated MeOH in CH$_2$Cl$_2$ to give a pale-yellow gum as P1 (0.280 g, 55.6%). $^1$H NMR (CDCl$_3$). δ 7.30 (d, 1H, J=8.2 Hz), 7.23 (d, 1H, J=2.1 Hz), 7.03 (t, 1H, J=7.7 Hz), 6.94 (dd, 1H, J=8.2, 1.9 Hz), 6.54 (dd, 1H, J=7.9, 2.2 Hz), 6.47 (d, 1H, J=7.8 Hz), 6.45 (d, 1H, J=2.1 Hz), 4.81 (d, 1H, J=5.7 Hz), 3.59 (br. s., 2H), 3.15 (q, 1H, J=6.6 Hz), 2.71-2.91 (m, 2H), 2.33 (s, 3H). MS m/z (ESI) 325.15 (MH$^+$).

syn-tert-butyl-3-(3-aminophenyl)-2-(3,4-dichlorophenyl)-3-hydroxypropyl(methyl)carbamate: A solution of syn-1-(3-aminophenyl)-2-(3,4-dichlorophenyl)-3-(methylamino)propan-1-ol (0.275 g, 0.85 mmol) and TEA (0.130 mL; 0.93 mmol) in dichloromethane (4 mL) and MeOH (1 mL) was cooled to 0° C. Boc-anhydride (0.216 mL, 0.93 mmol) in dichloromethane (1 mL) was added into the above reaction mixture slowly. After the addition, the reaction was allowed to stir at room temperature overnight. The reaction mixture was diluted with CH$_2$Cl$_2$ (50 mL), washed with 1N NaOH (20 mL) and water (50 mL), dried over MgSO$_4$, and then evaporated to dry. The crude product was added to a silica gel column and was eluted with 0-100% EtOAc in hexane to give a brown gum as the desired product (0.368 g, 102% along with 13% of the di-Boc by-product). Since the $^1$H NMR spectrum of the crude in CDCl$_3$ showed the presence of the expected product, the crude mixture was taken to the next step without further purification.

syn-Boc-N-(3-2-(3,4-dichlorophenyl)-1-hydroxy-3-(methylamino)propyl)phenyl)-1,1,1-trifluoromethanesulfonamide: A solution of syn-tert-butyl-3-(3-aminophenyl)-2-(3,4-dichlorophenyl)-3-hydroxypropyl(methyl) carbamate (0.368 g, 0.75 mmol) and TEA (0.262 mL, 1.88 mmol) in dichloromethane (4 mL) was cooled to 0° C. Tf$_2$O (0.203 mL, 1.20 mmol) was added to the above reaction mixture slowly. Ten minutes after the addition, a mixture of NaOH (3.76 mL, 7.53 mmol) and MeOH (8 mL) was added into the reaction mixture, and the stirring continued overnight. The mixture was diluted with CH$_2$Cl$_2$ (100 mL), washed with water (100 mL×2), dried over MgSO$_4$, and evaporated to dryness. The crude product was used for next step directly.

(1R,2S)—N-(3-(2-(3,4-dichlorophenyl)-1-hydroxy-3-(methylamino)propyl)phenyl)-1,1,1-trifluoromethanesulfonamide: syn-tert-butyl-2-(3,4-dichlorophenyl)-3-hydroxy-3-(3-(trifluoromethyl sulfonamido)phenyl)propyl(methyl) carbamate (0.368 g, 0.66 mmol) was dissolved in MeOH (10 mL) at room temperature. 5 mL of concentrated HCl in MeOH (5 mL) was added slowly. The final concentration of HCl was about 3N. The reaction was stirred at room temperature for 1 hour. The reaction mixture was diluted with chloroform (100 mL) and then basified with 1N NaOH. The layers were separated, and aqueous layer was extracted with CHCl$_3$ (50 mL×2). Based on LCMS, the aqueous layer was found to have the majority of the possible product, and the organic layer had a very small amount of the product. The aqueous layer was acidified by diluted HCl (3N) and extracted with CHCl$_3$ (50 mL×3). The resulting CHCl$_3$ layer contained a trace of the desired product based on LCMS. Water was removed from the aqueous layer by evaporation to give a mixture of NaCl and the desired product. This crude product was loaded onto a basic alumina column and was eluted with 50% MeOH in EtOAc to give a pink-orange solid as the desired product (0.205 g, 67.9%). $^1$H NMR (MeOD) δ 7.37 (s, 1H), 7.39 (d, 1H, J=5.9 Hz), 6.91-7.14 (m, 5H), 6.68 (d, 1H, J=7.2 Hz), 4.77 (d, 1H, J=6.7 Hz), 3.15-3.25 (m, 1H), 2.90-3.08 (m, 2H), 2.40 (s, 3H). MS m/z (ESI) 457.1 (MH$^+$).

Separation of enantiomers of syn-N-(3-(2-(3,4-dichlorophenyl)-1-hydroxy-3-(methylamino)propyl)phenyl)-1,1,1-trifluoromethanesulfonamide: The two chiral compounds were purified twice by SFC (ADH column, 24% iPrOH with 2% isopropylamine) as Peak 1 and Peak 2. Each fraction was concentrated separately. The free base of the desired products were diluted each with 2 mL of CH$_2$Cl$_2$, and 0.5 mL of 2M HCl in ether was added and then evaporated the volatiles to give enantiomeric HCl salts as a brownish solids. $^1$H NMR (MeOD) δ 7.36 (d, 1H, J=7.9 Hz), 7.30 (d, 1H, J=2.4 Hz), 7.25 (t, 1H, J=7.9 Hz), 7.07-7.12 (m, 2H), 6.98-7.03 (m, 2H), 5.07 (d, 1H, J=4.3 Hz), 3.57 (dd, 1H, J=12.8, 9.8 Hz), 3.47 (dd, 1H, J=12.8, 5.5 Hz), 2.70 (s, 3H), one proton covered under MeOH. MS m/z (ESI) 457.03 (MH$^+$). Compound ID No. 127 obtained from the second eluting fraction was assigned (1R,2S) configuration based on its $^1$H NMR as well as its higher inhibitory activity on the hNET compared to the (1S,2S) enantiomer.

Example 128—Synthesis of Compound ID No. 128 ((1R,2R)-2-(3,4-dichlorophenyl)-3-(methylamino)-1-(2-(methylsulfinyl)phenyl)propan-1-ol)

3-Amino-2-(3,4-dichlorophenyl)-1-(2-(methylthio)phenyl)propan-1-ol: To a stirred solution of 2-(3,4-dichlorophenyl)acetonitrile (5.6 g, 30.10 mmol) in 60 mL dry THF at −75° C. (dry ice-acetone bath) under nitrogen, was added drop-wise the n-butyllithium, which produced a canary yellow solution. After 20 minutes of stirring at −75° C., a solution of 2-(methylthio)benzaldehyde (3.88 mL, 30.10 mmol) in 20 mL THF was added drop-wise (color fades). After 30 minutes stirring at −75° C., the reaction was quenched with a solution of acetic acid (2.1 mL, 36.68 mmol) in 5 mL THF drop-wise. After stirring the resulting clear solution for 15 minutes, the borane tetrahydrofuran complex (100.0 mL, 100.0 mmol) was added drop-wise, the dry ice bath was removed, and the mixture was allowed to warm to room temperature (gas evolution observed). It was then heated at mild reflux for 2 hours. The mixture was chilled to 0° C. with an ice bath, 2N HCl (60 mL) was cautiously added drop-wise, the ice bath removed, and the mixture was heated at mild reflux for 2 hours. After cooling, volatiles were evaporated under reduced pressure. The residue was diluted to white solution-suspension with chloroform (150 mL), cooled to 0° C., and vigorously stirred. The mixture was made basic by drop-wise addition of 1N NaOH, the layers separated, and the aqueous layer was extracted with chloroform (2×). The organic layers were combined, washed with half-saturated brine, and dried over MgSO$_4$. Concentration to dryness afforded a white amorphous solid (10.3 g), which was used as such for the next reaction. The nitrile was reduced with borane-DMS in THF in standard fashion. The $^1$H NMR spectrum of the crude in CDCl$_3$ showed the presence of the expected mixture of anti- and syn-structures, hence the crude mixture was taken to the next step without further purification.

Ethyl (2-(3,4-dichlorophenyl)-3-hydroxy-3-(2-(methylsulfinyl)phenyl)propyl)-carbamate: To a stirred ice-cooled solution of 3-amino-2-(3,4-dichlorophenyl)-1-(2-(methylthio)phenyl)propan-1-ol (10.3 g, 30.09 mmol) and TEA (6.27 mL, 45.0 mmol) in 140 mL of DCM was added drop-wise a solution of ethyl chloroformate (3.8 mL, 39.57 mmol) in 40 mL DCM. The mixture was stirred for 2 hours and then concentrated to near dryness by evaporating off the solvents in vacuo. The residue was partitioned between ether and aqueous sodium bicarbonate and extracted with ether (2×). The organics were combined, washed with brine, dried, and concentrated to give crude product (10.0 g) as a white amorphous solid. Approximately half was subjected to chromatography (ISCO, 220 g) eluting with a 0-50% EtOAc/hexanes gradient to afford two products: anti pair of enantiomers (1.0 g) and syn pair of enantiomers (1.6 g). $^1$H NMR in CDCl$_3$ showed the presence of the expected structure.

anti-2-(3,4-dichlorophenyl)-3-(methylamino)-1-(2-(methylthio)phenyl) propan-1-ol: To the stirred ice-cooled borane tetrahydrofuran complex (15 mL, 15.00 mmol) was added drop-wise a solution of ethyl (2S,3S/2R,3R)-2-(3,4-dichlorophenyl)-3-hydroxy-3-(2-(methylthio)phenyl)propylcarbamate (1.6 g, 3.86 mmol) in dry THF. The mixture was warmed to room temperature and heated at mild reflux for 3 hours. The clear solution was chilled with an ice bath and cautiously treated with drop-wise addition of 3N HCl (10 mL). The resulting solution was warmed to room temperature and heat at reflux for 2 hours. The volatiles were evaporated in vacuo, the residue was diluted with 15 mL water and 60 mL chloroform, and cooled on ice bath. The mixture was then made basic with drop-wise addition of 2N NaOH. The layers were separated, and the aqueous layer was extracted with chloroform (2×). The organic layers were combined, washed with half-saturated brine, and dried over MgSO$_4$. The solvents were evaporated to afford a crude product (1.3 g), which was subjected to flash chromatography on silica eluting with chloroform, then 0-3% MeOH/chloroform (ammoniated) to give purified product. This product was subjected to chiral SFC to give P1 enantiomer (0.550 g) and P2 enantiomer (0.560 g). P1 and P2 were separately taken in 12 mL of ether and converted to corresponding hydrochlorides by adding HCl/MeOH (15% solution) until acidic. The volatiles were removed, and the resulting solid was triturated with ether, collected, washed with fresh ether, and dried in vacuo to give the respective HCl salts. $^1$H NMR in CDCl$_3$ showed the presence of the expected structure. MS m/z (ESI) 356.07 (MH$^+$).

(1R,2R)-tert-butyl-2-(3,4-dichlorophenyl)-3-hydroxy-3-(2-(methylthio)phenyl) propyl(methyl)carbamate: To a stirred ice-cooled solution of (1R,2R)-2-(3,4-dichlorophenyl)-3-(methylamino)-1-(2-(methylthio)phenyl)propan-1-ol (0.380 g, 1.07 mmol) and TEA (0.163 mL, 1.17 mmol) in 4 mL DCM was added drop-wise a solution of Boc-anhydride (0.272 mL, 1.17 mmol) in 1 mL DCM. The clear solution was allowed to gradually warm to room temperature over 2 hours. The volatiles were removed, and the residue was dissolved in chloroform and subjected to ISCO chromatography, eluting with a 0-40% EtOAc/hexanes gradient to give purified t-butyl (2S,3S)-2-(3,4-dichlorophenyl)-3-hydroxy-3-(2-(methylthio)phenyl) propyl(methyl) carbamate (0.390 g, 80%). $^1$H NMR in CDCl$_3$ showed the presence of the expected structure.

anti-tert-butyl-2-(3,4-dichlorophenyl)-3-hydroxy-3-(2-(methylsulfinyl)phenyl) propyl(methyl)carbamate: To a stirred solution of t-butyl (2S,3S or 2R,3R)-2-(3,4-dichlorophenyl)-3-hydroxy-3-(2-(methylthio)phenyl)propyl (methyl)carbamate (0.230 g, 0.50 mmol) in THF and water at room temperature was added sodium periodate (0.350 g, 1.64 mmol). The mixture was stirred for 8 hours, and then the volatiles were removed by evaporation in vacuo. The aqueous residue was extracted with DCM (2×), and the organics were washed with half-saturated brine and dried. The resulting crude product subjected to ISCO chromatography eluting with a 0-100% EtOAc/hexanes gradient to afford the desired product. $^1$H NMR in CDCl$_3$ showed the presence of the expected structure.

anti-2-(3,4-dichlorophenyl)-3-(methylamino)-1-(2-(methylsulfinyl)phenyl) propan-1-ol: To a solution of t-butyl (2S,3S or 2R,3R)-2-(3,4-dichlorophenyl)-3-hydroxy-3-(2-(methylsulfinyl)phenyl)propyl(methyl)carbamate (0.200 g, 0.42 mmol) in DCM was added drop-wise TFA (0.200 mL, 2.60 mmol). The mixture was allowed to stir at room temperature for 1 hour. The volatiles were removed, and the residue was dissolved in 50 mL DCM and shaken with saturated sodium bicarbonate (6 mL). The organics were dried and concentrated in vacuo overnight to give (1S,2S)-2-(3,4-dichlorophenyl)-3-(methylamino)-1-(2-(methylsulfinyl)phenyl)propan-1-ol (0.147 g, 94%). $^1$H NMR in CDCl$_3$ showed the presence of the expected structure. MS m/z (ESI) 372.14 (MH$^+$). Since the Compound ID No. 128 obtained from the first-eluting peak during the chiral SFC separation of anti-2-(3,4-dichlorophenyl)-3-(methylamino)-

1-(2-(methylsulfinyl)phenyl) propan-1-ol was less potent at hNET than the other enantiomer, it is presumed to be (1R,2R)-configured.

Example 129—Synthesis of Compound ID No. 129 ((6S,7S)-4-methyl-6-(naphthalen-2-yl)-7-phenyl-1,4-oxazepan-3-one)

2-Bromo-N-((2S,3S)-3-hydroxy-2-(naphthalen-2-yl)-3-phenylpropyl)-N-methylacetamide: A solution of the hydrochloride salt of (1S,2S)-3-(methylamino)-2-(naphthalen-2-yl)-1-phenylpropan-1-ol (4.95 g, 16.99 mmol) and triethylamine (4.24 mL, 30.58 mmol) in dichloromethane (50 mL) was cooled to 0° C. 2-Bromoacetyl bromide (4.11 g, 20.39 mmol) was added into the above reaction mixture slowly at 0° C., and the reaction mixture was warmed to room temperature and stirred for 10 minutes. The mixture was diluted with DCM (100 mL), washed with water (100 mL×2), dried over MgSO$_4$, and evaporated to dryness. The crude product was loaded onto a silica gel column and was eluted with 0-100% EtOAc in hexane to give the desired product as a yellow gum (4.75 g, 50.9%). $^1$H NMR in CDCl$_3$ was consistent with desired product (6S,7S)-4-methyl-6-(naphthalen-2-yl)-7-phenyl-1,4-oxazepan-3-one: A suspension of sodium hydride (0.409 g, 10.22 mmol) in DMF (15 mL) was cooled to 0° C. 2-Bromo-N-((2S,3S)-3-hydroxy-2-(naphthalen-2-yl)-3-phenylpropyl)-N-methylacetamide (2.16 g, 3.93 mmol) in DMF (5 mL) was added into the above reaction mixture slowly at 0° C., and the reaction mixture was stirred for 20 minutes at which point the MS analysis showed mainly the desired product (MH+ at 332). The mixture was diluted with DCM (300 mL), washed with water (2×300 mL), dried through MgSO$_4$, and evaporated to dryness. The crude product was purified by silica gel column chromatography using 0-100% EtOAc in hexane as eluent, giving the product as a colorless foam (1.08 g, 83%, 95% purity). $^1$H NMR (CDCl$_3$) δ 7.72 (d, 2H, J=8.0 Hz), 7.68-7.82 (m, 1H), 7.52 (s, 1H), 7.39-7.50 (m, 2H), 7.07-7.22 (m, 6H), 4.88 (d, 1H, J=10.1 Hz), 4.66 (d, 1H, J=15.4 Hz), 4.56 (d, 1H, J=15.9 Hz), 4.05 (dd, 1H, J=14.8, 3.0 Hz), 3.83 (dd, 1H, J=14.4, 6.3 Hz), 3.44 (ddd, 1H, J=9.8, 6.6, 3.0 Hz), 3.00 (s, 3H). MS m/z (ESI) 332 (MH+).

Example 130—Synthesis of Compound ID No. 130 ((1R,2R or 1S,2S)-2-(naphthalen-2-yl)-1-phenyl-3-(2,2,2-trifluoroethylamino)propan-1-ol)

anti-3-hydroxy-2-(naphthalen-2-yl)-3-phenylpropanenitrile: A 22-L three neck round bottom flask equipped with a mechanical stirrer, nitrogen inlet, thermometer, and addition funnel with septum was charged with THF (12 L) and diisopropylamine (0.180 L, 1260.28 mmol) and chilled to −78° C. N-butyllithium (0.490 L, 1224.28 mmol) was added and stirred for 5 minutes. A solution of 2-(naphthalen-2-yl)acetonitrile (206.9 g, 1.2 mol) in THF (2 L) was added drop-wise over 45 minutes and the resulting solution stirred for 30 minutes. Benzaldehyde (0.122 L, 1200.27 mmol) was added drop-wise over 5 minutes and stirred for an additional 20 minutes before the reaction was quenched by the addition of acetic acid (150 g) in THF (250 mL) at −72° C. The layers separated, and the aqueous layer was extracted with Et$_2$O (2×1 L). The combined organic extracts were washed with brine (1 L), dried over MgSO$_4$, and concentrated in vacuo to give the crude product (379.6 g, 116%). Recrystallization from THF (640 mL) hexanes (800 mL) at 40° C. gave 3-hydroxy-2-(naphthalen-2-yl)-3-phenylpropanenitrile (228 g, 69.4%). Recrystallization with THF and hexane at 40° C. gave 174 g (53%) anti isomer contaminated with about 5.2 g of the syn isomer. $^1$H NMR in CDCl$_3$ showed the presence of the expected structure.

anti-3-Amino-2-(naphthalen-2-yl)-1-phenylpropan-1-ol: anti-3-hydroxy-2-(naphthalen-2-yl)-3-phenylpropanenitrile (3.13 g, 11.45 mmol) was dissolved in THF (85 mL), stirred in a 100 mL flask fitted with a Dean-Stark trap and condenser, and heated to 85° C. To this colorless solution was added, via gas tight syringe, in several portions, the borane (30 mL, 30.00 mmol) as a 1.0 M solution in THF. Bubbling occurred with each addition. The reaction mixture was stirred and heated to 80° C. for 2 hours and then allowed to cool to room temperature. 10 mL MeOH was added cautiously. Vigorous reaction occurred early in the addition and dissipated towards the end of the 10 mL addition. It was reheated to reflux and distilled into a Dean-Stark trap for 30 minutes. It was cooled to room temperature, and 150 mL of 10% sodium bicarbonate in water was added. The aqueous phase was extracted with CH$_2$Cl$_2$ three times. Organic layers were combined, washed with brine, dried with MgSO$_4$, filtered, and evaporated to form a crude semi-solid. This semi-solid was dried overnight. The impure product was taken to the next step without further purification. MS m/z (ESI) 278.3 (MH$^+$). $^1$H NMR spectrum of the crude material in CDCl$_3$ showed the presence of the expected structure.

anti-2,2,2-trifluoro-N-(3-hydroxy-2-(naphthalen-2-yl)-3-phenylpropyl) acetamide: anti3-amino-2-(naphthalen-2-yl)-1-phenylpropan-1-ol (1.78 g, 6.42 mmol) was diluted in CH$_2$Cl$_2$ (100 mL) at room temperature. Triethylamine (2 mL, 14.35 mmol) was added, and the reaction mixture was cooled to 0° C. in an ice bath. 2,2,2-Trifluoroacetic anhydride (0.892 mL, 6.42 mmol) was added in one portion to the vigorously stirred solution. Vapor and heat were noticeable with the addition as well as the clear colorless solution immediately turning slight yellow. After the addition, the reaction was stirred at room temperature for 2 hours. The reaction was diluted with DCM to a volume of about 75 mL and washed twice with 50 mL of 1N HCl and once with 50 mL of saturated aqueous NaHCO$_3$, dried with MgSO$_4$, filtered, and evaporated, leaving an oil that was dried overnight (1.900 g, 79%). $^1$H NMR spectrum of the crude material in CDCl$_3$ showed the presence of the expected structure, hence the 2,2,2-Trifluoro-N-((2S,3S)/(2R,3R)-3-hydroxy-2-(naphthalen-2-yl)-3-phenylpropyl)acetamide was taken to the next step without purification. MS m/z (ESI) 396.3 (MNa$^+$).

(1R,2R or 1S,2S)-2-(naphthalen-2-yl)-1-phenyl-3-(2,2,2-trifluoro-ethylamino)propan-1-ol: To a hot stirred solution of anti-2,2,2-trifluoro-N-(3-hydroxy-2-(naphthalen-2-yl)-3-phenylpropyl) acetamide (0.85 g, 2.28 mmol) in THF (11.4 mL), heated to 80° C., was added via gas tight syringe in several portions, the borane (1.0M THF Solution) (11.38 ml, 11.38 mmol). Bubbling occurred with each addition. The reaction was kept at a constant 80° C., which produced a mild reflux. After 1 hour and 20 minutes, the heat was turned down to 55° C., and the reaction was allowed to react at that temperature. After an additional 2 hours of refluxing, the reaction was cooled to room temperature. 5 mL of MeOH was added drop-wise causing a vigorous gas evolution. After the gas evolution subsided, 1 mL of 1.0M HCl in dioxane was added, and the mixture was heated to reflux for 15 minutes. The reaction mixture was cooled to room temperature and evaporated in vacuo. 10% NaHCO$_3$ was added, and the aqueous layer was extracted three times with an equal volume of CH$_2$Cl$_2$. Organic phases were combined, dried with MgSO$_4$, filtered, and evaporated to afford the desired product as a clear oil. The crude product was dissolved in CH$_2$Cl$_2$ and purified using an 80 gram ISCO column eluting with a ramp of 0-100% EtOAc/hexane. About 0.600 g of desired product was isolated mixed with starting material. This material was separated into the final two compounds (1S,2S)-2-(naphthalen-2-yl)-1-phenyl-3-(2,2,2-trifluoroethylamino)propan-1-ol and it's (1R,2R) enantiomer were isolated as free base (0.158 g, 19.31%). Enantiomer 1: $^1$H NMR (CDCl$_3$) δ 7.66-7.80 (m, 3H), 7.57 (s, 1H), 7.39-7.47 (m, 2H), 7.09-7.20 (m, 6H), 5.13 (d, 1H, J=7.3 Hz), 4.75 (br. s., 1H), 3.37-3.45 (m, 1H), 3.29-3.37 (m, 1H), 3.15-3.29 (m, 3H), 1.66 (br. s., 1H). MS m/z (ESI) 360.3 (MH$^+$). Enantiomer 2: $^1$H NMR (CDCl$_3$) δ 7.64-7.80 (m, 3H), 7.57 (s, 1H), 7.35-7.50 (m, 2H), 7.10-7.20 (m, 6H), 5.13 (d, 1H, J=7.3 Hz), 4.76 (br. s., 1H), 3.36-3.47 (m, 1H), 3.29-3.36 (m, 1H), 3.14-3.29 (m, 3H), 1.67 (br. s., 1H). MS m/z (ESI) 360.3 (MH$^+$). Compound ID No. 130 was recovered from the first-eluting fraction. Both enantiomers were equipotent at hNET and their absolute configuration could not be assigned.

Example 131—Synthesis of Compound ID No. 131 (1-((S)-2-methoxypyrrolidin-1-yl)-2-((1S,2S)-3-(methylamino)-2-(naphthalen-2-yl)-1-phenyl-propoxy)ethanone)

tert-butyl (2S,3S)-3-(2-((S)-2-methoxypyrrolidin-1-yl)-2-oxoethoxy)-2-(naphthalen-2-yl)-3-phenylpropyl(methyl)carbamate: A mixture of ethyl 2-((1S,2S)-3-(tert-butoxycarbonyl(methyl)amino)-2-(naphthalen-2-yl)-1-phenylpropoxy)acetate (Compound ID No. 35) (0.160 g, 0.34 mmol), diisopropylethylamine (DIEA) (0.162 mL, 0.93 mmol), and (S)-3-methoxypyrrolidine (0.110 g, 1.09 mmol) in EtOH was subjected to microwave conditions at 130° C. for 30 hours. The amber solution was concentrated, and the resulting crude product was subjected to ISCO chromatography eluting with a 0-100% EtOAc/hexanes gradient to give purified tert-butyl ((2S,3S)-3-(2-((S)-3-methoxypyrrolidin-1-yl)-2-oxoethoxy)-2-(naphthalen-2-yl)-3-phenylpropyl)(methyl)carbamate (0.070 g, 39.2%). $^1$H NMR of this compound in CDCl$_3$ showed the presence of the expected mixture of diastereomers. MS m/z (ESI) 533.5 (MH$^+$).

Compound ID No. 131: A mixture of tert-butyl (2S,3S)-3-(2-((S)-2-methoxypyrrolidin-1-yl)-2-oxoethoxy)-2-(naphthalen-2-yl)-3-phenylpropyl(methyl)carbamate (0.070 g, 0.13 mmol) and HCl (2 mL, 8.00 mmol) was allowed to stir at room temperature for 0.5 hours. The reaction mixture was then concentrated to near dryness, and the solid was washed with ether (3×) and dried in vacuo at 60° C. overnight to give purified 1-((S)-3-methoxypyrrolidin-1-yl)-2-((1S,2S)-3-(methylamino)-2-(naphthalen-2-yl)-1-phenylpropoxy)ethanone (0.0396 g, 64.9%). MS m/z (ESI) 433.3 (MH$^+$).

Example 132—Synthesis of Compound ID No. 132 ((RS)-3-(2-methoxyphenyl)-N-methyl-2-(naphthalen-2-yl)propan-1-amine hydrochloride)

Compound ID No. 132 is the racemate of Compound ID No. 57, and was prepared using the methods set forth in Example 57, except that the enantiomer separation step was omitted.

Example 133—Synthesis of Compound ID No. 133 ((5)-2-(3-amino-2-(naphthalen-2-yl)propyl)phenol hydrochloride)

To an air-free Schlenck flask under a stream of N$_2$ was added Compound No. 133a (321 mg, 0.69 mmol), 5% Pd/C (120 mg), CH$_3$OH (4 mL), and THF (4 mL). System was carefully evacuated and backfilled with H$_2$ followed by addition of a stir bar and balloon. The suspension was allowed to stir under a H$_2$ balloon for 16 hours. Catalyst was filtered through celite, and the filtrate was dried over MgSO$_4$ and concentrated. Residue was purified via silica gel flash chromatography to give 178 mg (0.47 mmol, 68%) of a colorless gum. The Boc group was removed by dissolving a sample of the gum (172 mg, 0.45 mmol) in 4 mL of CH$_3$OH and adding 4 mL of 4N HCl in dioxane at 0° C. After 1 hour at 0° C., the cooling bath was removed, and the solution was allowed to warm to room temperature overnight. In the morning, the solvents were removed in vacuo to give 147 mg (0.44 mmol, 99%) of a white powder. $^1$H NMR (400 MHz, CD$_3$OD) δ 7.89 (d, J=8.5 Hz, 1H), 7.86-7.80 (m, 2H), 7.72 (d, J=1.1 Hz, 1H), 7.51-7.43 (m, 3H), 7.03-6.97 (m, 1H), 6.84 (dd, J=7.5, 1.6 Hz, 1H), 6.78 (dd, J=8.1, 0.9 Hz, 1H), 6.62 (td, J=7.4, 1.1 Hz, 1H), 3.71-3.64 (m, 1H), 3.62-3.49 (m, 1H), 3.42-3.34 (m, 1H), 3.14 (dd, J=13.5, 7.6 Hz, 1H), 2.98 (dd, J=13.4, 7.0 Hz, 1H). HRMS (ESI-TOF) calculated for C$_{19}$H$_{20}$NO (MH$^+$) 278.1539, found 278.1545 (+1.92 ppm, 0.6 mmu). This racemate was separated into its enantiomers using a chiral stationary phase supercritical fluid chromatography. The second eluting enantiomer was isolated (38 mg of HCl salt). $^1$H NMR (500 MHz, DMSO-d6) δ 2.89 (dd, J=13.6, 7.5 Hz, 1H), 3.03 (dd, J=13.6, 7.5 Hz, 1H), 3.48 (dd, J=9.0, 4.1 Hz, 2H), 6.37-8.00 (m, 11H). Since this enantiomer is more potent at hNET than the second-eluting enantiomer, it was presumed to be (S)-configured.

Example 133a—Synthesis of Compound No. 133a ((RS)-tert-butyl (3-(2-(benzyloxy)phenyl)-2-(naphthalen-2-yl)propyl)carbamate)

The aldol condensation using sodium ethoxide, ethanol, 2-benzyloxybenzaldehyde (1.07 g, 5.05 mmol), and 2-naphthylacetonitirle (836 mg, 5.0 mmol) was performed in the usual way to give 1.73 g (4.8 mmol, 96%) of a yellow solid. The conjugate reduction was performed in the usual way with (580 mg, 1.6 mmol) of the aldol condensate to give 332 mg (0.9 mmol, 56%) of a crude yellow oil. The oil was then dissolved in 10 mL of THF and cooled to 0° C. Triethylamine (0.55 mL, 3.84 mmol) and DMAP (ca. 5 mg) were then added followed by Boc$_2$O (415 mg, 1.9 mmol). The solution was allowed to warm to room temperature overnight. In the morning 1 mL of water and 10 mL of diethyl ether were added. The contents were poured into a separatory funnel and extracted with ether (2×15 mL) The organics were dried over Na$_2$SO$_4$, filtered, and concentrated. The residue was purified via silica gel flash chromatography (10% EtOAc in hexanes) to give 321 mg (0.69 mmol, 77%) of a colorless gum. $^1$H NMR (400 MHz, CD$_3$OD) δ 7.80-7.63 (m, 3H), 7.51-7.25 (m, 9H), 7.06 (t, J=7.6 Hz, 1H), 6.94 (dd, J=25.5, 7.8 Hz, 2H), 6.72 (t, J=7.4 Hz, 1H), 5.03 (dd, J=27.7, 11.8 Hz, 2H), 3.40 (s, 3H), 3.13-2.99 (m, 2H), 1.29 (s, 9H).

Example 134—Synthesis of Compound ID No. 134 ((RS)—N-methyl-2-(naphthalen-2-yl)-3-(o-tolyl)propan-1-amine hydrochloride)

Compound ID No. 134 is the racemate of Compound ID No. 39, and was prepared using the methods set forth in Example 39, except that the enantiomer separation step was omitted.

Example 135—Synthesis of Compound ID No. 135 ((1RS,2RS)-3-(dimethylamino)-2-(naphthalen-2-yl)-1-(thiophen-2-yl)propan-1-ol))

The monomethyl analogue of this compound (anti-3-(methylamino)-2-(naphthalen-2-yl)-1-(thiophen-2-yl)propan-1-ol) is described as Compound ID No. 40 in Example 40. Compound ID No. 135 was prepared by reductive methylation of this precursor. $^1$H NMR δ 8.42 (br. S, 1H), 8.21 (br. S, 1H), 7.76-7.93 (m, 2H), 7.71 (s, 1H), 7.42-7.55 (m, 2H), 7.38 (dd, J=8.5, 1.7 Hz, 1H), 7.24-7.32 (m, 1H), 6.67-6.78 (m, 1H), 6.60 (d, J=2.6 Hz, 1H), 6.50 (d, J=3.8 Hz, 1H), 5.20 (dd, J=8.3, 3.4 Hz, 1H), 3.51-3.76 (m, 1H), 3.12-3.53 (m, 9H), 2.41-2.67 (m, 5H). MS m/z (ESI) 312.2 (MH$^+$).

Example 136—Synthesis of Compound ID No. 136 (((2RS,3RS)-3-(benzo[d][1,3]dioxol-5-yl)-3-methoxy-N-methyl-2-(naphthalen-2-yl)propan-1-amine))

Anti and syn-3-(benzo[d][1,3]dioxol-5-yl)-3-hydroxy-2-(naphthalen-2-yl)propanenitrile were prepared by reacting the carbanion derived from naphthyl acetonitrile and LDA with benzo[d][1,3]dioxole-5-carbaldehyde at −78° C. A mixture of anti- and syn-isomer was obtained which could not be separated. This material was reduced to anti and syn-3-(benzo[d][1,3]dioxol-5-yl)-3-methoxy-2-(naphthalen-2-yl)propan-1-amine as follows. An oven-dried round-bottom flask with a stir bar was charged with a solution of 0.8 g (2.52 mmol) of a mixture of anti and syn-3-(benzo[d][1,3]dioxol-5-yl)-3-hydroxy-2-(naphthalen-2-yl)propanenitrile and dry THF (7 mL) placed under nitrogen. Next, 2.5 equivalents (6.30 mL, 6.30 mmol) of 1M Borane-THF solution was added via syringe. This mixture was refluxed at 60° C. for one hour during which the reaction progress was checked with TLC. The reaction was quenched with cautious addition of sat'd aqueous NaHCO$_3$. The reaction mixture was poured from the reaction vessel into a separatory funnel. The layers were separated, the aqueous layer was extracted with EtOAc (3×25 mL), and the combined organic layers were washed with water and brine and dried over MgSO$_4$, filtered, and concentrated using a rotary evaporator. The product obtained was mixed with 5 mL of 2N HCl and stirred for an hour and a half to break the boron complexes. The solution was then evaporated in vacuo to furnish a white powder. DCM was then added, which dissolved the compound. Addition of hexane produced a white precipitate which was filtered, dried and lyophilized. A 1:1 anti:syn mixture was obtained as a white solid after crystallizing with DCM and hexane. MS m/z (ESI) 322.28 (M+1)$^+$. This material was converted to anti-Ethyl-3-(benzo[d][1,3]dioxol-5-yl)-3-methoxy-2-(naphthalen-2-yl)propylcarbamate as follows. The starting material (0.5 g, 1.397 mmol) was suspended in 10 mL of anhydrous DCM, and triethylamine (3 equivalents, 0.584 mL, 4.19 mmol) was then added. This was followed by addition of 1.2 equivalents (0366 g, 1.677 mmol) of Boc anhydride. The reaction mixture was stirred at room temperature for two hours and was monitored for completion by TLC. On completion, the reaction was quenched with saturated NaHCO$_3$. The layers were separated, the aqueous layer was extracted with DCM (3×25 mL), and the combined organic layers were washed with water and brine and dried over MgSO$_4$. The combined organic layers were concentrated using a rotary evaporator. The resulting residue was purified by flash chromatography over silica gel (elution with 40% EtOAc in hexanes) to afford the anti-carbamate.

Conversion to Compound ID No. 136 was performed as follows. An oven-dried round-bottom flask with a stir bar was charged with 0.100 g (0.237 mmol) of anti-ethyl-3-(benzo[d][1,3]dioxol-5-yl)-3-methoxy-2-(naphthalen-2-yl) propylcarbamate and dissolved in 2 mL of dry THF and placed under nitrogen. Next, 2.5 equivalents (0.593 mL, 0.593 mmol) of 1M borane-THF solution was added via syringe. This mixture was refluxed at 60° C. for 1 hour and was checked for completion with TLC. The reaction was quenched with cautious addition of NaHCO$_3$. The reaction was poured from the reaction vessel into a separatory funnel. The layers were separated, the aqueous layer was extracted with EtOAc (3×25 mL), and the combined organic layers were washed with water and brine and dried over MgSO$_4$. The combined organic layers were concentrated using a rotary evaporator. The product obtained was mixed with 5 mL of 2N HCl. Concentration in vacuo afforded a white powder that was then washed with ether and dried. $^1$H NMR (500 MHz, DMSO-d6) δ 7.64 (s, 1H), 7.70-7.93 (m, 2H), 7.40-7.56 (m, 3H), 7.31 (dd, J=8.5, 1.5 Hz, 1H), 6.74 (d, J=1.5 Hz, 1H), 6.59-6.69 (m, 1H), 6.51 (dd, J=8.1, 1.7 Hz, 1H), 5.90 (d, J=7.0 Hz, 2H), 4.51 (d, J=9.2 Hz, 1H), 3.63 (d, J=8.5 Hz, 1H), 3.45-3.58 (m, 2H), 3.14 (s, 3H), 2.56 (t, J=5.3 Hz, 3H). MS m/z (ESI) δ 336.22 (M+1)$^+$.

Example 137—Synthesis of Compound ID No. 137 ((RS)-3-(2-fluorophenyl)-2-(naphthalen-2-yl)propan-1-amine hydrochloride)

The aldol condensation using sodium ethoxide, ethanol, 2-fluorobenzaldehyde (683 mg, 5.5 mmol), and 2-naphthylacetonitrile (836 mg, 5.0 mmol) was performed in the usual way to give 1.33 g (4.87 mmol, 97%) of a pale yellow solid. The reduction was performed in the usual way with a portion of the aldol condensate (527 mg, 1.93 mmol) to give 500 mg (1.8 mmol, 93%) of a crude yellow oil. The oil was then dissolved in 10 mL of THF and cooled to 0° C. DIEA (0.63 mL, 3.6 mmol) and DMAP (ca. 5 mg) were added followed by Boc$_2$O (468 mg, 2.15 mmol). The solution was allowed to warm to room temperature overnight. In the morning, 1 mL of water and 10 mL of diethyl ether were added. The contents were poured into a separatory funnel and extracted with ether (2×15 mL). The organics were dried over Na$_2$SO$_4$, filtered, and concentrated. The residue was purified via silica gel flash chromatography (10% EtOAc in hexanes) to give 494 mg (1.3 mmol, 67%) of a colorless gum. The Boc group was removed by dissolving a portion of the colorless gum (231 mg, 0.61) in 4 mL of CH$_3$OH and adding 4 mL of 4N HCl in dioxane at 0° C. After 1 hour at 0° C., the cooling bath was removed, and the solution was allowed to warm to room temperature overnight. In the morning, the solvents were removed in vacuo to give 183 mg (0.58 mmol, 95%) of a white powder. $^1$H NMR (400 MHz, CD$_3$OD) δ 7.88 (d, J=8.5 Hz, 1H), 7.85-7.78 (m, 2H), 7.69 (s, 1H), 7.53-7.45 (m, 2H), 7.44 (dd, J=8.6, 1.8 Hz, 1H), 7.21-7.11 (m, 1H), 7.08-6.99 (m, 2H), 6.95 (ddd, J=8.6, 6.8, 1.1 Hz, 1H), 3.47-3.33 (m, 3H), 3.22 (dd, J=13.7, 5.4 Hz, 1H), 3.06 (dd, J=13.6, 7.4 Hz, 1H). HRMS (ESI-TOF) calculated for C$_{19}$H$_{19}$FN (MH$^+$) 281.1529, found 281.1532 (+0.97 ppm, 0.3 mmu).

Example 138—Synthesis of Compound ID No. 138 ((R)-3-(2-fluorophenyl)-N-methyl-2-(naphthalen-2-yl)propan-1-amine hydrochloride)

Compound ID No. 138 is the enantiomer of the compound in Example 17. The combined fractions of the first eluting enantiomer were concentrated in vacuo and converted to an HCl salt, which afforded 156 mg of Compound ID No. 138, which was shown by the described SCF system to have 99% enantiomeric excess. $^1$H NMR (300 MHz, CDCl$_3$) δ 2.64 (s, 3H), 2.97-3.12 (m, 1H), 3.15-3.27 (m, 1H), 3.36-3.70 (m, 3H), 6.86-7.07 (m, 3H), 7.09-7.24 (m, 1H), 7.35-7.57 (m, 3H) 7.75-7.97 (m, 3H). Since this enantiomer was less potent at hNET than the first-eluting enantiomer, it was presumed to be (R)-configured.

Example 139—Synthesis of Compound ID No. 139 (±)-N-methyl-3-(5-methylthiophen-2-yl)-2-(naphthalen-2-yl)propan-1-amine))

Compound ID No. 139 is the racemate of Compound ID No. 44. It was prepared exactly as for Compound ID No. 44, but without the enantiomer separation step. Its spectroscopic properties are identical to that of Compound ID No. 44.

Example 140—Synthesis of Compound ID No. 140 ((R)-2-(3-(methylamino)-2-(naphthalen-2-yl)propyl) phenol hydrochloride)

Compound ID No. 140 is the enantiomer of the compound in Example 52. The combined fractions of the second eluting enantiomer were concentrated in vacuo and converted to an HCl salt, which afforded 35.6 mg of Compound ID No. 140. $^1$H NMR (500 MHz, DMSO-d6) δ ppm 2.50 (d, J=1.8 Hz, 3H), 2.88 (dd, J=13.4, 7.9 Hz, 2H), 3.04 (dd, J=13.6, 6.6 Hz, 2H), 3.39 (q, J=7.0 Hz, 1H), 6.46-7.97 (m, 11H).

Example 141—Synthesis of Compound ID No. 141 ((1R,2S)-1-(3,5-difluorophenyl)-3-(methylamino)-2-(naphthalen-2-yl)propan-1-ol)

Syn-3-(3,5-difluorophenyl)-3-hydroxy-2-(naphthalen-2-yl)propanenitrile was prepared as follows. 2-naphthylacetonitrile (2 g, 11.96 mmol) was placed in an oven-dried round bottom flask with stirrer, and 170 mL of dry THF was added under nitrogen. Diisopropylamine (2 mL, 14.35 mmol) was added, and the mixture was stirred and cooled to −78° C. for 20 minutes. 2.5 M Butyllithium (5.74 mL, 14.35 mmol) was then added slowly with a syringe. After 30 minutes, 1.2 equivalents of 3,5-difluoro-benzaldehyde (2 mL, 14.35 mmol) was added drop-wise via syringe slowly. The reaction was monitored by TLC. After 20 minutes, the reaction was quenched quickly with 10 mL 2.1 THF/acetic acid (add all at once). Cold bath was removed, and the reaction was allowed to reach room temperature slowly. Water was added, and the layers were separated. The aqueous layer was extracted with EtOAc (3x), and the combined organic layers were washed with water and brine and dried over MgSO$_4$. The combined organic layers were concentrated using a rotary evaporator. The resulting residue was purified by flash chromatography over silica gel (elution with 15% to 40% EtOAc in hexanes) to afford the two diastereomers. The more polar compound was isolated and was assigned the RS/SR-stereochemistry. $^1$H NMR (CDCl$_3$) δ 7.92-7.79 (m, 3H), 7.75 (s, 1H), 7.59-7.50 (m, 2H), 7.32 (dd, 1H, J=8.48 Hz, 1.70 Hz), 6.92-6.73 (m, 3H), 5.08 (d, 1H, J=6.59 Hz), 4.24 (dd, 1H, J=6.78 Hz).

The compound described above was reduced as follows. An oven-dried round-bottom flask with a stir bar was charged with 2.5 g (8.08 mmol) of syn-3-(3,5-difluorophenyl)-3-hydroxy-2-(naphthalen-2-yl)propanenitrile and dissolved in 25 mL of dry THF and placed under nitrogen. Next, 32 mL (4 equivalents, 32.3 mmol) of 1M borane-THF solution was added via syringe. This mixture was stirred at 60° C. for two days. The reaction was checked for completion monitored with TLC. The reaction was quenched with cautious addition of NaHCO$_3$. The reaction was poured from the reaction vessel into a separatory funnel. The layers were separated, the aqueous layer was extracted with EtOAc (3×25 mL), and the combined organic layers were washed with water and brine and dried over MgSO$_4$. The combined organic layers were concentrated using a rotary evaporator. The residue was dissolved in DCM, and then 5 mL of 1N HCl was added with stirring. The solvents were then evaporated off in vacuo. The product was dried, washed with ether, dried and lyophilized. $^1$H NMR (CD3OD) (for the mixture of diastereomers) δ 7.87-7.73 (m, 6H), 7.62 (m, 2H), 7.50-7.41 (m, 4H), 7.37-7.24 (m, 2H), 6.78 (m, 5.15 (d, 1H, J=4.33 Hz), 5.03 (d, 1H, J=8.85 Hz), 3.76-3.63 (m, 1H), 3.56-3.39 (m, 5H). MS m/z (ESI) 314.34 (MH$^+$).

syn-tert-Butyl-3-(3,5-difluorophenyl)-3-hydroxy-2-(naphthalen-2-yl)propylcarbamate was prepared as follows. A suspension of 2.8 g (8.94 mmol) of 3-amino-1-(3,5-difluorophenyl)-2-(naphthalen-2-yl)propan-1-ol in 20 mL of DCM was treated with triethylamine (26.8 mmol, 3.74 ml). This was followed by addition of 1.25 equivalents (11.17 mmol, 2.438 g) of Boc$_2$O. The reaction mixture was stirred at room temperature overnight. The reaction progress was checked for completion by TLC. On completion, the reaction was quenched with saturated NaHCO$_3$. The layers were separated, the aqueous layer was extracted with DCM (3×25 mL), and the combined organic layers were washed with water and brine and dried over MgSO$_4$. The combined organic layers were concentrated using a rotary evaporator. The resulting residue was purified by flash chromatography over silica gel (elution with 15-30% EtOAc in hexanes) to afford the product. $^1$H NMR (CDCl$_3$) δ 7.84-7.64 (m, 3H), 7.59 (s, 1H), 7.49-7.37 (m, 2H), 6.71 (d, 2H, J=6.4 Hz), 6.54 (t, 1H, J=9.04, 8.48 Hz), 5.03 (d, 1H, J=4.14 Hz, J=3.96 Hz), 4.77 (s, 2H), 3.98-3.80 (m, 1H), 3.35-3.21 (m, 1H), 3.18-3.06 (m, 1H), 1.43 (s, 9H). MS (ESI) m/z 436.22=(M+Na$^+$).

Compound ID No. 141 was then prepared as follows. An oven-dried round-bottom flask with a stir bar was charged with 1 g (2.419 mmol) of syn-tert-Butyl-3-(3,5-difluorophenyl)-3-hydroxy-2-(naphthalen-2-yl)propylcarbamate and dissolved in 15 mL of dry THF and placed under nitrogen. Next, 9.67 mL (9.67 mmol) of 1M borane-THF solution was added via syringe. This mixture was stirred at 60° C. overnight. The reaction was monitored by TLC. The reaction was quenched with cautious addition of NaHCO$_3$. The reaction was poured from the reaction vessel into a separatory funnel. The layers were separated, the aqueous layer was extracted with EtOAc (3×25 mL), and the combined organic layers were washed with water and brine, and dried over MgSO$_4$. The combined organic layers were concentrated using a rotary evaporator. The resulting residue was purified by flash chromatography over silica gel (elution with 1% TEA in 5% MeOH in DCM). The solvents were evaporated using a rotary evaporator. 1N HCl (3 mL) was added, and the product was lyophilized. The product was dissolved in MeOH and allowed to crystallize at 4° C. in the presence of ether. White crystals were isolated and dried. This was subjected to chiral SFC to separate the two enantiomers. The second-eluting enantiomer was Compound ID No. 141. Since it was more potent at hNET than the first eluting enantiomer, it was assigned (1R,2S)-configuration. $^1$H NMR (500 MHz, DMSO-d6) δ 8.30-8.51 (m, 1H) 8.73-8.96 (m, 1H), 7.78 (d, J=8.8 Hz, 1H), 7.47 (dd, J=6.3, 3.2 Hz, 2H), 7.62, 7.29 (dd, J=8.4, 1.7 Hz, 1H), 6.97 (s, 1H) (s, 1H), 6.80 (d, J=6.7 Hz, 2H),) 5.99 (d, J=4.6 Hz, 1H), 5.16 (t, J=4.3 Hz), 7.86 (d, J=4.3 Hz, 2H), 3.53 (d, J=4.6 Hz, 1H), 3.40 (d, J=3.7 Hz, 2H). MS m/z (ESI) 328.34 (MH⁺).

Example 142—Synthesis of Compound ID No. 142 ((1S,2R)-1-(3,5-difluorophenyl)-3-(methylamino)-2-(naphthalen-2-yl)propan-1-ol)

Compound ID No. 142 is the enantiomer of Compound ID No. 141. It was first-eluting from SFC separation of the racemate. Since it is less potent at hNET than its enantiomer, it was assigned (1S,2R) configuration. Its spectroscopic properties were identical to that of Compound ID No. 141.

Example 143—Synthesis of Compound ID No. 143 ((1S,2S)-1-(2,3-dihydrobenzo[b][1,4]dioxin-6-yl)-3-(methylamino)-2-(naphthalen-2-yl)propan-1-ol)

Anti-3-(2,3-dihydrobenzo[b][1,4]dioxin-6-yl)-3-hydroxy-2-(naphthalen-2-yl)propanenitrile was prepared in a standard fashion by adding a LDA-derived carbanion from naphthyl acetonitrile to a solution of 2,3-dihydrobenzo[b][1,4]dioxine-6-carbaldehyde at −78° C. followed by separation of the anti- and syn-stereoisomers. This pure diastereomer was then reduced to the corresponding primary amine using borane-THF. This compound was converted to anti-ethyl-3-(2,3-dihydrobenzo[b][1,4]dioxin-6-yl)-3-hydroxy-2-(naphthalen-2-yl)propylcarbamate in the manner outlined for other compounds provided herein. Finally, this carbamate was reduced using borane-THF. An oven-dried round-bottom flask with a stir bar was charged with 0.13 g, 0.298 mmol of anti-ethyl-3-(2,3-dihydrobenzo[b][1,4]dioxin-6-yl)-3-hydroxy-2-(naphthalen-2-yl)propylcarbamate and dissolved in 1 mL of dry THF and placed under nitrogen. Next, 2.5 equivalents (0.746 mL, 0.746 mmol) of 1M borane-THF solution was added via syringe. This mixture was refluxed at 60° C. overnight while monitoring the reaction with TLC. The reaction was quenched with cautious addition of NaHCO₃. The reaction was poured from the reaction vessel into a separatory funnel. The layers were separated, the aqueous layer was extracted with EtOAc (3×25 mL), and the combined organic layers were washed with water and brine and dried over MgSO₄. The combined organic layers were concentrated using a rotary evaporator. The crude product obtained was mixed with 2 mL of 2N HCl and stirred to break the boron complexes. The solution was then evaporated in vacuo which left a white product. DCM was then added, and the resulting suspension was leached by agitating and stirring to remove impurities. This left a white powder that was lyophilized. The enantiomers were then separated using SFC. The first-eluting enantiomer was Compound ID No. 143. Based on its higher potency at hNET than that of the second-eluting enantiomer, Compound ID No. 143 was assigned (S,S)-configuration. ¹H NMR (500 MHz, DMSO-d6) δ 7.76-7.85 (m, 3H), 7.68 (s, 1H), 7.44-7.53 (m, 2H), 7.35 (dd, J=8.54, 1.53 Hz, 1H), 6.70 (d, J=1.83 Hz, 1H), 6.53-6.67 (m, 2H), 5.06 (br. s., 1H), 4.81 (d, J=8.24 Hz, 1H), 4.08-4.14 (m, 4H), 3.65-3.79 (m, 1H), 3.53-3.65 (m, 2H), 2.54 (t, J=5.34 Hz, 3H). MS m/z (ESI) 350.2 (MH⁺).

Example 144—Synthesis of Compound ID No. 144 ((1R,2R)-3-(methylamino)-2-(naphthalen-2-yl)-1-(thiophen-2-yl)propan-1-ol))

Compound ID No. 144 is the enantiomer of Compound ID. No. 47, and its preparation is detailed in Example 47. Compound ID No. 47 was the second-eluting enantiomer, and Compound ID No. 144 was the first-eluting enantiomer. Based on its lower potency at hNET relative to its enantiomer, Compound ID No. 144 was assigned (1R,2R)-configuration. It was spectroscopically identical to Compound ID No. 47.

Example 145—Synthesis of Compound ID No. 145 ((1RS,2RS)-1-(2,3-dihydrobenzo[b][1,4]dioxin-6-yl)-3-(methylamino)-2-(naphthalen-2-yl)propan-1-ol))

Compound ID No. 145 is the racemate of Compound ID No. 143, and its preparation was as described in Example 143. It was spectroscopically identical to Compound ID No. 143.

Example 146—Synthesis of Compound ID No. 146 ((2S,3S)-3-chloro-N-methyl-2-(naphthalen-2-yl)-3-phenylpropan-1-amine)

(1R,2S)-3-hydroxy-N-methyl-2-(naphthalen-2-yl)-3-phenylpropan-1-amine) was prepared as described in Example 9. This compound (70 mg) was then dissolved in 3 mL of DCM, and to this was added 1.0 mL of thionyl chloride. The resulting mixture was stirred under dark at room temperature for 30 minutes. Concentration under rotary evaporation yielded a quick syrupy liquid. ¹H NMR (CD₃OD) δ 7.85-7.69 (m, 4H), 7.66 (s, 1H), 7.49-7.41 (m, 3H), 7.33-7.04 (m, 4H), 5.38 (d, J=9.4 Hz, 1H), 4.07-3.07 (m, 4H), 2.69 (s, 3H). MS m/z (ESI) 310.19 (MH+). Invertive substitution was assumed.

Example 147—Synthesis of Compound ID No. 147 ((1R,2R)-2-((methylamino)methyl)-1,4-diphenylbutan-1-ol)

The first-eluting anti-enantiomer carbamate described in Example 27 (ethyl 2-(hydroxy(phenyl)methyl)-4-phenylbutylcarbamate, 72 mg, 0.22 mmol) was dissolved in THF (2 mL) and added drop-wise via syringe over about 5 minutes to LiAlH₄ (0.605 mL, 0.60 mmol, 1 M in THF) in THF (2 mL) at 55° C. under nitrogen. The reaction mixture was then heated at reflux for 1.5 hours. LCMS indicated near complete conversion to product, and the reaction mixture was quenched carefully with sat. aq. Na₂SO₄, then sat. aq. NaHCO₃. Ether was added, the ether layer was isolated, and the aq. layer was extracted twice more with ether. The ether layers were combined, washed with sat. NaHCO₃, brine, dried (Na₂SO₄), filtered, and concentrated in vacuo to afford an oil (49 mg). ¹H NMR spectroscopy in the presence of the TBPTA shift reagent indicated a vicinal coupling constant of 9.7 Hz, consistent with anti-relative configuration. ¹H NMR and MS spectra confirm the proposed structure. This material was dissolved in CH₂Cl₂, to which was added 4 M HCl/dioxane (0.20 mL) The mixture was concentrated, and the resulting residue was triturated with ether, and concentrated in vacuo to afford a foamy solid. Compound ID No. 147's enantiomer was derived from the second-eluting anti-carbamate described in Example 27. Based on its lower potency at hNET than its enantiomer, Compound ID No. 147 is assigned the (1R,2R)-configuration. Its corresponding syn-enantiomers are Compound ID Nos. 27 and 66.

Example 148—Synthesis of Compound ID No. 148 ((1RS,2RS)-2-(4-chlorophenyl)-3-(methylamino)-1-phenylpropan-1-ol)

Syn and anti-2-(4-chlorophenyl)-3-hydroxy-3-phenylpropanenitrile was prepared in a standard fashion by reacting a LDA-derived carbanion from 4-chlorophenylacetonitrile with a solution of benzaldehyde at −78° C. in THF followed by work-up to give a mixture of anti- and syn-stereoisomeric nitriles which could not be separated by crystallization or silica gel chromatography. These compounds (1.23 g, 4.77 mmol) were dissolved in tetrahydrofuran (25 mL), heated at 75° C., and to this mixture was added the borane-methyl sulfide complex (5.97 mL, 11.93 mmol) dropwise via syringe. The reaction mixture was then heated at 75° C. for 2 hours while collecting the liberated methyl sulfide in a Dean-Stark trap. The reaction mixture was cooled to room temperature and concentrated to remove the THF. The residue was dissolved in EtOAc and carefully washed twice with sat'd NaHCO$_3$, brine, dried (Na$_2$SO$_4$), filtered, and concentrated to give the crude primary amine (1.41 g). To a suspension of this material (773 mg, 2.95 mmol) in dichloromethane (15 mL) was slowly added triethylamine (1.646 mL, 11.81 mmol). The clear solution thus obtained was cooled to 0° C., and the ethyl carbonochloridate (0.339 mL, 3.54 mmol) was added drop-wise via syringe. The reaction mixture was then stirred at 0° C. for several minutes, then allowed to warm to room temperature and continuously stirred for 1.5 hours. The reaction mixture was diluted with DCM and washed with 1N HCl, sat'd NaHCO$_3$, brine, dried (Na$_2$SO$_4$), filtered and concentrated to a residue (900 mg) that was purified via silica gel chromatography to give the pure anti-carbamate (yield 360 mg). The racemic anti-carbamate was reduced in the following way. To a solution of lithium aluminum hydride in THF (1M, 2.92 mL, 2.92 mmol) and additional THF (3 mL) at 55° C. under nitrogen was added the ethyl 2-(4-chlorophenyl)-3-hydroxy-3-phenylpropylcarbamate (355 mg, 1.06 mmol) in THF (3 mL) drop-wise via syringe over 5 minutes. The reaction mixture was heated at reflux for 2 hours. When the reaction was complete as checked by LCMS, the reaction mixture was quenched carefully with sat'd aq Na$_2$SO$_4$, then sat'd NaHCO$_3$. The aqueous solution was diluted with ether with stirring, then the ether layer was isolated. The aqueous layer extracted twice more with ether. The ether layers were combined, washed with brine, dried (Na$_2$SO$_4$), filtered and concentrated (316 mg). The product was dissolved in DCM, and 4M HCl/dioxane (0.6 mL) was added with stirring. This suspension, on concentration, produced a white foamy solid that was suspended in ether, filtered, and washed with ether. The solid was dried via drying pistol (yield 312 mg). $^1$H NMR (500 MHz, DMSO-d6) δ 7.17 (t, J=7.9 Hz, 4H), 7.02-7.12 (m, 6H), 1.73-1.78 (m, 1H), 4.77 (d, J=7.9 Hz, 1H), 2.97-3.09 (m, 2H), 2.80 (dd, J=11.3, 6.1 Hz, 1H), 3.60 (s, 1H), 2.26 (s, 3H).

Example 149—Synthesis of Compound ID No. 149 ((1S,2RS)-2-(4-bromophenyl)-3-(methyl amino)-1-phenylpropan-1-ol)

2-(4-bromophenyl)-3-hydroxy-3-phenylpropanenitrile (anti/syn ratio=3:1) was prepared in the following way. A 250 mL round bottom flask equipped with a magnetic stirring bar, nitrogen inlet, and septum was charged with THF (100 mL) and 1.8 M LDA (22.67 mL, 40.81 mmol). After cooling to −78° C., 2-(4-bromophenyl)acetonitrile (8 g, 40.81 mmol) was added. After stirring for 60 minutes, benzaldehyde (4.12 mL, 40.81 mmol) was added via syringe. The reaction was left stirred at −78° C. for 5 hours, after which, the reaction was quenched by the addition of water (50 mL) at the same temperature. The aqueous layer was extracted with Et$_2$O (2×200 mL)), and the combined organic extracts were washed with brine (100 mL) and dried (MgSO$_4$). Concentration of the extracts in vacuo gave the crude aldol. ISCO purification on silica gel eluting with 0-30% of ethyl acetate in hexane afforded the product as 3:1 anti:syn mixture (5 g). Recrystallization from DCM (90 mL) and hexane (120 mL) at 0° C. overnight afforded an anti/syn >3/1 mixture (4.3 g) that was taken to the next step. MS m/z (ESI) 324.0/326.0 (MH+). This material was reduced to the primary amine in the following way. A solution of 2-(4-bromophenyl)-3-hydroxy-3-phenylpropanenitrile (4.3 g, 14.23 mmol) in 50 mL THF was heated to a gentle reflux at 76° C. and treated with borane-methyl sulfide complex (21.50 mL, 43 mmol) added drop-wise over 5 minutes. Liberated dimethyl sulfide was collected in a Dean-Stark trap. After 3.5 hours, the mixture was allowed to cool to ambient temperature and concentrated in vacuo, and the residue was dissolved in ethyl acetate (100 ml). This solution was washed with saturated aq. NaHCO$_3$, brine, dried (MgSO$_4$), filtered, and concentrated to give the crude product (4.13 g) that was carried to the next carbamate formation step. MS m/z (ESI) 306.0/308.0 (MH+).

A solution of the HCl salt of 3-amino-2-(4-bromophenyl)-1-phenylpropan-1-ol (5 g, 16.33 mmol) and triethylamine (5.69 mL, 40.82 mmol) in DCM (50 ml) was chilled to 0° C. To the chilled solution was added ethyl carbonochloridate (1.882 mL, 19.60 mmol) over 10 minutes. Ice bath was removed, and the solution was allowed to warm to room temperature for 3 hours. LCMS (t=1.12 minutes, M−H$_2$O+1=362) showed completion of reaction. Reaction solution was reduced to 5 mL (in DCM) by rotary evaporation. Ethyl acetate (200 ml) was added, and the solution was sequentially washed with 0.1N HCl (2×50 mL), saturated sodium bicarbonate (50 ml), and brine (50 mL), then dried over MgSO$_4$, filtered and concentrated in vacuo. Residual solvents were evaporated to give crude product as a form. ISCO purification eluting with 0-50% of ethyl acetate in hexane over 15 minutes afforded the product as oil (2.9 g). NMR showed ~4:1 ratio of anti vs. syn. MS m/z (ESI) 360.0/362.0 (MH−H$_2$O)$^+$. A mixture of ethyl 2-(4-bromophenyl)-3-hydroxy-3-phenylpropylcarbamate (3 g, 7.93 mmol) and 50 mL THF were transferred to a 100-mL 3-neck round bottom flask equipped with a magnetic stirrer, addition funnel, thermometer, Dean-Stark trap, a condenser, and a nitrogen inlet. The solution was heated to a gentle reflux (66° C.) during which a solution of borane-methyl sulfide complex (27.8 mL, 55.52 mmol) was added slowly over 10 minutes. During the reaction, the liberated dimethyl sulfide was collected (bp 38° C.). After 7 hours, the reaction mixture was cooled to room temperature and carefully quenched by slow addition of methanol (20 mL). The methanol was distilled, and the crude products were re-dissolved in ethyl acetate and washed with brine. After drying over sodium sulfate, the organic phase was filtered and concentrated to give the crude product as a solid residue (2.55 g). The SFC separation of the anti/syn mixture produced two peaks. From Peak 1, the solvent was evaporated, and the residue was dissolved in 1.5 mL of dioxane containing 4 M HCl. After stirring for 10 minutes, the solvent was removed, and the solid was washed with ether and dried under vacuum to afford the product as the anti-isomer, which was Compound ID No. 149 (850 mg). $^1$H NMR (500 MHz, DMSO-d6) δ 6.06 (d, J=3.1 Hz, 1H), 4.73 (d, J=2.7 Hz, 1H), 3.29 (s, 2H), 3.51 (br. s., 1H), 2.50 (d, J=1.8 Hz, 3H). MS m/z (ESI) 320/322 (MH+).

Example 150—Synthesis of Compound ID No. 150 ((1RS,2SR)-2-(4-bromo-3-chlorophenyl)-3-(methylamino)-1-phenylpropan-1-ol)

A 250 mL round bottom flask equipped with a magnetic stirring bar, nitrogen inlet, and septum was charged with THF (200 mL) and 1.8 M LDA (12.3 mL, 22.2 mmol). After cooling to −78° C., 2-(4-bromo-3-chlorophenyl)acetonitrile (5.12 g, 22.2 mmol) was added. After 60 minutes, benzaldehyde (2.2 mL, 22 mmol) was added via syringe. After stirring at −78° C. for 3 hours, the reaction was quenched by the addition of water (20 mL) while stirring at −78° C. The aqueous layer was extracted with $Et_2O$ (2×50 mL), and the combined organic extracts were washed with brine (50 mL), dried ($MgSO_4$), and concentrated in vacuo to give the crude aldol. ISCO purification on silica gel eluting with 0-30% of ethyl acetate in hexane afforded the aldol product as 3:1 anti:syn mixture (3 g). This material (3 g, 8.91 mmol) was dissolved in THF (150 mL) and heated to a gentle reflux at 76° C. and treated with borane-dimethylsulfide (13.5 mL, 27.0 mmol), adding drop-wise over 5 minutes. The liberated dimethyl sulfide was collected in a Dean-Stark trap. After 3.5 hours, the mixture was allowed to cool to ambient temperature, quenched with 10 mL of ethanol, and concentrated in vacuo, and the residue was dissolved in ethyl acetate (100 mL) The combined extracts were washed with saturated aq. $NaHCO_3$, brine, dried ($MgSO_4$), filtered, and concentrated to give a residue. This material was dissolved in $CH_2Cl_2$, filtered to remove inorganic materials, and concentrated in vacuo to afford the amine as anti/syn mix products (2.5 g). This material (2.5 g, 7.3 mmol) was combined with triethylamine (2.6 mL, 18 mmol) in $CH_2Cl_2$ (100 mL) and chilled to 0° C. To the chilled solution was added ethyl carbonochloridate (0.85 mL, 8.8 mmol) over 10 minutes. The ice bath was removed, and the solution was allowed to warm to room temperature for 12 hours. The reaction mixture was concentrated in vacuo to approximately 5 mL, diluted with ethyl acetate (200 mL), washed with 0.1 N HCl (2×150 mL), saturated sodium bicarbonate (150 mL), and brine (200 mL), dried over $MgSO_4$, filtered, and concentrated in vacuo to give the product as a foam (2.6 g). The mixture of diastereomeric carbamates was purified on ISCO eluting with 0-40% of ethyl acetate in hexane over 15 minutes. Tubes 14-19 were collected as isomer 1, and tubes 20-27 were collected as isomer 2. Isomer 1 (750 mg) was deduced as syn on the basis of its $^1H$ NMR spectrum in the presence of the TBPTA Shift reagent showed ($J_{1,2}=3$ Hz). For isomer 2 (800 mg), $^1H$ NMR with the identical shift reagent (TBPTA) indicated "anti" stereochemistry ($J_{1,2}=9.3$ Hz). Carbamate isomer 1 (syn, 750 mg, 1.82 mmol) and 25 mL THF were transferred to a 100 mL 3-neck round bottom flask equipped with a magnetic stirrer, addition funnel, thermometer, and Dean-Stark trap fitted with a condenser and nitrogen inlet. The solution was heated to a gentle reflux, and a solution of borane-methyl sulfide complex (4.5 mL, 9.1 mmol) was added drop-wise over 10 minutes. The dimethyl sulfide distillate was collected. and after 4 hours, the reaction was completed.

The reaction was cooled to room temperature, and ethanol (5 mL) was added, causing an exotherm with gas evolution. The reaction mixture was then concentrated in vacuo to remove ethanol and trimethyl borate. The free amine was converted to the HCl salt by dissolving in dioxane, addition of 4 N HCl in dioxane (0.5 mL), and concentration in vacuo. The residue was washed with ether, ethyl acetate in hexane (1:1), and hexane and dried in vacuo to provide the titled compound as the HCl salt. Compound ID No. 150 is the racemate of Compound ID No. 21, and its spectroscopic data is identical to that of Compound ID No. 21.

Example 151—Synthesis of Compound ID No. 151
((1S,2S)-2-(3,4-dichlorophenyl)-1-(3-iodophenyl)-3-(methylamino)propan-1-ol hydrochloride)

To a stirred ice-cooled borane-THF complex (12 mL, 12.00 mmol) was added drop-wise a solution of Compound No. 151a (1.3 g, 2.63 mmol) in dry THF. The mixture was warmed to room temperature and heated to mild reflux for 3 hours. The clear solution was chilled with an ice bath and cautiously treated with drop-wise addition of 3N HCl (10 mL) The resulting solution was warmed to room temperature and heated at reflux for 2 hours. The volatiles were removed on a rotary evaporator, and the aqueous layer was diluted with water (15 mL) followed by addition of chloroform (60 mL). This mixture was then cooled with an ice bath and made alkaline with drop-wise addition of 2N NaOH. These layers were separated and extracted aqueous with chloroform (2×15 mL) The combined organics were washed with brine then dried. The resulting crude product (ca. 1.1 g) was subjected to flash chromatography on silica eluting with chloroform, then 0-3% MeOH/chloroform (ammoniated) to give 1.0 g of purified anti product. The racemate was resolved by SFC, and the first-eluting enantiomer (Compound ID No. 151) was assumed to be 1S,2S-configured based on its higher potency on hNET. $^1H$ NMR data were consistent with the desired structure.

Example 151a—Synthesis of Compound No. 151a
(ethyl (2RS,3RS)-2-(3,4-dichlorophenyl)-3-hydroxy-3-(3-iodophenyl)propylcarbamate)

To a stirred ice-cooled solution of Compound No. 151b (4.25 g, 10.07 mmol) and triethylamine (2.091 mL, 15.0 mmol) in DCM (60 mL) was added drop-wise a solution of ethyl chloroformate (1.249 mL, 13.0 mmol) in DCM (10 mL). The mixture was stirred for 2 hours, and then concentrated to near dryness on a rotary evaporator. The resulting residue was partitioned between ether and aqueous sodium bicarbonate, and then extracted with ether (2×15 mL) The organics fractions were combined, washed with brine, dried, and concentrated to give 4.8 g of the crude product. This was subjected to silica gel chromatography eluting with a 0-50% EtOAc/hexanes gradient to give in order purified (yet racemic) syn isomer (2.0 g) followed by purified anti isomer (1.3 g) as solids. The anti isomer was used as in the next step without further purification.

Example 151b—Synthesis of Compound No. 151b
(3-amino-2-(3,4-dichlorophenyl)-1-(3-iodophenyl)propan-1-ol)

To a stirred solution of the 2-(3,4-dichlorophenyl)acetonitrile (1.86 g, 10.00 mmol) in dry THF (20 mL) at −75° C. was added drop-wise the n-BuLi (2.5M, 4.00 mL, 10.0 mmol). After 20 minutes stirring at −75° C., a solution of the 3-iodobenzaldehyde (2.320 g, 10.00 mmol) in THF (10 mL) was added drop-wise. After 30 minutes stirring at −75° C., a solution of acetic acid (0.715 mL, 12.49 mmol) in THF (2 mL) was added drop-wise. After stirring for 15 minutes, the borane-THF complex (35.0 mL, 35.00 mmol) was added drop-wise, and the dry ice bath was removed. The mixture was allowed to warm to room temperature and then heated at mild reflux for 2 hours. The mixture was chilled to 0° C. with an ice bath followed by drop-wise addition of 2N HCl (20 ml). The ice bath was then removed, and the mixture was heated at mild reflux for 2 hours, cooled, and the volatiles removed in vacuo. The white suspension was diluted with chloroform (150 mL), cooled to 0° C., and vigorously stirred while adding 1N NaOH drop-wise. The resulting layers were separated, and the aqueous layer was extracted with chloroform (2×). The combined organics layers were washed with brine and dried. Concentration to dryness afforded 4.5 g of a white solid (>100%), which was used as such in the next step without further purification.

Example 152—Synthesis of Compound ID No. 152 ((1R,2S)-2-(3,4-dichlorophenyl)-1-(2-iodophenyl)-3-(methylamino)propan-1-ol hydrochloride)

To a stirred ice-cooled borane-THF complex (1.0 M, 27.0 mL, 27.0 mmol) was added drop-wise a solution of Compound No. 152a (3.7 g, 7.49 mmol) in dry THF. The mixture was warmed to room temperature and heated to mild reflux for 3 hours. The clear solution was chilled with an ice bath and cautiously treated with drop-wise addition of 3N HCl (10 mL). The resulting solution was warmed to room temperature and heated at reflux for 2 hours. The volatiles were removed on a rotary evaporator, and the aqueous layer was diluted with water (15 mL) followed by addition of chloroform (60 mL). This mixture was then cooled with an ice bath and made alkaline with drop-wise addition of 2N NaOH. These layers were separated and then extracted aqueous with chloroform (2×15 mL) The combined organics were washed with brine then dried. The resulting crude product was subjected to flash chromatography on silica eluting with chloroform, then 0-3% MeOH/chloroform (ammoniated) to give 400 mg of purified syn product. The racemate was resolved by SFC, and the first-eluting enantiomer (Compound ID No. 152) was assumed to be 1R,2S-configured based on its higher potency on hNET. $^1$H NMR data were consistent with the desired structure.

Example 152a—Synthesis of Compound No. 152a (ethyl (2RS,3RS)-2-(3,4-dichlorophenyl)-3-hydroxy-3-(2-iodophenyl)propyl carbamate)

To a stirred ice-cooled solution of Compound No. 152b (6.3 g, 14.93 mmol) and triethylamine (3.1 mL, 22.24 mmol) in DCM (60 mL) was added drop-wise a solution of ethyl chloroformate (1.9 mL, 19.8 mmol) in DCM (10 mL). The mixture was stirred for 2 hours, and then concentrated to near dryness on a rotary evaporator. The resulting residue was partitioned between ether and aqueous sodium bicarbonate, then extracted with ether (2×15 mL). The organics fractions were combined, washed with brine, dried, and concentrated to give 4.8 g of the crude product. This was subjected to silica gel chromatography eluting with a 0-50% EtOAc/hexanes gradient to give in order purified (yet racemic) syn isomer (3.70 g) followed by purified anti isomer (0.650 g) as solids. The syn isomer was used as in the next step without further purification.

Example 152b—Synthesis of Compound No. 152b (3-amino-2-(3,4-dichlorophenyl)-1-(2-iodophenyl)propan-1-ol)

To a stirred solution of 2-(3,4-dichlorophenyl)acetonitrile (2.80 g, 15.05 mmol) in dry THF (20 mL) at −75° C. was added drop-wise n-BuLi (2.5M, 6.02 mL, 15.05 mmol). After 20 minutes stirring at −75° C., a solution of the 2-iodobenzaldehyde (3.49 g, 15.05 mmol) in THF (10 mL) was added drop-wise. After 30 minutes stirring at −75° C., a solution of acetic acid (1.05 mL, 18.34 mmol) in THF (4 mL) was added drop-wise. After stirring for 15 minutes, the borane-THF complex (1.0 M, 52.0 mL, 52.0 mmol) was added drop-wise, and the dry ice bath was removed. The mixture was allowed to warm to room temperature and then heated at mild reflux for 2 hours. The mixture was chilled to 0° C. with an ice bath followed by drop-wise addition of 2N HCl (20 mL). The ice bath was then removed, and the mixture was heated at mild reflux for 2 hours and cooled. The volatiles were removed in vacuo. The white suspension was diluted with chloroform (150 mL), cooled to 0° C., and vigorously stirred while adding 1N NaOH drop-wise. The resulting layers were separated, and the aqueous layer was extracted with chloroform (2×). The combined organics layers were washed with brine and dried. Concentration to dryness afforded 6.3 g of a white solid (99%), which was used as such in the next step without further purification.

Example 153—Synthesis of Compound ID No. 153 ((1R,2R)-2-(3,4-dichlorophenyl)-3-(methylamino)-1-(thiophen-3-yl)propan-1-ol)

Compound ID No. 153 is the enantiomer of Compound ID No. 106, and its preparation is described in Example 106. It was the second-eluting enantiomer. Based on its lower potency at hNET relative to Compound ID No. 106, Compound ID No. 153 was assigned (1R,2R)-configuration.

Example 154—Synthesis of Compound ID No. 154 ((1R,2R)-2-(3,4-dichlorophenyl)-3-(methylamino)-1-(3-(methylthio)phenyl)propan-1-ol)

Compound ID No. 154 is the enantiomer of Compound ID No. 120, and its preparation is described in Example 120. It was the second-eluting enantiomer. Based on its lower potency at hNET relative to Compound ID No. 120, Compound ID No. 154 was assigned (1R,2R)-configuration.

Example 155—Synthesis of Compound ID No. 155 ((1RS,2RS)-2-(3,4-dichlorophenyl)-3-(methylamino)-1-(pyridin-4-yl)propan-1-ol)

A mixture of anti- and syn-2-(3,4-dichlorophenyl)-3-hydroxy-3-(pyridin-4-yl)propanenitrile was prepared using a standard LDA-mediated reaction of 3,4-dichlorophenylacetonitrile with 4-pyridine carboxaldehyde at −78° C. in THF. The mixture of diastereomers was reduced to the corresponding primary amines as follows. An oven-dried round-bottom flask with a stir bar was charged with a solution of 2-(3,4-dichlorophenyl)-3-hydroxy-3-(pyridin-4-yl)propanenitrile (1.0 g, 3.41 mmol) in 15 mL of dry THF and placed under nitrogen. Next, 4 equivalents (13.64 mL, 13.64 mmol) of 1M borane-THF solution were added via syringe. After stirring at 60° C. overnight, the mixture was quenched with cautious addition of NaHCO$_3$. The reaction was poured from the reaction vessel into a separatory funnel. The layers were separated, the aqueous layer was extracted with EtOAc (3×50 mL), and the combined organic layers were washed with water and brine, then dried over MgSO$_4$. The combined organic layers were concentrated using a rotary evaporator. Dioxane containing HCl was added to the residue, and the resulting mixture was stirred for one half hour. After concentration in vacuo, the crude product was dissolved in MeOH. Addition of ether produced a turbid mixture that was left for one half hour. The off-white crystals were filtered, washed with ether, dried and lyophilized. MS m/z (ESI) 297.21 and 299.18 (MH+). This primary amine (0.45 g, 1.281 mmol) was dissolved in 10 mL of anhydrous DCM containing 3 equivalents (0.536 mL, 3.84 mmol) triethylamine. Then 1.1 equivalents (0.308 g, 1.409 mmol) of di-t-butyl dicarbonate were added, and the reaction mixture was stirred at room temperature for about 1 hour. On completion (TLC monitoring), the reaction was quenched with saturated NaHCO$_3$. The layers were separated, and the aqueous layer was extracted with DCM (3×25 mL). The combined organic layers were washed with water and brine and dried over MgSO$_4$. The combined organic layers were concentrated using a rotary evaporator. The resulting residue was purified by flash chromatography over silica gel (elution with 70% EtOAc in hexanes) that furnished two diastereomers. The anti-isomer was obtained as a white solid. MS m/z (ESI) 396.10 (100.0%), 398.10 (64.7%), 397.10 (21.4%). This material was reduced as follows. An oven-dried round-bottom flask with a stir bar was charged with a solution of the anti-carbamate, (0.4 g, 1.057 mmol) in 5 mL of dry THF and placed under nitrogen. Next, 4 equivalents (2.85 mL, 2.85 mmol) of 1M borane-THF solution were added via syringe. The resulting mixture was stirred at 60° C. overnight and then quenched by cautious addition of NaHCO$_3$. The reaction mixture was poured into a reparatory funnel. The layers were separated, and the aqueous layer was extracted with EtOAc (3×50 mL). The combined organic layers were washed with water and brine and dried over MgSO$_4$. The combined organic layers were concentrated using a rotary evaporator. Dioxane containing HCl was added to the residue which produced a white suspension. The solvents were evaporated under vacuum, and the crude product was dried into a solid that was dissolved in MeOH. Slow addition of anhydrous ether produced a turbid solution. After one half hour, the off white crystals were filtered and washed with ether, dried and lyophilized. $^1$H NMR (CD$_3$OD) δ 8.76 (d, 2H, J=5.3 Hz), 7.92 (d, 2H, J=5.7 Hz), 7.57-7.46 (m, 2H), 7.28-7.18 (m, 1H), 5.21 (d, 1H, J=8.1 Hz), 3.79-3.67 (m, 1H), 3.56-3.38 (m, 2H), 2.74 (s, 3H). MS m/z (ESI) 310.06 (100.0%), 312.06 (64.0%), 311.07 (16.4%).

Example 156—Compound ID No. 156 ((1S,2S)-2-(3,4-dichlorophenyl)-3-(methylamino)-1-(2-(methylthio)phenyl)propan-1-ol)

To a stirred solution of 2-(3,4-dichlorophenyl)acetonitrile (5.6 g, 30 mmol) in dry THF (60 mL) at −78° C. was added drop-wise n-BuLi (2.5 M in hexanes, 12.0 mL, 1.0 equiv). After 20 minutes stirring at −78° C., a solution of 2-(methylthio)benzaldehyde (3.9 mL, 30 mmol) in THF (20 mL) was added drop-wise. After 30 minutes stirring at −78° C., a solution of acetic acid (2.1 mL, 36.68 mmol) in THF (5 mL) was added drop-wise. After stirring the resulting clear solution for 15 minutes, the borane tetrahydrofuran complex (100 mL, 100 mmol) was added drop-wise, and the dry ice bath was removed. The mixture was allowed to warm to room temperature (gas evolution observed) and then heated at mild reflux for 2 hours. The mixture was chilled to 0° C., and 2N HCl (60 mL) was cautiously added drop-wise. The ice bath was removed, and the mixture was heated at reflux for 2 hours and cooled. Volatiles were removed in vacuo. The suspension was diluted with chloroform (150 mL), cooled to 0° C., and vigorously stirred while making basic by drop-wise addition of 1 N NaOH. The layers were separated, the aqueous layer was extracted with chloroform (2×), and the organics were combined, washed with half-saturated brine, dried, and concentrated in vacuo to afford a white amorphous solid (10.3 g) which was presumed to be the primary amine. This material (10.3 g, 30.1 mmol) was combined with Et$_3$N (6.3 mL, 45 mmol) in DCM (140 mL) and was added drop-wise to a solution of ethyl chloroformate (3.8 mL, 40 mmol) in DCM (40 mL). The mixture was stirred for 2 hours and concentrated to near dryness on rotovap. The residue was partitioned between ether and aqueous sodium bicarbonate and extracted with ether (2×). The organics were combined, washed with brine, dried, and concentrated to give crude ethyl carbamate (10 g) as a white amorphous solid. Approximately half was subjected to chromatography (ISCO 220 g column) eluting with a 0-50% EtOAc/hexanes gradient to give in isomer 1 (1.0 g) followed by isomer 2 (1.6 g, used as such in the following step). Isomer 2 (1.6 g, 3.86 mmol) dissolved in THF was added drop-wise to the stirred ice-cooled borane tetrahydrofuran complex (15 mL, 15.00 mmol) in dry THF. The mixture was warmed to room temperature and then heated at mild reflux for 3 hours. The clear solution was chilled with an ice bath, and then 3N HCl (10 mL) was added drop-wise cautiously. The resulting solution was warmed to room temperature and heated at reflux for 2 hours. After removal of volatiles in vacuo, the aqueous suspension was diluted with water (15 mL) and chloroform (60 mL), cooled in ice bath, and made basic with drop-wise addition of 2N NaOH. The layers separated, and the aqueous layer was extracted with chloroform (2×). The organics were washed with half-saturated brine, dried, and concentrated in vacuo. The resulting crude product (1.3 g) was subjected to flash chromatography on silica eluting with chloroform, then 0-3% MeOH/chloroform (ammoniated) to give purified racemic anti diastereomer. This material was submitted to SFC separation to give a first-eluting enantiomer (550 mg) followed by the second eluting enantiomer (560 mg). The second-eluting enantiomer was converted to the HCl salt. Based on its potency at hNET relative to it is enantiomer, it is presumed to be (1S,2S)-configured. $^1$H NMR spectroscopic data and MS analysis were consistent with the proposed structure.

Example 157—Synthesis of Compound ID No. 157 ((1R,2R)-2-(3,4-dichlorophenyl)-1-(6-methoxypyridin-2-yl)-3-(methylamino)propan-1-ol)

2-(3,4-dichlorophenyl)acetonitrile (3.50 g, 18.8 mmol) was taken up in THF (30 mL) and diethyl ether (30 mL), and cooled to −78° C. in an acetone-dry ice bath. BuLi (8.1 mL, 20 mmol, 1.6 M in hexane) was added drop-wise, and the temperature was maintained below −60° C. Once the last drop had been added, the reaction was allowed to stir for 15 minutes. This solution became orange clear. 6-methoxypicolinaldehyde (2.3 mL, 19 mmol) dissolved in THF (20 mL) was added slowly drop-wise, and the temperature was maintained below −60° C. Solution was dark brown/black clear at this point and was allowed to stir for 1.5 hours at −75° C. The reaction was quenched with acetic acid (1.6 mL, 28 mmol) dissolved in 5 mL of diethyl ether, added drop-wise while the reaction was cooled in the dry ice acetone bath. The temperature was maintained below −60° C. LCMS revealed mostly one peak with the desired mass. The reaction was worked up by adding 100 mL of water, and layers were separated. The aqueous phase was extracted with ethyl acetate three times. The combined organic layers were washed with brine, dried over MgSO$_4$, and concentrated in vacuo to afford 8.14 grams of a clear amber oil. LCMS revealed a peak that was consistent with desired material. The material was absorbed onto silica gel and ran through an ISCO 80 gram column, eluting with CH$_2$Cl$_2$/EtOAc. The broad peak looked to be a mixture of diastereomers in a ratio around 1.5:1. It was not determined which diastereomeric pair is the more predominant pair (0.988 g). The spiked shoulder from that broad peak looked to be a mixture of diastereomers in a ratio around 4:1 (4.39 g). These two samples were recombined (5.2 g, 16.1 mmol), dissolved in THF (150 mL), stirred in a 500 mL flask fitted with a dean stark trap and condenser, and heated to 85° C. To this colorless solution was added, via gas tight syringe in several portions, the 2.0 M borane dimethysulfide complex in THF (16.1 mL, 32.1 mmol). Bubbling occurred with each addition. The reaction was heated to 95° C., which produced a vigorous reflux. After stirring for 1.5 hours, during which time the solvent was removed from the dean stark trap (removing most of the dimethyl sulfide), LCMS showed mainly one peak with a desired mass. The reaction was removed from heat and stirred until the reaction had reached room temperature, at which point 20 mL MeOH was added drop-wise at first. Vigorous reaction occurred early in the addition and dissipated towards the end of the addition. The mixture was reheated to reflux and distilled into a Dean Stark trap for 30 minutes, then cooled to room temperature. The mixture was combined with 350 mL of 10% $NaHCO_3$ in water and extracted with $CH_2Cl_2$ three times. The organics were combined, washed with brine, dried with $MgSO_4$, filtered, and evaporated to crude semi-solid. This material was pumped down overnight to afford 3-amino-2-(3,4-dichlorophenyl)-1-(6-methoxypyridin-2-yl)propan-1-ol (5.51 g, 99%). Purity was judged sufficient for the next step. This material (5.0 g, 15 mmol) was diluted in $CH_2Cl_2$ (80 mL) at room temperature, and $Et_3N$ (3.2 mL, 23 mmol) was added. The reaction mixture was cooled to 0° C. Ethyl chloroformate (1.75 mL, 18.3 mmol) was added slowly at 0° C. After the addition, the reaction was stirred at room temperature overnight. The reaction was worked up by diluting with 150 mL of $CH_2Cl_2$, sat. aq. $NaHCO_3$ (75 mL) and water (125 mL). This mixture was shaken several times, and then the layers were separated. The aqueous fraction was extracted with two more equal portions of $CH_2Cl_2$. All organics were combined and dried with $MgSO_4$, filtered, and evaporated to a crude oil. This material was dissolved in $CH_2Cl_2$ and purified in parallel by passing through three 80 gram silica ISCO columns with a ramp from 20-40% EtOAc/Hexane. This diluted chromatography was used to get separation of the diastereomers. Diastereomers were identified on the ISCO trace as well as through TLC. Three samples were collected. Sample 1 was the "syn" diastereomeric pair, sample 2 was a mixture of both pairs, and sample 3 was the "anti" diastereomeric pair. A total of about 83% yield of the desired carbamates were obtained, about 90% purity judging roughly by NMR. Total mass of about 5.6 grams.

The pure anti fraction (0.35 g, 0.88 mmol) was dissolved in THF (6.6 mL) and stirred in a 100 mL flask fitted with a Dean Stark trap and condenser. To this colorless solution was added, via gas tight syringe in several portions, the 2.0 M borane dimethysulfide complex in THF (2.2 ml, 4.4 mmol). Bubbling occurred with each addition. The reaction was heated to 80° C., which produced a vigorous reflux. The reaction was allowed to stir for 10 hours at reflux, solvent was removed from the Dean Stark trap, and the product was allowed to sit at room temperature overnight, at which point LCMS showed mostly desired product. The reaction was quenched by addition of 10 mL MeOH (added drop-wise). A vigorous reaction occurred early in the addition, and it dissipated towards the end of the 10 mL addition. The reaction was heated to reflux and distilled into a Dean Stark trap for 30 minutes. After cooling to room temperature, 10% $NaHCO_3$ (150 mL) was added, and the reaction was extracted with $CH_2Cl_2$ three times. Organics were combined, washed with brine, dried with $MgSO_4$, filtered and evaporated to crude semi-solid, which was taken up in $CH_2Cl_2$ and run through an 80 grain ISCO column (eluted with 20% $MeOH/CH_2Cl_2$). Good separation was achieved, and 180 mg of the racemic product was separated on a Multigram III SFC system with a 30 mm×250 mm Chiral ADH column: sample was diluted in about 5 mL of EtOH [0.5% isopropylamine], and stacked injections of 0.35 mL each were run using 17.5% of i-PrOH [1% isopropylamine] isocratic at 100 mL/minute. Two fractions were obtained, each of which was concentrated, dissolved in diethyl ether, then treated with HCl in diethyl ether, and concentrated in vacuo to afford 75 mg samples. The HCl salt of the second eluting enantiomer included Compound ID No. 157. Based on its lower potency at hNET relative to the first-eluting enantiomer (Compound ID No. 167), the configuration was assigned as (1R,2R). $^1$H NMR spectroscopic data and MS analysis were consistent with the proposed structure.

Example 158—Synthesis of Compound ID No. 158 ((1S,2S)-2-(3,4-dichlorophenyl)-1-(2-ethylphenyl)-3-(methylamino)propan-1-ol)

To a stirred solution of the 2-(3,4-dichlorophenyl)acetonitrile (2.80 g, 15.1 mmol) in dry THF (30 mL) at −78° C. was added drop-wise n-BuLi (6.1 mL, 15.1 mmol, 2.5 M in hexanes). After 20 minutes stirring, a solution of the 2-ethylbenzaldehyde (2.02 g, 15.1 mmol) in THF (15 mL) was added drop-wise (color fades). After 30 minutes stirring, a solution of acetic acid (1.05 mL, 18.3 mmol) in THF (3 mL) was added drop-wise. After stirring the resulting clear solution for 15 minutes, the borane-tetrahydrofuran complex (52.0 mL, 52.0 mmol, 1 M in THF) was added drop-wise, the dry ice bath was removed, and the mixture was allowed to warm to room temperature (gas evolution observed) and then was heated at mild reflux for 2 hours. The mixture was chilled to 0° C. with an ice bath, and 2 N HCl (30 mL) was cautiously added drop-wise. The ice bath was removed, and the mixture was heated at mild reflux for 2 hours and cooled. The volatiles were removed in vacuo, and the resulting white suspension was diluted with chloroform (150 mL) and water (10 mL) and cooled to 0° C. The vigorously stirred mixture was made basic by drop-wise addition of 2 N NaOH. The layers were separated, the aqueous layer extracted with chloroform (2×), and the organics were combined, washed with half-saturated brine, and dried over $MgSO_4$. Concentration to dryness afforded crude white amorphous solid product (5.0 g), which was used as such.

To a stirred ice-cooled solution of the above crude product (3-amino-2-(3,4-dichlorophenyl)-1-(2-ethylphenyl)propan-1-ol, 5.0 g, 15.42 mmol) and $Et_3N$ (3.1 mL, 22.24 mmol) in $CH_2Cl_2$ (80 mL) was added drop-wise a solution of ethyl chloroformate (1.9 mL, 20 mmol) in $CH_2Cl_2$ (20 mL). The mixture was stirred for 2 hours and concentrated to near dryness in vacuo, and the residue partitioned between ether and aqueous sodium bicarbonate. The aqueous phase was extracted with ether (2×), and the organics were combined, washed with brine, dried over $MgSO_4$, and concentrated to give crude product (4.8 g) as a white amorphous solid. This was subjected to chromatography (ISCO 220 g) eluting with a 0-50% EtOAc/hexanes gradient to give in order 2 g of syn isomer followed by 2 g of anti isomer.

To the stirred ice-cooled borane tetrahydrofuran complex (17 mL, 17.0 mmol) was added drop-wise a solution of the anti-fraction described above (2.0 g, 5.05 mmol) in dry THF. The mixture was warmed to room temperature and heated at mild reflux for 3 hours. The clear solution was chilled with an ice bath and cautiously treated with drop-wise addition of 3 N HCl (10 mL). The resulting solution was warmed to room temperature and heated at reflux for 2 hours. The volatiles were removed by concentration in vacuo, and the residue was partitioned between water (15 mL) and chloroform (60 mL), cooled in an ice bath, and made basic with drop-wise addition of 2 N NaOH. The layers were separated, and the aqueous phase was extracted with chloroform (2×). The combined organic layers were washed with half-saturated brine and dried over MgSO$_4$. The resulting crude product (2 g) was subjected to flash chromatography on silica, eluting with chloroform, then 0-3% MeOH/chloroform (ammoniated) to give 1.6 g of purified anti isomer. This racemate was subjected to SFC to give a first-eluting enantiomer (650 mg) followed by a second-eluting enantiomer enantiomer (650 mg). P1 and P2 were separately taken in 12 mL of ether, to approximately half of each free base enantiomer solution. The other half was concentrated and saved. HCl/MeOH (15% solution) was added until acidic, and the mixture was allowed to stand at room temperature. The resulting solids were collected, washed with fresh ether, and dried in vacuo to give the respective HCl salts. The HCl salt of the second-eluting enantiomer included Compound ID No. 158. Based on its potency at hNET (6 nM), an (1S,2S)-configuration was assigned. $^1$H NMR spectroscopic data and MS analysis were consistent with the proposed structure.

Example 159—Compound ID No. 159 ((1S,2S)-2-(3,4-dichlorophenyl)-1-(3-ethylphenyl)-3-(methylamino)propan-1-ol)

2-(3,4-dichlorophenyl)acetonitrile (5.8 g, 30 mmol) was dissolved in ether (35 mL)/THF (15 mL) and cooled to −78° C. n-BuLi (20.9 mL, 33.5 mmol, 1.6 M in hexanes) was added slowly, and the reaction was stirred at −78° C. for 20 minutes. 3-bromobenzaldehyde (6.20 g, 33.5 mmol) in THF (15 mL) was added drop-wise, maintaining the temperature under −60° C. After the addition, the reaction was stirred at −75° C. for another hour. Then, acetic acid (2.6 mL, 46 mmol) was added at −75° C. to quench the reaction. The reaction mixture was warmed to room temperature, and the organic layer was separated from the aqueous layer. The aqueous layer was extracted with Ether (100 mL×3), and the combined organic layer was dried through MgSO$_4$ and evaporated to give an orange oil (12.9 g), which was used for the next step directly without further purification, assuming 30 mmol of the product.

The above crude product was dissolved in THF (55 mL) and preheated to 76° C. A solution of borane-methyl sulfide complex (52.5 mL, 105 mmol) in THF was added drop-wise over 30 minutes, and a Dean-Stark trap was set up to collect liberated Me$_2$S. Twelve hours after the addition, LCMS indicated near complete reaction. The reaction mixture was cooled in a cold water bath and quenched by slow addition of MeOH (20 mL), maintaining the temperature under 25° C. After gas evolution ceased, the reaction mixture was heated to 64° C. for 10-15 minutes when the B(OMe)$_3$-MeOH complex was collected in a Dean-Stark trap. The reaction mixture was concentrated to give a pale-yellow oil. The pale-yellow oil was dissolved in 200 mL of CH$_2$Cl$_2$, washed with sat. aq. NaHCO$_3$, washed with brine, dried with MgSO$_4$, and concentrated to a volume of approx. 100 mL for the next step.

The aminoalcohol product of the previous step, (3-amino-1-(3-bromophenyl)-2-(3,4-dichlorophenyl)propan-1-ol, 11.25 g, 30 mmol), was diluted in CH$_2$Cl$_2$ (100 mL) and combined with Et$_3$N (6.3 mL, 45 mmol). The reaction mixture was cooled to 0° C., and ethyl carbonochloridate (3.5 mL, 36 mmol) was added slowly at 0° C. After the addition, the reaction was stirred at room temperature for several hours. Three hours later, LCMS indicated near complete reaction, and the mixture was washed with 0.5 N HCl (150 mL), sat. NaHCO$_3$ (100 mL), and water (100 mL), and dried over MgSO. Filtration and concentration in vacuo afforded a pale-yellow oil. The pale-yellow oil was purified by silica gel chromatography and eluted with 0-100% EtOAc in Hexane to give two desired collections: anti-isomer (second-eluting 4.70 g, 3-step yield: 35%, 95% purity), and the syn-isomer collection (first-eluting, 5.16 g, 3-step yield: 38.5%, 95% purity).

The second fraction (anti-isomer, ethyl (2RS,3RS)-3-(3-bromophenyl)-2-(3,4-dichlorophenyl)-3-hydroxypropylcarbamate, 4.60 g, 10.3 mmol) in THF (50 mL) was pre-heated at 76° C. A solution of BH$_3$-THF (25.7 mL, 25.7 mmol, 1 M in THF) was added drop-wise over 15 minutes. Six hours after the addition, LCMS indicated near complete reaction, and the mixture was cooled to room temperature and stirred overnight. The reaction mixture was cooled in a cold water bath and was treated with 5 mL HCl and then 10 mL of MeOH slowly to quench extra BH$_3$, maintaining the temperature under 25° C. After gas evolution had ceased, the reaction mixture was heated to 64° C. for 10-15 minutes and then concentrated to a pale-yellow oil. The reaction mixture was concentrated to give a yellow gum. This residue was stirred in CHCl$_3$ (100 mL)/sat. NaHCO$_3$ for 10 minutes, the organic layer was separated, and the aqueous layer was extracted with CHCl$_3$ (20 mL×2). The combined organic layers were dried over MgSO$_4$ and evaporated to give a yellow oil, which was added to a silica gel column and eluted with 0-10% MeOH in CH$_2$Cl$_2$ to give the desired product (2.69 g).

The above product ((1RS,2RS)-1-(3-bromophenyl)-2-(3,4-dichlorophenyl)-3-(methylamino)propan-1-ol, 920 mg, 2.36 mmol), triethylborane (7.09 mL, 7.09 mmol), PdCl$_2$ (dppf) (173 mg, 0.24 mmol), and K$_2$CO$_3$ (1307 mg, 9.46 mmol) were combined in acetonitrile (8 mL) and refluxed at 85° C. overnight. After 16 hours, the reaction mixture was diluted with 200 mL CH$_2$Cl$_2$, washed with half-sat. NaHCO$_3$, water, and brine, dried over MgSO$_4$, and evaporated to give a dark-brown gum. The dark-brown crude product was added to a silica gel column and was eluted with 0-5% ammoniated MeOH in CH$_2$Cl$_2$ to give a brown oil. Due to difficult separation, this chromatographic purification was repeated two more times. A pure fraction was isolated (115 mg, 95% purity based on $^1$H NMR and LCMS). This material was subjected to SFC separation (ADH column, 9% EtOH with 0.5% isopropylamine). The first-eluting enantiomer required some additional purification and was chromatographed with 0-5% ammoniated MeOH in CH$_2$Cl$_2$. The relevant fractions were collected and concentrated. The residue was diluted with 2 mL of CH$_2$Cl$_2$, and 0.5 mL of 2M HCl in ether was added, and then the residue was concentrated in vacuo to give the HCl salt of the first-eluting enantiomer as a white solid (25.6 mg, 20.1% recovery).

The second-eluting enantiomer was purified in exactly the same manner. Compound ID No. 159 included the HCl salt of the second-eluting enantiomer (white solid, 31.1 mg, 24.4% recovery). Since the Compound ID No. 159 was more potent at hNET than the first-eluting enantiomer, Compound ID No. 159 was assigned the (1S,2S)-configuration. $^1$H NMR spectroscopic data and MS analysis were consistent with the proposed structure.

Example 160—Synthesis of Compound ID No. 160 ((1S,2S)-2-(3,4-dichlorophenyl)-1-(2-methoxyphenyl)-3-(methylamino)propan-1-ol)

2-(3,4-dichlorophenyl)acetonitrile (4.52 g, 24.3 mmol) was taken up in ether (30 mL) and THF (30 mL) and cooled to −78° C. n-BuLi (16.4 mL, 26.2 mmol, 1.6 M in hexane) was added drop-wise, maintaining the temperature below −60° C., and the mixture was allowed to stir for 15 minutes. 2-methoxybenzaldehyde (3.31 g, 24.3 mmol) dissolved in THF (20 mL) was added slowly drop-wise to maintain the temperature below −55° C. After stirring for 1 hour at −75° C., the reaction was quenched by addition of acetic acid (2.1 mL, 36 mmol) dissolved in 5 mL of diethyl ether, maintaining internal temperature below −55° C. The reaction was worked up by adding 100 mL of water, separating the layers, and extracting the aqueous phase two times with EtOAc. The combined organic layers were washed with sat. aq. $NaHCO_3$, dried with $MgSO_4$, filtered, and evaporated to a thick clear, pale yellow oil (7.6 grams). This residue was dissolved in $CH_2Cl_2$, 50 grams of silica gel was added, and the mixture was evaporated to dryness. The solid dispersion was split into two equal portions and ran through two separate 80 gram ISCO columns eluting with 0-60% EtOAc/Hexane. Two fractions were isolated that contained diastereomeric mixtures of the desired product. These were combined to give the desired product 2-(3,4-dichlorophenyl)-3-hydroxy-3-(2-methoxyphenyl)propanenitrile (6.80 g, 87%).

This material was dissolved in THF (185 mL) and added to a 500 mL flask fitted with a Dean Stark trap and condenser. The solution was heated to 75° C., and to this colorless solution was added, via gas tight syringe in several portions, the borane-methyl sulfide complex (26.4 ml, 52.8 mmol). Bubbling occurred with each addition. The reaction was heated to 75° C., which produced a mild reflux. After 4 hours reflux, the reaction was worked up by cooling to 0° C., upon which 4 M HCl in dioxane (9 mL) was added, followed by the very slow addition of MeOH (20 mL). After copious gas evolution had ceased, the reaction was heated to 75° C. for 30 minutes, collecting and disposing of the distillate through the Dean Stark trap. The reaction was then cooled to room temperature and concentrated in vacuo. The residue was dissolved in $CH_2Cl_2$ and shaken with 10% aq. $NaHCO_3$. These layers were separated, the aqueous phase was extracted with two more equal portions of $CH_2Cl_2$, and the combined organic layers were dried with $MgSO_4$, filtered, and evaporated to a yellow foamy oil (3-amino-2-(3,4-dichlorophenyl)-1-(2-methoxyphenyl)propan-1-ol, 6.85 g, 99%).

This material was dissolved in $CH_2Cl_2$ (110 mL), $Et_3N$ (4.39 mL, 31.5 mmol) was added, and the reaction mixture was cooled to 0° C. Ethyl carbonochloridate (2.42 mL, 25.2 mmol) was added slowly at 0° C. After the addition, the reaction was stirred at room temperature for 1.5 hours. LCMS confirmed near complete reaction, and the reaction was worked up by diluting with 150 mL of $CHCl_3$, 75 mL of sat. aq. $NaHCO_3$, and water (125 mL). This mixture was shaken several times, and then the layers were separated. The aqueous phase was extracted with two more equal portions of $CHCl_3$. All organics were combined, dried with $MgSO_4$, filtered, and evaporated to a yellow foamy oil (9.42 g). The residue was dissolved in $CH_2Cl_2$ and absorbed onto about 100 g of silica gel. This solid dispersion was portioned in half, and half was run through two 80 gram normal phase ISCO columns. Careful separation resulted in a pure antisample (2.72 g).

This material (ethyl (2RS,3RS)-2-(3,4-dichlorophenyl)-3-hydroxy-3-(2-methoxyphenyl)propylcarbamate, 2.72 g, 6.83 mmol) and 50 mL THF were transferred to a 500 mL flask equipped with a magnetic stirrer, addition funnel, thermometer, and Dean-Stark trap fitted with a condenser and nitrogen inlet. A solution of borane-methyl sulfide complex (17.1 mL, 34.1 mmol) was added slowly, and the solution was heated to reflux (75° C.). Dimethyl sulfide was removed from the Dean-Stark trap over 30 minutes, and then the reaction was allowed to heat at that temperature for an additional hour. Another 10 mL of borane-methyl sulfide complex was added, dimethyl sulfide was removed from the Dean-Stark trap over 30 minutes, and the reaction was allowed to heat at 75° C. on a timer for 18 hours and then allowed to sit at room temperature for the rest of the weekend. LCMS indicated near complete reaction, and the reaction was quenched by addition of MeOH (15 mL), followed by 4M HCl in dioxane (5 mL) After stirring for 20 minute, volatiles were removed in vacuo. The residue was taken back up in $CH_2Cl_2$ (200 mL), sat. sodium carbonate (50 mL), and water (50 mL). The layers were separated, and the organic phase was extracted three times with $CH_2Cl_2$. All organics were combined, dried with $MgSO_4$, filtered, and evaporated. The residue was taken up in $CHCl_3$ and absorbed onto silica gel. Separation with an 80 gram normal phase ISCO column and 0-20% MeOH/$CHCl_3$ as the eluent afforded the product in high purity (1.24 g).

A portion of this material (450 mg) was submitted for SFC separation. The two enantiomeric fractions were returned, concentrated in vacuo, redissolved in $CHCl_3$, and washed with 10% $NaHCO_3$. The aq. layer was back extracted with $CHCl_3$, and the combined layers were dried over $MgSO_4$ and evaporated to clear oils. Each was dissolved in ether, to which 2 M HCl in ether was added, and the sample concentrated in vacuo to give solids. The first-eluting enantiomer HCl included 215 mg, and the second-eluting enantiomer HCl salt, which is Compound ID No. 160 included 220 mg. Based on the greater hNET potency of Compound ID No. 160 relative to the first-eluting enantiomer, (1S,2S)-configuration was assigned. $^1H$ NMR and MS spectral data were consistent with the proposed structure.

Example 161—Synthesis of Compound ID No. 161 ((1R,2S)-1-(3-bromophenyl)-2-(3,4-dichlorophenyl)-3-(methylamino)propan-1-ol)

2-(3,4-dichlorophenyl)acetonitrile (5.78 g, 30.5 mmol) was dissolved in ether (35 mL)/THF (15 mL) and cooled to −78° C. n-BuLi (20.9 mL, 33.5 mmol) was added slowly, and the reaction was stirred at −78° C. for 20 minutes. 3-bromobenzaldehyde (6.20 g, 33.5 mmol) in THF (15 mL) was added drop-wise, maintaining the temperature under −60° C. After the addition, the reaction was stirred at −78° C. for another hour. The reaction was quenched by the addition of acetic acid (2.6 mL, 46 mmol)−78° C. and was warmed to room temperature, and the organic layer was separated from the aqueous layer. The aqueous layer was extracted with ether (100 mL×3), and the combined organic layers were dried over $MgSO_4$ and evaporated to give an orange oil, which was used for next step directly without further purification, assuming <30 mmole of the product.

This material, (3-(3-bromophenyl)-2-(3,4-dichlorophenyl)-3-hydroxypropanenitrile, 12.9 g, 30 mmol) in THF (55 mL) was preheated at 76° C., and a solution of borane-methyl sulfide complex (52.5 mL, 105 mmol) in THF was added drop-wise over 30 minutes. A Dean-Stark trap was set up to collect liberated $SMe_2$. Twelve hours after the addition, LCMS indicated near complete reaction, and the reaction mixture was cooled in a cold water bath and quenched by slow addition of 4M HCl in dioxane (10 mL) and 20 mL of MeOH, maintaining the temperature under 25° C. After gas evolution had ceased, the reaction mixture was heated to 64° C., and the $B(OMe)_3$-MeOH complex was collected in a Dean-Stark trap. The reaction mixture was concentrated to give a pale-yellow oil, diluted in 200 mL of CH$_2$Cl$_2$, basified with sat. NaHCO$_3$, washed with brine, dried over MgSO$_4$, and concentrated to about 100 mL for the next step directly without further purification, assuming the product <30 mmoles.

This material (3-amino-1-(3-bromophenyl)-2-(3,4-dichlorophenyl)propan-1-ol, 11.25 g, 30 mmol) was diluted in CH$_2$Cl$_2$ (100 mL) at room temperature, and Et$_3$N (6.27 mL, 45.00 mmol) was added. The reaction mixture was cooled to 0° C., and ethyl carbonochloridate (3.5 mL, 36 mmol) was added slowly at 0° C. After the addition, the reaction was stirred at room temperature. After three hours, LCMS confirmed a near complete reaction. The reaction was worked up by washing with 0.5 N HCl (150 mL), sat NaHCO$_3$ (100 mL), and water (100 mL), dried through MgSO$_4$, and then evaporated to give a pale yellow oil. This residue was added to a silica gel column and was eluted with 0-100% EtOAc in Hexane to separate the diastereoisomers. The syn-isomer eluted first and was evaporated to give a pale-yellow oil (5.16 g, 3-step yield: 38.5%, 95% purity). The anti-isomer eluted second and was evaporated to give a pale-yellow oil (4.70 g, 3-step yield: 35%, 95% purity).

The syn isomer (ethyl (2RS,3SR)-3-(3-bromophenyl)-2-(3,4-dichlorophenyl)-3-hydroxypropylcarbamate, 5.1 g, 11.41 mmol) in THF (60 mL) was preheated at 76° C., and borane-methyl sulfide complex (5.4 mL, 57 mmol) in THF (20 mL) was added drop-wise over 30 minutes. A Dean-Stark trap was set up to collect liberated SMe$_2$. After the reaction was refluxed for 24 hours, it was cooled to room temperature, and LCMS indicated nearly complete conversion.

The reaction mixture was cooled in a cold water bath and was quenched with 4M HCl in Dioxane (5 mL) followed by MeOH (30 mL), maintaining the temperature under 25° C. After the copious gas evolution ceased, the reaction mixture was heated to 64° C., and the B(OMe)$_3$-MeOH complex was collected in a Dean-Stark trap. The reaction mixture was concentrated to give a yellow gum as a HCl salt of the desired product. The HCl salt was stirred in CHCl$_3$ (200 mL)/sat. NaHCO$_3$ for 10 minutes, the organic layer separated, and the aqueous layer extracted with CHCl$_3$ (50 mL×2). The combined CHCl$_3$ layer was dried through MgSO$_4$ and evaporated to give a yellow oil. The yellow oil was added to a silica gel column and was eluted with 0-5% MeOH in CH$_2$Cl$_2$ to afford the desired product (3.79 g, 85% yield, 95% purity). A sample (308 mg) of this material was subjected to SFC separation (ADH column, 20% EtOH with 0.5% isopropylamine), and two enantiomeric fractions were collected. The first-eluting enantiomer contained a significant amount of unknown contaminant from SFC system ($^1$H NMR) and was purified by acidification with TFA (2 mL) for 5 minutes, neutralized with 1 N NaOH (15 mL×2), dried through MgSO$_4$, and concentrated to a yellow oil. The yellow oil was purified by silica gel chromatography, eluting with 0-5% ammoniated MeOH in CH$_2$Cl$_2$ to give the desired product, as a colorless gel. This material was diluted with 2 mL of CH$_2$Cl$_2$, 0.5 mL of 2 M HCl in ether was added, and the material was then concentrated in vacuo to give its HCl salt, as a white solid (111.3 mg, 33% recovery, 98% purity). This HCl salt of the first-eluting enantiomer included Compound ID No. 161. $^1$H NMR and MS data were consistent with the proposed structure. The second-eluting enantiomer was purified and converted to its HCl salt in exactly the same manner (110.6 mg, 32.8% recovery, 98% purity). Since the first-eluting enantiomer (Compound ID No. 161) was more potent at hNET than the second-eluting enantiomer, the (1R,2S)-configuration was assign to Compound ID No. 161.

Example 162—Synthesis of Compound ID No. 162 ((1R,2R)-1-(3-bromophenyl)-2-(3,4-dichlorophenyl)-3-(methylamino)propan-1-ol hydrochloride)

Compound ID No. 162 is the enantiomer of the compound in Example 76. The combined fractions of the first eluting enantiomer were concentrated in vacuo and converted to an HCl salt, which afforded 31 mg of Compound ID No. 162, which was shown by the described SCF system to have 99% enantiomeric excess. $^1$H NMR (300 MHz, CDCl$_3$) δ 7.38 (t, J=1.6 Hz, 1H), 7.29 (ddd, J=8.5, 1.3, 1.2 Hz, 1H), 7.25 (d, J=5.1 Hz, 1H), 7.13 (d, J=2.1 Hz, 1H), 7.02 (t, J=7.8 Hz, 1H), 6.89 (d, J=7.6 Hz, 1H), 6.82 (dd, J=8.2, 2.1 Hz, 1H), 4.91 (d, J=8.0 Hz, 1H), 3.19 (dd, J=12.1, 9.8 Hz, 1H), 3.01 (dd, J=12.4, 3.1 Hz, 1H), 2.85 (dd, J=7.9, 3.1 Hz, 1H), 2.50 (s, 3H). Since this enantiomer was less potent at hNET than the first-eluting enantiomer, it was presumed to be (1R,2R)-configured.

Example 163—Synthesis of Compound ID No. 163 ((1R,2S)-2-(3,4-dichlorophenyl)-3-(methylamino)-1-(3-(methylthio)phenyl)propan-1-ol hydrochloride)

Compound No. 163c (5.1 g, 12.31 mmol) in THF (60 mL) was preheated at 76° C. for gentle-refluxing. Borane•dimethylsulfide complex (5.84 mL, 61.54 mmol) was added drop-wise over 30 minutes, and a Dean-Stark trap was set up to collect liberated SMe$_2$. The material was refluxed overnight and cooled to room temperature. The reaction mixture was cooled in a cold water bath and treated with 4M HCl in dioxane (5.0 mL) to generate a HCl salt. Then 30 mL of MeOH was added slowly to quench extra BH$_3$, maintaining the temperature under 25° C. Gas bubbles were formed as MeOH was added. The reaction mixture was heated to 64° C. (to make sure all of BH$_3$ was quenched) for three hours when the B(OMe)$_3$-MeOH complex was collected in a Dean-Stark trap. The reaction mixture was concentrated to give a white solid as an HCl salt of the desired product. The HCl salt was stirred in CHCl$_3$ (100 mL)/NaHCO$_3$ (saturated) for 10 minutes, the organic layer was separated from the aqueous, and the aqueous layer was extracted with CHCl$_3$ (20 mL×2). The combined CHCl$_3$ layer was dried over MgSO$_4$ and evaporated to give a yellow stinky oil. The yellow oil was added to a silica gel column and was eluted with 0-10% MeOH in CH$_2$Cl$_2$. The collected fractions gave the crude racemate as a colorless gel 3.43 g (78% yield). The racemate was separated into its component enantiomers using SFC (ADH column, 20% EtOH with 0.5% dimethylethylamine) resulting in enantiomer retention times of 7.3 and 9.4 minutes, respectively. The combined fractions of the first eluting enantiomer were concentrated in vacuo and acidified in the usual way yielding 100 mg of Compound ID No. 163 as an HCl salt, which was shown by the SCF system to have >95% enantiomeric excess. $^1$H NMR (300 MHz, CDCl$_3$) δ 7.28 (d, J=8.4 Hz, 1H) 7.05-7.21 (m, 3H) 6.93 (s, 1H) 6.89 (d, J=8.0 Hz, 1H) 6.82 (d, J=7.2 Hz, 1H) 4.91 (br. s., 1H) 3.12-3.26 (m, 1H) 2.75-2.94 (m, 2H) 2.37 (s, 6H). Since this compound was the more potent syn-enantiomer at hNET, it was presumed to be (1R,2S)-configured.

Example 163a—Synthesis of Compound No. 163a ((2RS,3SR)-2-(3,4-dichlorophenyl)-3-hydroxy-3-(3-(methylthio)phenyl)propanenitrile)

2-(3,4-dichlorophenyl)acetonitrile (5.8 g, 30.55 mmol) was dissolved in THF (15 mL) and diethyl ether (35 mL)

then cooled to −75° C. n-Butyl lithium (13.44 mL, 33.61 mmol) was added slowly, and the reaction was stirred at −75° C. for 20 minutes. 3-(methylthio)benzaldehyde (5.12 g, 33.61 mmol) in THF (15 mL) was added drop-wise, maintaining the temperature under −70° C. After the addition, the reaction was stirred at −75° C. for another hour. Then, acetic acid (2.62 mL, 45.83 mmol) was added at −75° C. to quench the reaction. The reaction mixture was warmed to room temperature and diluted with saturated NaHCO$_3$ (50 mL), and the organic layer was separated from the aqueous layer. The aqueous layer was extracted with ether (100 mL×2), and the combined organic layer was dried through MgSO$_4$ and evaporated to give an oil, which was used in the next step without further purification. $^1$H NMR data matched the proposed structures.

Example 163b—Synthesis of Compound No. 163b ((1RS,2SR)-3-amino-2-(3,4-dichlorophenyl)-1-(3-(methylthio)phenyl)propan-1-ol)

Compound No. 163a (10.15 g, 30 mmol) in THF (55 mL) was preheated at 76° C. for gentle refluxing. The solution of borane dimethyl sulfide complex (45.0 mL, 90.0 mmol) in THF was added drop-wise over 15 minutes, and a Dean-Stark trap was set up to collect liberated dimethylsulfide. The reaction was allowed to stir while heating for 4 hours. Upon cooling, the reaction mixture was cooled in a cold water bath and quenched with extra BH$_3$ with 20 mL of MeOH slowly, maintaining the temperature under 25° C. Gas bubbles were formed as MeOH was added. The reaction mixture was heated to 64° C. (to make sure all of BH$_3$ was quenched) for 10-15 minutes when the B(OMe)$_3$-MeOH complex was collected in a Dean-Stark trap. The reaction mixture was concentrated to give a pale-yellow foam as the desired product which was used in the next step without further purification. $^1$H NMR data matched the proposed structures.

Example 163c—Synthesis of Compound No. 163c (ethyl((2RS,3SR)-2-(3,4-dichlorophenyl)-3-hydroxy-3-(3-(methylthio)phenyl)propyl)carbamate)

Compound No. 163b (11.36 g, 30.0 mmol) was diluted in CH$_2$Cl$_2$ (100 mL) at room temperature, and TEA (12.54 mL, 90.0 mmol) was added. The reaction mixture was cooled to 0° C. Ethyl chloroformate (3.46 mL, 36.00 mmol) was added slowly at 0° C. After the addition, the reaction was stirred at room temperature for several hours. The reaction was washed with 0.5 N HCl (150 mL), saturated NaHCO$_3$ (100 mL), and water (100 mL), dried over MgSO$_4$, and then evaporated to give a yellow oil. The yellow oil was added to a silica gel column and was eluted with 0-100% EtOAc in hexane to give three fractions: anti isomer, syn isomer, and an unknown. The anti isomer fraction was evaporated to give a pale-yellow oil (4.85 g), and the desired syn-isomer fraction was evaporated to give a pale-yellow oil (5.14 g). The syn isomer was taken on to the next step without further purification. $^1$H NMR data matched the proposed structures.

Example 164—Synthesis of Compound ID No. 164 ((1S,2S)-2-(3,4-dichlorophenyl)-1-(2-iodophenyl)-3-(methylamino)propan-1-ol)

To a stirred solution of 2-(3,4-dichlorophenyl)acetonitrile (2.80 g, 15.1 mmol) in dry THF (30 mL) at −78° C. (dry ice-acetone bath) was added drop-wise the n-BuLi (canary yellow solution). After 20 minutes stirring at −78° C., a solution of the 2-iodobenzaldehyde (3.49 g, 15.1 mmol) in THF (15 mL) was added drop-wise (color fades). After 30 minutes stirring at −78° C., a solution of acetic acid (1.05 mL, 18.3 mmol) in THF (3 mL) was added drop-wise. After stirring the resulting clear solution for 15 minutes, borane-tetrahydrofuran complex (52.0 mL, 52.0 mmol, 1 M in THF) was added drop-wise, the dry ice bath was removed, and the mixture was allowed to warm to room temperature (gas evolution observed) and then heated at mild reflux for 2 hours. The mixture was then cooled with an ice bath, and the reaction was quenched by the addition of 2 N HCl (30 mL, drop-wise). The ice bath was removed, and the mixture was heated at mild reflux for 2 hours and then cooled. The volatiles were removed on rotovap, and the resulting white suspension was diluted with chloroform (250 mL), cooled to 0° C., and vigorously stirred with 1N NaOH. The layers were separated, the aqueous layer was extracted with chloroform (2×), and the organics were combined, washed with half-saturated brine, and dried over MgSO$_4$. Concentration to dryness afforded a white amorphous solid (6.30 g), which was used below.

To a stirred ice-cooled solution of this material (3-amino-2-(3,4-dichlorophenyl)-1-(2-iodophenyl)propan-1-ol, 6.30 g, 14.9 mmol) and Et$_3$N (3.1 mL, 22 mmol) in CH$_2$Cl$_2$ (80 mL) was added drop-wise a solution of ethyl chloroformate (1.9 mL, 20 mmol) in CH$_2$Cl$_2$ (20 mL). The mixture was stirred for 2 hours and concentrated to near dryness on rotovap, and the residue was partitioned between ether and aqueous sodium bicarbonate. The aqueous phase was extracted with ether (2×), and the organics were combined, washed with brine, dried, and concentrated to give crude product (6.5 g) as a white amorphous solid. This material was subjected to chromatography (ISCO 220 g) eluting with a 0-50% EtOAc/hexanes gradient to give in order 3.7 g of syn isomer followed by 0.65 g of anti isomer.

To a stirred ice-cooled borane-tetrahydrofuran complex (6.0 mL, 6.0 mmol 1 M in THF) was added drop-wise a solution of the anti-carbamate described above (0.65 g, 1.3 mmol) in dry THF. The mixture was warmed to room temperature and heated at mild reflux for 3 hours. The clear solution was chilled with an ice bath and cautiously quenched by drop-wise addition of 3 N HCl (10 mL). The resulting solution was warmed to room temperature and heated at reflux for 2 hours, the volatiles were removed on rotovap, diluted with water (15 mL) and chloroform (60 mL), cooled in an ice bath, and made basic with drop-wise addition of 2 N NaOH, and the layers separated. The aqueous phase was extracted with chloroform (2×), and the combined organics were washed with half-saturated brine and dried over MgSO$_4$. The resulting crude product (0.6 g) was subjected to flash chromatography on silica gel eluting with chloroform, then 0-3% MeOH/chloroform (ammoniated) to give 0.5 g of the pure racemic anti product. This material was subjected to SFC separation, which afforded the first-eluting enantiomer (200 mg) followed by the second-eluting enantiomer (220 mg). Both enantiomers had unrelated 8-10% impurity present (by 1H NMR) and were separately purified by LC to give 150 mg samples of both enantiomers. These were separately taken in 6 mL of ether, and 15% HCl in MeOH was added. The samples were concentrated in vacuo, and the resulting solids were triturated with ether, collected, and dried in vacuo to give the respective HCl salts (112.2 and 146 mg, respectively). Compound ID No. 164 included the second-eluting enantiomer HCl salt. Its $^1$H NMR and MS spectral data were consistent with the proposed structure. Based on the greater potency of Compound ID No. 164 at hNET to the first-eluting enantiomer, it was assigned the (1S,2S)-configuration.

Example 165—Synthesis of Compound ID No. 165 ((1R,2S)-2-(3,4-dichlorophenyl)-1-(3-iodophenyl)-3-(methylamino)propan-1-ol)

To a stirred solution of 2-(3,4-dichlorophenyl)acetonitrile (1.86 g, 10.0 mmol) in dry THF (20 mL) at −78° C. was added drop-wise n-BuLi (4.0 mL, 10 mmol, 2.5 M in hexanes). After 20 minutes stirring at −78° C., a solution of the 3-iodobenzaldehyde (2.32 g, 10.0 mmol) in THF (10 mL) was added drop-wise. After 30 minutes stirring at −78° C., a solution of acetic acid (0.720 mL, 12.5 mmol) in THF (2 mL) was added drop-wise. After stirring the resulting clear solution for 15 minutes, borane-tetrahydrofuran complex (35.0 mL, 35.0 mmol, 1 M in THF) was added drop-wise, the dry ice bath was removed, and the mixture was allowed to warm to room temperature (gas evolution observed) and then heated at mild reflux for 2 hours. The mixture was chilled to 0° C. with an ice bath, 2 N HCl (20 mL) was cautiously added drop-wise, the ice bath was removed, and mixture was heated at mild reflux for 2 hours. After cooling, the volatiles were removed on rotovap, and the white suspension was diluted with chloroform (150 mL), cooled to 0° C., and vigorously stirred with 1 N NaOH. The layers were separated, the aqueous layer was extracted with chloroform (2×), and the organics were combined, washed with half-saturated brine, and dried over $MgSO_4$. Concentration to dryness afforded a white amorphous solid (4.5 g), which was used as such below.

To a stirred ice-cooled solution of this material (3-amino-2-(3,4-dichlorophenyl)-1-(3-iodophenyl)propan-1-ol, 4.25 g, 10.1 mmol) and $Et_3N$ (2.09 mL, 15.0 mmol) in $CH_2Cl_2$ (60 mL) was added drop-wise a solution of ethyl chloroformate (1.25 mL, 13.0 mmol) in $CH_2Cl_2$ (10 mL). The mixture was stirred for 2 hours and concentrated to near dryness on rotovap. The residue was partitioned between ether and aqueous sodium bicarbonate and extracted with ether (2×), and the organics were combined, washed with brine, dried, and concentrated to give crude product (4.8 g) as a white amorphous solid. This was subjected to chromatography (ISCO 220 g) eluting with a 0-50% EtOAc/hexanes gradient to give in order purified "syn" isomer (2.0 g) followed by purified "anti" isomer (1.3 g) as amorphous syrupy solids.

The aforementioned syn isomer ethyl ((2RS,3SR)-2-(3,4-dichlorophenyl)-3-hydroxy-3-(3-iodophenyl)propylcarbamate, 2.0 g, 4.05 mmol) in 10 mL THF was added to the stirred ice-cooled borane tetrahydrofuran complex (15.0 mL, 15.0 mmol). The mixture was warmed to room temperature and heated at mild reflux for 3 hours. The clear solution was then chilled with an ice bath and cautiously quenched by the drop-wise addition of 3 N HCl (10 mL). The resulting solution was warmed to room temperature and heated at reflux for 2 hours, the volatiles were removed on rotovap, the aqueous phase was diluted with water (15 mL) and chloroform (60 mL), cooled in an ice bath and made basic with drop-wise addition of 2 N NaOH, and the layers were separated. The aqueous phase was extracted with chloroform (2×), and the combined organics were washed with half-saturated brine, dried, and concentrated in vacuo. The resulting crude product (1.1 g) was subjected to flash chromatography on silica eluting with chloroform, then 0-3% MeOH/chloroform (ammoniated) to give purified product (0.9 g). This material was subjected to SFC separation to give a first-eluting enantiomer (370 mg) and a second-eluting enantiomer (390 mg). These materials were separately taken in 12 mL of ether, and 15% HCl in MeOH was added until acidic. The resulting solids were collected, washed with fresh ether, and dried in vacuo to give the respective HCl salts. Compound ID No. 165 included the HCl salt of the first-eluting enantiomer. Based on its higher potency at hNET to the second-eluting enantiomer, it was assigned the (1R,2S)-configuration. $^1H$ NMR and MS spectral data were consistent with the proposed structure.

Example 166—Synthesis of Compound ID No. 166 ((1S,2S)-2-(3,4-dichlorophenyl)-1-(5-methoxypyridin-3-yl)-3-(methylamino)propan-1-ol hydrochloride)

Compound ID No. 166 is the enantiomer of the compound in Example 109. The combined fractions of the second eluting enantiomer were concentrated in vacuo and converted to an HCl salt, which afforded Compound ID No. 166. Since this enantiomer was more potent at hNET than the first-eluting enantiomer, it was presumed to be (1S,2S)-configured. $^1H$ NMR spectroscopic data and MS analysis were consistent with the proposed structure.

Example 167—Synthesis of Compound ID No. 167 ((1S,2S)-2-(3,4-dichlorophenyl)-1-(6-methoxypyridin-2-yl)-3-(methylamino)propan-1-ol)

Compound ID No. 167 is the first eluting enantiomer described in Example 157. It was assigned (1S,2S) configuration based on its higher potency at hNET relative to the second-eluting enantiomer (Compound ID No. 157). Spectral data were identical to that of Compound ID No. 157.

Example 168—Synthesis of Compound ID No. 168 ((1S,2S) or (1R,2R)-2-(3,4-dichlorophenyl)-1-(3-(dimethylamino)phenyl)-3-(methylamino)propan-1-ol)

The preparation of this compound is described in Example 108. Compound ID No. 168 is the first eluting enantiomer described in Example 108. The potencies of both compounds at hNET are similar, and it is not possible to assign absolute configuration to either.

Example 169—Synthesis of Compound ID No. 169 ((1R,2R)-1-(6-chloropyridin-3-yl)-3-(methylamino)-2-(naphthalen-2-yl)propan-1-ol)

The preparation of Compound ID No. 169 is described in Example 26, in which it is the first-eluting enantiomer. Based on its lower potency at hNET relative to Compound ID No. 26, it was assigned an (1R,2R)-configuration.

Example 170—Synthesis of Compound ID No. 170 ((1R,2S)-2-(3,4-dichlorophenyl)-3-(methylamino)-1-(2-(methylsulfonyl)phenyl)propan-1-ol hydrochloride)

To a solution of Compound No. 170a (95 mg, 0.19 mmol) in DCM was added drop-wise TFA (100 μL, 1.30 mmol). This solution was stirred at room temperature for 1 hour. The volatiles were then removed, and the resulting residue was taken in DCM (5 mL), made basic by shaking with excess saturated sodium bicarbonate, and extracted with DCM. The organics were concentrated to dryness to give the free base product. This was taken in ether (4 mL) and made acidic with HCl/MeOH, and concentrated to dryness. The residue was triturated with ether (2×), and the white solid was collected and dried in vacuo to give the product (52.1 mg, 64.6%). $^1$H NMR spectroscopic data and MS analysis were consistent with the proposed structure.

Example 170a—Synthesis of Compound No. 170a (tert-butyl tert-butyl((2R,3S)-2-(3,4-dichlorophenyl)-3-hydroxy-3-(2-(methylsulfonyl)phenyl)propyl)(methyl)carbamate)

To a stirred solution of Compound No. 170b (110 mg, 0.24 mmol) in THF and water at room temperature was added solid oxone (560 mg, 0.91 mmol). The mixture (with slight turbidity) was stirred at room temperature for 6 hours. The volatiles were then evaporated and diluted with DCM (15 mL). This mixture was made basic with addition of saturated sodium bicarbonate. The aqueous was extracted with DCM. The organic layer was separated, dried, and concentrated to give the crude product as a clear syrup (110 mg). This was subjected to ISCO chromatography (0-50% EtOAc/hexanes gradient) to give Compound No. 170a (100 mg, 85%) as a foamy solid. This compound was used in the next step without further purification. $^1$H NMR spectroscopic data and MS analysis were consistent with the proposed structure.

Example 170b—Synthesis of Compound No. 170b (tert-butyl ((2R,3S)-2-(3,4-dichlorophenyl)-3-hydroxy-3-(2-(methylthio)phenyl)propyl)(methyl)carbamate)

To a stirred, ice-cooled solution of Compound No. 170c (220 mg, 0.62 mmol) and triethylamine (0.095 mL, 0.68 mmol) in 4 mL DCM was added drop-wise a solution of Boc$_2$O (0.158 mL, 0.68 mmol) in DCM. The mixture was allowed to gradually warm to room temperature over 2 hours. The volatiles were then removed, and the resulting residue was dissolved in chloroform and subjected to ISCO chromatography (0-30% EtOAc/hexanes gradient) to give purified Compound No. 170b (220 mg, 78%). $^1$H NMR and MS spectral data were consistent with the proposed structure.

Example 170c—Synthesis of Compound No. 170c ((1R,2S)-2-(3,4-dichlorophenyl)-3-(methylamino)-1-(2-(methylthio)phenyl)propan-1-ol hydrochloride)

To a stirred solution of 2-(3,4-dichlorophenyl)acetonitrile (5.6 g, 30 mmol) in dry THF (60 mL) at −78° C. was added drop-wise the n-BuLi (2.5 M in hexanes, 12.0 mL, 1.0 equiv). After 20 minutes stirring at −78° C., a solution of the 2-(methylthio)benzaldehyde (3.9 mL, 30 mmol) in THF (20 mL) was added drop-wise. After 30 minutes stirring at −78° C., a solution of acetic acid (2.1 mL, 36.68 mmol) in THF (5 mL) was added drop-wise. After stirring the resulting clear solution for 15 minutes, the borane tetrahydrofuran complex (100 mL, 100 mmol) was added drop-wise, the dry ice bath was removed, and the mixture was allowed to warm to room temperature (gas evolution observed) and then heated at mild reflux for 2 hours. The mixture was chilled to 0° C., and 2N HCl (60 mL) was cautiously added drop-wise. The ice bath was removed, and the mixture was heated at reflux for 2 hours and then cooled. The volatiles were removed in vacuo. The suspension was diluted with chloroform (150 mL), cooled to 0° C., and vigorously stirred while making basic by drop-wise addition of 1 N NaOH. The layers were separated, the aqueous layer was extracted with chloroform (2×), and the organics were combined, washed with half-saturated brine, dried, and concentrated in vacuo to afford a white amorphous solid (10.3 g), which was presumed to be the primary amine. This material (10.3 g, 30.1 mmol) was combined with Et$_3$N (6.3 mL, 45 mmol) in DCM (140 ml) and was added drop-wise to a solution of ethyl chloroformate (3.8 mL, 40 mmol) in DCM (40 mL). The mixture was stirred for 2 hours and concentrated to near dryness on rotovap, and the residue was partitioned between ether and aqueous sodium bicarbonate and extracted with ether (2×). The organics were combined, washed with brine, dried, and concentrated to give crude ethyl carbamate (10 g) as a white amorphous solid. Approximately half was subjected to chromatography (ISCO 220 g column) eluting with a 0-50% EtOAc/hexanes gradient to give isomer 1 (1.0 g) followed by isomer 2 (1.6 g, used as such in the following step). Isomer 1 (1.0 g, 2.41 mmol) dissolved in THF (15 mL) was added drop-wise to the stirred ice-cooled borane tetrahydrofuran complex (10 mL, 10.00 mmol) in dry THF. The mixture was warmed to room temperature and then heated at mild reflux for 3 hours. The clear solution was chilled with an ice bath, and then 3N HCl (10 mL) was added drop-wise cautiously. The resulting solution was warmed to room temperature and heated at reflux for 2 hours. After removal of volatiles in vacuo, the aqueous suspension was diluted with water (15 mL) and chloroform (60 mL), cooled in ice bath, and made basic with drop-wise addition of 2N NaOH. The layers were separated, the aqueous layer was extracted with chloroform (2×), and the organics were washed with half-saturated brine, dried, and concentrated in vacuo. The resulting crude product (1.1 g) was subjected to flash chromatography on silica eluting with chloroform, then 0-3% MeOH/chloroform (ammoniated) to give 0.9 g of the purified racemic syn diastereomer. This material was submitted to SFC separation to give a first-eluting enantiomer (370 mg) followed by a second eluting enantiomer (320 mg). The first-eluting enantiomer was converted to the HCl salt. Based on its potency at hNET relative to it is enantiomer, it was presumed to be (1R,2S)-configured. $^1$H NMR spectroscopic data and MS analysis were consistent with the proposed structure.

Example 171—Synthesis of Compound ID No. 171 ((1R,2R)-2-(3,4-dichlorophenyl)-1-(2-methoxypyridin-3-yl)-3-(methylamino)propan-1-ol hydrochloride)

Compound No. 171c (1.2 g, 3.01 mmol) was dissolved in 15 mL THF, stirred, and heated to 80° C. To this colorless solution was added, via gas tight syringe in several portions, the borane reagent (1.0M in THF, 15.03 mL, 15.03 mmol). Bubbling occurred with each addition. The reaction was kept at a constant 80° C., which produced a mild reflux for 10 hours. Upon cooling, the reaction was quenched with careful addition of 5 mL of MeOH. After the bubbling subsided, 1 mL of 1.0M HCl in dioxane was added, and the mixture was heated to reflux for 15 minutes and then cooled to room temperature. The volatiles were evaporated on a rotary evaporator. 10% NaHCO$_3$ was added, and the aqueous layer was extracted three times with an equal volume of CH$_2$Cl$_2$. The organic extracts were combined, washed with water, dried with MgSO$_4$, filtered, and evaporated in vacuo. The crude was then immediately purified by chromatography (elution with 0-30% MeOH/CH$_2$Cl$_2$) giving a fraction (1.1 g) of the anti-pair of enantiomers as determined by the $^1$H-NMR analysis (large J-value of 6.7 Hz). 600 mg of the racemic anti-sample was submitted for SFC chiral separation, which gave enantiomer retention times of 6.32 and 6.42 minutes, respectively. The combined fractions of the second eluting enantiomer were concentrated in vacuo and acidified in the usual way yielding 100 mg of Compound ID No. 163 as an HCl salt, which was shown by the SCF system to have >99% enantiomeric excess. $^1$H NMR (500 MHz, CDCl$_3$) δ ppm 8.01 (dd, J=5.19, 2.14 Hz, 1H) 7.70 (dd, J=7.33, 1.83 Hz, 1H) 7.32 (d, J=1.83 Hz, 1H) 7.22-7.28 (m, 1H) 6.97 (dd, J=8.24, 2.14 Hz, 1H) 6.86 (dd, J=7.33, 4.88 Hz, 1H) 5.27 (d, J=6.71 Hz, 1H) 3.76 (s, 3H) 3.14-3.22 (m, 1H) 3.10 (ddd, J=7.48, 3.97, 3.82 Hz, 1H) 2.98 (dd, J=11.90, 3.36 Hz, 1H) 2.47 (s, 3H). Since this enantiomer is less potent at hNET than the first-eluting enantiomer, it was presumed to be (1R,2R)-configured.

Example 171a—Synthesis of Compound No. 171a (2-(3,4-dichlorophenyl)-3-hydroxy-3-(2-methoxypyridin-3-yl)propanenitrile)

A solution of 2-(3,4-dichlorophenyl)acetonitrile (2.92 g, 15.68 mmol) in 20 mL THF and 20 mL diethyl ether was placed under nitrogen in an oven dried round bottom flask with stirrer. After cooling to −75° C. in an acetone dry ice bath, butyllithium (6.77 mL, 16.93 mmol) (2.5 M in hexane) was added drop-wise. Internal temperature was monitored and maintained below −60° C. After the addition, the reaction was allowed to stir for 15 minutes. To this, 2-methoxynicotinaldehyde (2.15 g, 15.68 mmol) dissolved in 20 mL of THF was added drop-wise, maintaining the temperature below −60° C. The reaction mixture was allowed to stir for 1.5 hours at −75° C. and then quenched at the same temperature with a solution of acetic acid (1.346 mL, 23.52 mmol in 10 mL of THF), and the cold bath was removed. After adding 100 mL of water, the two layers were separated in a separatory funnel. The aqueous layer was extracted with ethyl acetate (3×). The combined organic layers were washed with brine, dried over MgSO$_4$, filtered, and evaporated in vacuo. The crude product was purified by chromatography (elution with ethyl acetate/CH$_2$Cl$_2$ 0-100%) to yield Compound No. 171a (4.64 g, 92%). $^1$H NMR spectroscopic data and MS analysis were consistent with the proposed structure.

Example 171b—Synthesis of Compound No. 171b (3-amino-2-(3,4-dichlorophenyl)-1-(2-methoxypyridin-3-yl)propan-1-ol)

Compound No. 171a was dissolved in 115 mL THF and heated to 80° C. in a 100 mL flask equipped with a stirrer and water condenser. To this colorless solution was added, via gas tight syringe in several portions, the borane reagent (28.7 mL, 28.72 mmol) as a 1.0 M solution in THF. The heating was allowed to continue which produced a gentle reflux for 5 hours. The reaction mixture was cooled and quenched with slow addition of MeOH (10 mL) Vigorous reaction occurred early in the addition and dissipated towards the end of the addition. The reaction mixture was then reheated to reflux for 30 minutes. After cooling to room temperature, 150 mL of 10% sodium bicarbonate in water was added, and the aqueous phase was extracted with CH$_2$Cl$_2$ three times. The organic layers were combined, washed with brine, dried with MgSO$_4$, filtered, evaporated, and dried to a clear, oily semi-solid (4.58 g) as a mixture of diastereomers. This mixture of diastereomers was carried on to the following step without any further purification.

Example 171c—Synthesis of Compound No. 171c (tert-butyl 2-(3,4-dichlorophenyl)-3-hydroxy-3-(2-methoxypyridin-3-yl)propyl)carbamate)

To a vigorously stirring mixture of Compound No. 171b (4.58 g, 14.00 mmol) and TEA (2.93 mL, 21.00 mmol) in 100 mL CH$_2$Cl$_2$ was added ethyl chloroformate (1.606 mL, 16.80 mmol) in one portion at room temperature. After stirring overnight, the reaction mixture was diluted with water (125 mL) and CH$_2$Cl$_2$ (150 mL). The organic layer was separated, and the aqueous phase was extracted with two more equal portions of CH$_2$Cl$_2$. All the organic layers were combined, dried with MgSO$_4$, filtered, and evaporated to a crude oil (5.56 g). This material was used in the next step without further purification. $^1$H NMR spectroscopic data and MS analysis were consistent with the proposed structure.

Example 172—Synthesis of Compound ID No. 172 (N-(3-((1R,2R)-2-(3,4-dichlorophenyl)-1-methoxy-3-(methylamino)propyl)phenyl)-1,1,1-trifluoromethanesulfonamide hydrochloride)

Compound No. 172b (20 mg, 0.03 mmol) was stirred in 3N HCl (MeOH/water=3:1; 1 mL) at room temperature for one hour. LCMS showed the desired product, and the reaction mixture was evaporated to dry to give 14.5 mg (0.029 mmol, 95%) of a foam-like solid as the desired product. $^1$H NMR (300 MHz, CD$_3$OD) δ 7.37 (d, J=8.3 Hz, 1H) 7.32 (d, J=7.5 Hz, 1H) 7.28 (br. s., 0H) 7.20-7.27 (m, 2H) 7.18 (br. s., 1H) 7.00 (dd, J=8.3, 1.9 Hz, 1H) 4.88 (d, J=9.4 Hz, 1H) 3.77 (dd, J=12.6, 8.1 Hz, 1H) 3.38-3.44 (m, 1H) 3.37 (s, 3H) 3.20 (td, J=8.5, 6.0 Hz, 1H) 2.74 (s, 3H). Since this enantiomer was less potent at hNET than the second-eluting enantiomer, it was presumed to be (1R,2R)-configured. $^1$H NMR spectroscopic data and MS analysis were consistent with the proposed structure.

Example 172a—Synthesis of Compound No. 172a (tert-butyl ((2R,3R)-3-(3-aminophenyl)-2-(3,4-dichlorophenyl)-3-methoxypropyl)carbamate)

Compound ID No. 24 (311 mg, 0.96 mmol) and TEA (0.147 mL, 1.05 mmol) in dichloromethane (4 mL)/MeOH (1 mL) were cooled to 0° C. Boc$_2$O (0.244 mL, 1.05 mmol) in dichloromethane (1 mL) was added into the above reaction mixture slowly. After the addition, the reaction was stirred at room temperature for several hours. The reaction mixture was diluted with CH$_2$Cl$_2$ (50 mL), washed with 1N NaOH (20 mL) and water (50 mL), dried through MgSO$_4$, and then evaporated to dryness. The crude product was added to a silica gel column and was eluted with 0-100% EtOAc in hexane to give a light-yellow gum as the desired product (261.8 mg, 64.4% yield, 98% purity). $^1$H NMR (300 MHz, CDCl$_3$) δ 7.30 (br. s., 1H) 7.26 (d, J=8.4 Hz, 1H) 7.00 (t, J=7.4 Hz, 2H) 6.50 (d, J=8.0 Hz, 1H) 6.54 (br. s., 2H) 4.72 (d, J=6.3 Hz, 1H) 3.43-3.97 (m, 4H) 3.22 (br. s., 1H) 2.54 (br. s., 3H) 1.36 (br. s., 9H).

Example 172b—Synthesis of Compound No. 172b (tert-butyl ((2R,3R)-2-(3,4-dichlorophenyl)-3-methoxy-3-(3-(trifluoromethylsulfonamido)phenyl)propyl)carbamate)

Compound No. 172a (261 mg, 0.61 mmol) and triethylamine (155 mg, 1.53 mmol) in dichloromethane (3 mL) were cooled to 0° C. Trifluoromethanesulfonic anhydride (277 mg, 0.98 mmol) was added into the above reaction mixture slowly and then allowed to be warmed to room temperature. The O-trifyl product was suspected and was hydrolyzed by the addition of a mixture of sodium hydroxide (2.454 mL, 6.14 mmol). MeOH (5 mL) was added into the reaction mixture above, and the mixture was stirred for 1 hour. The mixture was diluted with CH$_2$Cl$_2$ (100 mL), washed with water (100 mL×2), dried through MgSO$_4$, and evaporated to dryness. The crude product was added to a silica gel column and was eluted with 0-100% EtOAc in hexane to give a colorless gum as the desired product (152 mg) containing 20-30% unknown based on LC/MS and $^1$H NMR. The sample was submitted to SFC Chiral purification (ADH column, 20% iPrOH with 1% isopropylamine) The third-eluting peak was collected (20 mg, 0.035 mmol, retention time=7.65 minutes). The fourth-eluting peak was the enantiomer and was shown by the SCF system to have 94% enantiomeric excess.

Example 173—Human DAT (Dopamine Transporter) Uptake Assay Protocol

This protocol was designed to measure inhibition of uptake by the human dopamine transporter. The reagents were human DAT (HEK293F) cells, GBR 12909 (Sigma), nomifensine, neurotransmitter transporter uptake assay kit (Molecular Devices), freestyle 293 expression medium (Invitrogen), 10× Hank's Balanced Salt Solution (HBSS; Invitrogen), 1 M HEPES (Mediatech), Biocoat poly-D-lysine 96-well, black, clear plates (Becton, Dickinson), and 500 pt polypropylene U-bottom 96-well plates (Fisher). The Assay Buffer (AB) was 1×HBSS and 0.02 M HEPES.

The HEK293F cells were transfected with the human dopamine transporter and frozen in 1 mL aliquots at about 1E+07 cells/mL. On the day of the experiment, the cells were removed from −80° C. or liquid nitrogen and thawed in a room temperature water bath. The cells were dilute to about 1-2E+06 with Freestyle medium. A 1 mL sample (1:2 dilution) was prepared, and the cells were counted. The cells were spun at 1100 rpm for 5 minutes, and the medium was aspirated off. The cells were resuspend in medium at 1.5E+06 cells/mL for about 60,000 cells per well. 40 µL of cells were dispensed per well in the Biocoat plates. The plates were spun at 1100 rpm for 1 minute to improve homogeneity of the cell layer and were incubated at 37° C. for a minimum of 3 hours.

12 µL of test compound (10 mM) in DMSO was added to the wells, and nomifensine was used as a control. GBR 12909 (final assay concentration of 10 µM) was used for background signal. The neurotransmitter transporter dye was prepared in AB prior to use.

Data were analyzed by calculating percent effect: (a) [1-(singlicate minus plate background signal)/(plate total signal minus plate background)]×100%, (b) IC$_{50}$, and (c) K$_i$ using the Cheng-Prusoff equation below and an Activity-Base or XLfit template.

$$K_i = \frac{IC_{50}}{1 + ([dye]/K_m)}$$ where $K_m$ is the value for the dye (55.5% at 20 minute read)

Due to the proprietary nature of the dye formulation, all dye concentrations were expressed as a percentage of the vendor-recommended dye reconstitution. Thus, the above calculations were valid when both [dye] and K$_1$ were expressed in the same units (%). Compounds were tested in triplicate (n=3).

Example 174—Human NET (Norepinephrine Transporter) Uptake Assay Protocol

This protocol was designed to measure inhibition of uptake by the human norepinephrine transporter. The reagents were human NET (HEK293F) cells, desipramine (Sigma), nomifensine, neurotransmitter transporter uptake assay kit (Molecular Devices), freestyle 293 expression medium (Invitrogen), 10× Hank's Balanced Salt Solution (HBSS; Invitrogen), 1 M HEPES (Mediatech), Biocoat poly-D-lysine 96-well, black, clear plates (Becton, Dickinson), and 500 µL polypropylene U-bottom 96-well plates (Fisher). The Assay Buffer (AB) was 1×HBSS and 0.02 M HEPES.

The HEK293F cells were transfected with the human norepinephrine transporter and frozen in 1 mL aliquots at about 1E+07 cells/mL. On the day of the experiment, the cells were removed from −80° C. or liquid nitrogen and thawed in a room temperature water bath. The cells were dilute to about 1-2E+06 with Freestyle medium. A 1 mL sample (1:2 dilution) was prepared, and the cells were counted. The cells were spun at 1100 rpm for 5 minutes, and the medium was aspirated off. The cells were resuspend in medium at 1.5E+06 cells/mL for about 60,000 cells per well. 40 µL of cells were dispensed per well in the Biocoat plates. The plates were spun at 1100 rpm for 1 minute to improve homogeneity of the cell layer and were incubated at 37° C. for a minimum of 3 hours.

12 µL of test compound (10 mM) in DMSO was added to the wells, and nomifensine was used as a control. Desipramine (final assay concentration of 10 µM) was used for background signal. The neurotransmitter transporter dye was prepared in AB prior to use.

Data were analyzed by calculating percent effect: (a) [1-(singlicate minus plate background signal)/(plate total signal minus plate background)]×100%, (b) IC$_{50}$, and (c) K$_i$ using the Cheng-Prusoff equation below and an Activity-Base or XLfit template.

$$K_i = \frac{IC_{50}}{1 + ([dye]/K_m)}$$ where $K_m$ is the value for the dye (55.5% at 20 minute read)

Due to the proprietary nature of the dye formulation, all dye concentrations were expressed as a percentage of the vendor-recommended dye reconstitution. Thus, the above calculations were valid when both [dye] and K$_m$ were expressed in the same units (%). Compounds were tested in triplicate (n=3).

Example 175—Human SERT (Serotonin Transporter) Uptake Assay Protocol

This protocol was designed to measure inhibition of uptake by the human serotonin transporter. The reagents were human SERT (HEK293F) cells, fluoxetine (Sigma), nomifensine, neurotransmitter transporter uptake assay kit (Molecular Devices), freestyle 293 expression medium (Invitrogen), 10× Hank's Balanced Salt Solution (HBSS; Invitrogen), 1 M HEPES (Mediatech), Biocoat poly-D-lysine 96-well, black, clear plates (Becton, Dickinson), and 500 µL polypropylene U-bottom 96-well plates (Fisher). The Assay Buffer (AB) was 1λ HBSS and 0.02 M HEPES.

The HEK293F cells were transfected with the human serotonin transporter and frozen in 1 mL aliquots at about 1E+07 cells/mL. On the day of the experiment, the cells were removed from −80° C. or liquid nitrogen and thawed in a room temperature water bath. The cells were dilute to about 1-2E+06 with Freestyle medium. A 1 mL sample (1:2 dilution) was prepared, and the cells were counted. The cells were spun at 1100 rpm for 5 minutes, and the medium was aspirated off. The cells were resuspend in medium at 1.5E+06 cells/mL for about 60,000 cells per well. 40 μL of cells were dispensed per well in the Biocoat plates. The plates were spun at 1100 rpm for 1 minute to improve homogeneity of the cell layer and were incubated at 37° C. for a minimum of 3 hours.

12 μL of test compound (10 mM) in DMSO was added to the wells, and nomifensine was used as a control. Fluoxetine (final assay concentration of 10 μM) was used for background signal. The neurotransmitter transporter dye was prepared in AB prior to use.

Data were analyzed by calculating percent effect: (a) [1-(singlicate minus plate background signal)/(plate total signal minus plate background)]×100%, (b) $IC_{50}$, and (c) $K_i$ using the Cheng-Prusoff equation below and an Activity-Base or XLfit template.

$$K_i = \frac{IC_{50}}{1 + ([dye]/K_m)} \text{ where } K_m \text{ is the value for the dye} \\ (55.5\% \text{ at } 20 \text{ minute read})$$

Due to the proprietary nature of the dye formulation, all dye concentrations were expressed as a percentage of the vendor-recommended dye reconstitution. Thus, the above calculations were valid when both [dye] and $K_m$ were expressed in the same units (%). Compounds were tested in triplicate (n=3).

Example 176—Human ERG (hERG) Assay

The voltage-dependent potassium channel encoded by the human ether-a-go-go-related gene (hERG) is believed to play a key role in repolarisation of the ventricular cardiac action potential. Changes in its activity, caused either by inherited mutations of the gene sequence or pharmacological modification, can lead to prolongation of action potential duration. This can lead to prolongation of the QT interval recorded in man on an electrocardiogram and to a potentially fatal cardiac arrhythmia known as Torsades de Pointes.

hERG currents were recorded from hERG-expressing CHO cells. The biophysical and pharmacological characterization of the hERG currents in these cells was performed. The sequence of the gene expressed in this cell line exhibited 100% identity at the nucleotide level with published hERG sequences (GenBank® Accession Numbers U04270 and NM_000238).

The pre- and post-compound hERG current was evoked by a single voltage pulse consisting of a 20 s period holding at −70 mV, a 160 ms step to −60 mV (to obtain an estimate of leak), a 100 ms step back to −70 mV, a 1 s step to +40 mV, a 2 s step to −30 mV, and finally a 500 ms step to −70 mV. In between the pre- and post-compound voltage pulses, there was no clamping of the membrane potential. Currents were leak-subtracted based on the estimate of current evoked during the +10 mV step at the start of the voltage pulse protocol. The current signal was sampled at 2.5 k Hz. For each compound, the $IC_{50}$ value was determined.

Example 177—Cytochrome P450 Inhibition Assays

Recombinant enzymes, 3A4 and 2D6, generated using the ABL yeast expression system were used. For CYP3A4, the enzyme amount was 2 pmol per well, and the substrate (7-benzyloxy-4-(trifluoromethyl) coumarin; BFC) was used at 15 μM. The assay mixture also included $K_2HPO_4$ (pH 7.4; conc. 0.1 M) and NADPH (conc. 1 mM). The incubation time was 30 minutes, and the reference inhibitor was A-naphthoflavone. For CYP2D6, the enzyme amount was 2 pmol per well, and the substrate (7-methoxy-4-(aminomethyl)-coumarin; MAMC) was used at 20 μM. The assay mixture also included $K_2HPO_4$ (pH 7.4; conc. 0.1 M) and NADPH (conc. 0.06 mM). The incubation time was 35 minutes, and the reference inhibitor was quinidine.

Briefly, 0.6 μL of serially diluted compound was added to 75 μL water. 10 μL of diluted compound in water was then added to each assay plate. 20 μL of a $K_2HPO4$, enzyme, and substrate mixture was added. After 10 minutes of room temperature pre-incubation, 10 μL of NADPH was added, and the plates were placed at 37° C. for 30 or 35 minutes depending on the enzyme being tested. After the incubation was complete, 20 μL of 0.1% Tris/ACN was added to the plate. The plate was read on a FluorStar fluorescence plate reader.

Example 178—Biological Activities

The compounds made as described in Example 1-131 were tested using the assays described in Examples 132-136. The results were compiled as set forth in Tables 2. Selected compounds (Compound ID NOs. 173-182) were evaluated for comparison purposes (Table 3). These results demonstrate that the compounds provided herein can be used to inhibit reuptake of serotonin, norepinephrine, dopamine, or combinations thereof. In some cases, a compound provided herein can inhibit the reuptake of one or more of serotonin, norepinephrine, and dopamine with a $K_i$ value of less than 50 nM while having an $IC_{50}$ value for a human CYP2D6 polypeptide and/or a human ERG polypeptide that is greater than 1 μM.

TABLE 2

Biological activity results.

| Compound ID No. | Compound Reference No. | hNET $K_i$ (nM) | hDAT $K_i$ (nM) | hSERT $K_i$ (nM) | hERG $IC_{50}$ (μm) | CYP3A4 $IC_{50}$ (μm) | CYP2D6 $IC_{50}$ (μm) |
|---|---|---|---|---|---|---|---|
| 1 | 13341668 | 0.7 | 20.7 | 1.9 | 33 | | 1.1 |
| 2 | 13337869 | 1 | 5.5 | 2.5 | 15 | | 0.17 |
| 3 | 13322896 | 1.3 | 5.2 | 0.6 | 33 | 20 | 1.3 |
| 4 | 13224752 | 1.4 | 10.9 | 2.5 | 11 | 20 | 0.3 |
| 5 | 13261591 | 1.4 | 10.1 | 2.8 | 6.5 | 18 | 0.24 |

TABLE 2-continued

Biological activity results.

| Compound ID No. | Compound Reference No. | hNET K$_i$ (nM) | hDAT K$_i$ (nM) | hSERT K$_i$ (nM) | hERG IC$_{50}$ (μm) | CYP3A4 IC$_{50}$ (μm) | CYP2D6 IC$_{50}$ (μm) |
|---|---|---|---|---|---|---|---|
| 6 | 13342106 | 1.4 | 39.2 | 0.8 | 25 | | 0.76 |
| 7 | 13366080 | 1.4 | 6.6 | 3.6 | 33 | 5.9 | 0.034 |
| 8 | 13371132 | 1.4 | 10.8 | 1.3 | | | |
| 9 | 13228373 | 1.5 | 42.3 | 5.7 | 9.5 | 8.6 | 0.21 |
| 10 | 13245751 | 1.5 | 7.3 | 11.7 | 9.1 | 20 | 0.12 |
| 11 | 13224757 | 1.6 | 11.1 | 4.2 | 11 | 6.7 | 0.096 |
| 12 | 13305851 | 1.6 | 52.6 | 2.7 | 8.4 | 20 | 0.88 |
| 13 | 13349532 | 1.6 | 19.7 | 5.4 | 19 | 17 | 0.4 |
| 14 | 13366816 | 1.6 | 79.3 | 3.1 | 33 | 20 | 3.7 |
| 15 | 13331487 | 1.7 | 42.5 | 2.4 | 12 | 20 | 0.2 |
| 16 | 13311940 | 1.8 | 6.6 | 6.3 | 5 | 19 | 0.23 |
| 17 | 13320979 | 1.8 | 21.6 | 2.2 | 7.9 | 6.4 | 0.12 |
| 18 | 13342139 | 1.8 | 31.9 | 0.4 | 4.6 | | 0.33 |
| 19 | 13366419 | 1.9 | 17 | 4.3 | 33 | 20 | 20 |
| 20 | 13368447 | 1.9 | 36.1 | 3.2 | 4.7 | | |
| 21 | 13309710 | 2 | 32.4 | 66.4 | 23 | 20 | 0.47 |
| 22 | 13344312 | 2 | 56.7 | 2.1 | 15 | 15 | 0.18 |
| 23 | 13366125 | 2 | 65.6 | 5.6 | 21 | 20 | 4.9 |
| 24 | 13326653 | 2.2 | 21.9 | 71.4 | 33 | 20 | 1.4 |
| 25 | 13341411 | 2.2 | 105.6 | 22.7 | 33 | | 0.32 |
| 26 | 13366118 | 2.2 | 53.5 | 1.6 | 7.5 | 20 | 0.027 |
| 27 | 13267551 | 2.3 | 96.7 | 251.5 | | | |
| 28 | 13283201 | 2.4 | 43.8 | 3.4 | 15 | 9.6 | 0.16 |
| 29 | 13342110 | 2.4 | 37.2 | 1.1 | 11 | | 0.65 |
| 30 | 13368783 | 2.4 | 14.3 | 1 | 29 | | |
| 31 | 13370608 | 2.4 | 24.6 | 1.9 | | | |
| 32 | 13322893 | 2.7 | 15.8 | 0.7 | 22 | 20 | 0.56 |
| 33 | 13342019 | 2.7 | 13.2 | 1.4 | 33 | | 0.55 |
| 34 | 13366421 | 2.7 | 28.5 | 7.5 | 33 | 20 | 12 |
| 35 | 13342107 | 2.8 | 70.8 | 3.7 | 13 | | 0.32 |
| 36 | 13273128 | 2.9 | 17 | 7 | 6.2 | 11 | 0.17 |
| 37 | 13283197 | 3 | 63.6 | 54.6 | | | |
| 38 | 13203584 | 3.1 | 49.9 | 16.9 | 12 | 8.7 | 0.083 |
| 39 | 13281862 | 3.1 | 34.3 | 12.6 | 8.2 | 8.4 | 0.17 |
| 40 | 13225597 | 3.2 | 114.2 | 3.3 | 4.1 | 19 | 0.96 |
| 41 | 13225601 | 3.2 | 10.6 | 52.5 | | 19 | 0.13 |
| 42 | 13320726 | 3.2 | 89.5 | 0.3 | 27 | 3.4 | 1.1 |
| 43 | 13267866 | 3.3 | 7.3 | 19.7 | 7.1 | 8.1 | 0.11 |
| 44 | 13299100 | 3.3 | 74.1 | 12.2 | 3.3 | 8 | 1 |
| 45 | 13368878 | 3.3 | 8.9 | 2.4 | | | |
| 46 | 13228482 | 3.4 | 37.5 | 24.2 | 20 | 16 | 0.17 |
| 47 | 13270298 | 3.5 | 15 | 2.2 | 4.8 | 20 | 0.17 |
| 48 | 13289328 | 3.8 | 78 | 2.3 | 33 | 15 | 0.58 |
| 49 | 13309941 | 3.8 | 213.4 | 5.6 | 25 | 20 | 1.7 |
| 50 | 13341669 | 3.8 | 36.5 | 2.9 | 17 | | 0.8 |
| 51 | 13376700 | 3.9 | 140.9 | 2.6 | | | |
| 52 | 13298151 | 4.1 | 26.7 | 20.4 | 12 | 20 | 0.9 |
| 53 | 13232819 | 4.5 | 9.8 | 17.3 | 9.8 | 20 | 0.41 |
| 54 | 13243687 | 4.5 | 971.5 | 2.4 | | | |
| 55 | 13283198 | 4.6 | 1634.6 | 1.8 | | 20 | 0.81 |
| 56 | 13270295 | 4.7 | 40.4 | 6.7 | 22 | 11 | 0.24 |
| 57 | 13299102 | 5 | 20.2 | 5.9 | 4.7 | 3.3 | 0.19 |
| 58 | 13270525 | 5.1 | 127.2 | 5.9 | 2.1 | 9.6 | 0.12 |
| 59 | 13328855 | 5.2 | 111.8 | 35.6 | 21 | 20 | 1.5 |
| 60 | 13328420 | 5.3 | 83.2 | 10.7 | 28 | 20 | 0.56 |
| 61 | 13242271 | 5.8 | 14.6 | 0.9 | 9.8 | 20 | 0.3 |
| 62 | 13270294 | 6.5 | 45 | 9.9 | 25 | 20 | 1 |
| 63 | 13320582 | 6.7 | 78.2 | 853.3 | 33 | 8.3 | 2.8 |
| 64 | 13342119 | 7.2 | 9.4 | 11.3 | 20 | | 5.1 |
| 65 | 13324681 | 7.5 | 18.1 | 243.4 | 19 | 7.8 | 0.043 |
| 66 | 13267288 | 8.1 | 28.9 | 46.7 | 15 | 20 | 0.26 |
| 67 | 13361259 | 8.2 | 69.7 | 0.7 | 15 | 20 | 0.33 |
| 68 | 13369076 | 8.4 | 55.5 | 29.7 | | | |
| 69 | 13287084 | 9 | 21.9 | 21.2 | 9.5 | 20 | 0.51 |
| 70 | 13270228 | 9.5 | 48.5 | 142.5 | 31 | 20 | 0.22 |
| 71 | 13372931 | 10 | 17.9 | 4.4 | | | |
| 72 | 13270293 | 10.1 | 100.3 | 27.6 | 33 | 20 | 0.76 |
| 73 | 13247827 | 10.2 | 56.6 | 16 | 31 | 20 | 0.79 |
| 74 | 13287085 | 10.3 | 109 | 13.6 | 20 | 8.1 | 0.79 |
| 75 | 13273126 | 10.4 | 504.9 | 2.1 | | 16 | 0.56 |
| 76 | 13303502 | 11.9 | 21.2 | 222.4 | 3 | 3.6 | 0.14 |
| 77 | 13373098 | 12.4 | 44.7 | 3 | 4.5 | | 5.7 |
| 78 | 13332464 | 14.3 | 26.1 | 15.3 | 12 | 20 | 1.1 |
| 79 | 13370736 | 14.4 | 73.3 | 6.4 | | | |

TABLE 2-continued

Biological activity results.

| Compound ID No. | Compound Reference No. | hNET $K_i$ (nM) | hDAT $K_i$ (nM) | hSERT $K_i$ (nM) | hERG $IC_{50}$ (μm) | CYP3A4 $IC_{50}$ (μm) | CYP2D6 $IC_{50}$ (μm) |
|---|---|---|---|---|---|---|---|
| 80 | 13287456 | 14.5 | 52.2 | 34.7 | 33 | 19 | 2 |
| 81 | 13371279 | 14.7 | 1360 | 13 | | | |
| 82 | 13228464 | 15.3 | 9.8 | 15.3 | 19 | 20 | 0.99 |
| 83 | 13094210 | 15.7 | 46.7 | 5.1 | 4.3 | | |
| 84 | 13376701 | 16.2 | 39.2 | 3.3 | | | |
| 85 | 13326301 | 16.4 | 246.6 | 16.1 | 21 | 20 | 1 |
| 86 | 13228816 | 16.7 | 9.9 | 2.7 | 0.85 | 20 | 0.29 |
| 87 | 13242217 | 18.1 | 114.3 | 6.1 | 17 | 0.94 | 0.066 |
| 88 | 13314785 | 18.1 | 80.4 | 4.6 | 23 | 20 | 1.6 |
| 89 | 13322895 | 21.4 | 25 | 1.8 | 6.6 | 20 | 1.8 |
| 90 | 13338191 | 22.6 | 86.2 | 25.4 | 12 | | 0.59 |
| 91 | 13097910 | 23.2 | 248.8 | 177.8 | 31 | | |
| 92 | 13331486 | 28 | 216.2 | 9.3 | 33 | 20 | 0.81 |
| 93 | 13334801 | 29.5 | 136.6 | 1.1 | 13 | | 1.2 |
| 94 | 13320573 | 32.8 | 52.6 | 366.6 | 33 | 18 | 3 |
| 95 | 13364611 | 33.5 | 30.7 | 36.9 | 33 | 11 | 0.41 |
| 96 | 13328422 | 36.8 | 158.2 | 9.9 | 33 | 20 | 1.1 |
| 97 | 13322960 | 38.2 | 22.6 | 78.4 | 8 | 15 | 0.18 |
| 98 | 13320581 | 38.8 | 216 | 166.7 | 33 | 20 | 0.85 |
| 99 | 13324636 | 41 | 287.4 | 43.2 | 33 | 20 | 3.6 |
| 100 | 13321139 | 43.8 | 27.4 | 361.3 | 21 | 8.2 | 0.064 |
| 101 | 13332457 | 54.4 | 73 | 2736.4 | | 20 | 3.5 |
| 102 | 13303500 | 55.2 | 29.3 | 86.2 | | 5.7 | 0.12 |
| 103 | 13305857 | 57.6 | 91.9 | 58.6 | | 20 | 11 |
| 104 | 13351506 | 60.6 | 94.6 | 656.2 | | 0.27 | 0.066 |
| 105 | 13230850 | 64.6 | 18.1 | 137.5 | | 20 | 2.1 |
| 106 | 13308441 | 80.6 | 19.7 | 741.8 | | 20 | 3.9 |
| 107 | 13305701 | 82.2 | 125.5 | 726.9 | | 19 | 2.4 |
| 108 | 13305597 | 88.5 | 57.1 | 754.2 | | 20 | 2.2 |
| 109 | 13363016 | 120 | 66.7 | 646.2 | | 20 | 1.1 |
| 110 | 13311883 | 142 | 24 | 677.4 | 6.8 | 17 | 1.9 |
| 111 | Paroxetine | | | | | | |
| 112 | 13320725 | 148.4 | 273.3 | 154.2 | | 18 | 2.9 |
| 113 | 13270300 | 167.5 | 1569.9 | 5.2 | | 16 | 0.22 |
| 114 | 13245752 | 170.6 | 27 | 660.8 | 11 | 20 | 5.3 |
| 115 | 13328854 | 177.2 | 126.8 | 641.7 | | 20 | 15 |
| 116 | 13334197 | 195 | 39.7 | 1691.7 | | 20 | 5.5 |
| 117 | 13322959 | 235.8 | 12.9 | 796.3 | | 20 | 3.9 |
| 118 | 13366077 | 252.5 | 138.6 | 36.6 | 24 | 20 | 4.1 |
| 119 | 13326650 | 257.3 | 75.5 | 1783.9 | | 7.9 | 2.4 |
| 120 | 13303494 | 261.7 | 88.5 | 661.6 | | 9 | 20 |
| 121 | 13329271 | 269.5 | 5 | 2845.3 | | 20 | 3.4 |
| 122 | 13328652 | 273.2 | 49.6 | 124 | | 20 | 6.6 |
| 123 | 13334795 | 290.5 | 378.7 | 12 | | | 3 |
| 124 | 13334794 | 337.9 | 15.3 | 166.8 | | 4.8 | 2.4 |
| 125 | 13303501 | 370.6 | 65.3 | 724.7 | | 20 | 3.9 |
| 126 | 13366127 | 499.9 | 125 | 107.1 | | 20 | 15 |
| 127 | 13328856 | 649 | 80.5 | 3280 | | 20 | 19 |
| 128 | 13332636 | 2630 | 193 | 3040 | | 20 | 20 |
| 129 | 13366724 | 3670 | 43.5 | 3370 | | | 3.7 |
| 130 | 13337429 | 4570 | 87.3 | 3370 | | | |
| 131 | 13381274 | | | | | | |
| 132 | 13279931 | 10.3 | 41.8 | 12.4 | 4.7 | | |
| 133 | 13298150 | 34.6 | 52.7 | 115.7 | | 10 | 0.58 |
| 134 | 13259059 | 6 | 56.8 | 7.8 | 6.2 | 9.9 | 0.22 |
| 135 | 13270299 | 11.7 | 58.1 | 21.4 | 3.1 | 20 | 0.91 |
| 136 | 13270719 | 37.4 | 64.5 | 15.7 | 5.4 | 3.4 | 0.19 |
| 137 | 13273127 | 23.2 | 77.7 | 31.8 | 7.8 | 3.7 | 0.11 |
| 138 | 13320978 | 47.4 | 87.2 | 75.8 | | 11 | 0.37 |
| 139 | 13253992 | 5 | 88.7 | 6.4 | 3.1 | 13 | 0.62 |
| 140 | 13298152 | 25.9 | 91.6 | 28.3 | 6.1 | 20 | 0.86 |
| 141 | 13296640 | 32.6 | 91.9 | 296.2 | | 20 | 0.37 |
| 142 | 13298144 | 13.8 | 95.3 | 207.8 | | 20 | 0.66 |
| 143 | 13283202 | 6.6 | 105.8 | 7.9 | 15 | 7.6 | 0.16 |
| 144 | 13283194 | 23.5 | 112.8 | 10 | 6.1 | 20 | 1.6 |
| 145 | 13270301 | 10.9 | 133.7 | 9.4 | 11 | 19 | 0.31 |
| 146 | 13242221 | 9.3 | 143.8 | 10.1 | 15 | 1.3 | 0.092 |
| 147 | 13267552 | 45.7 | 120.6 | 800.3 | | | |
| 148 | 13250685 | 8.5 | 114.5 | 191.2 | | | |
| 149 | 13251189 | 7.7 | 128.7 | 118.7 | | | |
| 150 | 13267189 | 6.3 | 31.8 | 51.5 | | | |
| 151 | 13320727 | 20.4 | 31.4 | 45.2 | 3.8 | 2.1 | 0.13 |
| 152 | 13322451 | 126.1 | 31.8 | 935.1 | | 2 | 0.044 |
| 153 | 13308428 | 3.9 | 33.8 | 7.5 | 1.6 | 20 | 1.4 |

TABLE 2-continued

Biological activity results.

| Compound ID No. | Compound Reference No. | hNET $K_i$ (nM) | hDAT $K_i$ (nM) | hSERT $K_i$ (nM) | hERG IC$_{50}$ (μm) | CYP3A4 IC$_{50}$ (μm) | CYP2D6 IC$_{50}$ (μm) |
|---|---|---|---|---|---|---|---|
| 154 | 13303499 | 37.1 | 40.3 | 38.4 | 2.2 | 6.9 | 0.29 |
| 155 | 13270733 | 17.8 | 46.6 | 73.7 |  | 20 | 1.4 |
| 156 | 13320772 | 17.2 | 48.5 | 22.4 | 4.1 | 9.5 | 0.17 |
| 157 | 13328622 | 88.4 | 53.4 | 140.4 |  | 20 | 0.58 |
| 158 | 13320641 | 6.3 | 55.4 | 38.6 | 4.4 | 3.8 | 0.098 |
| 159 | 13320572 | 55.4 | 55.8 | 69.5 |  | 2.5 | 0.17 |
| 160 | 13312320 | 9.1 | 83.5 | 9.2 | 8 | 3.5 | 0.49 |
| 161 | 13326651 | 38.5 | 103 | 616.3 |  | 9.2 | 0.16 |
| 162 | 13303497 | 107.6 | 110.3 | 806.1 |  | 4.9 | 0.79 |
| 163 | 13320512 | 80 | 110.4 | 192.4 |  | 14 | 0.73 |
| 164 | 13322452 | 41.6 | 113.4 | 78.1 | 4.1 | 5.3 | 0.25 |
| 165 | 13321142 | 38.6 | 118.2 | 341.3 | 3.8 | 2.9 | 0.081 |
| 166 | 13363017 | 92.4 | 131.5 | 36.9 |  | 0.24 | 0.63 |
| 167 | 13328653 | 10.8 | 131.8 | 18.8 | 12 | 20 | 0.4 |
| 168 | 13305595 | 89.3 | 144.1 | 177.7 |  | 4.6 | 0.78 |
| 169 | 13366126 | 212.2 | 145.9 | 268 |  | 20 | 1.3 |
| 170 | 13329113 | 306.5 | 40 | 2010 |  | 4.8 | 0.38 |
| 171 | 13350716 | 453.7 | 92 | 1848.4 |  | 20 | 2 |
| 172 | 13331217 | 625.1 | 101.9 | 1261.5 | 4.7 | 0.2 | 0.97 |

TABLE 3

Biological activity results for selected reference compounds.

| Compound ID No. | Compound Reference No. | Structure | Name | hNET $K_i$ (nM) | hDAT $K_i$ (nM) | hSERT $K_i$ (nM) | hERG IC$_{50}$ (μM) | CYP 3A4 IC$_{50}$ (μM) | CYP 2D6 IC$_{50}$ (μM) |
|---|---|---|---|---|---|---|---|---|---|
| 173 | PRC200-SS | 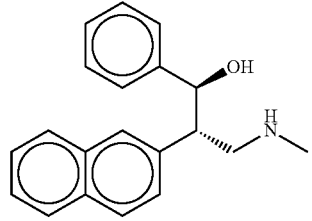 | AZD1858 MCJ001-SS | 0.5 | 4.6 | 1.2 | 8.8 |  |  |
| 174 | 10050326 | 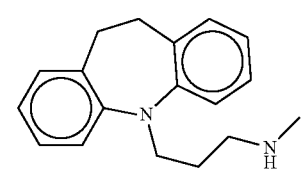 | Desipramine | 1.8 | 4566.3 | 19.1 | 13 |  |  |
| 175 | 10529749 | 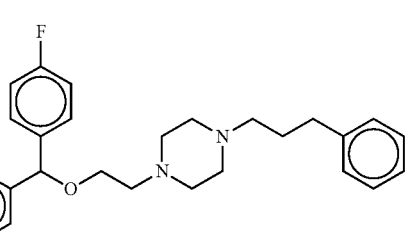 | GBR12909 | 137.7 | 8.7 | 167.6 | 0.47 |  |  |

TABLE 3-continued

Biological activity results for selected reference compounds.

| Compound ID No. | Compound Reference No. | Structure | Name | hNET $K_i$ (nM) | hDAT $K_i$ (nM) | hSERT $K_i$ (nM) | hERG $IC_{50}$ (μM) | CYP 3A4 $IC_{50}$ (μM) | CYP 2D6 $IC_{50}$ (μM) |
|---|---|---|---|---|---|---|---|---|---|
| 176 | 10582649 | 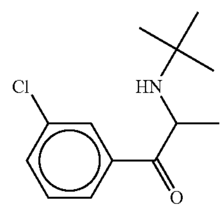 | Buproprion | 3641.5 | 172.9 | 13310.8 | 69 | | |
| 177 | 10610390 | 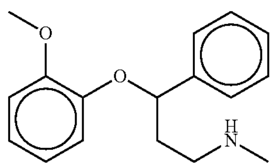 | Nisoxetine | 1.3 | 82.5 | 54.4 | | | |
| 178 | 12528553 | 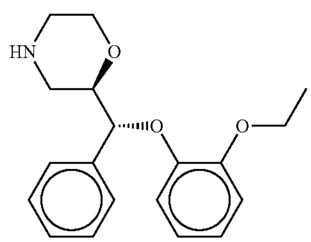 | Reboxetine | 2.9 | 5260 | 99.5 | | | |
| 179 | 12971996 | 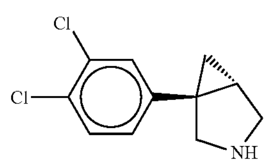 | DOV | 38.6 | 42.3 | 59 | 21 | 8.8 | 7 |
| 180 | 13098793 | 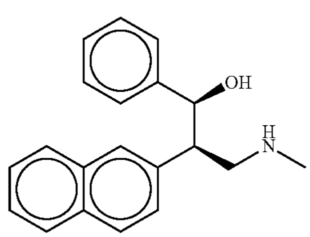 | PRC-200 isomer | 2.9 | 47.5 | 14.8 | 32 | | |
| 181 | 13115612 | 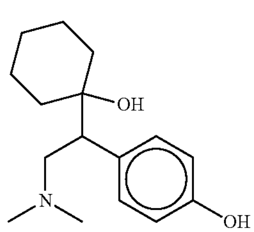 | Desvenlafaxine | 668.1 | 3726.4 | 4.1 | | | |

TABLE 3-continued

Biological activity results for selected reference compounds.

| Compound ID No. | Compound Reference No. | Structure | Name | hNET $K_i$ (nM) | hDAT $K_i$ (nM) | hSERT $K_i$ (nM) | hERG IC$_{50}$ (μM) | CYP 3A4 IC$_{50}$ (μM) | CYP 2D6 IC$_{50}$ (μM) |
|---|---|---|---|---|---|---|---|---|---|
| 182 | 12013473 | 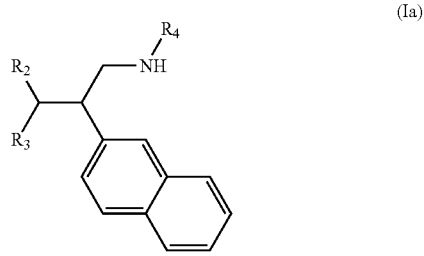 | Paroxetine | 145 | 387.5 | 0.8 | 5.4 | 20 | 3.1 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of formula I:

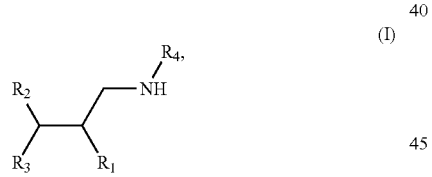

wherein $R_1$ is selected from naphthalen-2-yl, and phenyl substituted at the 3- or 4-position or 3- and 4-positions with a substituent selected from halogen and lower alkyl;

$R_2$ is a 5- or 6-membered aromatic heterocycle each of which is substituted with substituents selected from halo, methylsulfanyl, methanesulfonyl, hydroxyl, methyl, ethyl, alkoxy, dimethylamino, and 1,1,1-trifluoromethanesulfonamide;

optionally, two adjacent alkoxy groups are connected to form a 5- or 6-membered ring;

$R_3$ is hydrogen, hydroxyl, lower alkoxy, or halo; and $R_4$ is hydrogen or lower alkyl.

2. The compound of claim 1, wherein $R_2$ is substituted with one or two substituents.

3. The compound of claim 1, having the formula Ia or Ib:

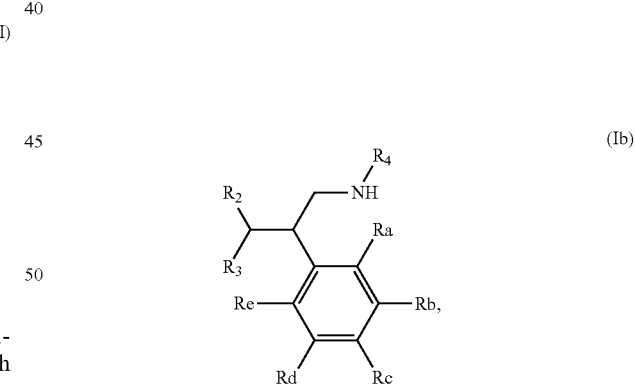

wherein $R_a$, $R_b$, $R_c$, $R_d$, and $R_e$ are selected from hydrogen, lower alkyl, and halo.

4. The compound of claim 3, wherein at least two of $R_a$, $R_b$, $R_c$, $R_d$, and $R_e$ are hydrogen.

5. The compound of claim 4, wherein the remaining $R_a$, $R_b$, $R_c$, $R_d$, and $R_e$ are independently selected from ethyl, chloro, and bromo.

6. The compound of claim 3, wherein $R_a$, $R_d$, and $R_e$ are hydrogen; and $R_b$ and $R_c$ are independently selected from ethyl, chloro, and bromo.

7. A compound of formula II:

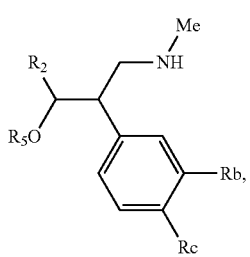

wherein

R$_2$ is a 5- or 6-membered aromatic heterocycle each of which is substituted with substituents selected from halo, methylsulfanyl, methanesulfonyl, ethyl, alkoxy, dimethylamino, and 1,1,1-trifluoromethanesulfonamide;

R$_5$ is hydrogen or lower alkyl; and

R$_b$ and R$_c$ are independently hydrogen, halo, or lower alkyl.

8. The compound of claim 7, wherein each of R$_b$ and R$_c$ is not hydrogen.

9. A compound of formula I:

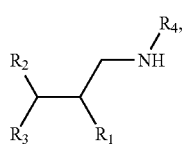

wherein

R$_1$ is a phenyl substituted at the 3 or 4 position or 3- and 4-positions with a substituent selected from halogen and lower alkyl;

R$_2$ is selected from phenyl and a 5- or 6-membered aromatic heterocycle each of which is optionally substituted with substituents selected from halo, methylsulfanyl, methanesulfonyl, hydroxyl, methyl, ethyl, alkoxy, dimethylamino, and 1,1,1-trifluoromethanesulfonamide;

optionally, two adjacent alkoxy groups are connected to form a 5- or 6-membered ring;

R$_3$ is hydrogen, hydroxyl, lower alkoxy, or halo; and

R$_4$ is hydrogen or lower alkyl, wherein said compound has the formula Ia:

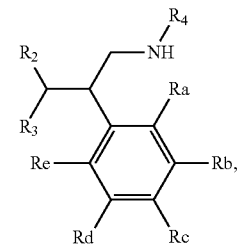

wherein at least two of R$_a$, R$_b$, R$_c$, R$_d$, and R$_e$ are hydrogen, and wherein the remaining R$_a$, R$_b$, R$_c$, R$_d$, and R$_e$ are independently selected from ethyl, chloro, and bromo.

10. A compound of formula I:

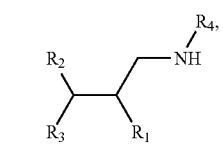

wherein

R$_1$ is a phenyl substituted at the 3 or 4 position or 3- and 4-positions with a substituent selected from halogen and lower alkyl;

R$_2$ is selected from phenyl and a 5- or 6-membered aromatic heterocycle each of which is optionally substituted with substituents selected from halo, methylsulfanyl, methanesulfonyl, hydroxyl, methyl, ethyl, alkoxy, dimethylamino, and 1,1,1-trifluoromethanesulfonamide;

optionally, two adjacent alkoxy groups are connected to form a 5- or 6-membered ring;

R$_3$ is hydrogen, hydroxyl, lower alkoxy, or halo; and

R$_4$ is hydrogen or lower alkyl, wherein said compound has the formula Ia:

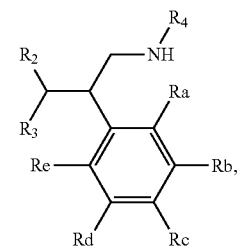

wherein R$_a$, R$_d$, and R$_e$ are hydrogen; and R$_b$ and R$_c$ are independently selected from ethyl, chloro, and bromo.

* * * * *